United States Patent
Lindsley et al.

(10) Patent No.: US 9,540,371 B2
(45) Date of Patent: Jan. 10, 2017

(54) SUBSTITUTED QUINAZOLIN-4(3H)-ONES, PYRIDO[3,4-D]PYRIMIDIN-4(3H)-ONES, PYRIDO[3,2-D]PYRIMIDIN-4(3H)-ONES AND PYRIDO[2,3-D]PYRIMIDIN-4(3H)-ONES AS POSITIVE ALLOSTERIC MODULATORS OF MUSCARINIC ACETYCHOLINE RECEPTOR M1

(71) Applicant: Vanderbilt University, Nashville, TN (US)

(72) Inventors: Craig W. Lindsley, Brentwood, TN (US); P. Jeffrey Conn, Nashville, TN (US); Shaun R. Stauffer, Brentwood, TN (US); Joseph David Panarese, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 14/787,722

(22) PCT Filed: Apr. 28, 2014

(86) PCT No.: PCT/US2014/035744
§ 371 (c)(1),
(2) Date: Oct. 28, 2015

(87) PCT Pub. No.: WO2014/179237
PCT Pub. Date: Nov. 6, 2014

(65) Prior Publication Data
US 2016/0102090 A1 Apr. 14, 2016

Related U.S. Application Data

(60) Provisional application No. 61/817,284, filed on Apr. 29, 2013.

(51) Int. Cl.
| | | |
|---|---|---|
| *A61K 31/519* | (2006.01) | |
| *C07D 471/04* | (2006.01) | |
| *C07D 403/10* | (2006.01) | |
| *C07D 401/10* | (2006.01) | |

(52) U.S. Cl.
CPC ........... *C07D 471/04* (2013.01); *C07D 401/10* (2013.01); *C07D 403/10* (2013.01)

(58) Field of Classification Search
CPC ............................ A61K 31/519; C07D 471/04
USPC ............... 514/264.1, 303; 544/279; 546/118; 548/361.1, 377.1
See application file for complete search history.

(56) References Cited

U.S. PATENT DOCUMENTS

| | | |
|---|---|---|
| 5,962,457 A | 10/1999 | Chenard et al. |
| 2006/0247244 A1 | 11/2006 | Erguden et al. |
| 2011/0112119 A1 | 5/2011 | Peters et al. |
| 2013/0123236 A1 | 5/2013 | Lindsley et al. |

FOREIGN PATENT DOCUMENTS

WO 2013103931 7/2013

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Hackam, et al. JAMA, 296(14), 2006, 1731-1732.*
Osborne, et al. Spectrochimica Acta, Part A: Molecular and Biomolecular Spectroscopy, 56A(6), 2000, 1079-1100.*
PCT/US2014/035744 International Search Report and Written Opinion of the Intentional Searching Authority dated Aug. 26, 2014 (8 pages).
PCT/US2014/035744 International Preliminary Report on Patentability dated Nov. 3, 2015 (2 pages.).
Bridges et al. "Chemical Lead Optimization of a Pan Gq mAChR M1, M3, M5 Positive Allosteric Modulator (PAM) Lead, Part II, Development of Potent and Highly Selective M1 PAM," Bioorg Med Chem Lett (Mar. 15, 2010) vol. 20 (6), pp. 1972-1975. p. 1, para 3-p. 3, para 1; p. 6, Fig 2; Fig 4; p. 9, Fig 5.
Reid et al. "Discovery and Optimization of a Novel, Selective and Brain Penetrant M1 Positive Allosteric Modulator (PAM): The development of ML 169, an MLPCN probe," Bioorganic & Medicinal Chemistry Letters (2011) vol. 21 pp. 2697-2701, p. 2699, Table 2.
PCT/US2014/035700 International Search Report and Written Opinion dated Oct. 1, 2014 (10 pages).

(Continued)

*Primary Examiner* — Douglas M Willis

(74) *Attorney, Agent, or Firm* — Michael Best & Friedrich LLP

(57) ABSTRACT

In one aspect, the invention relates to 3-benzylquinazolin-4(3H)-one analogs, derivatives thereof, and related compounds, which are useful as positive allosteric modulators of the muscarinic acetylcholine receptor $M_1$ (mAChR $M_1$); synthesis methods for making the compounds; pharmaceutical compositions comprising the compounds; and methods of treating neurological and psychiatric disorders associated with muscarinic acetylcholine receptor dysfunction using the compounds and compositions. This abstract is intended as a scanning tool for purposes of searching in the particular art and is not intended to be limiting of the present invention. Exemplary 3-benzylquinazolin-4(3H)-one compounds include compounds of formula (I):

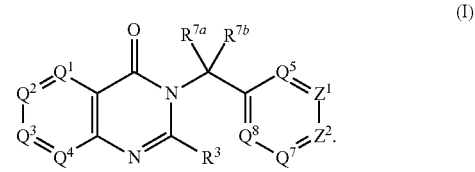

12 Claims, No Drawings

(56) References Cited

OTHER PUBLICATIONS

Morrison and Boyd, Organic Chemistry, (5th Ed., 1987), Chapter 13, entitled "Aromaticity," pp. 477-497.
T. W. Greene, P. G. M. Wuts, Wiley-Interscience, "Protective Groups in Organic Synthesis," 1999.
Almarasson, O., et. al., "Crystal Engineering of the Composition of Pharmaceutical Phases. Do Pharmaceutical Co-crystals Represent a New Path to Improved Medicines?" The Royal Society of Chemistry, 1889-1896, 2004.
Levey, A.I., et al., J Neurosci. 1991, 11, 3218-3226.
Liu et al., "Quinoxalin-2(1-H)-One Derivatives As Inhibitors Against Hepatitis C Virus" J. Med. Chem. 2011, 54, 5747.

* cited by examiner

SUBSTITUTED QUINAZOLIN-4(3H)-ONES, PYRIDO[3,4-D]PYRIMIDIN-4(3H)-ONES, PYRIDO[3,2-D]PYRIMIDIN-4(3H)-ONES AND PYRIDO[2,3-D]PYRIMIDIN-4(3H)-ONES AS POSITIVE ALLOSTERIC MODULATORS OF MUSCARINIC ACETYCHOLINE RECEPTOR M1

CROSS-REFERENCE TO RELATED APPLICATIONS

This application is a U.S. national stage filing under 35 U.S.C. 371 of International Application No. PCT/US2014/035744, filed Apr. 28, 2014, which claims priority to U.S. Provisional Patent Application No. 61/817,284, filed Apr. 29, 2013, each of which is incorporated herein by reference in its entirety.

STATEMENT REGARDING FEDERALLY SPONSORED RESEARCH

This invention was made with U.S. Government support under grant numbers RO1MH082867 and U01MH087965, awarded by the National Institute of Mental Health (NIMH). The U.S. government has certain rights in the invention.

BACKGROUND

Alzheimer's disease (AD) is a neurodegenerative disease affecting the elderly, which results in progressive impairment of memory, language skills and severe behavioral deficits. Hallmarks of the disease include degeneration of cholinergic neurons in the cerebral cortex, hippocampus, basal forebrain and other regions of the brain important for memory and cognition. Other hallmarks of AD include neurofibrillary tangles composed of hyperphosphorylated tau and accumulation of amyloid β peptide (Aβ). Aβ is a 39-43 amino acid peptide produced in the brain by proteolytic processing of β-amyloid precursor protein (APP) by the β-amyloid cleaving enzyme (BACE) and gamma secretase which leads to accumulation of Aβ in the brain, where Aβ 1-40 and 1-42 are the principal aggregate-forming species of Aβ.

Schizophrenia is a debilitating psychiatric disorder characterized by a combination of negative (blunted affect, withdrawal, anhedonia) and positive (paranoia, hallucinations, delusions) symptoms as well as marked cognitive deficits. While schizophrenia remains an idiopathic disorder, it appears to be produced by a complex interaction of biological, environmental, and genetic factors. Over 40 years ago it was found that phencyclidine (PCP) induces a psychotic state in humans that is very similar to that observed in schizophrenic patients. The finding that the main mode of action of PCP is that of a non-competitive antagonist of the N-methyl-D-aspartate (NMDA) subtype of ionotropic glutamate receptor stimulated a series of studies that have led to the development of the NMDA receptor hypofunction model of schizophrenia. Besides schizophrenia, dysfunction of glutamatergic pathways has been implicated in a number of disease states in the human central nervous system (CNS) including cognitive deficits, dementias, Parkinson's disease, Alzheimer's disease and bipolar disorder.

NMDA receptor function can be modulated by activation of G Protein-Coupled Receptors (GPCRs) that are known to physically and/or functionally interact with the NMDA receptor. The NMDA receptor hypofunction hypothesis is a proposal to explain the underlying cause of schizophrenia. According to this hypothesis, any agent that can potentiate NMDA receptor currents, either directly by action on modulatory sites on the NMDA receptor (e.g., the glycine co-agonist binding site) or indirectly by activation of GPCRs known to potentiate NMDA receptor function (e.g. the $M_1$ mAChR), has the potential to ameliorate the symptoms of schizophrenia. In both preclinical and in clinical studies, Xanomeline, an $M_1/M_4$ preferring orthosteric agonist has proved efficacious with regard to positive, negative and cognitive symptoms, indicating that $M_1$ activation is a reasonable approach to the treatment of schizophrenia. More recently, the selective $M_1$ allosteric agonist TBPB demonstrated efficacy in multiple preclinical models of schizophrenia.

Positive allosteric modulators are compounds that bind to a target, such as a receptor, and can enhance the affinity or efficacy of an orthosteric agonist. For example, a selective muscarinic $M_1$ positive allosteric modulator would preferentially bind to the muscarinic $M_1$ receptor which would result in an increased affinity at that receptor for acetylcholine (ACh), the endogenous agonist for the muscarinic $M_1$ receptor, or an increase in the efficacy induced by ACh. In some systems, the compound may also have an intrinsic activity to activate the receptor in the absence of orthosteric ligand. As another example, a dual $M_1/M_4$ positive allosteric modulator would induce a potentiating effect at both the $M_1$ and $M_4$ muscarinic receptors, but not necessarily to an identical extent at both receptors. Positive allosteric modulation (potentiation), therefore, can be an attractive mechanism for enhancing appropriate physiological receptor activation.

Cholinergic neurotransmission involves the activation of nicotinic acetylcholine receptors (nAChRs) or the muscarinic acetylcholine receptors (mAChRs) by the binding of the endogenous orthosteric agonist acetylcholine (ACh). Acetylcholinesterase inhibitors, which inhibit the hydrolysis of ACh, have been approved in the United States for use in the palliative, but not disease-modifying, treatment of the cognitive deficits in AD patients. An alternative approach to pharmacologically increase the effects of ACh could be accomplished through the use of positive allosteric modulators either alone or possibly in combination with other mAChR agonists. mAChRs are widely expressed throughout the body. The mAChRs are members of the family A GPCRs and include five subtypes, designated $M_1$-$M_5$. $M_1$, $M_3$ and $M_5$ mainly couple to Gq and activate phospholipase C whereas $M_2$ and $M_4$ mainly couple to $G_{i/o}$ and associated effector systems. These five distinct mAChR subtypes have been identified in the mammalian central nervous system where they are prevalent and differentially expressed. $M_1$-$M_5$ mAChRs have varying roles in cognitive, sensory, motor and autonomic functions. Activation of various muscarinic receptors, particularly the $M_1$ subtype, has been proposed as a mechanism to enhance cognition in disorders such as AD. Thus, without wishing to be bound by theory, it is believed that selective positive allosteric modulators of mAChR subtypes that regulate processes involved in cognitive function could prove superior to AChE inhibitors for treatment of AD and related disorders as it is postulated that these compounds would exhibit improved selectivity for specific mAChRs Evidence suggests that the most prominent adverse effects of AChE inhibitors and other cholinergic agents are mediated by activation of peripheral $M_2$ and $M_3$ mAChRs and include bradycardia, GI distress, excessive salivation, and sweating. In contrast, $M_1$ has been viewed as the most likely subtype for mediating the effects on cognition, attention mechanisms, and sensory processing. Because of this, considerable effort has been focused on developing selective $M_1$ agonists and positive allosteric modulators for the treatment of AD. Unfortunately, these efforts have been largely unsuccessful because of an inability to develop compounds that are highly selective for the $M_1$ mAChR. Because of this, mAChR agonists that have been tested in clinical studies induce the same adverse effects of AChE inhibitors by activation of peripheral mAChRs. To fully understand the physiological roles of individual mAChR subtypes and to further explore the therapeutic utility of mACh receptors in AD and other disorders, it can be important to develop compounds that are highly selective positive allosteric modulators of $M_1$ and other individual mAChR subtypes.

Previous attempts to develop activators that are highly selective for individual mAChR subtypes have failed because of the high conservation of the orthosteric ACh binding site. To circumvent problems associated with targeting the highly conserved orthosteric ACh site, a number of groups have shifted their focus to developing compounds that act at allosteric sites on mAChRs that are removed from the orthosteric site and are less highly conserved. This approach is proving to be successful in developing selective ligands for multiple GPCR subtypes. In the case of mAChRs, a major goal has been to develop allosteric ligands that selectively increase activity of $M_1$ or other mAChR subtypes. Allosteric activators can include allosteric agonists, that act at a site removed from the orthosteric site to directly activate the receptor in the absence of ACh as well as positive allosteric modulators (PAMs), which do not activate the receptor directly but potentiate activation of the receptor by the endogenous orthosteric agonist ACh. Also, it is possible for a single molecule to have both allosteric potentiator and allosteric agonist activity.

Phase III trials have shown that orthosteric mAChR activators can have efficacy in improving cognitive performance in AD patients. Moreover, data indicate that administration of $M_1$ activators decreases behavioral disturbances, including delusions, hallucinations, outbursts, and other symptoms in patients suffering from neurodegenerative diseases such as Alzheimer's disease. However, dose limiting adverse effects that may be due to lack of $M_1$ mAChR selectivity led to failed launches of previous $M_1$ agonists. In some cases, evidence suggests that mAChR activation also has the potential to be disease-modifying in that these agents may lower Aβ in AD patients. Interestingly, the $M_1$-selective allosteric agonist TBPB was found to display effects on the processing of APP toward the non-amyloidogenic pathway and decrease Aβ 1-40 and 1-42 production in vitro. These data suggest that selective activation of $M_1$ may provide a novel approach for both symptomatic and disease modifying the treatment of Alzheimer's disease.

Despite advances in muscarinic receptor (mAChR) research, there is still a scarcity of compounds that are potent, efficacious and selective positive allosteric modulators of the $M_1$ mAChR that are also effective in the treatment of neurological and psychiatric disorders associated with cholinergic activity, or other neurologic diseases in which the muscarinic $M_1$ receptor may be involved. These needs and other needs are addressed by the present invention.

SUMMARY

In accordance with the purpose(s) of the invention, as embodied and broadly described herein, the invention, in one aspect, relates to substituted 3-benzylquinazolin -4(3H)-one analogs useful as positive allosteric modulators (i.e., potentiators) of the muscarinic acetylcholine receptor $M_1$ (mAChR $M_1$), methods of making same, pharmaceutical compositions comprising same, and methods of treating neurological and psychiatric disorders associated with muscarinic acetylcholine receptor dysfunction using same.

Disclosed are compounds having a structure represented by a formula:

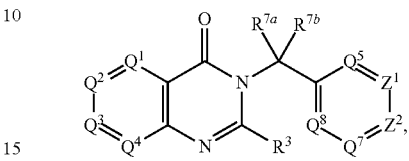

wherein each of $Z^1$ and $Z^2$ are independently selected from $Q^6$ or $CR^4$, provided that $Z^1$ and $Z^2$ are not simultaneously $Q^6$ or simultaneously $CR^4$; wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$; wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO$_2R^{30}$; wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from $Ar^2$, —$L^2$—$Ar^2$, and $Cy^1$; wherein $L^2$ is selected from —$CR^{8a}R^{8b}$—, —O—, —$NR^9$—, —S—, —(S=O)—, and —(SO$_2$)—; wherein each of $R^{8a}$ and $R^{8b}$ is independently selected from hydrogen, C1-C6 alkyl, C1-C6 haloalkyl, and C1-C6 polyhaloalkyl; wherein $R^9$ is selected from hydrogen and C1-C6 alkyl; wherein $Ar^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2,3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein $Ar^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein Ar$^2$ is pyrazolyl substituted with substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein Cy$^1$ is a C2-C5 heterocycloalkyl or C2-C5 heterocycloalkenyl, and wherein Cy$^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of R$^{7a}$ and R$^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

Also disclosed are pharmaceutical compositions comprising a therapeutically effective amount of one or more disclosed compounds, or pharmaceutically acceptable salt, hydrate, solvate, or polymorph thereof, and a pharmaceutically acceptable carrier.

Also disclosed are methods for the treatment of a neurological and/or psychiatric disorder associated with muscarinic acetylcholine receptor dysfunction in a mammal comprising the step of administering to the mammal an effective amount of at least one disclosed compound or pharmaceutically acceptable salt, hydrate, solvate, or polymorph thereof.

Also disclosed are methods for potentiation of muscarinic acetylcholine receptor activity in at least one cell, comprising the step of contacting the cell with an effective amount of at least one disclosed compound or pharmaceutically acceptable salt, hydrate, solvate, or polymorph thereof.

Also disclosed are methods for potentiation of muscarinic acetylcholine receptor activity in at least one cell, comprising the step of contacting the cell with an effective amount of at least one disclosed compound or pharmaceutically acceptable salt, hydrate, solvate, or polymorph thereof.

Also disclosed are methods for enhancing cognition in a mammal, comprising the step of administering to the mammal an effective amount of at least one disclosed compound or pharmaceutically acceptable salt, hydrate, solvate, or polymorph thereof.

Also disclosed are uses of a disclosed compound, a disclosed product of making, or a pharmaceutically acceptable salt, hydrate, solvate, or polymorph thereof.

Also disclosed are uses of a disclosed compound, a disclosed product of making, or a pharmaceutically acceptable salt, hydrate, solvate, or polymorph thereof, in the manufacture of a medicament for the treatment of a disorder associated with a muscarinic acetylcholine receptor dysfunction in a mammal.

Also disclosed are methods for the manufacture of a medicament to activate the mAChR M$_4$ in a mammal comprising combining at least one disclosed compound or at least one disclosed product of making with a pharmaceutically acceptable carrier or diluent.

Also disclosed are kits comprising at least one disclosed compound, or a pharmaceutically acceptable salt, hydrate, solvate, or polymorph thereof, and one or more of: (a) at least one agent known to increase mAChR M$_1$ activity; (b) at least one agent known to decrease mAChR M$_1$ activity; (c) at least one agent known to treat a disorder associated with cholinergic activity; (d) instructions for treating a disorder associated with cholinergic activity; (e) instructions for treating a disorder associated with mAChR M$_1$ receptor activity; or (f) instructions for administering the compound in connection with cognitive or behavioral therapy.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "allosteric site" refers to a ligand binding site that is topographically distinct from the orthosteric binding site.

As used herein, the term "modulator" refers to a molecular entity (e.g., but not limited to, a ligand and a disclosed compound) that modulates the activity of the target receptor protein.

As used herein, the term "ligand" refers to a natural or synthetic molecular entity that is capable of associating or binding to a receptor to form a complex and mediate, prevent or modify a biological effect. Thus, the term "ligand" encompasses allosteric modulators, inhibitors, activators, agonists, antagonists, natural substrates and analogs of natural substrates.

As used herein, the terms "natural ligand" and "endogenous ligand" are used interchangeably, and refer to a naturally occurring ligand, found in nature, which binds to a receptor.

As used herein, the term "orthosteric site" refers to the primary binding site on a receptor that is recognized by the endogenous ligand or agonist for that receptor. For example, the orthosteric site in the mAChR $M_1$ receptor is the site that acetylcholine binds.

As used herein, the term "mAChR $M_1$ receptor positive allosteric modulator" refers to any exogenously administered compound or agent that directly or indirectly augments the activity of the mAChR $M_1$ receptor in the presence or in the absence of acetylcholine, or another agonist, in an animal, in particular a mammal, for example a human. In one aspect, a mAChR $M_1$ receptor positive allosteric modulator increases the activity of the mAChR $M_1$ receptor in a cell in the presence of extracellular acetylcholine. The cell can be Chinese hamster ovary (CHO-K1) cells transfected with human mAChR $M_1$. The cell can be Chinese hamster ovary (CHO-K1) cells transfected with rat mAChR $M_1$ receptor. The cell can be Chinese hamster ovary (CHO-K1) cells transfected with a mammalian mAChR $M_1$. The term "mAChR $M_1$ receptor positive allosteric modulator" includes a compound that is a "mAChR $M_1$ receptor allosteric potentiator" or a "mAChR $M_1$ receptor allosteric agonist," as well as a compound that has mixed activity comprising pharmacology of both a "mAChR $M_1$ receptor allosteric potentiator" and a "mAChR $M_1$ receptor allosteric agonist". The term "mAChR $M_1$ receptor positive allosteric modulator also includes a compound that is a "mAChR $M_1$ receptor allosteric enhancer."

As used herein, the term "mAChR $M_1$ receptor allosteric potentiator" refers to any exogenously administered compound or agent that directly or indirectly augments the response produced by the endogenous ligand (such as acetylcholine) when the endogenous ligand binds to the orthosteric site of the mAChR $M_1$ receptor in an animal, in particular a mammal, for example a human. The mAChR $M_1$ receptor allosteric potentiator binds to a site other than the orthosteric site, that is, an allosteric site, and positively augments the response of the receptor to an agonist or the endogenous ligand. In one aspect, an allosteric potentiator does not induce desensitization of the receptor, activity of a compound as a mAChR $M_1$ receptor allosteric potentiator provides advantages over the use of a pure mAChR $M_1$ receptor orthosteric agonist. Such advantages can include, for example, increased safety margin, higher tolerability, diminished potential for abuse, and reduced toxicity.

As used herein, the term "mAChR $M_1$ receptor allosteric enhancer" refers to any exogenously administered compound or agent that directly or indirectly augments the response produced by the endogenous ligand (such as acetylcholine) in an animal, in particular a mammal, for example a human. In one aspect, the allosteric enhancer increases the affinity of the natural ligand or agonist for the orthosteric site. In another aspect, an allosteric enhancer increases the agonist efficacy. The mAChR $M_1$ receptor allosteric potentiator binds to a site other than the orthosteric site, that is, an allosteric site, and positively augments the response of the receptor to an agonist or the endogenous ligand. An allosteric enhancer has no effect on the receptor by itself and requires the presence of an agonist or the natural ligand to realize a receptor effect.

As used herein, the term "mAChR $M_1$ receptor allosteric agonist" refers to any exogenously administered compound or agent that directly activates the activity of the mAChR $M_1$ receptor in the absence of the endogenous ligand (such as acetylcholine) in an animal, in particular a mammal, for example a human. The mAChR $M_1$ receptor allosteric agonist binds to a site that is distinct from the orthosteric acetylcholine site of the mAChR $M_1$ receptor. Because it does not require the presence of the endogenous ligand, activity of a compound as a mAChR $M_1$ receptor allosteric agonist provides advantages over the use of a pure mAChR $M_1$ receptor allosteric potentiator, such as more rapid onset of action.

As used herein, the term "mAChR $M_1$ receptor neutral allosteric ligand" refers to any exogenously administered compound or agent that binds to an allosteric site without affecting the binding or function of agonists or the natural ligand at the orthosteric site in an animal, in particular a mammal, for example a human. However, a neutral allosteric ligand can block the action of other allosteric modulators that act via the same site.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more neurological and/or psychiatric disorder associated with muscarinic acetylcholine receptor dysfunction prior to the administering step. In some aspects of the disclosed method, the subject has been diagnosed with a need for positive allosteric modulation of muscarinic acetylcholine receptor activity prior to the administering step. In some aspects of the disclosed method, the subject has been diagnosed with a need for partial agonism of muscarinic acetylcholine receptor activity prior to the administering step. In some aspects of the disclosed method, the subject has been diagnosed with a neurological and/or psychiatric disorder, e.g. schizophrenia, Alzheimer's disease, a cognitive disorder, or neuropathic pain prior to the administering step. In some aspects of the disclosed method, the subject has been identified with a disorder treatable by activation of the mAChR $M_1$ receptor and/or a need for activation/agonism of mAChR $M_1$ activity prior to the administering step. In some aspects of the disclosed method, the subject has been identified with anxiety or a related disorder prior to the administering step. In one aspect, a subject can be treated prophylactically with a compound or composition disclosed herein, as discussed herein elsewhere.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by modulation of mAChR $M_1$" means having been subjected to a physical examination by a person of skill, for example, a physician, and found to have a condition that can be diagnosed or treated by a compound or composition that can modulate mAChR $M_1$. As a further example, "diagnosed with a need for modulation of mAChR $M_1$" refers to having been subjected to a physical examination by a person of skill, for example, a physician, and found to have a condition characterized by mAChR $M_1$ activity. Such a diagnosis can be in reference to a disorder, such as a neurodegenerative disease, and the like, as discussed herein. For example, the term "diagnosed with a need for positive allosteric modulation of muscarinic acetylcholine receptor activity" refers to having been subjected to a physical examination by a person of skill, for example, a physician, and found to have a condition that can be diagnosed or treated by positive allosteric modulation of muscarinic acetylcholine receptor activity. For example, "diagnosed with a need for partial agonism of muscarinic acetylcholine receptor activity" means having been subjected to a physical examination by a person of skill, for example, a physician, and found to have a condition that can be diagnosed or treated by partial agonism of muscarinic acetylcholine receptor activity. For example, "diagnosed with a need for treatment of one or more neurological and/or psychiatric disorder associated with acetylcholine dysfunction" means having been subjected to a physical examination by a person of skill, for example, a physician, and found to have one or more neurological and/or psychiatric disorder associated with acetylcholine dysfunction, including, for example, but not limited to, muscarinic receptor deficient schizophrenia and Alzheimer's disease.

As used herein, the phrase "identified to be in need of treatment for a disorder," or the like, refers to selection of a subject based upon need for treatment of the disorder. For example, a subject can be identified as having a need for treatment of a disorder (e.g., a disorder related to mAChR $M_1$ activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, a target receptor (e.g. a muscarinic acetylcholine receptor), or other biological entity together in such a manner that the compound can affect the activity of the target, either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro- drugs, which become biologically active or more active after they have been placed in a predetermined physiological environment.

As used herein, "$EC_{50}$," is intended to refer to the concentration of a substance (e.g., a compound or a drug) that is required for 50% activation or enhancement of a biological process, or component of a process. For example, $EC_{50}$ can refer to the concentration of agonist that provokes a response halfway between the baseline and maximum response in an appropriate assay of the target activity. For example, an $EC_{50}$ for the mAChR $M_1$ receptor can be determined in an in vitro or cell-based assay system. Such in vitro assay systems frequently utilize a cell line that either expresses endogenously a target of interest, or has been transfected with a suitable expression vector that directs expression of a recombinant form of the target such as the mAChR $M_1$ receptor. For example, the $EC_{50}$ for mAChR $M_1$ can be determined using Chinese hamster ovary (CHO-K1) cells transfected with human mAChR $M_1$. Alternatively, the $EC_{50}$ for mAChR $M_1$ can be determined using Chinese hamster ovary (CHO-K1) cells transfected with rat mAChR $M_1$. In another example, the $EC_{50}$ for mAChR $M_1$ can be determined using Chinese hamster ovary (CHO-K1) cells transfected with a mammalian mAChR $M_1$.

As used herein, "$IC_{50}$," is intended to refer to the concentration of a substance (e.g., a compound or a drug) that is required for 50% inhibition of a biological process, or component of a process. For example, $IC_{50}$ refers to the half maximal (50%) inhibitory concentration (IC) of a substance as determined in a suitable assay. For example, an $IC_{50}$ for mAChR $M_1$ receptor can be determined in an in vitro or cell-based assay system. Frequently, receptor assays, including suitable assays for mAChR $M_1$, make use of a suitable cell-line, e.g. a cell line that either expresses endogenously a target of interest, or has been transfected with a suitable expression vector that directs expression of a recombinant form of the target such as mAChR $M_1$. For example, the $IC_{50}$ for mAChR $M_1$ can be determined using Chinese hamster ovary (CHO-K1) cells transfected with human mAChR $M_1$. Alternatively, the $IC_{50}$ for mAChR $M_1$ can be determined using Chinese hamster ovary (CHO-K1) cells transfected with rat mAChR $M_1$. In another example, the $IC_{50}$ for mAChR $M_1$ can be determined using Chinese hamster ovary (CHO-K1) cells transfected with a mammalian mAChR $M_1$.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$—$OA^2$ or —$OA^1$—$(OA^2)_a$—$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain $(4n+2)\pi$ electrons. A further discussion of aromaticity is found in Morrison and Boyd, *Organic Chemistry*, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon- carbon bond. For example, biaryl can be two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C═O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N -ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula —($A^1$O(O)C—$A^2$—C(O)O)$_a$— or —($A^1$O(O)C—$A^2$—OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1$O$A^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula —($A^1$O—$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo, " "halogen" or "halide", as used herein can be used interchangeably and refer to F, Cl, Br, or I.

The terms "pseudohalide, " "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl, " as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo [d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H- chromenyl, 1H-pyrazolo[4,3-c]pyridin-3-yl; 1H-pyrrolo[3,2-b]pyridin-3-yl; and 1H- pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxy" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$,""$R^2$,""$R^3$,""$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°: —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched)alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$—(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, —(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R• is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, —(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, —(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, *Wiley-Interscience*, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

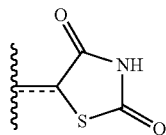

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di -substituted amino, acyloxy, cyano, carboxy, carboalkoxy, alkylcarboxamide, substituted alkyl-carboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non- superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically- labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., *The Royal Society of Chemistry*, 1889-1896, 2004. Examples of co-crystals include p -toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

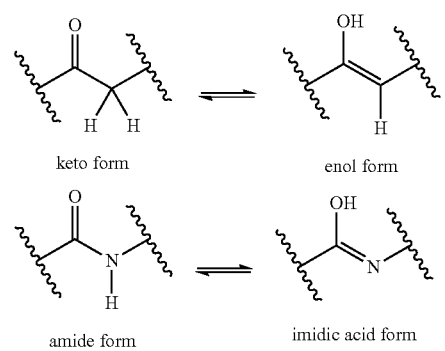

keto form      enol form amide form      imidic acid form

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

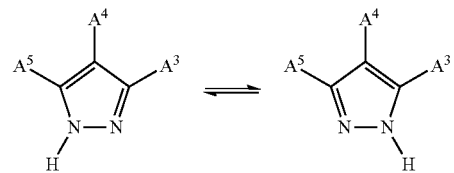

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

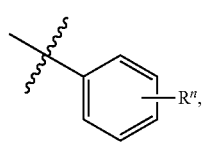

which is understood to be equivalent to a formula:

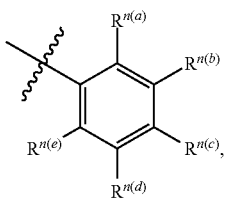

wherein n is typically an integer. That is, R" is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's *Reagents for Organic Synthesis*, Volumes 1-17 (John Wiley and Sons, 1991); *Rodd's Chemistry of Carbon Compounds*, Volumes 1-5 and supplemental volumes (Elsevier Science Publishers, 1989); *Organic Reactions*, Volumes 1-40 (John Wiley and Sons, 1991); March's *Advanced Organic Chemistry*, (John Wiley and Sons, 4th Edition); and *Larock's Comprehensive Organic Transformations* (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful as positive allosteric modulators of the muscarinic acetylcholine receptor $M_1$ (mAChR $M_1$). More specifically, in one aspect, the present invention relates to compounds that allosterically modulate mAChR $M_1$ receptor activity, affecting the sensitivity of mAChR $M_1$ receptors to agonists without acting as orthosteric agonists themselves. The compounds can, in one aspect, exhibit subtype selectivity.

In one aspect, the disclosed compounds exhibit positive allosteric modulation of mAChR $M_1$ response to acetylcholine as an increase in response to non-maximal concentrations of acetylcholine in Chinese hamster ovary (CHO-K1) cells transfected with rat mAChR $M_1$ in the presence of the compound, compared to the response to acetylcholine in the absence of the compound. In further aspect, the Chinese hamster ovary (CHO-K1) cells are transfected with human mAChR $M_1$. In yet a further aspect, Chinese hamster ovary (CHO-K1) cells are transfected with mAChR $M_1$ of a mammal.

In one aspect, the compounds of the invention are useful in the treatment neurological and psychiatric disorders associated with muscarinic acetylcholine receptor dysfunction and other diseases in which muscarinic acetylcholine receptors are involved, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to a compound having a structure represented by a formula:

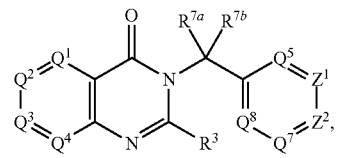

wherein each of $Z^1$ and $Z^2$ are independently selected from $Q^6$ or $CR^4$, provided that $Z^1$ and $Z^2$ are not simultaneously $Q^6$ or simultaneously $CR^4$; wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$; wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO$_2R^{30}$; wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from $Ar^2$, —$L^2$—$Ar^2$, and $Cy^1$; wherein $L^2$ is selected from —$CR^{8a}R^{8b}$—, —O—, —$NR^9$—, —S—, —(S=O)—, and —(SO$_2$)—; wherein each of $R^{8a}$ and $R^{8b}$ is independently selected from hydrogen, C1-C6 alkyl, C1-C6 haloalkyl, and C1-C6 polyhaloalkyl; wherein $R^9$ is selected from hydrogen and C1-C6 alkyl; wherein $Ar^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2, 3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein $Ar^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein $Ar^2$ is pyrazolyl substituted with substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein $Cy^1$ is a C2-C5 heterocycloalkyl or C2-C5 heterocycloalkenyl, and wherein $Cy^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of $R^{7a}$ and $R^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In various aspects, the invention relates to a compound having a structure represented by a formula:

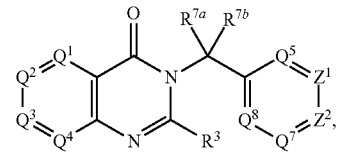

wherein each of $Z^1$ and $Z^2$ are independently selected from $Q^6$ or $CR^4$, provided that $Z^1$ and $Z^2$ are not simultaneously $Q^6$ or simultaneously $CR^4$; wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$; wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO$_2R^{30}$; wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from $Ar^2$, —$L^2$—$Ar^2$, and $Cy^1$; wherein $L^2$ is selected from —$CR^{8a}R^{8b}$—, —O—, —$NR^9$—, —S—, —(S=O)—, and —(SO$_2$)—; wherein each of $R^{8a}$ and $R^{8b}$ is independently selected from hydrogen, C1-C6 alkyl, C1-C6 haloalkyl, and C1-C6 polyhaloalkyl; wherein $R^9$ is selected from hydrogen and C1-C6 alkyl; wherein $Ar^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2, 3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein $Ar^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein $Cy^1$ is a C2-C5 heterocycloalkyl or C2-C5 heterocycloalkenyl, and wherein $Cy^1$ is substituted with 0-3 substituents independently selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of $R^{7a}$ and $R^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In various aspects, the invention relates to a compound having a structure represented by a formula:

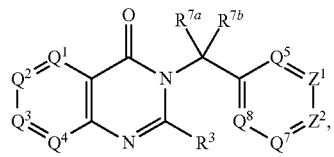

wherein each of $Z^1$ and $Z^2$ are independently selected from $Q^6$ or $CR^4$, provided that $Z^1$ and $Z^2$ are not simultaneously $Q^6$ or simultaneously $CR^4$; wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$, wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —$C(OH)R^{20a}R^{20b}$, and —$SO_2R^{30}$; wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with 0-3 substituents independently selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from $Ar^2$, —$L^2$—$Ar^2$, and $Cy^1$; wherein $L^2$ is selected from —$CR^{8a}R^{8b}$—, —O—, —$NR^9$—, —S—, —(S=O)—, and —($SO_2$)—; wherein each of $R^{8a}$ and $R^{8b}$ is independently selected from hydrogen, C1-C6 alkyl, C1-C6 haloalkyl, and C1-C6 polyhaloalkyl; wherein $R^9$ is selected from hydrogen and C1-C6 alkyl; wherein $Ar^2$ is pyrazolyl substituted with substituted with 1-3 substituents independently selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino; and wherein $Cy^1$ is a C2-C5 heterocycloalkyl or C2-C5 heterocycloalkenyl, and wherein $Cy^1$ is substituted with 0-3 substituents independently selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of $R^{7a}$ and $R^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In various aspects, the invention relates to a compound having a structure represented by a formula:

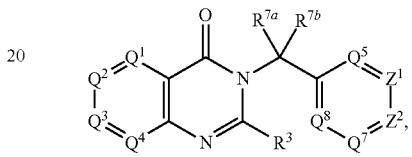

wherein each of $Z^1$ and $Z^2$ are independently selected from $Q^6$ or $CR^4$, provided that $Z^1$ and $Z^2$ are not simultaneously $Q^6$ or simultaneously $CR^4$; wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$, wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —$C(OH)R^{20a}R^{20b}$, and —$SO_2R^{30}$; wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with 0-3 substituents independently selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino; wherein $R^4$ is $Cy^1$; wherein $L^2$ is selected from —$CR^{8a}R^{8b}$—, —O—, —$NR^9$—, —S—, —(S=O)—, and —($SO_2$)—; wherein each of $R^{8a}$ and $R^{8b}$ is independently selected from hydrogen, C1-C6 alkyl, C1-C6 haloalkyl, and C1-C6 polyhaloalkyl; wherein $R^9$ is selected from hydrogen and C1-C6 alkyl; wherein $Cy^1$ is a C2-C5 heterocycloalkyl or C2-C5 heterocycloalkenyl, and wherein $Cy^1$ is substituted with 0-3 substituents independently selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of $R^{7a}$ and $R^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In various aspects, the invention relates to a compound having a structure represented by a formula:

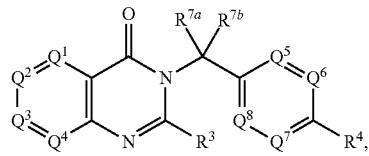

wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$, wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO$_2R^{30}$, wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from $Ar^2$, —L$^2$—$Ar^2$, and $Cy^1$; wherein $L^2$ is selected from —CR$^{8a}R^{8b}$—, —O—, —NR$^9$—, —S—, —(S=O)—, and —(SO$_2$)—; wherein each of $R^{8a}$ and $R^{8b}$ is independently selected from hydrogen, C1-C6 alkyl, C1-C6 haloalkyl, and C1-C6 polyhaloalkyl; wherein $R^9$ is selected from hydrogen and C1-C6 alkyl; wherein $Ar^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2,3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein $Ar^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein $Ar^2$ is pyrazolyl substituted with substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein $Cy^1$ is a C2-C5 heterocycloalkyl or C2-C5 heterocycloalkenyl, and wherein $Cy^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of $R^{7a}$ and $R^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In various aspects, the invention relates to a compound having a structure represented by a formula:

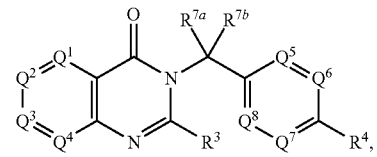

wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$, are N; wherein $R^{1a}$, $R^{1b}$, $R^{1c}$, and $R^{1d}$, when present is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$; wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, $R^{2d}$, and when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO$^{30}$; wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from $Ar^2$, —L$^2$—$Ar^2$, and $Cy^1$; wherein $L^2$ is selected from —CR$^{8a}R^{8b}$—, —O—, —NR$^9$—, —S—, —(S=O)—, and —(SO$_2$)—; wherein each of $R^{8a}$ and $R^{8b}$ is independently selected from hydrogen, C1-C6 alkyl, C1-C6 haloalkyl, and C1-C6 polyhaloalkyl; wherein R⁹ is selected from hydrogen and C1-C6 alkyl; wherein Ar² is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2,3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein Ar² is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino; and wherein Cy¹ is a C2-C5 heterocycloalkyl or C2-C5 heterocycloalkenyl, and wherein Cy¹ is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of $R^{7a}$ and $R^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In various aspects, the invention relates to a compound having a structure represented by a formula:

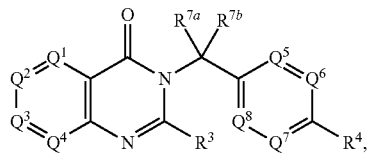

wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$, wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO₂$R^{30}$, wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and Ar¹; wherein Ar¹ is selected from phenyl, indenyl, and naphthalenyl; and substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from Ar², —L²—Ar², and Cy¹; wherein L² is selected from —$CR^{8a}R^{8b}$—, —O—, —$NR^9$—, —S—, —(S═O)—, and —(SO₂)—; wherein each of $R^{8a}$ and $R^{8b}$ is independently selected from hydrogen, C1-C6 alkyl, C1-C6 haloalkyl, and C1-C6 polyhaloalkyl; wherein R⁹ is selected from hydrogen and C1-C6 alkyl; wherein Ar² is pyrazolyl substituted with substituted with 1-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino; and wherein Cy¹ is a C2-C5 heterocycloalkyl or C2-C5 heterocycloalkenyl, and wherein Cy¹ is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of $R^{7a}$ and $R^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In various aspects, the invention relates to a compound having a structure represented by a formula:

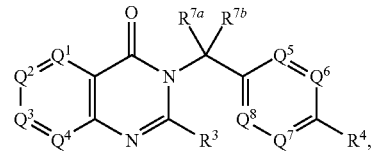

wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$, wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO₂$R^{30}$, wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and Ar¹; wherein Ar¹ is selected from phenyl, indenyl, and naphthalenyl; and substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino; wherein R$^4$ is Cy$^1$; wherein L$^2$ is selected from —CR$^{8a}$R$^{8b}$—, —O—, —NR$^9$—, —S—, —(S=O)—, and —(SO$_2$)—; wherein each of R$^{8a}$ and R$^{8b}$ is independently selected from hydrogen, C1-C6 alkyl, C1-C6 haloalkyl, and C1-C6 polyhaloalkyl; wherein R$^9$ is selected from hydrogen and C1-C6 alkyl; wherein Cy$^1$ is a C2-C5 heterocycloalkyl or C2-C5heterocycloalkenyl, and wherein Cy$^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of R$^{7a}$ and R$^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In various aspects, the invention relates to a compound having a structure represented by a formula:

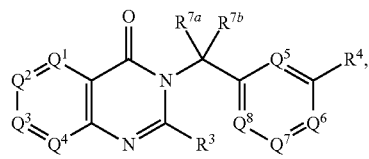

wherein Q$^1$ is selected from N and CR$^{1a}$; wherein Q$^2$ is selected from N and CR$^{1b}$; wherein Q$^3$ is selected from N and CR$^{1c}$; wherein Q$^4$ is selected from N and CR$^{1d}$; and wherein 0, 1, or 2 of Q$^1$, Q$^2$, Q$^3$, and Q$^4$ are N; wherein each of R$^{1a}$, R$^{1b}$, R$^{1c}$, and R$^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein Q$^5$ is selected from N and CR$^{2a}$; wherein Q$^6$ is selected from N and CR$^{2b}$; wherein Q$^7$ is selected from N and CR$^{2c}$; wherein Q$^8$ is selected from N and CR$^{2d}$; and wherein 0, 1, or 2 of Q$^5$, Q$^6$, Q$^7$, and Q$^8$ are N; wherein each of R$^{2a}$, R$^{2b}$, R$^{2c}$, and R$^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)R$^{20a}$R$^{20b}$, and —SO$_2$R$^{30}$; wherein each of R$^{20a}$ and R$^{20b}$ is independently selected from hydrogen, C1-C3 alkyl, C1-C3 haloalkyl; and C1-C3 polyhaloalkyl; and wherein R$^{30}$ is selected from C1-C3 alkyl, C1-C3 haloalkyl; and C1-C3 polyhaloalkyl; wherein R$^3$ is selected from hydrogen, C1-C3 alkyl, C1-C3 haloalkyl, C1-C3 polyhaloalkyl, cyclopropyl, and Ar$^1$; wherein Ar$^1$ is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein R$^4$ is selected from Ar$^2$, —L$^2$—Ar$^2$, and Cy$^1$; wherein L$^2$ is selected from —CR$^{8a}$R$^{8b}$—, —O—, —NR$^9$—, —S—, —(S=O)—, and —(SO$_2$)—; wherein each of R$^{8a}$ and R$^{8b}$ is independently selected from hydrogen, C1-C6 alkyl, C1-C6 haloalkyl, and C1-C6 polyhaloalkyl; wherein R$^9$ is selected from hydrogen and C1-C6 alkyl; wherein Ar$^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2, 3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein Ar$^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein Ar$^2$ is pyrazolyl substituted with substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein Cy$^1$ is a C2-C5 heterocycloalkyl or C2-C5 heterocycloalkenyl, and wherein Cy$^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of R$^{7a}$ and R$^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In various aspects, the invention relates to a compound having a structure represented by a formula:

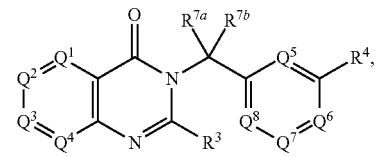

wherein Q$^1$ is selected from N and CR$^{1a}$; wherein Q$^2$ is selected from N and CR$^{1b}$; wherein Q$^3$ is selected from N and CR$^{1c}$; wherein Q$^4$ is selected from N and CR$^{1d}$; and wherein 0, 1, or 2 of Q$^1$, Q$^2$, Q$^3$, and Q$^4$ are N; wherein each of R$^{1a}$, R$^{1b}$, R$^{1c}$, and R$^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein Q$^5$ is selected from N and CR$^{2a}$; wherein Q$^6$ is selected from N and CR$^{2b}$; wherein Q$^7$ is selected from N and CR$^{2c}$; wherein Q$^8$ is selected from N and CR$^{2d}$; and wherein 0, 1, or 2 of Q$^5$, Q$^6$, Q$^7$, and Q$^8$ are N; wherein each of R$^{2a}$, R$^{2b}$, R$^{2c}$, and R$^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)R$^{20a}$R$^{20b}$, and —SO$_2$R$^{30}$; wherein each of R$^{20a}$ and R$^{20b}$ is independently selected from hydrogen, C1-C3 alkyl, C1-C3 haloalkyl; and C1-C3 polyhaloalkyl; and wherein R$^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with 0-3 substituents independently selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from $Ar^2$, —$L^2$—$Ar^2$, and $Cy^1$; wherein $L^2$ is selected from —$CR^{8a}R^{8b}$—, —O—, —$NR^9$—, —S—, —(S=O)—, —($SO_2$)—; wherein each of $R^{8a}$ and $R^{8b}$ is independently selected from hydrogen, C1-C6 alkyl, C1-C6 haloalkyl, and C1-C6 polyhaloalkyl; wherein $R^9$ is selected from hydrogen and C1-C6 alkyl; wherein $Ar^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2,3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein $Ar^2$ is substituted with 0-3 substituents independently selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino; and wherein $Cy^1$ is a C2-C5 heterocycloalkyl or C2-C5 heterocycloalkenyl, and wherein $Cy^1$ is substituted with 0-3 substituents independently selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of $R^{7a}$ and $R^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In various aspects, the invention relates to a compound having a structure represented by a formula:

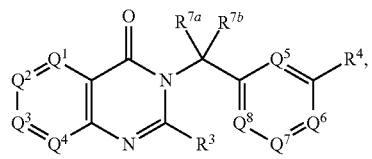

wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino;

wherein $Q^5$ is selected from N and $CR^{2a}$; wherein $Q^6$ is selected from N and $CR^{2b}$; wherein $Q^7$ is selected from N and $CR^{2c}$; wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —$C(OH)R^{20a}R^{20b}$, and —$SO_2R^{30}$, wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with 0-3 substituents independently selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from $Ar^2$, —$L^2$—$Ar^2$, and $Cy^1$; wherein $L^2$ is selected from —$CR^{8a}R^{8b}$—, —O—, —$NR^9$—, —S—, —(S=O)—, and —($SO_2$)—; wherein each of $R^{8a}$ and $R^{8b}$ is independently selected from hydrogen, C1-C6 alkyl, C1-C6 haloalkyl, and C1-C6 polyhaloalkyl; wherein $R^9$ is selected from hydrogen and C1-C6 alkyl; wherein $Ar^2$ is pyrazolyl substituted with substituted with 1-3 substituents independently selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino; and wherein $Cy^1$ is a C2-C5 heterocycloalkyl or C2-C5 heterocycloalkenyl, and wherein $Cy^1$ is substituted with 0-3 substituents independently selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of $R^{7a}$ and $R^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In various aspects, the invention relates to a compound having a structure represented by a formula:

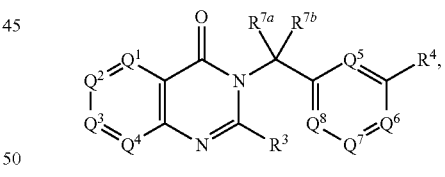

wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$; wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)R$^{20a}$R$^{20b}$, and —SO$_2$R$^{30}$, wherein each of R$^{20a}$ and R$^{20b}$ is independently selected from hydrogen, C1-C3 alkyl, C1-C3 haloalkyl; and C1-C3 polyhaloalkyl; and wherein R$^{30}$ is selected from C1-C3 alkyl, C1-C3 haloalkyl; and C1-C3 polyhaloalkyl; wherein R$^3$ is selected from hydrogen, C1-C3 alkyl, C1-C3 haloalkyl, C1-C3 polyhaloalkyl, cyclopropyl, and Ar$^1$; wherein Ar$^1$ is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein R$^4$ is Cy$^1$; wherein L$^2$ is selected from —CR$^{8a}$R$^{8b}$—, —O—, —NR$^9$—, —S—, —(S═O)—, and —(SO$_2$)—; wherein each of R$^{8a}$ and R$^{8b}$ is independently selected from hydrogen, C1-C6 alkyl, C1-C6 haloalkyl, and C1-C6 polyhaloalkyl; wherein R$^9$ is selected from hydrogen and C1-C6 alkyl; wherein Cy$^1$ is a C2-05 heterocycloalkyl or C2-C5 heterocycloalkenyl, and wherein Cy$^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of R$^{7a}$ and R$^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In a further aspect, a compound can have a structure listed herein. In a further aspect, the compounds can be selected from two or more of the structures listed herein.

In a further aspect, the invention relates to a compound having a structure represented by a formula:

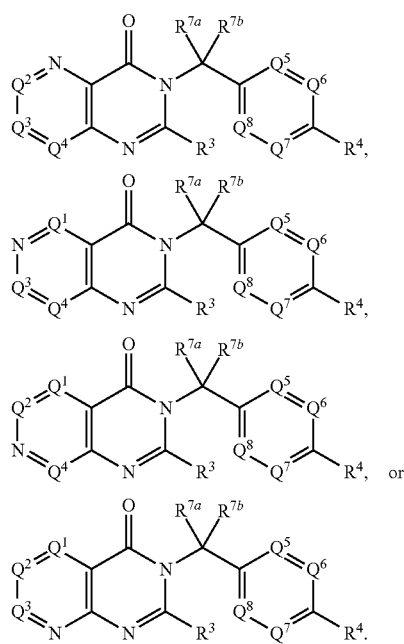

In a further aspect, the invention relates to a compound having a structure represented by a formula:

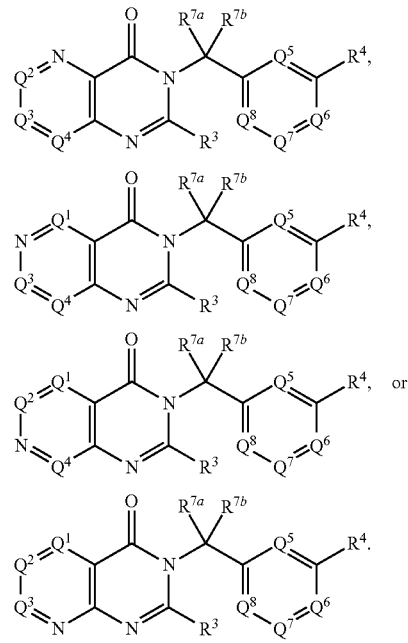

In a further aspect, the invention relates to a compound having a structure represented by a formula:

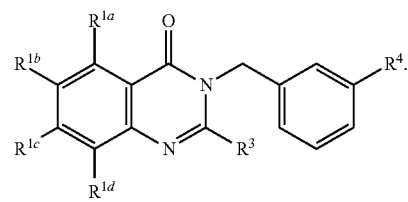

In a further aspect, the invention relates to a compound having a structure represented by a formula:

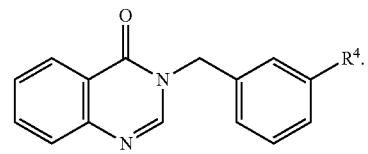

In a further aspect, the invention relates to a compound having a structure represented by a formula:

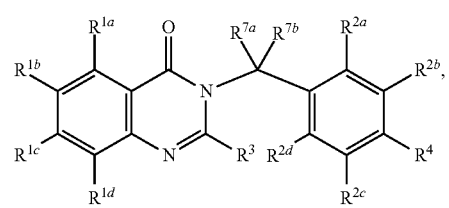

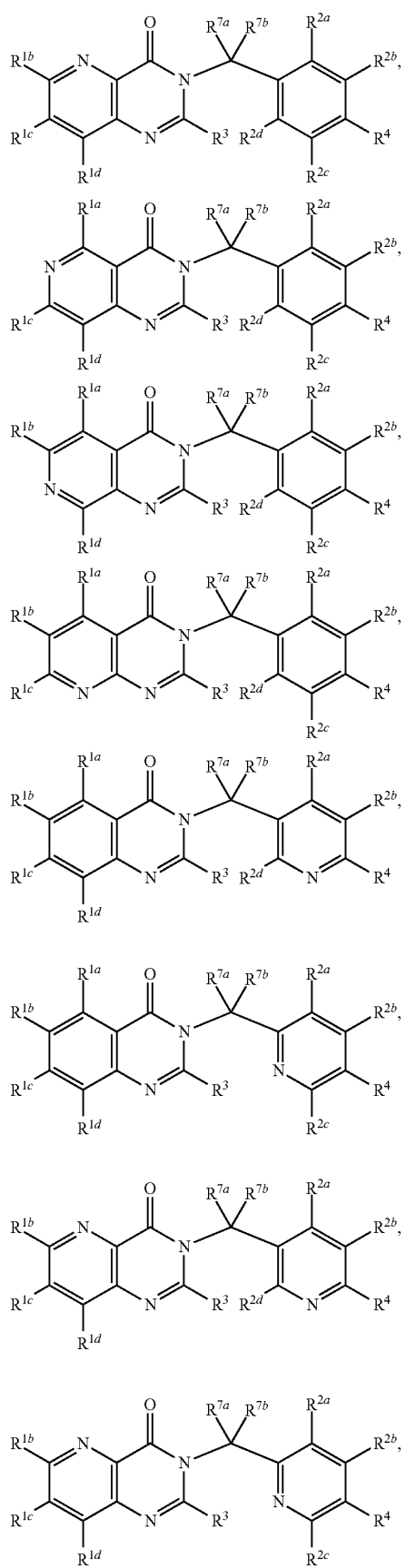
In a further aspect, the invention relates to a compound having a structure represented by a formula:

-continued
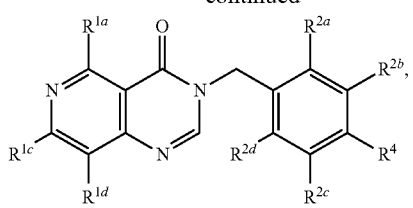
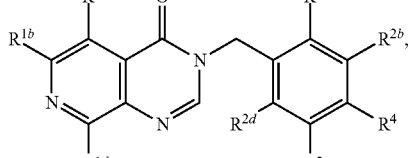
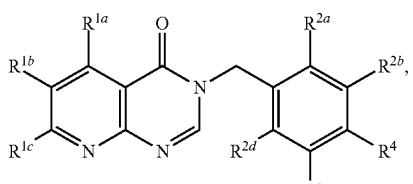
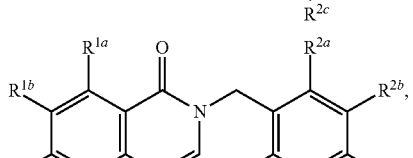
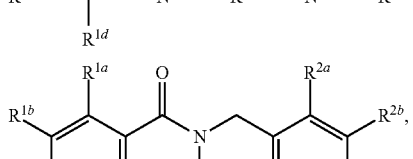
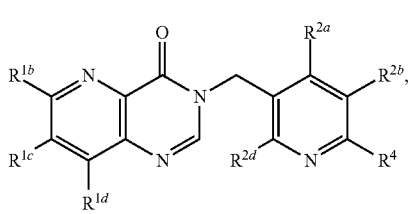
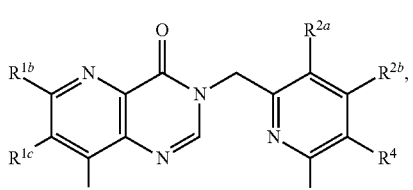
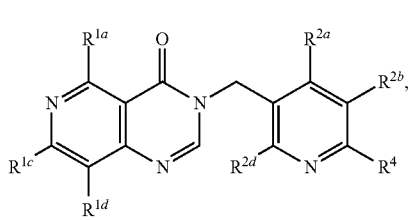
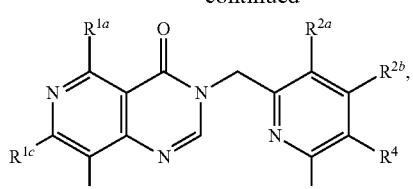
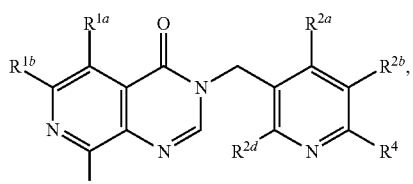
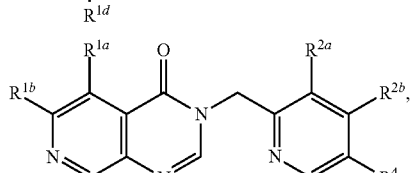
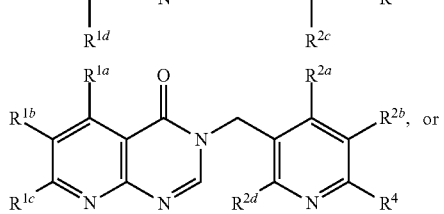
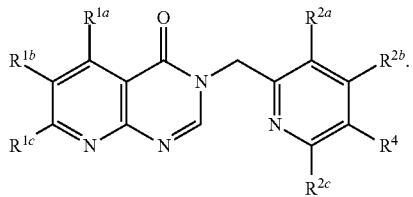
In a further aspect, the invention relates to a compound having a structure represented by a formula:
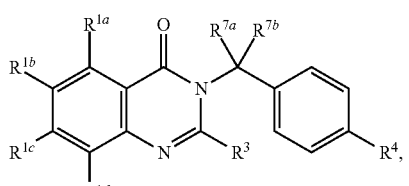
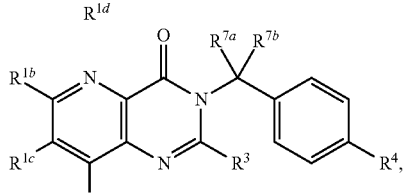
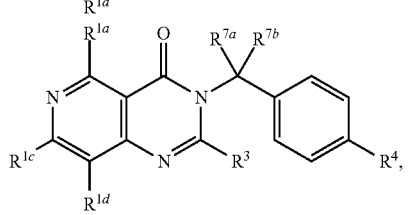

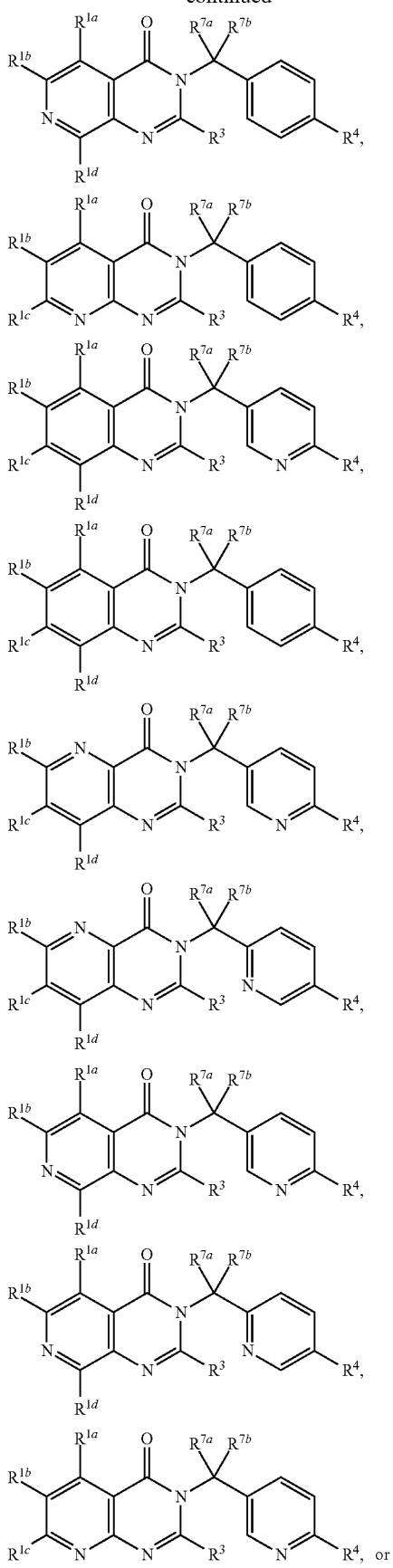
In a further aspect, the invention relates to a compound having a structure represented by a formula:

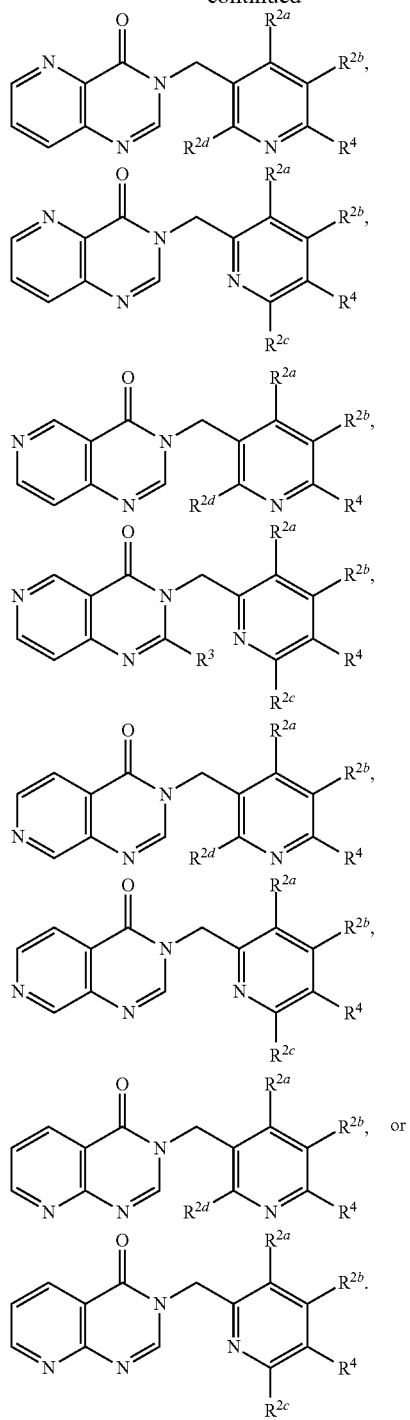
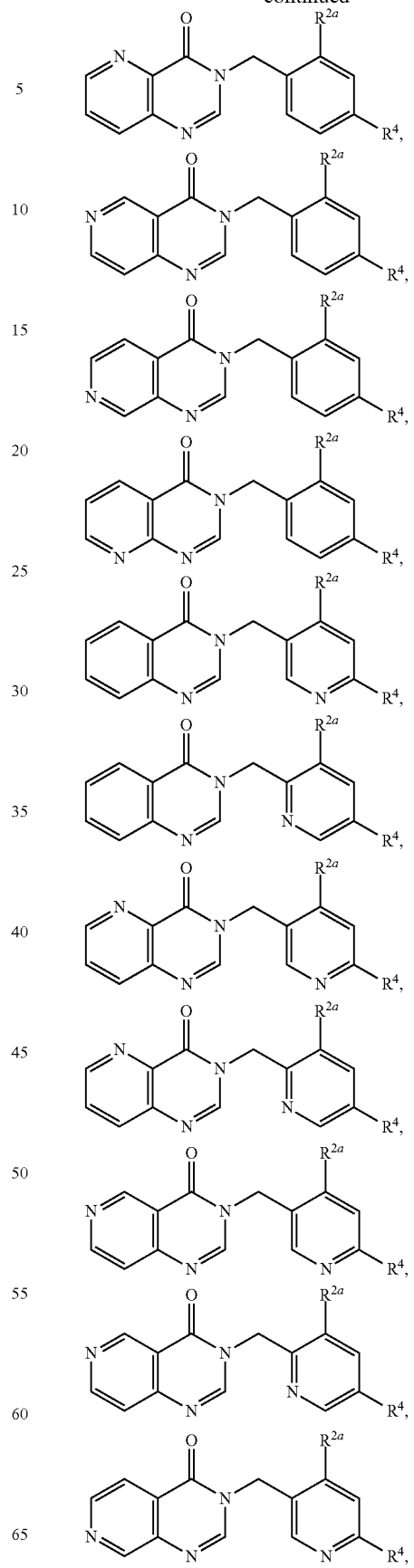
In a further aspect, the invention relates to a compound having a structure represented by a formula:
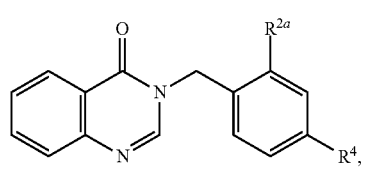

-continued
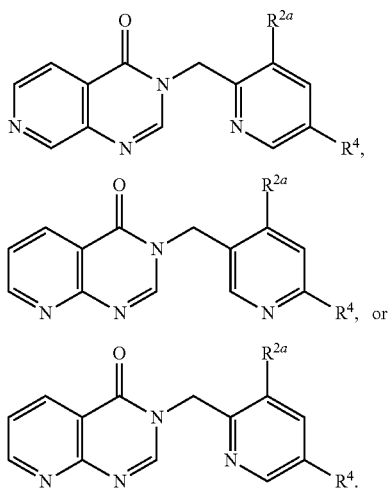
In a further aspect, the invention relates to a compound having a structure represented by a formula:
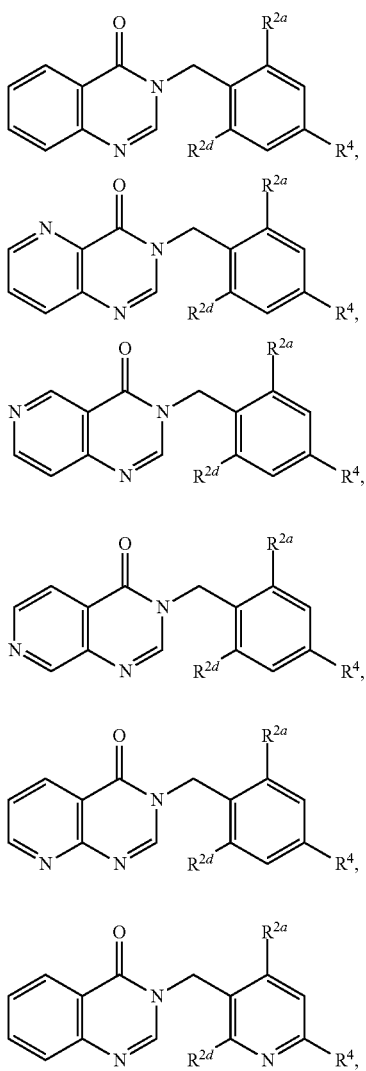
-continued
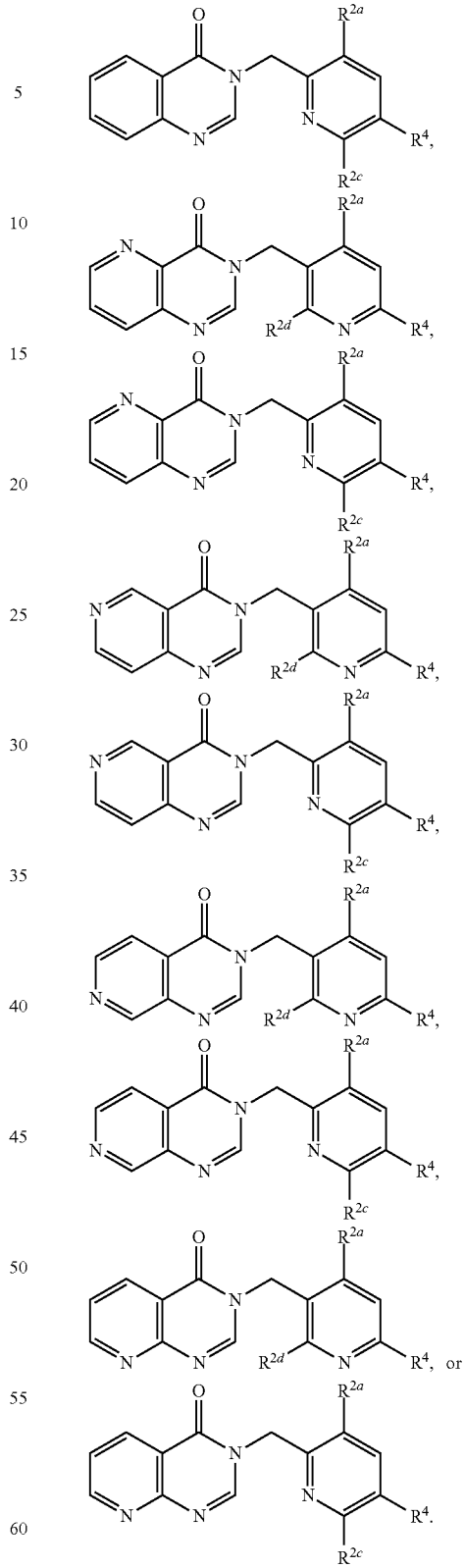
a. L² Groups
In one aspect, L² is selected from —CR$^{8a}$R$^{8b}$—, —O—, —NR$^9$—, —S—, —(S═O)—, and —(SO$_2$)—. In a further aspect, L² is selected from —O—, —NR$^9$—, —S—, —(S=O)—, and —(SO$_2$)—. In a still further aspect, L$^2$ is selected from —CR$^{8a}$R$^{8b}$—, —NR$^9$—, —S—, —(S=O)—, and —(SO$_2$)—. In a yet further aspect, L$^2$ is selected from —CR$^{8a}$R$^{8b}$—, —O—, —S—, —(S=O)—, and —(SO$_2$)—. In an even further aspect, L$^2$ is selected from —CR$^{8a}$R$^{8b}$—, —O—, —NR$^9$—, —(S=O)—, and —(SO$_2$)—. In a still further aspect, L$^2$ is selected from —CR$^{8a}$R$^{8b}$—, —O—, —NR$^9$—, —S—, and —(SO$_2$)—. In a yet further aspect, L$^2$ is selected from —CR$^{8a}$R$^{8b}$—, —O—, —NR$^9$—, —S—, and —(S=O)—.

In various aspects, L$^2$ is —O— or —NR$^8$—. In a further aspect, L$^2$ is —O— or —S—. In a still further aspect, L$^2$ is selected from —S—, —S=O)—, and —(SO$_2$)—. In a yet further aspect, L$^2$ is selected from —O—, —S—, —(S=O)—, and —(SO$_2$)—. In an even further aspect, L$^2$ is selected from —O—, —S—, and —NR$^9$—. In a still further aspect, L$^2$ is selected from —CR$^{8a}$R$^{8b}$—, —O—, and —NR$^9$—. In a yet further aspect, L$^2$ is selected from —NR$^9$—, —S—, —(S=O)—, and —(SO$_2$)—.

In a further aspect, L$^2$ is —O—. In a still further aspect, L$^2$ is —NR$^8$—. In a yet further aspect, L$^2$ is —NH—. In an even further aspect, L$^2$ is —NCH$_3$—. In a still further aspect, L$^2$ is —CR$^{8a}$R$^{8b}$—. In a yet further aspect, L$^2$ is —S—. In an even further aspect, L$^2$ is —(S=O)—. In a still further aspect, L$^2$ is —(SO$_2$)—.

b. Q Groups (Q$^1$, Q$^2$, Q$^3$ AND Q$^4$)

In one aspect, Q$^1$ is selected from N and CR$^{1a}$; Q$^2$ is selected from N and CR$^{1b}$; Q$^3$ is selected from N and CR$^{1c}$; Q$^4$ is selected from N and CR$^{1b}$; and wherein 0, 1, or 2 of Q$^1$, Q$^2$, Q$^3$, and Q$^4$ are N.

In a further aspect, 0 or 1 of Q$^1$, Q$^2$, Q$^3$, and Q$^4$ is N. In a still further aspect, 1 or 2 of Q$^1$, Q$^2$, Q$^3$, and Q$^4$ is N. In a yet further aspect, 1 of Q$^1$, Q$^2$, Q$^3$, and Q$^4$ is N. In an even further aspect, 2 of Q$^1$, Q$^2$, Q$^3$, and Q$^4$ are N. In a still further aspect, each of Q$^1$, Q$^2$, Q$^3$, and Q$^4$ is not N.

In a further aspect, Q$^1$ is CR$^{1a}$; Q$^2$ is CR$^{1b}$; Q$^3$ is CR$^{1c}$; and Q$^4$ is CR$^{1d}$. In a yet further aspect, Q$^1$ is CR$^{1a}$; Q$^2$ is CR$^{1b}$; Q$^3$ is CR$^{1c}$; and Q$^4$ is N. In a still further aspect, Q$^1$ is CR$^{1a}$; Q$^2$ is CR$^{1b}$; Q$^3$ is N; and Q$^4$ is CR$^{1d}$. In an even further aspect, Q$^1$ is CR$^{1a}$; Q$^2$ is N; Q$^3$ is CR$^{1c}$; and Q$^4$ is CR$^{1d}$. In a still further aspect, Q$^1$ is N; Q$^2$ is CR$^{1b}$; Q$^3$ is CR$^{1c}$; and Q$^4$ is CR$^{1d}$.

In a further aspect, each of Q$^1$ and Q$^3$ is N; Q$^2$ is CR$^{1b}$; and Q$^4$ is CR$^{1d}$. In an even further aspect, each of Q$^1$ and Q$^2$ is N; Q$^3$ is CR$^{1c}$; and Q$^4$ is CR$^{1d}$. In a yet further aspect, each of Q$^1$ and Q$^4$ is N; Q$^2$ is CR$^{1b}$; and Q$^3$ is CR$^{1c}$. In a still further aspect, each of Q$^2$ and Q$^3$ is N; Q$^1$ is CR$^{1a}$; and Q$^4$ is CR$^{1d}$. In an even further aspect, each of Q$^2$ and Q$^4$ is N; Q$^1$ is CR$^{1a}$; and Q$^3$ is CR$^{1c}$. In a still further aspect, each of Q$^3$ and Q$^4$ is N; Q$^1$ is CR$^{1a}$; and Q$^2$ is CR$^{1b}$.

c. Q Groups (Q$^5$, Q$^6$, Q$^7$ AND Q$^8$)

In one aspect, Q$^5$ is selected from N and CR$^{2a}$; Q$^6$ is selected from N and CR$^{2b}$; Q$^7$ is selected from N and CR$^{2c}$; Q$^8$ is selected from N and CR$^{2d}$; and wherein 0, 1, or 2 of Q$^5$, Q6, Q$^7$, and Q$^8$ are N.

In a further aspect, 0 or 1 of Q$^5$, Q$^6$, Q$^7$, and Q$^8$ is N. In a still further aspect, 1 or 2 of Q$^5$, Q$^6$, Q$^7$, and Q$^8$ is N. In a yet further aspect, 1 of Q$^5$, Q$^6$, Q$^7$, and Q$^8$ is N. In an even further aspect, 2 of Q$^5$, Q$^6$, Q$^7$, and Q$^8$ are N. In a still further aspect, each of Q$^5$, Q$^6$, Q$^7$, and Q$^8$ is not N.

In a further aspect, Q$^5$ is CR$^{2a}$; Q$^6$ is CR$^{2b}$; Q$^7$ is CR$^{2c}$, and Q$^8$ is CR$^{2d}$. In a yet further aspect, Q$^5$ is CR$^{2a}$; Q$^6$ is CR$^{2b}$; Q$^7$ is CR$^{2c}$; and Q$^8$ is N. In a still further aspect, Q$^5$ is CR$^{2a}$; Q$^6$ is CR$^{2b}$; Q$^7$ is N; and Q$^8$ is CR$^{2d}$. In an even further aspect, Q$^5$ is CR$^{2a}$; Q$^6$ is N; Q$^7$ is CR$^{2c}$; and Q$^8$ is CR$^{2d}$. In a still further aspect, Q$^5$ is N; Q$^6$ is CR$^{2b}$; Q$^7$ is CR$^{2c}$; and Q$^8$ is CR$^{2d}$.

In a further aspect, each of Q$^5$ and Q$^7$ is N; Q$^6$ is CR$^{2b}$; and Q$^8$ is CR$^{2d}$. In an even further aspect, each of Q$^5$ and Q$^6$ is N; Q$^7$ is CR$^{2c}$; and Q$^8$ is CR$^{2d}$. In a yet further aspect, each of Q$^5$ and Q$^8$ is N; Q$^6$ is CR$^{2b}$; and Q$^7$ is CR$^{2c}$. In a still further aspect, each of Q$^6$ and Q$^7$ is N; Q$^5$ is CR$^{2a}$; and Q$^8$ is CR$^{2d}$. In an even further aspect, each of Q$^6$ and Q$^8$ is N; Q$^5$ is CR$^{2a}$; and Q$^7$ is CR$^{2c}$. In a still further aspect, each of Q$^7$ and Q$^8$ is N; Q$^5$ is CR$^{2a}$; and Q$^6$ is CR$^{2b}$.

d. Z$^1$ AND Z$^2$

In one aspect, each of Z$^1$ and Z$^2$ are independently selected from Q$^6$ or CR$^4$, provided that Z$^1$ and Z$^2$ are not simultaneously Q$^6$ or simultaneously CR$^4$.

In a further aspect, Z$^1$ is Q$^6$ and Z$^2$ is CR$^4$. In a still further aspect, Z$^1$ is CR$^4$ and Z$^2$ is Q$^6$.

e. R$^1$ Groups

In one aspect, each of R$^{1a}$, R$^{1b}$, R$^{1c}$, and R$^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino.

In one aspect, each of R$^{1a}$, R$^{1b}$, R$^{1c}$, and R$^{1d}$, when present, is independently selected from hydrogen, halogen, C1-C6 alkyl, C1-C6 alkenyl, C1-C6 alkynyl, C1-C6 haloalkyl, C1-C6 polyhaloalkyl, C1-C6 alkoxy, C1-C6 alkoxy-C1-C6 alkyl, C1-C6 haloalkyl-oxy-C1-C6 alkyl, C1-C6 polyhaloalkyl-oxy-C1-C6 alkyl, C1-C6 alkylamino, C1-C6 dialkylamino, C3-C8 cycloalkyl, and C3-C8 heterocycloalkyl.

In a further aspect, each of R$^{1a}$, R$^{1b}$, R$^{1c}$, and R$^{1d}$, when present, is independently selected from hydrogen, halogen, C1-C3 alkyl, C1-C3 haloalkyl, C1-C3 polyhaloalkyl, C1-C3 alkoxy, C1-C3 alkoxy-C1-C3 alkyl, C1-C3 alkylamino, C1-C3 haloalkyl-oxy-C1-C3 alkyl, C1-C3 polyhaloalkyl-oxy-C1-C3 alkyl, and C1-C3 dialkylamino. In a still further aspect, each of R$^{1a}$, R$^{1b}$, R$^{1c}$, and R$^{1d}$, when present, is independently selected from hydrogen, —F, —Cl, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —CH(CH$_3$)$_2$, —CH$_2$OCH$_3$, —(CH$_2$)$_2$OCH$_3$, —OCH$_2$F, —OCHF$_2$, —OCF$_3$, —OCH$_2$Cl, —OCHCl$_2$, —OCCl$_3$, —OCH$_2$CF$_3$, —CH(CH$_3$)(CF$_3$), —CH$_2$OCF$_3$, —(CH$_2$)$_2$OCF$_3$, —OCH$_2$CCl$_3$, —CH(CH$_3$)(CCl), —CH$_2$OCCl$_3$, —(CH$_2$)$_2$OCCl$_3$, —NHCH$_3$, —NHCH$_2$CH$_3$, —NHCH(CH$_3$)$_2$, —N(CH$_3$)$_2$, —N(CH$_3$)CH$_2$CH$_3$, and —N(CH$_3$)CH(CH$_3$)$_2$. In a yet further aspect, each of R$^{1a}$, R$^{1b}$, R$^{1c}$, and R$^{1d}$, when present, is independently selected from hydrogen, —F, —Cl, —CH$_3$, —CF$_3$, and —CCl$_3$, —OCH$_3$, —OCH$_2$CH$_3$, —CH$_2$OCH$_3$, —OCF$_3$, —OCH$_2$CF$_3$, —CH$_2$OCF$_3$, —NHCH$_3$, —NHCH$_2$CH$_3$, —NHCH(CH$_3$)$_2$, and —N(CH$_3$)$_2$.

In a further aspect, each of R$^{1a}$, R$^{1b}$, R$^{1c}$, and R$^{1d}$, when present, is independently selected from hydrogen, C1-C3 alkyl, C1-C3 haloalkyl, C1-C3 polyhaloalkyl, C1-C3 alkoxy, C1-C3 alkoxy-C1-C3 alkyl, C1-C3 alkylamino, C1-C3 haloalkyl-oxy-C1-C3 alkyl, C1-C3 polyhaloalkyl-oxy-C1-C3 alkyl, and C1-C3 dialkylamino. In a still further aspect, each of R$^{1a}$, R$^{1b}$, R$^{1c}$, and R$^{1d}$, when present, is independently selected from hydrogen, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —CH(CH$_3$)$_2$, —CH$_2$OCH$_3$, —(CH$_2$)$_2$OCH$_3$, —OCH$_2$F, —OCHF$_2$, —OCF$_3$, —OCH$_2$Cl, —OCHCl$_2$, —OCCl$_3$, —OCH$_2$CF$_3$, —CH(CH$_3$)(CF$_3$), —CH$_2$OCF$_3$, —(CH$_2$)$_2$OCF$_3$, —OCH$_2$CCl$_3$, —CH(CH$_3$)(CCl$_3$), —CH$_2$OCCl$_3$, —(CH$_2$)$_2$OCCl$_3$, —NHCH$_3$, —NHCH$_2$CH$_3$, —NHCH(CH$_3$)$_2$, —N(CH$_3$)$_2$, —(CH$_3$)CH$_2$CH$_3$, and —N(CH$_3$)CH(CH$_3$)$_2$. In a yet further aspect, each of R$^{1a}$, R$^{1b}$, R$^{1c}$, and R$^{1d}$, when present, is independently selected from hydrogen, —CH$_3$, —CF$_3$, and —CCl$_3$, —OCH$_3$, —OCH$_2$CH$_3$, —CH$_2$OCH$_3$, —OCF$_3$, —OCH$_2$CF$_3$, —CH$_2$OCF$_3$, —NHCH$_3$, —NHCH$_2$CH$_3$, —NHCH(CH$_3$)$_2$, and —N(CH$_3$)$_2$.

In a further aspect, each of R$^{1a}$, R$^{1b}$, R$^{1c}$, and R$^{1d}$, when present, is independently selected from halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino. In a further aspect, each of R$^{1a}$, R$^{1b}$, R$^{1c}$, and R$^{1d}$, when present, is independently selected from halogen, C1-C3 alkyl, C1-C3 haloalkyl, C1-C3 polyhaloalkyl, C1-C3 alkoxy, C1-C3 alkoxy-C1-C6 alkyl, C1-C3 alkylamino, C1-C3 haloalkyl-oxy-C1-C3 alkyl, C1-C3 polyhaloalkyl-oxy-C1-C3 alkyl, and C1-C3 dialkylamino. In a still further aspect, each of R$^{1a}$, R$^{1b}$, R$^{1c}$, and R$^{1d}$, when present, is independently selected from —F, —Cl, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —CH(CH$_3$)$_2$, —CH$_2$OCH$_3$, —(CH$_2$)$_2$OCH$_3$, —OCH$_2$F, —OCHF$_2$, —OCF$_3$, —OCH$_2$Cl, —OCHCl$_2$, —OCCl$_3$, —OCH$_2$CF$_3$, —CH(CH$_3$)(CF$_3$), —CH$_2$OCF$_3$, —(CH$_2$)$_2$OCF$_3$, —OCH$_2$CCl$_3$, —CH(CH$_3$)(CCl$_3$), —CH$_2$OCCl$_3$, —(CH$_2$)$_2$OCCl$_3$, —NHCH$_3$, —NHCH$_2$CH$_3$, —NHCH(CH$_3$)$_2$, —N(CH$_3$)$_2$, —N(CH$_3$)CH$_2$CH$_3$, and —N(CH$_3$)CH(CH$_3$)$_2$. In a yet further aspect, each of R$^{1a}$, R$^{1b}$, R$^{1c}$, and R$^{1d}$, when present, is independently selected from —F, —Cl, —CH$_3$, —CF$_3$, and —CCl$_3$, —OCH$_3$, —OCH$_2$CH$_3$, —CH$_2$OCH$_3$, —OCF$_3$, —OCH$_2$CF$_3$, —CH$_2$OCF$_3$, —NHCH$_3$, —NHCH$_2$CH$_3$, —NHCH(CH$_3$)$_2$, and —N(CH$_3$)$_2$.

In a further aspect, each of R$^{1a}$, R$^{1b}$, R$^{1c}$, and R$^{1d}$, when present, is independently selected from hydrogen, halogen, C1-C6 alkyl, C1-C6 haloalkyl, and C1-C6 polyhaloalkyl. In a still further aspect, each of R$^{1a}$, R$^{1b}$, R$^{1c}$, and R$^{1d}$, when present, is independently selected from hydrogen, halogen, C1-C3 alkyl, C1-C3 haloalkyl, and C1-C3 polyhaloalkyl. In a yet further aspect, each of R$^{1a}$, R$^{1b}$, R$^{1c}$, and R$^{1d}$, when present, is independently selected from hydrogen, —F, —Cl, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, and —CH$_2$CCl$_3$. In an even further aspect, each of R$^{1a}$, R$^{1b}$, R$^{1c}$, and R$^{1d}$, when present, is independently selected from hydrogen, —F, —Cl, —CH$_3$, —CF$_3$, and —CCl$_3$.

In a further aspect, each of R$^{1a}$, R$^{1b}$, R$^{1c}$, and R$^{1d}$, when present, is independently selected from hydrogen, C1-C6 alkyl, C1-C6 haloalkyl, and C1-C6 polyhaloalkyl. In an even further aspect, each of R$^{1a}$, R$^{1b}$, R$^{1c}$, and R$^{1d}$, when present, is independently selected from hydrogen, C1-C3 alkyl, C1-C3 haloalkyl, and C1-C3 polyhaloalkyl. In a still further aspect, each of R$^{1a}$, R$^{1b}$, R$^{1c}$, and R$^{1d}$, when present, is independently selected from hydrogen, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, and —CH$_2$CCl$_3$. In a yet further aspect, each of R$^{1a}$, R$^{1b}$, R$^{1c}$, and R$^{1d}$, when present, is independently selected from hydrogen, —CH$_3$, —CF$_3$, and —CCl$_3$.

In a further aspect, each of R$^{1a}$, R$^{1b}$, R$^{1c}$, and R$^{1d}$, when present, is independently selected from hydrogen, halogen, C1-C6 alkoxy, C1-C6 alkoxy-C1-C6 alkyl, C1-C6 haloalkyl-oxy-C1-C6 alkyl, and C1-C6 polyhaloalkyl-oxy-C1-C6 alkyl. In a still further aspect, each of R$^{1a}$, R$^{1b}$, R$^{1c}$, and R$^{1d}$, when present, is independently selected from hydrogen, halogen, C1-C3 alkoxy, C1-C3 alkoxy-C1-C3 alkyl, C1-C3 haloalkyl-oxy-C1-C3 alkyl, and C1-C3 polyhaloalkyl-oxy-C1-C3 alkyl. In a yet further aspect, each of R$^{1a}$, R$^{1b}$, R$^{1c}$, and R$^{1d}$, when present, is independently selected from hydrogen, —F, —Cl, —OCH$_3$, —OCH$_2$CH$_3$, —CH(CH$_3$)$_2$, —CH$_2$OCH$_3$, —(CH$_2$)$_2$OCH$_3$, —OCH$_2$F, —OCHF$_2$, —OCF$_3$, —OCH$_2$Cl, —OCHCl$_2$, —OCCl$_3$, —OCH$_2$CF$_3$, —CH(CH$_3$)(CF$_3$), —CH$_2$OCF$_3$, —(CH$_2$)$_2$OCF$_3$, —OCH$_2$CCl$_3$, —CH(CH$_3$)(CCl$_3$), —CH$_2$OCCl$_3$, and —(CH$_2$)$_2$OCCl$_3$. In an even further aspect, each of R$^{1a}$, R$^{1b}$, R$^{1c}$, and R$^{1d}$, when present, is independently selected from hydrogen, —F, —Cl, —OCH$_3$, —OCH$_2$CH$_3$, —CH$_2$OCH$_3$, —OCF$_3$, —OCH$_2$CF$_3$, and —CH$_2$OCF$_3$.

In a further aspect, each of R$^{1a}$, R$^{1b}$, R$^{1c}$, and R$^{1d}$, when present, is independently selected from hydrogen, C1-C6 alkoxy, C1-C6 alkoxy-C1-C6 alkyl, C1-C6 haloalkyl-oxy -C1-C6 alkyl, and C1-C6 polyhaloalkyl-oxy-C1-C6 alkyl. In a still further aspect, each of R$^{1a}$, R$^{1b}$, R$^{1c}$, and R$^{1d}$, when present, is independently selected from hydrogen, C1-C3 alkoxy, C1-C3 alkoxy-C1-C3 alkyl, C1-C3 haloalkyl-oxy-C1-C3 alkyl, and C1-C3 polyhaloalkyl-oxy -C1-C3 alkyl. In a still further aspect, each of R$^{1a}$, R$^{1b}$, R$^{1c}$, and R$^{1d}$, when present, is independently selected from hydrogen, —OCH$_3$, —OCH$_2$CH$_3$, —CH(CH$_3$)$_2$, —CH$_2$OCH$_3$, —(CH$_2$)$_2$OCH$_3$, —OCH$_2$F, —OCHF$_2$, —OCF$_3$, —OCH$_2$Cl, —OCHCl$_2$, —OCCl$_3$, —OCH$_2$CF$_3$, —CH(CH$_3$)(CF$_3$), —CH$_2$OCF$_3$, —(CH$_2$)$_2$OCF$_3$, —OCH$_2$CCl$_3$, —CH(CH$_3$)(CCl$_3$), —CH$_2$OCCl$_3$, and —(CH$_2$)$_2$OCCl$_3$. In an even further aspect, each of R$^{1a}$, R$^{1b}$, R$^{1c}$, and R$^{1d}$, when present, is independently selected from hydrogen, —OCH$_3$, —OCH$_2$CH$_3$, —CH$_2$OCH$_3$, —OCF$_3$, —OCH$_2$CF$_3$, and —CH$_2$OCF$_3$.

In a further aspect, each of R$^{1a}$, R$^{1b}$, R$^{1c}$, and R$^{1d}$, when present, is independently selected from hydrogen, halogen, C1-C6 alkylamino, and C1-C6 dialkylamino. In a still further aspect, each of R$^{1a}$, R$^{1b}$, R$^{1c}$, and R$^{1d}$, when present, is independently selected from hydrogen, halogen, C1-C3 alkylamino, and C1-C3 dialkylamino. In a yet further aspect, each of R$^{1a}$, R$^{1b}$, R$^{1c}$, and R$^{1d}$, when present, is independently selected from hydrogen, —F, —Cl, —NHCH$_3$, —NHCH$_2$CH$_3$, —NHCH(CH$_3$)$_2$, —N(CH$_3$)$_2$, —N(CH$_3$)CH$_2$CH$_3$, and —N(CH$_3$)CH(CH$_3$)$_2$. In an even further aspect, each of R$^{1a}$, R$^{1b}$, R$^{1c}$, and R$^{1d}$, when present, is independently selected from hydrogen, —F, —Cl, —NHCH$_3$, —NHCH$_2$CH$_3$, —NHCH(CH$_3$)$_2$, and —N(CH$_3$)$_2$.

In a further aspect, each of R$^{1a}$, R$^{1b}$, R$^{1c}$, and R$^{1d}$, when present, is independently selected from hydrogen, C1-C6 alkylamino, and C1-C6 dialkylamino. In a still further aspect, each of R$^{1a}$, R$^{1b}$, R$^{1c}$, and R$^{1d}$, when present, is independently selected from hydrogen, C1-C3 alkylamino, and C1-C3 dialkylamino. In a yet further aspect, each of R$^{1a}$, R$^{1b}$, R$^{1c}$, and R$^{1d}$, when present, is independently selected from hydrogen, —NHCH$_3$, —NHCH$_2$CH$_3$, —NHCH(CH$_3$)$_2$, —N(CH$_3$)$_2$, —N(CH$_3$)CH$_2$CH$_3$, and —N(CH$_3$)CH(CH$_3$)$_2$. In an even further aspect, each of R$^{1a}$, R$^{1b}$, R$^{1c}$, and R$^{1d}$, when present, is independently selected from hydrogen, —NHCH$_3$, —NHCH$_2$CH$_3$, —NHCH(CH$_3$)$_2$, and —N(CH$_3$)$_2$.

In a further aspect, each of R$^{1a}$, R$^{1b}$, R$^{1c}$, and R$^{1d}$, when present, is independently selected from hydrogen, —F, —Cl, —CF$_3$, and —CCl$_3$. In a yet further aspect, each of R$^{1a}$, R$^{1b}$, R$^{1c}$, and R$^{1d}$, when present, is independently selected from hydrogen, —CH$_3$, —CF$_3$, and —CCl$_3$.

In a further aspect, each of $R^{1a}$, $R^{1b}$, $R^{1c}$, and $R^{1d}$, when present, is independently selected from hydrogen, —F, —Cl, —Br, and —I. In an even further aspect, each of $R^{1a}$, $R^{1b}$, $R^{1c}$, and $R^{1d}$, when present, is independently selected from hydrogen, —F, and —Cl. In a still further aspect, each of $R^{1a}$, $R^{1b}$, $R^{1c}$, and $R^{1d}$, when present, is hydrogen.

In a further aspect, $R^{1a}$, when present, is selected from hydrogen, —F, and —Cl. In a still further aspect, $R^{1a}$, when present, is hydrogen. In a yet further aspect, $R^{1a}$, when present, is —F. In an even further aspect, $R^{1a}$, when present, is —Cl.

In a further aspect, $R^{1b}$, when present, is selected from hydrogen, —F, and —Cl. In a still further aspect, $R^{1b}$, when present, is hydrogen. In a yet further aspect, $R^{1b}$, when present, is —F. In an even further aspect, $R^{1b}$, when present, is —Cl.

In a further aspect, $R^{1c}$, when present, is selected from hydrogen, —F, and —Cl. In a still further aspect, $R^{1c}$, when present, is hydrogen. In a yet further aspect, $R1^{1c}$, when present, is —F. In an even further aspect, $R^{1c}$, when present, is —Cl.

In a further aspect, $R^{1d}$, when present, is selected from hydrogen, —F, and —Cl. In a still further aspect, $R^{1d}$, when present, is hydrogen. In a yet further aspect, $R^{1d}$, when present, is —F. In an even further aspect, $R^{1d}$, when present, is —Cl.

f. $R^2$ Groups

In one aspect, each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO$_2$R$^{30}$.

In one aspect, each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO$_2$R$^{30}$, provided that at least one $R^{2a}$, $R^{2b}$, $R^{2c}$, and $R^{2d}$, when present, is not hydrogen when Ar$^2$ is pyrazolyl.

In one aspect, each of $R^{2a}$, $R^{2b}$, $R^{2c}$, and $R^{2d}$, when present, is independently selected from hydrogen, halogen, cyano, C1-6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO$_2$R$^{30}$.

In a further aspect, each of $R^{2a}$, $R^{2b}$, $R^{2c}$, and $R^{2d}$, when present, is independently selected from hydrogen, halogen, cyano, C1-C3 alkyl, C1-C3 haloalkyl, C1-C3 polyhaloalkyl, C1-C3 alkoxy, C1-C3 alkoxy-C1-C3 alkyl, C1-C3 alkylamino, C1-C3 haloalkyl-oxy-C1-C3 alkyl, C1-C3 polyhaloalkyl-oxy-C1-C3 alkyl, C1-C3 dialkylamino, —C(OH)$R^{20a}R^{20b}$, and —SO$_2$R$^{30}$. In a still further aspect, each of $R^{2a}$, $R^{2b}$, $R^{2c}$, and $R^{2d}$, when present, is independently selected from hydrogen, —F, —Cl, cyano, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —CH(CH$_3$)$_2$, —CH$_2$OCH$_3$, —(CH$_2$)$_2$OCH$_3$, —OCH$_2$F, —OCHF$_2$, —OCF$_3$, —OCH$_2$Cl, —OCHCl$_2$, —OCCl$_3$, —OCH$_2$CF$_3$, —CH(CH$_3$)(CF$_3$), —CH$_2$OCF$_3$, —(CH$_2$)$_2$OCF$_3$, —OCH$_2$CCl$_3$, —CH(CH$_3$)(CCl$_3$), —CH$_2$OCCl$_3$, —(CH$_2$)$_2$OCCl$_3$, —NHCH$_3$, —NHCH$_2$CH$_3$, —NHCH(CH$_3$)$_2$, —N(CH$_3$)$_2$, —N(CH$_3$)CH$_2$CH$_3$, —N(CH$_3$)CH(CH$_3$)$_2$, —C(CH$_3$)$_2$(OH), —C(CH$_3$)(CF$_2$H)(OH), —C(CH$_3$)(CF$_3$)(OH), —C(CF$_2$H)$_2$(OH), —C(CF$_2$H)(CF$_3$)(OH), —C(CF$_3$)$_2$(OH), —CH$_2$(OH), —CH(CH$_3$)(OH), —CH(CF$_2$H)(OH), —CH(CF$_3$)(OH), —SO$_2$CH$_3$, —SO$_2$CF$_2$H, and —SO$_2$CF$_3$. In a yet further aspect, each of $R^{2a}$, $R^{2b}$, $R^{2c}$, and $R^{2d}$, when present, is independently selected from hydrogen, —F, —Cl, cyano, —CH$_3$, —CF$_3$, and —CCl$_3$, —OCH$_3$, —OCH$_2$CH$_3$, —CH$_2$OCH$_3$, —OCF$_3$, —OCH$_2$CF$_3$, —CH$_2$OCF$_3$, —NHCH$_3$, —NHCH$_2$CH$_3$, —NHCH(CH$_3$)$_2$, —N(CH$_3$)$_2$, —C(CH$_3$)$_2$(OH), —C(CH$_3$)(CF$_2$H)(OH), —C(CH$_3$)(CF$_3$)(OH), —CH$_2$(OH), —CH(CH$_3$)(OH), —CH(CF$_2$H)(OH), —CH(CF$_3$)(OH), —SO$_2$CH$_3$, —SO$_2$CF$_2$H, and —SO$_2$CF$_3$.

In a further aspect, each of $R^{2a}$, $R^{2b}$, $R^{2c}$, and $R^{2d}$, when present, is independently selected from hydrogen, cyano, C1-C3 alkyl, C1-C3 haloalkyl, C1-C3 polyhaloalkyl, C1-C3 alkoxy, C1-C3 alkoxy-C1-C3 alkyl, C1-C3 alkylamino, C1-C3 haloalkyl-oxy-C1-C3 alkyl, C1-C3 polyhaloalkyl-oxy-C1-C3 alkyl, C1-C3 dialkylamino, —C(OH)$R^{20a}R^{20b}$, and —SO$_2$R$^{30}$. In a still further aspect, each of $R^{2a}$, $R^{2b}$, $R^{2c}$, and $R^{2d}$, when present, is independently selected from hydrogen, cyano, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —CH(CH$_3$)$_2$, —CH$_2$OCH$_3$, —(CH$_2$)$_2$OCH$_3$, —OCH$_2$F, —OCHF$_2$, —OCF$_3$, —OCH$_2$Cl, —OCHCl$_2$, —OCCl$_3$, —OCH$_2$CF$_3$, —CH(CH$_3$)(CF$_3$), —CH$_2$OCF$_3$, —(CH$_2$)$_2$OCF$_3$, —OCH$_2$CCl$_3$, —CH(CH$_3$)(CCl$_3$), —CH$_2$OCCl$_3$, —(CH$_2$)$_2$OCCl$_3$, —NHCH$_3$, —NHCH$_2$CH$_3$, —NHCH(CH$_3$)$_2$, —N(CH$_3$)$_2$, —N(CH$_3$)CH$_2$CH$_3$, —N(CH$_3$)CH(CH$_3$)$_2$, —C(CH$_3$)$_2$(OH), —C(CH$_3$)(CF$_2$H)(OH), —C(CH$_3$)(CF$_3$)(OH), —C(CF$_2$H)$_2$(OH), —C(CF$_2$H)(CF$_3$)(OH), —C(CF$_3$)$_2$(OH), —CH$_2$(OH), —CH(CH$_3$)(OH), —CH(CF$_2$H)(OH), —CH(CF$_3$)(OH), —SO$_2$CH$_3$, —SO$_2$CF$_2$H, and —SO$_2$CF$_3$. In a yet further aspect, each of $R^{2a}$, $R^{2b}$, $R^{2c}$, and $R^{2d}$, when present, is independently selected from hydrogen, cyano, —CH$_3$, —CF$_3$, and —CCl$_3$, —OCH$_3$, —OCH$_2$CH$_3$, —CH$_2$OCH$_3$, —OCH$_2$CF$_3$, —CH$_2$OCF$_3$, —NHCH$_3$, —NHCH$_2$CH$_3$, —NHCH(CH$_3$)$_2$, —N(CH$_3$)$_2$, —C(CF$_2$H)$_2$(OH), —C(CF$_2$H)(CF$_3$)(OH), —C(CF$_3$)$_2$(OH), —CH(CF$_3$)(OH), —SO$_2$CH$_3$, —SO$_2$CF$_2$H, and —SO$_2$CF$_3$.

In a further aspect, each of $R^{2a}$, $R^{2b}$, $R^{2c}$, and $R^{2d}$, when present, is independently selected from halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino. In a further aspect, each of $R^{2a}$, $R^{2b}$, $R^{2c}$, and $R^{2d}$, when present is independently selected from halogen, C1-C3 alkyl, C1-C3 haloalkyl, C1-C3 polyhaloalkyl, C1-C3 alkoxy, C1-C3 alkoxy-C1-C6 alkyl, C1-C3 alkylamino, C1-C3 haloalkyl-oxy-C1-C3 alkyl, C1-C3 polyhaloalkyl-oxy-C1-C3 alkyl, C1-C3 dialkylamino, —C(OH)$R^{20a20b}$, and —SO$_{2R}^{30}$. In a still further aspect, each of $R^{2a}$, $R^{2b}$, $R^{2c}$, and $R^{2d}$, when present, is independently selected from —F, —Cl, cyano, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —CH(CH$_3$)$_2$, —CH$_2$OCH$_3$, —(CH$_2$)$_2$OCH$_3$, —OCH$_2$F, —OCHF$_2$, —OCF$_3$, —OCH$_2$Cl, —OCHCl$_2$, —OCCl$_3$, —OCH$_2$CF$_3$, —CH(CH$_3$)(CF$_3$), —CH$_2$OCF$_3$, —(CH$_2$)$_2$OCF$_3$, —OCH$_2$CCl$_3$, —CH(CH$_3$)(CCl$_3$), —CH$_2$OCCl$_3$, —(CH$_2$)$_2$OCCl$_3$, —NHCH$_3$, —NHCH$_2$CH$_3$, —NHCH(CH$_3$)$_2$, N(CH$_3$)$_2$, —N(CH$_3$)CH$_2$CH$_3$, —N(CH$_3$)CH(CH$_3$)$_2$, —C(CH$_3$)$_2$(OH), —C(CH$_3$)(CF$_2$H)(OH), —C(CH₃)(CF₃)(OH), —C(CF₂H)₂(OH), —C(CF₂H)(CF₃)(OH), —C(CF₃)₂(OH), —CH₂(OH), —CH(CH₃)(OH), —CH(CF₂H)(OH), —CH(CF₃)(OH), —SO₂CH₃, —SO₂CF₂H, and —SO₂CF₃. In a yet further aspect, each of R²ᵃ, R²ᵇ, R²ᶜ, and R²ᵈ, when present, is independently selected from —F, —Cl, cyano, —CH₃, —CF₃, and —CCl₃, —OCH₃, —OCH₂CH₃, —CH₂OCH₃, —OCF₃, —OCH₂CF₃, —CH₂OCF₃, —NHCH₃, —NHCH₂CH₃, —NHCH(CH₃)₂, —N(CH₃)₂, —C(CH₃)₂(OH), —C(CH₃)(CF₂H)(OH), —C(CH₃)(CF₃)(OH), —CH₂(OH), —CH(CH₃)(OH), —CH(CF₂H)(OH), —CH(CF₃)(OH), —SO₂CH₃, —SO₂CF₂H, and —SO₂CF₃.

In a further aspect, each of R²ᵃ, R²ᵇ, R²ᶜ, and R²ᵈ, when present, is independently selected from hydrogen, halogen, cyano, C1-C6 alkyl, C1-C6 haloalkyl, and C1-C6 polyhaloalkyl. In a still further aspect, each of R²ᵃ, R²ᵇ, R²ᶜ, and R²ᵈ, when present, is independently selected from hydrogen, halogen, cyano, C1-C3 alkyl, C1-C3 haloalkyl, and C1-C3 polyhaloalkyl. In a yet further aspect, each of R²ᵃ, R²ᵇ, R²ᶜ, and R²ᵈ, when present, is independently selected from hydrogen, —F, —Cl, cyano, —CH₃, —CH₂CH₃, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, and —CH₂CCl₃. In an even further aspect, each of R²ᵃ, R²ᵇ, R²ᶜ, and R²ᵈ, when present, is independently selected from hydrogen, cyano, —F, —Cl, —CH₃, —CF₃, and —CCl₃.

In a further aspect, each of R²ᵃ, R²ᵇ, R²ᶜ, and R²ᵈ, when present, is independently selected from hydrogen, C1-C6 alkyl, C1-C6 haloalkyl, and C1-C6 polyhaloalkyl. In an even further aspect, each of R²ᵃ, R²ᵇ, R²ᶜ, and R²ᵈ, when present, is independently selected from hydrogen, cyano, C1-C3 alkyl, C1-C3 haloalkyl, and C1-C3 polyhaloalkyl. In a still further aspect, each of R²ᵃ, R²ᵇ, R²ᶜ, and R²ᵈ, when present, is independently selected from hydrogen, —CH₃, —CH₂CH₃, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, and —CH₂CCl₃. In a yet further aspect, each of R²ᵃ, R²ᵇ, R²ᶜ, and R²ᵈ, when present, is independently selected from hydrogen, —CH₃, —CF₃, and —CCl₃.

In a further aspect, each of R²ᵃ, R²ᵇ, R²ᶜ, and R²ᵈ, when present, is independently selected from hydrogen, halogen, cyano, C1-C6 alkoxy, C1-C6 alkoxy-C1-C6 alkyl, C1-C6 haloalkyl-oxy-C1-C6 alkyl, C1-C6 polyhaloalkyl-oxy-C1-C6 alkyl, —C(OH)R²⁰ᵃR²⁰ᵇ, and —SO₂R³⁰. In a still further aspect, each of R²ᵃ, R²ᵇ, R²ᶜ, and R²ᵈ, when present, is independently selected from hydrogen, halogen, cyano, C1-C3 alkoxy, C1-C3 alkoxy-C1-C3 alkyl, C1-C3 haloalkyl-oxy-C1-C3 alkyl, C1-C3 polyhaloalkyl-oxy-C1-C3 alkyl, —C(OH)R²⁰ᵃR²⁰ᵇ, and —SO₂R³⁰. In a yet further aspect, each of R²ᵃ, R²ᵇ, R²ᶜ, R²ᵈ, when present, is independently selected from hydrogen, —F, —Cl, cyano, —OCH₃, —OCH₂CH₃, —CH(CH₃)₂, —CH₂OCH₃, —(CH₂)₂OCH₃, —OCH₂F, —OCHF₂, —OCH₂Cl, —OCCl₃, —OCH₂CF₃, —CH(CH₃)(CF₃), —CH₂OCF₃, —(CH₂)₂OCF₃, —OCH₂CCl₃, —CH(CH₃)(CCl₃), —CH₂OCCl₃, —(CH₂)₂OCCl₃, —C(CH₃)₂(OH), —C(CH₃)(CF₂H)(OH), —C(CH₃)(CF₃)(OH), —C(CF₂H)₂(OH), —C(CF₂H)(CF₃)(OH), —C(CF₃)₂(OH), —CH₂(OH), —CH(CH₃)(OH), —CH(CF₂H)(OH), —CH(CF₃)(OH), —SO₂CH₃, —SO₂CF₂H, and —SO₂CF₃. In an even further aspect, each of R²ᵃ, R²ᵇ, R²ᶜ, and R²ᵈ, when present, is independently selected from hydrogen, —F, —Cl, cyano, —OCH₃, —OCH₂CH₃, —CH₂OCH₃, —OCF₃, —OCH₂CF₃, —CH₂OCF₃, —C(CF₂H)₂(OH), —C(CF₂H)(CF₃)(OH), —C(CF₃)₂(OH), —CH(CF₃)(OH), —SO₂CH₃, —SO₂CF₂H, and —SO₂CF₃.

In a further aspect, each of R²ᵃ, R²ᵇ, R²ᶜ, and R²ᵈ, when present, is independently selected from hydrogen, C1-C6 alkoxy, C1-C6 alkoxy-C1-C6 alkyl, C1-C6 haloalkyl-oxy -C1-C6 alkyl, C1-C6 polyhaloalkyl-oxy-C1-C6 alkyl, —C(OH)R²⁰ᵃR²⁰ᵇ, and —SO₂R³⁰. In a still further aspect, each of R²ᵃ, R²ᵇ, R²ᶜ, and R²ᵈ, when present, is independently selected from hydrogen, C1-C3 alkoxy, C1-C3 alkoxy-C1-C3 alkyl, C1-C3 haloalkyl-oxy-C1-C3 alkyl, C1-C3 polyhaloalkyl-oxy-C1-C3 alkyl, —C(OH)R²⁰ᵃR²⁰ᵇ, and —SO₂R³⁰. In a still further aspect, each of R²ᵃ, R²ᵇ, R²ᶜ, and R²ᵈ, when present, is independently selected from hydrogen, —OCH₃, —OCH₂CH₃, —CH(CH₃)₂, —CH₂OCH₃, —(CH₂)₂OCH₃, —OCH₂F, —OCHF₂, —OCF₃, —OCH₂Cl, —OCHCl₂, —OCCl₃, —OCH₂CF₃, —CH(CH₃)(CF₃), —CH₂OCF₃, —(CH₂)₂OCF₃, —OCH₂CCl₃, —CH(CH₃)(CCl₃), —CH₂OCCl₃, —(CH₂)₂OCCl₃, —C(CH₃)₂(OH), —C(CH₃)(CF₂H)(OH), —C(CH₃)(CF₃)(OH), —C(CF₂H)₂(OH), —C(CF₂H)(CF₃)(OH), —C(CF₃)₂(OH), —CH₂(OH), —CH(CH₃)(OH), —CH(CF₂H)(OH), —CH(CF₃)(OH), —SO₂CH₃, —SO₂CF₂H, and —SO₂CF₃. In an even further aspect, each of R²ᵃ, R²ᵇ, R²ᶜ, and R²ᵈ, when present, is independently selected from hydrogen, —OCH₃, —OCH₂CH₃, —CH₂OCH₃, —OCF₃, —OCH₂CF₃, —CH₂OCF₃, —C(CH₃)₂(OH), —C(CH₃)(CF₂H)(OH), —C(CH₃)(CF₃)(OH), —CH₂(OH), —CH(CH₃)(OH), —CH(CF₂H)(OH), —CH(CF₃)(OH), —SO₂CH₃, —SO₂CF₂H, and —SO₂CF₃.

In a further aspect, each of R²ᵃ, R²ᵇ, R²ᶜ, and R²ᵈ, when present, is independently selected from hydrogen, halogen, cyano, C1-C6 alkylamino, and C1-C6 dialkylamino. In a still further aspect, each of R²ᵃ, R²ᵇ, R²ᶜ, and R²ᵈ, when present, is independently selected from hydrogen, halogen, cyano, C1-C3 alkylamino, and C1-C3 dialkylamino. In a yet further aspect, each of R²ᵃ, R²ᵇ, R²ᶜ, and R²ᵈ, when present, is independently selected from hydrogen, —F, —Cl, cyano, —NHCH₃, —NHCH₂CH₃, —NHCH(CH₃)₂, —N(CH₃)₂, —N(CH₃)CH₂CH₃, and —N(CH₃)CH(CH₃)₂. In an even further aspect, each of R²ᵃ, R²ᵇ, R²ᶜ, and R²ᵈ, when present, is independently selected from hydrogen, —F, —Cl, cyano, —NHCH₃, —NHCH₂CH₃, —NHCH(CH₃)₂, and —N(CH₃)₂.

In a further aspect, each of R²ᵃ, R²ᵇ, R²ᶜ, and R²ᵈ, when present, is independently selected from hydrogen, C1-C6 alkylamino, C1-C6 dialkylamino, —C(OH)R²⁰ᵃR²⁰ᵇ, and —SO₂R³⁰. In a still further aspect, each of R²ᵃ, R²ᵇ, R²ᶜ, and R²ᵈ, when present, is independently selected from hydrogen, C1-C3 alkylamino, C1-C3 dialkylamino, —C(OH)R²⁰ᵃR²⁰ᵇ, —SO₂R³⁰. In a yet further aspect, each of R²ᵃ, R²ᵇ, R²ᶜ, and R²ᵈ, when present, is independently selected from hydrogen, —NHCH₃, —NHCH₂CH₃, —NHCH(CH₃)₂, —N(CH₃)₂, —N(CH₃)CH₂CH₃, —N(CH₃)CH(CH₃)₂, —C(CH₃)₂(OH), —C(CH₃)(CF₂H)(OH), —C(CH₃)(CF₃)(OH), —C(CF₂H)₂(OH), —C(CF₂H)(CF₃)(OH), —C(CF₃)₂(OH), —CH₂(OH), —CH(CH₃)(OH), —CH(CF₂H)(OH), —CH(CF₃)(OH), —SO₂CH₃, —SO₂CF₂H, and —SO₂CF₃. In an even further aspect, each of R²ᵃ, R²ᵇ, R²ᶜ, and R²ᵈ, when present, is independently selected from hydrogen, —NHCH₃, —NHCH₂CH₃, —NHCH(CH₃)₂, —N(CH₃)₂, —C(CH₃)₂(OH), —CH₂(OH), —CH(CH₃)(OH), —CH(CF₂H)(OH), —CH(CF₃)(OH), —SO₂CH₃, —SO₂CF₂H, and —SO₂CF₃.

In a further aspect, each of R²ᵃ, R²ᵇ, R²ᶜ, and R²ᵈ, when present, is independently selected from hydrogen, cyano, —F, —Cl, —CF₃, and —CCl₃. In a yet further aspect, each of R²ᵃ, R²ᵇ, R²ᶜ, and R²ᵈ, when present, is independently selected from hydrogen, cyano, —CH₃, —CF₃, and —CCl₃.

In a further aspect, each of $R^{2a}$, $R_{2b}$, $R^{2c}$, and $R^{2d}$, when present, is independently selected from hydrogen, cyano, —F, —Cl, —Br, and —I. In an even further aspect, each of $R^{2a}$, $R^{2b}$, $R^{2c}$, and $R^{2d}$, when present, is independently selected from hydrogen, —F, —Cl, and cyano. In a still further aspect, each of $R^{2a}$, $R^{2b}$, $R^{2c}$, and $R^{2d}$, when present, is selected from hydrogen and cyano. In yet a further aspect, each of $R^{2a}$, $R^{2b}$, $R^{2c}$, and $R^{2d}$, when present, is hydrogen.

In a further aspect, $R^{2a}$, when present, is selected from hydrogen, cyano, —F, and —Cl. In a still further aspect, $R^{2a}$, when present, is hydrogen. In a yet further aspect, $R^{2a}$, when present, is —F. In an even further aspect, $R^{2a}$, when present, is —Cl. In a still further aspect, $R^{2a}$, when present, is cyano.

In a further aspect, $R^{2b}$, when present, is selected from hydrogen, cyano, —F, and —Cl. In a still further aspect, $R^{2b}$, when present, is hydrogen. In a yet further aspect, $R^{2b}$, when present, is —F. In an even further aspect, $R^{2b}$, when present, is —Cl. In a still further aspect, $R^{2b}$, when present, is cyano.

In a further aspect, $R^{2c}$, when present, is selected from hydrogen, cyano, —F, and —Cl. In a still further aspect, $R^{2c}$, when present, is hydrogen. In a yet further aspect, $R^{2c}$, when present, is —F. In an even further aspect, $R^{2c}$, when present, is —Cl. In a still further aspect, $R^{2c}$, when present, is cyano.

In a further aspect, $R^{2d}$, when present, is selected from hydrogen, —F, and —Cl. In a still further aspect, $R^{2d}$, when present, is hydrogen. In a yet further aspect, $R^{2d}$, when present, is —F. In an even further aspect, $R^{2d}$, when present, is —Cl. In a still further aspect, $R^{2d}$, when present, is cyano.

g. $R^3$ Groups

In one aspect, $R^3$ is selected from hydrogen, C1-C3 alkyl, C1-C3 haloalkyl, C1-C3 polyhaloalkyl, cyclopropyl and $Ar^1$. In a further aspect, $R^3$ is hydrogen.

In a further aspect, $R^3$ is selected from C1-C3 alkyl, C1-C3 haloalkyl, C1-C3 polyhaloalkyl, cyclopropyl and $Ar^1$. In a still further aspect, $R^3$ is selected from —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, cyclopropyl and $Ar^1$. In an even further aspect, $R^3$ is selected from —CH$_3$, —CF$_3$, —CCl$_3$, cyclopropyl and $Ar^1$. In a still further aspect, $R^3$ is $Ar^1$. In yet a further aspect, $R^3$ is cyclopropyl.

In a further aspect, $R^3$ is selected from hydrogen, C1-C3 alkyl, C1-C3 haloalkyl, C1-C3 polyhaloalkyl, cyclopropyl and $Ar^1$. In a still further aspect, $R^3$ is selected from hydrogen, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, cyclopropyl and $Ar^1$. In an even further aspect, $R^3$ is selected from hydrogen, —CH$_3$, —CF$_3$, —CCl$_3$, cyclopropyl and $Ar^1$. In a still further aspect, $R^3$ is $Ar^1$. In yet a further aspect, $R^3$ is cyclopropyl.

h. $R^4$ Groups

In one aspect, $R^4$ is selected from $Ar^2$, —$L^2$—$Ar^2$, and $Cy^1$. In a further aspect, $R^4$ is selected from $Ar^2$ and —$L^2$—$Ar^2$. In a still further aspect, $R^4$ is selected from $Ar^2$ and $Cy^1$.

In various aspects, $R^4$ is selected from $Ar^2$, —O—$Ar^2$, and $Cy^1$. In a further aspect, $R^4$ is selected from $Ar^2$ and —O—$Ar^2$.

In various aspects, $R^4$ is selected from $Ar^2$, —NR$^8$—$Ar^2$, and $Cy^1$. In a further aspect, $R^4$ is selected from $Ar^2$ and —NR$^8$—$Ar^2$.

In a further aspect, $R^4$ is $Ar^2$. In a still further aspect, $R^4$ is —$L^2$—$Ar^2$. In yet a further aspect, $R^4$ is $Cy^1$.

i. $R^7$ Groups

In one aspect, each of $R^{7a}$ and $R^{7b}$ is independently selected from hydrogen, C1-C6 alkyl, C1-C6 haloalkyl, and C1-C6 polyhaloalkyl. In a further aspect, each of $R^{7a}$ and $R^{7b}$ is hydrogen.

In a further aspect, each of $R^{7a}$ and $R^{7b}$ is independently selected from C1-C6 alkyl, C1-C6 haloalkyl, and C1-C6 polyhaloalkyl. In a still further aspect, each of $R^{7a}$ and $R^{7b}$ is independently selected from C1-C3 alkyl, C1-C3 haloalkyl, and C1-C3 polyhaloalkyl. In a yet further aspect, each of $R^{7a}$ and $R^{7b}$ is independently selected from —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, and —CH$_2$CCl$_3$. In an even further aspect, each of $R^{7a}$ and $R^{7b}$ is independently selected from —CH$_3$, —CF$_3$, and —CCl$_3$.

In a further aspect, each of $R^{7a}$ and $R^{7b}$ is independently selected from hydrogen, C1-C3 alkyl, C1-C3 haloalkyl, and C1-C3 polyhaloalkyl. In a still further aspect, each of $R^{7a}$ and $R^{7b}$ is independently selected from hydrogen, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —C$_2$CF$_3$, —CH$_2$CH$_2$Cl, —CH$_2$CHCl$_2$, and —CH$_2$CCl$_3$. In an even further aspect, each of $R^{7a}$ and $R^{7b}$ is independently selected from hydrogen, —CH$_3$, —CF$_3$, and —CCl$_3$.

In a further aspect, $R^{7a}$ is hydrogen and $R^{7b}$ is selected from hydrogen, C1-C6 alkyl, C1-C6 haloalkyl, and C1-C6 polyhaloalkyl. In a still further aspect, $R^{7a}$ is hydrogen and $R^{7b}$ is selected from hydrogen, C1-C3 alkyl, C1-C3 haloalkyl, and C1-C3 polyhaloalkyl. In a yet further aspect, $R^{7a}$ is hydrogen and $R^{7b}$ is selected from hydrogen, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, and —CH$_2$CCl$_3$. In an even further aspect, $R^{7a}$ is hydrogen and $R^{7b}$ is selected from hydrogen, —CH$_3$, —CF$_3$, and —CCl$_3$.

j. $R^8$ Groups

In one aspect, each of $R^{8a}$ and $R^{8b}$ is independently selected from hydrogen, C1-C6 alkyl, C1-C6 haloalkyl, and C1-C6 polyhaloalkyl. In a further aspect, each of $R^{8a}$ and $R^{8b}$ is hydrogen.

In a further aspect, each of $R^{8a}$ and $R^{8b}$ is independently selected from C1-C6 alkyl, C1-C6 haloalkyl, and C1-C6 polyhaloalkyl. In a still further aspect, each of $R^{8a}$ and $R^{8b}$ is independently selected from C1-C3 alkyl, C1-C3 haloalkyl, and C1-C3 polyhaloalkyl. In a yet further aspect, each of $R^{8a}$ and $R^{8b}$ is independently selected from —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, and —CH$_2$CCl$_3$. In an even further aspect, each of $R^{8a}$ and $R^{8b}$ is independently selected from —CH$_3$, —CF$_3$, and —CCl$_3$.

In a further aspect, each of $R^{8a}$ and $R^{8b}$ is independently selected from hydrogen, C1-C3 alkyl, C1-C3 haloalkyl, and C1-C3 polyhaloalkyl. In a still further aspect, each of $R^{8a}$ and $R^{8b}$ is independently selected from hydrogen, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, and —CH$_2$CCl$_3$. In an even further aspect, each of $R^{8a}$ and $R^{8b}$ is independently selected from hydrogen, —CH$_3$, —CF$_3$, and —CCl$_3$.

In a further aspect, $R^{8a}$ is hydrogen and $R^{8b}$ selected from hydrogen, C1-C6 alkyl, C1-C6 haloalkyl, and C1-C6 polyhaloalkyl. In a still further aspect, $R^{8a}$ is hydrogen and $R^{8b}$ is selected from hydrogen, C1-C3 alkyl, C1-C3 haloalkyl, and C1-C3 polyhaloalkyl. In a yet further aspect, $R^{8a}$ is hydrogen and $R^{8b}$ is selected from hydrogen, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, and —CH$_2$CCl$_3$. In an even further aspect, R$^{8a}$ is hydrogen and R$^{8b}$ is selected from hydrogen, —CH$_3$, —CF$_3$, and —CCl$_3$.

k. R$^9$ Groups

In one aspect, R$^9$ is selected from hydrogen and C1-C6 alkyl. In a further aspect, R$^9$ is hydrogen. In a still further aspect, R$^9$ is methyl.

In various aspects, R$^9$ is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a further aspect, R$^9$ is selected from hydrogen, methyl, ethyl, propyl, isopropyl, tert-butyl, sec-butyl, isobutyl, and tert-butyl. In a yet further aspect, R$^9$ is selected from hydrogen, methyl, ethyl, propyl, and isopropyl. In a still further aspect, R$^9$ is selected from hydrogen, hydrogen, methyl, and ethyl. In an even further aspect, R$^9$ is selected from hydrogen, hydrogen and ethyl.

l. R°

In one aspect, each of R$^{20a}$ and R$^{20b}$ is independently selected from hydrogen, C1-C3 alkyl, C1-C3 haloalkyl; and C1-C3 polyhaloalkyl. In a further aspect, each of R$^{20a}$ and R$^{20b}$ is hydrogen.

In a further aspect, each of R$^{20a}$ and R$^{20b}$ is independently selected from C1-C3 alkyl, C1-C3 haloalkyl, and C1-C3 polyhaloalkyl. In a yet further aspect, each of R$^{20a}$ and R$^{20b}$ is independently selected from —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, and —CH$_2$CCl$_3$. In an even further aspect, each of R$^{20a}$ and R$^{20b}$ is independently selected from —CH$_3$, —CF$_3$, and —CCl$_3$.

In a further aspect, each of R$^{20a}$ and R$^{20b}$ is independently selected from hydrogen, C1-C3 alkyl, C1-C3 haloalkyl, and C1-C3 polyhaloalkyl. In a still further aspect, each of R$^{20a}$ and R$^{20b}$ is independently selected from hydrogen, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, and —CH$_2$CCl$_3$. In an even further aspect, each of R$^{20a}$ and R$^{20b}$ is independently selected from hydrogen, —CH$_3$, —CF$_3$, and —CCl$_3$.

In a further aspect, R$^{20a}$ is hydrogen and R$^{20b}$ is selected from hydrogen, C1-C6 alkyl, C1-C6 haloalkyl, and C1-C6 polyhaloalkyl. In a still further aspect, R$^{20a}$ is hydrogen and R$^{20b}$ is selected from hydrogen, C1-C3 alkyl, C1-C3 haloalkyl, and C1-C3 polyhaloalkyl. In a yet further aspect, R$^{20a}$ is hydrogen and R$^{20b}$ is selected from hydrogen, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, and —CH$_2$CCl$_3$. In an even further aspect, R$^{20a}$ is hydrogen and R$^{20b}$ is selected from hydrogen, —CH$_3$, —CF$_3$, and —CCl$_3$ m. R$^{30}$ In one aspect, R$^{30}$ is selected from C1-C3 alkyl, C1-C3 haloalkyl; and C1-C3 polyhaloalkyl.

In a further aspect, R$^{30}$ is selected from C1-C3 alkyl, C1-C3 haloalkyl and C1-C3 polyhaloalkyl. In a still further aspect, R$^{30}$ is selected from —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$ and —CH$_2$CCl$_3$. In an even further aspect, R$^{30}$ is selected from —CH$_3$, —CF$_3$ and —CCl$_3$.

n. AR$^1$ Groups

In one aspect, Ar$^1$ is selected from is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a further aspect, Ar$^1$ is selected from is selected from phenyl, indenyl, and naphthalenyl; and substituted with 0-3 substituents independently selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, Ar$^1$ is selected from phenyl, indenyl, and naphthalenyl; and Ar$^1$ is unsubstituted.

In a further aspect, Ar$^1$ is selected from is selected from phenyl, indenyl, and naphthalenyl; and substituted with 0-3 substituents independently selected from —F, —Cl, hydroxyl, cyano, —NH$_2$, methyl, ethyl, propyl, isopropyl, tert-butyl, sec-butyl, isobutyl, tert -butyl, neopentyl, isopentyl, sec-pentyl, tert-pentyl, 3,3-dimethylbutan-2-yl, 3,3-dimethylpentan-2-yl, 2,3-dimethylbutan-2-yl, 2,3-dimethylpentan-2-yl, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$).

In a further aspect, Ar$^1$ is phenyl; and substituted with 0-3 substituents independently selected from —F, —Cl, hydroxyl, cyano, —NH$_2$, methyl, ethyl, propyl, isopropyl, tert-butyl, sec-butyl, isobutyl, tert-butyl, neopentyl, isopentyl, sec-pentyl, tert -pentyl, 3,3-dimethylbutan-2-yl, 3,3-dimethylpentan-2-yl, 2,3-dimethylbutan-2-yl, 2,3-dimethylpentan-2-yl, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$).

In a further aspect, Ar$^1$ is indenyl; and substituted with 0-3 substituents independently selected from —F, —Cl, hydroxyl, cyano, —NH$_2$, methyl, ethyl, propyl, isopropyl, tert-butyl, sec-butyl, isobutyl, tert-butyl, neopentyl, isopentyl, sec-pentyl, tert -pentyl, 3,3-dimethylbutan-2-yl, 3,3-dimethylpentan-2-yl, 2,3-dimethylbutan-2-yl, 2,3-dimethylpentan-2-yl, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$).

In a further aspect, Ar$^1$ is naphthalenyl; and substituted with 0-3 substituents independently selected from —F, —Cl, hydroxyl, cyano, —NH$_2$, methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, 2,3-dimethylpentan-2-yl, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$).

In a further aspect, Ar$^1$ is selected from is selected from phenyl, indenyl, and naphthalenyl; and substituted with 0-3 substituents independently selected from —F, —Cl, hydroxyl, cyano, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Ar$^1$ is phenyl; and substituted with 0-3 substituents independently selected from —F, —Cl, hydroxyl, cyano, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Ar$^1$ is indenyl; and substituted with 0-3 substituents independently selected from —F, —Cl, hydroxyl, cyano, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Ar$^1$ is naphthalenyl; and substituted with 0-3 substituents independently selected from —F, —Cl, hydroxyl, cyano, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Ar$^1$ is selected from is selected from phenyl, indenyl, and naphthalenyl; and substituted with 0-3 substituents independently selected from —F, —Cl, hydroxyl, cyano, —NH$_2$, methyl, ethyl, propyl, isopropyl, —OCH$_3$, —OCH$_2$CH$_3$, —OCH(CH$_3$)$_2$, —CH$_2$Cl, —CH$_2$CH$_2$F, —CH$_2$CH$_2$Cl, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^1$ is selected from is selected from phenyl, indenyl, and naphthalenyl; and substituted with 0-3 substituents independently selected from —F, —Cl, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In a yet further aspect, Ar$^1$ is selected from is selected from phenyl, indenyl, and naphthalenyl; and substituted with 0-3 substituents independently selected from —F, —Cl, methyl, —OCH$_3$, —CF$_3$, —CCl$_3$, —NHCH$_3$, and —N(CH$_3$)$_2$.

In a further aspect, Ar$^1$ is phenyl; and substituted with 0-3 substituents independently selected from —F, —Cl, hydroxyl, cyano, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^1$ is phenyl; and substituted with 0-3 substituents independently selected from —F, —Cl, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In a yet further aspect, Ar$^1$ is phenyl; and substituted with 0-3 substituents independently selected from —F, —Cl, methyl, —OCH$_3$, —CF$_3$, —CCl$_3$, —NHCH$_3$, and —N(CH$_3$)$_2$.

In a further aspect, Ar$^1$ is indenyl; and substituted with 0-3 substituents independently selected from —F, —Cl, hydroxyl, cyano, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^1$ is indenyl; and substituted with 0-3 substituents independently selected from —F, —Cl, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In a yet further aspect, Ar$^1$ is indenyl; and substituted with 0-3 substituents independently selected from —F, —Cl, methyl, —OCH$_3$, —CF$_3$, —CCl$_3$, —NHCH$_3$, and —N(CH$_3$)$_2$.

In a further aspect, $Ar^1$ is naphthalenyl; and substituted with 0-3 substituents independently selected from —F, —Cl, hydroxyl, cyano, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, $Ar^1$ is naphthalenyl; and substituted with 0-3 substituents independently selected from —F, —Cl, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In a yet further aspect, $Ar^1$ is naphthalenyl; and substituted with 0-3 substituents independently selected from —F, —Cl, methyl, —OCH$_3$, —CF$_3$, —CCl$_3$, —NHCH$_3$, and —N(CH$_3$)$_2$.

In a further aspect, $Ar^1$ is selected from $Ar^1$ is selected from phenyl, indenyl, and naphthalenyl; and $Ar^1$ is substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a still further aspect, $Ar^1$ is selected from phenyl, indenyl, and naphthalenyl; and $Ar^1$ is substituted with 1-2 substituents selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, $Ar^1$ is selected from phenyl, indenyl, and naphthalenyl; and $Ar^1$ is substituted with 2-3 substituents selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, $Ar^1$ is selected from phenyl, indenyl, and naphthalenyl; and $Ar^1$ is monosubstituted with the substituent selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino.

In a further aspect, $Ar^1$ is selected from $Ar^1$ is selected from phenyl, indenyl, and naphthalenyl; and $Ar^1$ is substituted with 1-3 substituents independently selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, $Ar^1$ is selected from phenyl, indenyl, and naphthalenyl; and $Ar^1$ is substituted with 1-2 substituents selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In a yet further aspect, $Ar^1$ is selected from phenyl, indenyl, and naphthalenyl; and $Ar^1$ is substituted with 2-3 substituents selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In an even further aspect, $Ar^1$ is selected from phenyl, indenyl, and naphthalenyl; and $Ar^1$ is monosubstituted with the substituent selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino.

In a further aspect, $Ar^1$ is selected from phenyl and indenyl; and $Ar^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, $Ar^1$ is selected from phenyl and indenyl; and $Ar^1$ is substituted with 0-3 substituents independently selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, $Ar^1$ is selected from phenyl and indenyl; and $Ar^1$ is unsubstituted.

In a further aspect, $Ar^1$ is selected from phenyl and naphthalenyl; and $Ar^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, $Ar^1$ is selected from phenyl and naphthalenyl; and $Ar^1$ is substituted with 0-3 substituents independently selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, $Ar^1$ is selected from phenyl and naphthalenyl; and wherein $Ar^1$ is unsubstituted.

In a further aspect, $Ar^1$ is selected from indenyl and naphthalenyl; and $Ar^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, $Ar^1$ is selected from indenyl and naphthalenyl; and $Ar^1$ is substituted with 0-3 substituents independently selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, $Ar^1$ is selected from indenyl and naphthalenyl; and $Ar^1$ is unsubstituted.

In a further aspect, $Ar^1$ is selected from phenyl, naphthalen-1-yl, and naphthalen-2-yl; and $Ar^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, $Ar^1$ is selected from phenyl, naphthalen-1-yl, and naphthalen-2-yl; and $Ar^1$ is substituted with 0-3 substituents independently selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, $Ar^1$ is selected from phenyl, naphthalen-1-yl, and naphthalen-2-yl; and $Ar^1$ is unsubstituted.

In a further aspect, $Ar^1$ is selected from phenyl and 1H-inden-1-yl, 1H-inden2-yl, 1H-inden-3-yl, 1H-inden-4-yl, 1H-inden-5-yl, 1H-inden-6-yl, and 1H-inden-7-yl; and $Ar^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, $Ar^1$ is selected from phenyl and 1H-inden-1-yl, 1H-inden-2-yl, 1H-inden-3-yl, 1H-inden-4-yl, 1H-inden-5-yl, 1H-inden-6-yl, and 1H-inden-7-yl; and $Ar^1$ is substituted with 0-3 substituents independently selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, $Ar^1$ is selected from phenyl and 1H-indenl-1-yl, 1H-inden-2-yl, 1H-inden-3-yl, 1H-inden-4-yl, 1H-inden-5-yl, 1H-inden-6-yl, and 1H-inden-7-yl; and $Ar^1$ is unsubstituted.

In a further aspect, $Ar^1$ is selected from 1H-inden-1-yl, 1H-inden-2-yl, 1-inden-3-yl, 1H-inden-4-yl, 1-inden-5-yl, 1H-inden-6-yl, 1H-inden-7-yl, naphthalen-1-yl, and naphthalen-2-yl; and $Ar^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, $Ar^1$ is selected from 1H-inden-1-yl, 1H-inden-2-yl, 1H-inden-3-yl, 1H-inden-4-yl, 1H-inden-5-yl, 1H-inden-6-yl, 1H-inden-7-yl, naphthalen- 1-yl, and naphthalen-2-yl; and Ar¹ is substituted with 0-3 substituents independently selected from halogen, hydroxyl, cyano, —NH₂, C1-C3 alkyl, C1-C3 alkoxy, C1-C3 haloalkyl, C1-C3 polyhaloalkyl, C1-C3 alkylamino, and C1-3 dialkylamino. In a still further aspect, Ar¹ is selected from 1H-inden-1-yl, 1H-inden-2-yl, 1H-inden-3-yl, 1H-inden-4-yl, 1H-inden-5-yl, 1H-inden-6-yl, 1H-inden-7-yl, naphthalen-1-yl, and naphthalen-2-yl; and Ar¹ is unsubstituted.

In a further aspect, Ar¹ is phenyl; and Ar¹ is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In yet a further aspect, Ar¹ is phenyl; and Ar¹ is substituted with 0-3 substituents independently selected from halogen, hydroxyl, cyano, —NH₂, C1-C3 alkyl, C1-C3 alkoxy, C1-C3 haloalkyl, C1-C3 polyhaloalkyl, C1-C3 alkylamino, and C1-C3 dialkylamino. In a still further aspect, Ar¹ is phenyl; and wherein Ar¹ is unsubstituted.

In a further aspect, Ar¹ is indenyl; and Ar¹ is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In a yet further aspect, Ar¹ is indenyl; and Ar¹ is substituted with 0-3 substituents independently selected from halogen, hydroxyl, cyano, —NH₂, C1-C3 alkyl, C1-C3 alkoxy, C1-C3 haloalkyl, C1-C3 polyhaloalkyl, C1-C3 alkylamino, and C1-C3 dialkylamino. In a still further aspect, Ar¹ is indenyl; and Ar¹ is unsubstituted.

In a further aspect, Ar¹ is 1H-inden-1-yl; and Ar¹ is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In a yet further aspect, Ar¹ is 1H-inden-1-yl; and Ar¹ is substituted with 0-3 substituents independently selected from halogen, hydroxyl, cyano, —NH₂, C1-C3 alkyl, C1-C3 alkoxy, C1-C3 haloalkyl, C1-C3 polyhaloalkyl, C1-C3 alkylamino, and C1-C3 dialkylamino. In a still further aspect, Ar¹ is 1H-inden-1-yl; and Ar¹ is unsubstituted.

In a further aspect, Ar¹ is 1H-inden-3-yl; and Ar¹ is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In a yet further aspect, Ar¹ is 1H-inden-3-yl; and Ar¹ is substituted with 0-3 substituents independently selected from halogen, hydroxyl, cyano, —NH₂, C1-C3 alkyl, C1-C3 alkoxy, C1-C3 haloalkyl, C1-C3 polyhaloalkyl, C1-C3 alkylamino, and C1-C3 dialkylamino. In a still further aspect, Ar¹ is 1H-inden-3-yl; and Ar¹ is unsubstituted.

In a further aspect, Ar¹ is 1H-inden-3-yl; and Ar¹ is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In a yet further aspect, Ar¹ is 1H-inden-3-yl; and Ar¹ is substituted with 0-3 substituents independently selected from halogen, hydroxyl, cyano, —NH₂, C1-C3 alkyl, C1-C3 alkoxy, C1-C3 haloalkyl, C1-C3 polyhaloalkyl, C1-C3 alkylamino, and C1-C3 dialkylamino. In a still further aspect, Ar¹ is 1H-inden-3-yl; and Ar¹ is unsubstituted.

In a further aspect, Ar¹ is 1H-inden-4-yl; and Ar¹ is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In a yet further aspect, Ar¹ is 1H-inden-4-yl; and Ar¹ is substituted with 0-3 substituents independently selected from halogen, hydroxyl, cyano, —NH₂, C1-C3 alkyl, C1-C3 alkoxy, C1-C3 haloalkyl, C1-C3 polyhaloalkyl, C1-C3 alkylamino, and C1-C3 dialkylamino. In a still further aspect, Ar¹ is 1H-inden-4-yl; and Ar¹ is unsubstituted.

In a further aspect, Ar¹ is 1H-inden-5-yl; and Ar¹ is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In a yet further aspect, Ar¹ is 1H-inden-5-yl; and Ar¹ is substituted with 0-3 substituents independently selected from halogen, hydroxyl, cyano, —NH₂, C1-C3 alkyl, C1-C3 alkoxy, C1-C3 haloalkyl, C1-C3 polyhaloalkyl, C1-C3 alkylamino, and C1-C3 dialkylamino. In a still further aspect, Ar¹ is 1H-inden-5-yl; and Ar¹ is unsubstituted.

In a further aspect, Ar¹ is 1H-inden-6-yl; and Ar¹ is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In a yet further aspect, Ar¹ is 1H-inden-6-yl; and Ar¹ is substituted with 0-3 substituents independently selected from halogen, hydroxyl, cyano, —NH₂, C1-C3 alkyl, C1-C3 alkoxy, C1-C3 haloalkyl, C1-C3 polyhaloalkyl, C1-C3 alkylamino, and C1-C3 dialkylamino. In a still further aspect, Ar¹ is 1H-inden-6-yl; and Ar¹ is unsubstituted.

In a further aspect, Ar¹ is 1H-inden-7-yl; and Ar¹ is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In a yet further aspect, Ar¹ is 1H-inden-7-yl; and Ar¹ is substituted with 0-3 substituents independently selected from halogen, hydroxyl, cyano, —NH₂, C1-C3 alkyl, C1-C3 alkoxy, C1-C3 haloalkyl, C1-C3 polyhaloalkyl, C1-C3 alkylamino, and C1-C3 dialkylamino. In a still further aspect, Ar¹ is 1H-inden-7-yl; and Ar¹ is unsubstituted.

In a further aspect, Ar¹ is naphthalenyl; and Ar¹ is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In a yet further aspect, Ar¹ is naphthalenyl; and Ar¹ is substituted with 0-3 substituents independently selected from halogen, hydroxyl, cyano, —NH₂, C1-C6 alkyl, C1-C3 alkoxy, C1-C3 haloalkyl, C1-C3 polyhaloalkyl, C1-C3 alkylamino, and C1-C3 dialkylamino. In a still further aspect, Ar¹ is naphthalenyl; and Ar¹ is unsubstituted.

In a further aspect, Ar¹ is naphthalen-1-yl; and Ar¹ is substituted with 0-3 substituents independently selected from halogen, hydroxyl, cyano, —NH₂, C1-C6 alkyl, C1-C6 alkoxy, C1-6 haloalkyl, C1-6 polyhaloalkyl, C1-6 alkylamino, and C1-6 dialkylamino. In a yet further aspect, Ar¹ is naphthalen-1-yl; and Ar¹ is substituted with 0-3 substituents independently selected from halogen, hydroxyl, cyano, —NH₂, C1-C3 alkyl, C1-C3 alkoxy, C1-C3 haloalkyl, C1-C3 polyhaloalkyl, C1-C3 alkylamino, and C1-C3 dialkylamino. In a still further aspect, Ar¹ is napthalen-1-yl; and Ar¹ is unsubstituted.

In a further aspect, Ar¹ is naphthalen-2-yl; and Ar¹ is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In a yet further aspect, Ar¹ is naphthalen-2-yl; and Ar$^1$ is substituted with 0-3 substituents independently selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, Ar$^1$ is napthalen-2-yl; and Ar$^1$ is unsubstituted.

o. AR2 Groups

In one aspect, Ar$^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane -2,3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl and triazolyl; and wherein Ar$^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein Ar$^2$ is pyrazolyl substituted with 1-3 substituents independently selected from halogen, hydroxyl, cyano, 13 NH$_2$, C1-C6 alkyl, C1-C6 alkoxy, C1-C6 haloalkyl, C1-C6 polyhaloalkyl, C1-C6 alkylamino, and C1-C6 dialkylamino.

In various aspects, Ar$^2$ is selected from furanyl, imidazolyl, pyrrolyl, pyridinyl, pyrimidinyl, pyrazinyl, benzofuranyl, benzothiophenyl, benzodioxolyl, benzoimidazolyl, benzoisoxazolyl, benzooxazolyl, benzooxadiazolyl, benzothiazolyl, dihydrobenzofuranyl, dihydroisobenzofuranyl, furopyridinyl, indazolyl, oxoindolinyl, indolyl, isoindolinyl, isoquinolinyl, pyrrolopyridinyl, naphthyridinyl, quinoxalinyl, quinazolinyl, quinolinyl, quinoxalinyl, and tetrahydroquinolinyl; and Ar$^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, and C1-C6 alkylamino; or wherein Ar$^2$ is pyrazolyl substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino.

In a further aspect, Ar$^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2,3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl and triazolyl; and wherein Ar$^2$ is substituted with 0-3 substituents independently selected from halogen, hydroxyl, cyano, —NH$_2$, C1-C3 alkyl, C1-C3 alkoxy, C1-C3 haloalkyl, C1-C3 polyhaloalkyl, and C1-C3 alkylamino; or wherein Ar$^2$ is pyrazolyl substituted with 1-3 substituents independently selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino.

In a further aspect, Ar$^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2,3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl and triazolyl; and Ar$^2$ is unsubstituted.

In one aspect, Ar$^2$ is pyrazolyl substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, C1-C6 dialkylamino, C3-C8 cycloalkyl, and C3-C8 heterocycloalkyl. In a further aspect, Ar$^2$ is pyrazolyl substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, C1-C6 dialkylamino, C3-C8 cycloalkyl, and C3-C8 heterocycloalkyl.

In a further aspect, Ar$^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2,3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl and triazolyl; and Ar$^2$ is substituted with 0-3 substituents independently selected from —F, —Cl, hydroxyl, cyano, —NH$_2$, methyl, ethyl, propyl, isopropyl, tert-butyl, sec-butyl, isobutyl, tert-butyl, neopentyl, isopentyl, sec-pentyl, tent-pentyl, 3,3-dimethylbutan-2-yl, 3,3-dimethylpentan-2-yl, 2,3-dimethylbutan-2-yl, 2,3-dimethylpentan-2-yl, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —H$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —CH$_2$I$_2$CH$_2$Br, —(CH$_2$)$_2$CH$_2$I, CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —H$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$); or wherein Ar$^2$ is pyrazolyl substituted with 1-3 substituents independently selected from —F, —Cl, hydroxyl, cyano, —NH$_2$, methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, 2,3-dimethylpentan-2-yl, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$).

In a further aspect, Ar$^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2,3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl and triazolyl; and Ar$^2$ is substituted with 0-3 substituents independently selected from —F, —Cl, hydroxyl, cyano, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$; or wherein Ar$^2$ is pyrazolyl substituted with 1-3 substituents independently selected from —F, —Cl, hydroxyl, cyano, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Ar$^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2,3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl and triazolyl; and Ar$^2$ is substituted with 0-3 substituents independently selected from —F, —Cl, hydroxyl, cyano, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —Cl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$; or wherein Ar$^2$ is pyrazolyl substituted with 1-3 substituents independently selected from —F, —Cl, hydroxyl, cyano, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —H$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$.

In a further aspect, Ar$^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2,3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl and triazolyl; and Ar$^2$ is substituted with 0-3 substituents independently selected from —F, —Cl, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —Cl$_3$, —NHCH$_3$, and —N(CH$_3$)$_2$; or wherein Ar$^2$ is pyrazolyl substituted with 1-3 substituents independently selected from —F, —Cl, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$.

In a further aspect, Ar$^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2,3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl and triazolyl; and Ar$^2$ is substituted with 0-3 substituents independently selected from —F, —Cl, methyl, —OCH$_3$, —CF$_3$, —Cl$_3$, —NHCH$_3$, and —N(CH$_3$)$_2$; or wherein Ar$^2$ is pyrazolyl substituted with 1-3 substituents independently selected from —F, —Cl, methyl, —OCH$_3$, —CF$_3$, —CCl$_3$, —NHCH$_3$, and —N(CH$_3$)$_2$.

In one aspect, Ar$^2$ is selected from benzoimidazolyl, dihydrobenzodioxinyl, imidazopyridinyl, indazolyl, isoquinolinyl, oxoindolinyl, pyridinyl, and quinolinyl; and wherein Ar$^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein Ar$^2$ is pyrazolyl substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino.

In a further aspect, Ar$^2$ is selected from benzoimidazolyl, dihydrobenzodioxinyl, imidazopyridinyl, indazolyl, isoquinolinyl, oxoindolinyl, pyridinyl, and quinolinyl; and wherein Ar$^2$ is substituted with 0-3 substituents independently selected from halogen, hydroxyl, cyano, —NH$_2$, C1-C3 alkyl, C1-C3 alkoxy, C1-C3 haloalkyl, C1-C3 polyhaloalkyl, C1-C3 alkylamino; or wherein Ar$^2$ is pyrazolyl substituted with 1-3 substituents independently selected from halogen, hydroxyl, cyano, —NH$_2$, C1-C3 alkyl, C1-C3 alkoxy, C1-C3 haloalkyl, C1-C3 polyhaloalkyl, and C1-C3 alkylamino.

In a further aspect, Ar$^2$ is selected from benzoimidazolyl, dihydrobenzodioxinyl, imidazopyridinyl, indazolyl, isoquinolinyl, oxoindolinyl, pyridinyl, and quinolinyl; and Ar$^2$ is unsubstituted.

In a further aspect, Ar$^2$ is selected from benzoimidazolyl, dihydrobenzodioxinyl, imidazopyridinyl, indazolyl, isoquinolinyl, oxoindolinyl, pyridinyl, and quinolinyl; and Ar$^2$ is substituted with 0-3 substituents independently selected from —F, —Cl, hydroxyl, cyano, —NH$_2$, methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, 2,3-dimethylpentan-2-yl, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —CH$_2$F, —CH$_2$Cl, —CH$_2$Br, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$); or wherein Ar$^2$ is pyrazolyl substituted with 1-3 substituents independently selected from —F, —Cl, hydroxyl, cyano, —NH$_2$, methyl, ethyl, propyl, isopropyl, tert-butyl, sec-butyl, isobutyl, tert-butyl, neopentyl, isopentyl, sec-pentyl, tert -pentyl, 3,3-dimethylbutan-2-yl, 3,3-dimethylpentan-2-yl, 2,3-dimethylbutan-2-yl, 2,3-dimethylpentan-2-yl, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$).

In a further aspect, Ar$^2$ is selected from benzoimidazolyl, dihydrobenzodioxinyl, imidazopyridinyl, indazolyl, isoquinolinyl, oxoindolinyl, pyridinyl, and quinolinyl; and Ar$^2$ is substituted with 0-3 substituents independently selected from —F, —Cl, hydroxyl, cyano, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CHCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$; or wherein Ar$^2$ is pyrazolyl substituted with 1-3 substituents independently selected from —F, —Cl, hydroxyl, cyano, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —(CH2)2CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —(CH$_2$)$_2$CHF$_2$, —(CH$_2$)$_2$CF$_3$, —(CH$_2$)$_2$CHCl$_2$, —(CH$_2$)$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Ar$^2$ is selected from benzoimidazolyl, dihydrobenzodioxinyl, imidazopyridinyl, indazolyl, isoquinolinyl, oxoindolinyl, pyridinyl, and quinolinyl; and Ar$^2$ is substituted with 0-3 substituents independently selected from —F, —Cl, hydroxyl, cyano, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$; or wherein Ar$^2$ is pyrazolyl substituted with 1-3 substituents independently selected from —F, —Cl, hydroxyl, cyano, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$.

In a further aspect, Ar$^2$ is selected from benzoimidazolyl, dihydrobenzodioxinyl, imidazopyridinyl, indazolyl, isoquinolinyl, oxoindolinyl, pyridinyl, and quinolinyl; and Ar$^2$ is substituted with 0-3 substituents independently selected from —F, —Cl, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$ —NHCH$_3$, and —N(CH$_3$)$_2$; or wherein Ar$^2$ is pyrazolyl substituted with 1-3 substituents independently selected from —F, —Cl, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$.

In a further aspect, Ar$^2$ is selected from benzoimidazolyl, dihydrobenzodioxinyl, imidazopyridinyl, indazolyl, isoquinolinyl, oxoindolinyl, pyridinyl, and quinolinyl; and Ar$^2$ is substituted with 0-3 substituents independently selected from —F, —Cl, methyl, —OCH$_3$, —CF$_3$, —CCl$_3$, —NHCH$_3$, and —N(CH$_3$)$_2$; or wherein Ar$^2$ is pyrazolyl substituted with 1-3 substituents independently selected from —F, —Cl, methyl, —OCH$_3$, —CF$_3$, —CCl$_3$, —NHCH$_3$, and —N(CH$_3$)$_2$.

In one aspect, Ar$^2$ is selected from 2H-indazol-4-yl, 1H-indazol-5-yl, 2H -indazol-5-yl, 1H-indazol-6-yl, 2,3-dihydrobenzo[b][1,4]dioxin-6-yl, quinolin-3-yl, quinolin -6-yl, 2-oxoindolin-5-yl, 1H-benzo[d]imidazol-6-yl, isoquinolin-6-yl, imidazo[1,2a]pyridin-6-yl, imidazo[1,5a]pyridin-6-yl, and pyridin-3-yl; and wherein Ar$^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein Ar$^2$ is selected from 1H-pyrazol-3-yl, 1H-pyrazol-4-yl, and 1H-pyrazol-5-yl; and wherein Ar$^2$ is substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino.

In a further aspect, Ar$^2$ is selected from 2H-indazol-4-yl, 1H-indazol-5-yl, 2H -indazol-5-yl, 1H-indazol-6-yl, 2,3-dihydrobenzo[b][1,4]dioxin-6-yl, quinolin-3-yl, quinolin -6-yl, 2-oxoindolin-5-yl, 1H-benzo[d]imidazol-6-yl, isoquinolin-6-yl, imidazo[1,2a]pyridin-6-yl, imidazo[1,5a]pyridin-6-yl, and pyridin-3-yl; and wherein Ar$^2$ is substituted with 0-3 substituents independently selected from halogen, hydroxyl, cyano, —NH$_2$, C1-3 alkyl, C1-C3 alkoxy, C1-C3 haloalkyl, C1-C3 polyhaloalkyl, C1-C3 alkylamino; or wherein Ar$^2$ is selected from 1H-pyrazol-3-yl, 1H-pyrazol- 4-yl, and 1H-pyrazol-5-yl; and wherein $Ar^2$ is substituted with 1-3 substituents independently selected from halogen, hydroxyl, cyano, —NH$_2$, C1-C3 alkyl, C1-C3 alkoxy, C1-C3 haloalkyl, C1-C3 polyhaloalkyl, C1-C3 alkylamino.

In a further aspect, $Ar^2$ is selected from 2H-indazol-4-yl, 1H-indazol-5-yl, 2H-indazol-5-yl, 1H-indazol-6-yl, 2,3-dihydrobenzo[b][1,4]dioxin-6-yl, quinolin-3-yl, quinolin-6-yl, 2-oxoindolin-5-yl, 1H-benzo[d]imidazol-6-yl, isoquinolin-6-yl, imidazo[1,2a]pyridin-6-yl, imidazo[1,5a]pyridin-6-yl, and pyridin-3-yl; and $Ar^2$ is unsubstituted.

In a further aspect, $Ar^2$ is selected from 2H-indazol-4-yl, 1H-indazol-5-yl, 2H-indazol-5-yl, 1H-indazol-6-yl, 2,3-dihydrobenzo[b][1,4]dioxin-6-yl, quinolin-3-yl, quinolin-6-yl, 2-oxoindolin-5-yl, 1H-benzo[d]imidazol-6-yl, isoquinolin-6-yl, imidazo[1,2a]pyridin-6-yl, imidazo[1,5a]pyridin-6-yl, and pyridin-3-yl; and $Ar^2$ is substituted with 0-3 substituents independently selected from —F, —Cl, hydroxyl, cyano, —NH$_2$, methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, 2,3-dimethylpentan-2-yl, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$); or wherein $Ar^2$ is selected from 1H-pyrazol-3-yl, 1H-pyrazol-4-yl, and 1H-pyrazol-5-yl; and wherein $Ar^2$ is substituted with 1-3 substituents independently selected from —F, —Cl, hydroxyl, cyano, —NH$_2$, methyl, ethyl, propyl, isopropyl, tert-butyl, sec-butyl, isobutyl, tert-butyl, neopentyl, isopentyl, sec-pentyl, tert-pentyl, 3,3-dimethylbutan-2—yl, 3,3-dimethylpentan-2-yl, 2,3-dimethylbutan-2-yl, 2,3-dimethylpentan-2-yl, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$).

In a further aspect, $Ar^2$ is selected from 2H-indazol-4-yl, 1H-indazol-5-yl, 2H-indazol-5-yl, 1H-indazol-6-yl, 2,3-dihydrobenzo[b][1,4]dioxin-6-yl, quinolin-3-yl, quinolin-6-yl, 2-oxoindolin-5-yl, 1H-benzo[d]imidazol-6-yl, isoquinolin-6-yl, imidazo[1,2a]pyridin-6-yl, imidazo[1,5a]pyridin-6-yl, and pyridin-3-yl; and $Ar^2$ is substituted with 0-3 substituents independently selected from —F, —Cl, hydroxyl, cyano, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH2)2CHF$_2$, —(CH$_2$)$_2$CF$_3$, —(CH$_2$)$_2$CHCl$_2$, —(CH$_2$)$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$; or wherein $Ar^2$ is selected from 1H-pyrazol-3-yl, 1H-pyrazol-4-yl, and 1H-pyrazol-5-yl; and wherein $Ar^2$ is substituted with 1-3 substituents independently selected from —F, —Cl, hydroxyl, cyano, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, $Ar^2$ is selected from 2H-indazol-4-yl, 1H-indazol-5-yl, 2H-indazol-5-yl, 1H-indazol-6-yl, 2,3-dihydrobenzo[b][1,4]dioxin-6-yl, quinolin-3-yl, quinolin-6-yl, 2-oxoindolin-5-yl, 1H-benzo[d]imidazol-6-yl, isoquinolin-6-yl, imidazo[1,2a]pyridin-6-yl, imidazo[1,5a]pyridin-6-yl, and pyridin-3-yl; and $Ar^2$ is substituted with 0-3 substituents independently selected from —F, —Cl, hydroxyl, cyano, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$; or wherein $Ar^2$ is selected from 1H-pyrazol-3-yl, 1H-pyrazol-4-yl, and 1H-pyrazol-5-yl; and wherein $Ar^2$ is substituted with 1-3 substituents independently selected from —F, —Cl, hydroxyl, cyano, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$.

In a further aspect, $Ar^2$ is selected from 2H-indazol-4-yl, 1H-indazol-5-yl, 2H-indazol-5-yl, 1H-indazol-6-yl, 2,3-dihydrobenzo[b][1,4]dioxin-6-yl, quinolin-3-yl, quinolin-6-yl, 2-oxoindolin-5-yl, 1H-benzo[d]imidazol-6-yl, isoquinolin-6-yl, imidazo[1,2a]pyridin-6-yl, imidazo[1,5a]pyridin-6-yl, and pyridin-3-yl; and $Ar^2$ is substituted with 0-3 substituents independently selected from —F, —Cl, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$; or wherein $Ar^2$ is selected from 1H-pyrazol-3-yl, 1H-pyrazol-4-yl, and 1H-pyrazol-5-yl; and wherein $Ar^2$ is substituted with 1-3 substituents independently selected from —F, —Cl, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and N(CH$_3$)$_2$.

In a further aspect, $Ar^2$ is selected from 2H-indazol-4-yl, 1H-indazol-5-yl, 2H-indazol-5-yl, 1H-indazol-6-yl, 2,3-dihydrobenzo[b][1,4]dioxin-6-yl, quinolin-3-yl, quinolin-6-yl, 2-oxoindolin-5-yl, 1H-benzo[d]imidazol-6-yl, isoquinolin-6-yl, imidazo[1,2a]pyridin-6-yl, imidazo[1,5a]pyridin-6-yl, and pyridin-3-yl; and $Ar^2$ is substituted with 0-3 substituents independently selected from —F, —Cl, methyl, —OCH$_3$, —CF$_3$, —CCl$_3$, —NHCH$_3$, and —N(CH$_3$)$_2$; or wherein Ar$^2$ is selected from 1H-pyrazol-3-yl, 1H-pyrazol-4-yl, and 1H -pyrazol-5-yl; and wherein Ar$^2$ is substituted with 1-3 substituents independently selected from —F, —Cl, methyl, —OCH$_3$, —CF$_3$, —CCl$_3$, —NHCH$_3$, and —N(CH$_3$)$_2$.

In a further aspect, Ar$^2$ is selected from furan-2-yl, furan-3-yl, 1H-imidazol- 1-yl, 1H-imidazol- 2-yl, 1H-imidazol-4-yl, 1H-imidazol- 5-yl, 1H-pyrrol-2-yl, 1H-pyrrol-3-yl, pyridin-2-yl, pyridin-3-yl, pyridin-4-yl, pyrimidin-2-yl, pyrimidin-4-yl, pyrimidin-5-yl, pyrazin-2-yl, benzofuran-5-yl, benzofuran-6-yl, benzo[b]thiophen-6-yl, benzo[d][1,3]-dioxol-5-yl, 1H-benzo[d]imidazol-6-yl, benzo[d]isoxazol-6-yl, benzo[d]oxazol-6-yl, benzo[c][1,2,5]oxadiazol-5-yl, benzo[d]thiazol-6-yl, 1,3-dihydroisobenzofuran-5-yl, 2,3-dihydrobenzofuran-6-yl, furo[2,3-b]pyridin-6-yl, furo[3,2-b]pyridin-6-yl, 1H-indazol-6-yl, 2H-indazol-5-yl, 3H-indazol-6-yl, 1H-indol-1-yl, 1H-indol-2-yl, 1H-indol-3-yl, 1H-indol-4-yl, 1H-indol-5-yl, 1H-indol-6-yl, 1H-indol-7-yl, isoindolin-5-yl, 2-oxoindolin-6-yl, 3-oxoindolin-6-yl, 1H-pyrrolo[2,3-b]pyridin-6-yl, 1H-pyrrolo[3,2-c]pyridin-6-yl, isoquinolin-6-yl, isoquinolin-7-yl, 1,8-naphthyridin-2-yl, 1,8-naphthyridin-3-yl, 1,5-naphthyridin-2-yl, quinoxalin-2-yl, quinoxalin-5-yl, quinoxalin-6-yl, quinazolin-2-yl, quinazolin-4-yl, quinazolin-7-yl, quinazolin-8-yl, quinolin-2-yl, quinolin- 3-yl, quinolin-6-yl, quinolin-7-yl, quinoxalin-2-yl, quinoxalin-5-yl, quinoxalin-6-yl, and 1,2,3,4-tetrahydroquinolin-7-yl; and Ar$^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-6 alkylamino, and C1-C6 dialkylamino; or wherein Ar$^2$ is selected from 1H-pyrazol-3-yl, 1H -pyrazol-4-yl, and 1H-pyrazol-5-yl; and wherein Ar$^2$ is substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino.

In a further aspect, Ar$^2$ is selected from furan-2-yl, furan-3-yl, 1H-imidazol- 1-yl, 1H-imidazol-2-yl, 1H-imidazol-4-yl, 1H-imidazol-5-yl, 1H-pyrrol-2-yl, 1H-pyrrol-3-yl, pyridin- 2-yl, pyridin- 3-yl, pyridin- 4-yl, pyrimidin-2-yl, pyrimidin-4-yl, pyrimidin-5-yl, pyrazin-2-yl, benzofuran-5-yl, benzofuran-6-yl, benzo[b]thiophen-6-yl, benzo[d][1,3]dioxol-5-yl, 1H-benzo[d]imidazol-6-yl, benzo[d]isoxazol-6-yl, benzo[d]oxazol-6-yl, benzo[c][1,2,5]oxadiazol-5-yl, benzo[d]thiazol-6-yl, 1,3-dihydroisobenzofuran-5-yl, 2,3-dihydrobenzofuran-6-yl, furo[2,3-b]pyridin-6-yl, furo[3,2-b]pyridin-6-yl, 1H-indazol-6-yl, 2H-indazol-5-yl, 3H-indazol-6-yl, 1H-indol-1-yl, 1H-indol-2-yl, 1H-indol-3-yl, 1H-indol-4-yl, 1H-indol-5-yl, 1H-indol-6-yl, 1H-indol-7-yl, isoindolin-5-yl, 2-oxoindolin-6-yl, 3-oxoindolin-6-yl, 1H-pyrrolo[2,3-b]pyridin-6-yl, 1H-pyrrolo[3,2-c]pyridin-6-yl, isoquinolin-6-yl, isoquinolin-7-yl, 1,8-naphthyridin-2-yl, 1,8-naphthyridin-3-yl, 1,5-naphthyridin-2-yl, quinoxalin-2-yl, quinoxalin-5-yl, quinoxalin-6-yl, quinazolin-2-yl, quinazolin-4-yl, quinazolin-7-yl, quinazolin-8-yl, quinolin-2-yl, quinolin-3-yl, quinolin-6-yl, quinolin-7-yl, quinoxalin-2-yl, quinoxalin-5-yl, quinoxalin-6-yl, and 1,2,3,4-tetrahydroquinolin-7-yl; and Ar$^2$ is substituted with 0-3 substituents independently selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino; or wherein Ar$^2$ is selected from 1H-pyrazol-3-yl, 1H -pyrazol-4-yl, and 1H-pyrazol-5-yl; and wherein Ar$^2$ is substituted with 1-3 substituents independently selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino.

In a further aspect, Ar$^2$ is selected from furan-2-yl, furan-3-yl, 1H-imidazol-1-yl, 1H-imidazol-2-yl, 1H-imidazol-4-yl, 1H-imidazol-5-yl, 1H-pyrrol-2-yl, 1H-pyrrol-3-yl, pyridin-2-yl, pyridin-3-yl, pyridin-4-yl, pyrimidin-2-yl, pyrimidin-4-yl, pyrimidin-5-yl, pyrazin-2-yl, benzofuran-5-yl, benzofuran-6-yl, benzo[b]thiophen-6-yl, benzo[d][1,3]dioxol-5-yl, 1H-benzo[d]imidazol-6-yl, benzo[d]isoxazol-6-yl, benzo[d]oxazol-6-yl, benzo[c][1,2,5]oxadiazol-5-yl, benzo[d]thiazol-6-yl, 1,3-dihydroisobenzofuran-5-yl, 2,3-dihydrobenzofuran-6-yl, furo[2,3-b]pyridin-6-yl, furo[3,2-b]pyridin-6-yl, 1H-indazol-6-yl, 2H-indazol-5-yl, 3H-indazol-6-yl, 1H-indol-1-yl, 1H-indol-2-yl, 1H-indol-3-yl, 1H-indol-4-yl, 1H-indol-5-yl, 1H-indol-6-yl, 1H-indol-7-yl, isoindolin-5-yl, 2-oxoindolin-6-yl, 3-oxoindolin-6-yl, 1H-pyrrolo[2,3-b]pyridin-6-yl, 1H-pyrrolo[3,2-c]pyridin-6-yl, isoquinolin-6-yl, isoquinolin-7-yl, 1,8-naphthyridin-2-yl, 1,8-naphthyridin-3-yl, 1,5-naphthyridin-2-yl, quinoxaline-2-yl, quinoxaline-5-yl, quinoxaline-6-yl, quinazolin-2-yl, quinazolin-4-yl, quinazolin-7-yl, quinazolin-8-yl, quinolin-2-yl, quinolin-3-yl, quinolin-6-yl, quinolin-7-yl, quinoxaline-2-yl, quinoxaline-5-yl, quinoxaline-6-yl, and 1,2,3,4-tetrahydroquinolin-7-yl; and wherein Ar$^2$ is unsubstituted.

In a further aspect, Ar$^2$ is selected from furan-2-yl, furan-3-yl, 1H-imidazol-1-yl, 1H-imidazol-2-yl, 1H-imidazol-4-yl, 1H-imidazol-5-yl, 1H-pyrrol-2-yl, and 1H-pyrrol-3-yl; and Ar$^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-6 alkylamino, and C1-C6 dialkylamino; or wherein Ar$^2$ is pyrazolyl substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, Ar$^2$ is selected from furan-2-yl, furan-3-yl, 1H -imidazol-1-yl, 1H-imidazol-2-yl, 1H-imidazol-4-yl, 1H-imidazol-5-yl, 1H-pyrazol-3-yl, 1H -pyrazol-4-yl, 1H-pyrazol-5-yl, 1H-pyrrol-2-yl, and 1H-pyrrol-3-yl; and Ar$^2$ is substituted with 0-3 substituents independently selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino; or wherein Ar$^2$ is selected from 1H-pyrazol-3-yl, 1H-pyrazol-4-yl, and 1H -pyrazol-5-yl; and wherein Ar$^2$ is substituted with 1-3 substituents independently selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, Ar$^2$ is selected from furan-2-yl, furan-3-yl, 1H-imidazol-1-yl, 1H-imidazol-2-yl, 1H-imidazol-4-yl, 1H-imidazol-5-yl, 1H-pyrrol-2-yl, and 1H-pyrrol-3-yl; and Ar$^2$ is unsubstituted.

In a further aspect, Ar$^2$ is selected from pyridin-2-yl, pyridin-3-yl, pyridin-4-yl, pyrimidin-2-yl, pyrimidin-4-yl, pyrimidin-5-yl, and pyrazin-2-yl; and Ar$^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein Ar$^2$ is selected from 1H-pyrazol-3-yl, 1H-pyrazol-4-yl, and 1H -pyrazol-5-yl; and wherein Ar$^2$ is substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, Ar$^2$ is pyrimidin-5-yl, and pyrazin-2-yl; and Ar$^2$ is substituted with 0-3 substituents independently selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1C-3 dialkylamino; or wherein Ar$^2$ is selected from 1H-pyrazol-3-yl, 1H-pyrazol-4-yl, and 1H-pyrazol-5-yl; and wherein Ar$^1$ is substituted with 1-3 substituents independently selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, Ar$^2$ is selected from pyridin-2-yl, pyridin-3-yl, pyridin-4-yl, pyrimidin-2-yl, pyrimidin-4-yl, pyrimidin-5-yl, and pyrazin-2-yl; and Ar$^2$ is unsubstituted.

In a further aspect, Ar$^2$ is selected from benzofuran-5-yl, benzofuran-6-yl, benzo[b]thiophen-6-yl, benzo[d][1,3]dioxol-5-yl, 1H-benzo[d]imidazol-6-yl, benzo[d]isoxazol-6-yl, benzo[d]oxazol-6-yl, benzo[c][1,2,5]oxadiazol-5-yl, benzo[d]thiazol-6-yl, 1,3-dihydroisobenzofuran-5-yl, 2,3-dihydrobenzofuran-6-yl, furo[2,3-b]pyridin-6-yl, furo[3,2-b]pyridin-6-yl, 1H-indazol-6-yl, 2H-indazol-5-yl, 3H-indazol-6-yl, 1H-indol-1-yl, 1H-indol-2-yl, 1H-indol-3-yl, 1H-indol-4-yl, 1H-indol-5-yl, 1H-indol-6-yl, 1H-indol-7-yl, isoindolin-5-yl, 2-oxoindolin—6-yl, 3-oxoindolin-6-yl, 1H-pyrrolo[2,3-b]pyridin- 6-yl, and 1H -pyrrolo[3,2-c]pyridin-6-yl; and Ar$^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein Ar$^2$ is selected from 1H-pyrazol-3-yl, 1H-pyrazol-4-yl, and 1H-pyrazol-5-yl; and wherein Ar$^2$ is substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-6 dialkylamino. In a yet further aspect, Ar$^2$ is selected from benzofuran-5-yl, benzofuran-6-yl, benzo[b]thiophen-6-yl, benzo[d][1,3]dioxol-5-yl, 1H-benzo[d]imidazol- 6-yl, benzo[d]isoxazol-6-yl, benzo[d]oxazol-6-yl, benzo[c][1,2,5]oxadiazol-5-yl, benzo[d]thiazol-6-yl, 1,3-dihydroisobenzofuran-5-yl, 2,3-dihydrobenzofuran-6-yl, furo[2,3-b]pyridin-6-yl, furo[3,2-b]-pyridin-6-yl, 1H-indazol-6-yl, 2H-indazol-5-yl, 3H-indazol-6-yl, 1H-indol-1-yl, 1H-indol-2-yl, 1H-indol-3-yl, 1H-indol-4-yl, 1H-indol-5-yl, 1H-indol-6-yl, 1H-indol-7-yl, isoindolin-5-yl, 2-oxoindolin-6-yl, 3-oxoindolin-6-yl, 1H-pyrrolo[2,3-b]pyridin-6-yl, and 1H -pyrrolo[3,2-c]pyridin-6-yl; and Ar$^2$ is substituted with 0-3 substituents independently selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino; or wherein Ar$^2$ is selected from 1H-pyrazol-3-yl, 1H-pyrazol-4-yl, and 1H-pyrazol-5-yl; and wherein Ar$^2$ is substituted with 1-3 substituents independently selected from halogen, hydroxyl, cyano, —NH$_2$, C1-C3 alkyl, C1-C3 alkoxy, C1-C3 haloalkyl, C1-C3 polyhalohaloalkyl, C1-C3 alkylamino, and C1-C3 dialkylamino. In a still further aspect, Ar$^2$ is selected from benzofuran-5-yl, benzofuran-6-yl, benzo[b]thiophen-6-yl, benzo[d][1,3]dioxol-5-yl, 1H-benzo[d]imidazol-6-yl, benzo[d]isoxazol-6-yl, benzo[d]oxazol-6-yl, benzo[c][1,2,5]oxadiazol-5-yl, benzo[d]thiazol -6-yl, 1,3-dihydroisobenzofuran-5-yl, 2,3-dihydrobenzofuran-6-yl, furo[2,3-b]pyridin-6-yl, furo[3,2-b]pyridin-6-yl, 1H-indazol-6-yl, 2H-indazol-5-yl, 3H-indazol-6-yl, 1H-indol-1-yl, 1H-indol-2-yl, 1H-indol-3-yl, 1H-indol-4-yl, 1H-indol-5-yl, 1H-indol-6-yl, 1H-indol-7-yl, isoindolin-5-yl, 2-oxoindolin-6-yl, 3-oxoindolin-6-yl, 1H-pyrrolo[2,3-b]pyridin-6-yl, and 1H -pyrrolo[3,2-c]pyridin-6-yl; and Ar$^2$ is unsubstituted.

In a further aspect, Ar$^2$ is selected from isoquinolin-6-yl, isoquinolin-7-yl, 1,8-naphthyridin-2-yl, 1,8-naphthyridin-3-yl, 1,5-naphthyridin-2-yl, quinoxaline-2-yl, quinoxaline-5-yl, quinoxaline-6-yl, quinazolin-2-yl, quinazolin-4-yl, quinazolin-7-yl, quinazolin-8-yl, quinolin-2-yl, quinolin-3-yl, quinolin-6-yl, quinolin-7-yl, quinoxaline-2-yl, quinoxaline-5-yl, quinoxaline-6-yl, and 1,2,3,4-tetrahydroquinolin-7-yl; and Ar$^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein Ar$^2$ is selected from 1H-pyrazol-3-yl, 1H-pyrazol-4-yl, and 1H -pyrazol-5-yl; and wherein Ar$^2$ is substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, Ar$^2$ is selected from isoquinolin-6-yl, isoquinolin-7-yl, 1,8-naphthyridin-2-yl, 1,8-naphthyridin-3-yl, 1,5—naphthyridin—2-yl, quinoxaline-2-yl, quinoxaline-5-yl, quinoxaline-6-yl, quinazolin-2-yl, quinazolin-4-yl, quinazolin-7-yl, quinazolin-8-yl, quinolin-2-yl, quinolin-3-yl, quinolin-6-yl, quinolin-7-yl, quinoxaline-2-yl, quinoxaline-5-yl, quinoxaline-6-yl, and 1,2,3,4-tetrahydroquinolin-7-yl; and Ar$^2$ is substituted with 0-3 substituents independently selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino; or wherein Ar$^2$ is selected from 1H-pyrazol-3-yl, 1H-pyrazol-4-yl, and 1H-pyrazol-5-yl; and wherein Ar$^2$ is substituted with 1-3 substituents independently selected from halogen, hydroxyl, cyano, —NH$_2$, C1-C3 alkyl, C1-C3 alkoxy, C1-C3 haloalkyl, C1-C3 polyhalohaloalkyl, C1-C3 alkylamino, and C1-C3 dialkylamino. In a still further aspect, Ar$^2$ is selected from isoquinolin- 6-yl, isoquinolin- 7-yl, 1,8-naphthyridin-2-yl, 1,8-naphthyridin-3-yl, 1,5-naphthyridin-2-yl, quinoxaline-2-yl, quinoxaline-5-yl, quinoxaline-6-yl, quinazolin-2-yl, quinazolin-4-yl, quinazolin-7-yl, quinazolin-8-yl, quinolin-2-yl, quinolin-3-yl, quinolin-6-yl, quinolin-7-yl, quinoxaline-2-yl, quinoxaline-5-yl, quinoxaline-6-yl, and 1,2,3,4-tetrahydroquinolin-7-yl; and Ar$^2$ is unsubstituted.

In a further aspect, Ar$^2$ is selected from 1H-imidazol-1-yl, pyridin-4-yl, 2H -indazol-5-yl, 1H-indazol-6-yl, isoquinolin-6-yl, and 1H-indol-6-yl; and Ar$^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein Ar$^2$ is selected from 1H-pyrazol-3-yl, 1H-pyrazol-4-yl, and 1H -pyrazol-5-yl; and wherein Ar$^2$ is substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a still further aspect, Ar$^2$ is selected from 1H-imidazol-1-yl, pyridin-4-yl, 2H-indazol-5-yl, 1H-indazol-6-yl, isoquinolin -6-yl, and 1H-indol-6-yl; and Ar$^2$ is substituted with 0-3 substituents independently selected from halogen, hydroxyl, cyano, —NH$_2$, C1-C6 alkyl, C1-C3 alkoxy, C1-C3 haloalkyl, C1-C3 polyhaloalkyl, C1-C3 alkylamino, and C1-C3 dialkylamino; or wherein Ar$^2$ is selected from 1H-pyrazol-3-yl, 1H-pyrazol-4-yl, and 1H-pyrazol-5-yl; and wherein Ar$^2$ is substituted with 1-3 substituents independently selected from halogen, hydroxyl, cyano, —NH$_2$, C1-C6 alkyl, C1-C3 alkoxy, C1-C3 haloalkyl, C1-C3 polyhalohaloalkyl, C1-C3 alkylamino, and C1-C3 dialkylamino. In a still further aspect, Ar$^2$ is selected from 1H-imidazol-1-yl, pyridin-4-yl, 2H-indazol—5-yl, 1H-indazol-6-yl, isoquinolin- 6-yl, and 1H-indol-6-yl; and Ar$^2$ is unsubstituted.

In a further aspect, Ar² is selected from 2H-indazol-4-yl, 2-methyl-2H-indazol-4-yl, 1H-indazol-5-yl, 3-methyl-1H-indazol-5-yl, 5-methyl-1H-indazol-5-yl, 2H-indazol-5-yl, 2-methyl-2H-indazol-5-yl, 1H-indazol-6-yl, 3-methyl-1H-indazol-6-yl, 2,3-dihydrobenzo[b][1,4]dioxin-6-yl, quinolin-3-yl, quinolin-6-yl, 2-oxoindolin-5-yl, 1H-benzo[d]imidazol-6-yl, 1-methyl-1H-benzo[d]imidazol-6-yl, isoquinolin-6-yl, imidazo[1,2a]pyridin-6-yl, imidazo[1,5a]pyridin-6-yl, and pyridin-3-yl.

p. CY¹ Groups

In one aspect, Cy¹ is a C2-C5 heterocycloalkyl or C2-C5 heterocycloalkenyl, and wherein Cy¹ is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group.

In a further aspect, Cy¹ is a C2-C5 heterocycloalkyl substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group.

In various aspects, Cy¹ is a C2-C5 heterocycloalkyl or C2-C5 heterocycloalkenyl, and wherein Cy¹ is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are covalently bonded, and together with the intermediate atoms, comprise an optionally substituted 3- to 6-membered fused ring group. In a further aspect, Cy¹ is tetrahydropyrazolopyridinyl. In a still further aspect, Cy¹ is dihydropyrazolopyridinyl. In a still further aspect, Cy¹ is 2-methyl—6,7-dihydro-2H-pyrazolo[4,3c]pyridin-5(4H)-yl.

In a further aspect, Cy¹ is a C2-C5 heterocycloalkyl substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are covalently bonded, and together with the intermediate atoms, comprise an optionally substituted 3- to 6-membered fused ring group. In a further aspect, Cy¹ is tetrahydropyrazolopyridinyl. In a still further aspect, Cy¹ is dihydropyrazolopyridinyl. In a still further aspect, Cy¹ is 2-methyl-6,7-dihydro-2H -pyrazolo[4, 3c]pyridin-5(4H)-yl.

In various aspects, Cy¹ is a C2-C5 heterocycloalkyl or C2-C5 heterocycloalkenyl, and wherein Cy¹ is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In a still further aspect, Cy¹ is a C2-C5 heterocycloalkyl or C2-C5 heterocycloalkenyl, and wherein Cy¹ is substituted with 0-3 substituents independently selected from halogen, hydroxyl, cyano, —NH₂, C1-C3 alkyl, C1-C3 alkoxy, C1-C3 haloalkyl, C1-C3 polyhalohaloalkyl, and C1-C3 alkylamino.

In a further aspect, Cy¹ is a C2-C5 heterocycloalkyl or C2-C5 heterocycloalkenyl, and wherein Cy¹ is substituted with 0-3 substituents independently selected from —F, —Cl, hydroxyl, cyano, —NH₂, methyl, ethyl, propyl, isopropyl, tert-butyl, sec-butyl, isobutyl, tert -butyl, neopentyl, isopentyl, sec-pentyl, tert-pentyl, 3,3-dimethylbutan-2-yl, 3,3-dimethylpentan-2-yl, 2,3-dimethylbutan-2-yl, 2,3-dimethylpentan-2-yl, —OCH₃, —OCH₂CH₃, —O(CH₂)₂CH₃, —OCH(CH₃)₂, —OCH(CH₂CH₃)₂(CH₃), —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH2)2CH₂Br, —(CH₂)₂CH₂I, —CHF₂, —CF₃, —CHCl₂, —CCl₃, —CHBr₂, —CBr₃, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —NHCH₃, —NHCH₂CH₃, —NH(CH₂)₂CH₃, NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), and —N(CH₂CH₃)(CH(CH₃)₂).

In a further aspect, Cy¹ is a C2-C5 heterocycloalkyl or C2-C5 heterocycloalkenyl, and wherein Cy¹ is substituted with 0-3 substituents independently selected from —F, —Cl, hydroxyl, cyano, —NH₂, methyl, ethyl, propyl, isopropyl, tert-butyl, sec-butyl, isobutyl, tert -butyl, —OCH₃, —OCH₂CH₃, —O(CH₂)₂CH₃, —OCH(CH₃)₂, —CH₂F, —CH₂Cl, —CH₂CH₂F, —CH₂CH₂Cl, —(CH₂)₂CH₂F, —(CH₂)₂CH₂Cl, —CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —NHCH₃, —NHCH₂CH₃, —NH(CH₂)₂CH₃, —NHCH(CH₃)₂, —N(CH₃)₂, —N(CH₃)CH₂CH₃, —N(CH₃)(CH₂)₂CH₃, —N(CH₃)CH(CH₃)₂, and —N(CH₂CH₃)₂.

In a further aspect, Cy¹ is a C2-C5 heterocycloalkyl or C2-C5 heterocycloalkenyl, and wherein Cy¹ is substituted with 0-3 substituents independently selected from —F, —Cl, hydroxyl, cyano, —NH₂, methyl, ethyl, propyl, isopropyl, —OCH₃, —OCH₂CH₃, —OCH(CH₃)₂, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, —CH₂CCl₃, —NHCH₃, —NHCH₂CH₃, —N(CH₃)₂, —N(CH₃)CH₂CH₃, and —N(CH₃)CH(CH₃)₂.

In a further aspect, Cy¹ is a C2-C5 heterocycloalkyl or C2-C5 heterocycloalkenyl, and wherein Cy¹ is substituted with 0-3 substituents independently selected from —F, —Cl, hydroxyl, —NH₂, methyl, ethyl, —OCH₃, —OCH₂CH₃, —CH₂F, —CH₂Cl, —CHF₂, —CF₃, —CH₂Cl, —CHCl₂, —CCl₃, —NHCH₃, and N(CH₃)₂.

In a further aspect, Cy¹ is a C2-C5 heterocycloalkyl or C2-C5 heterocycloalkenyl, and wherein Cy¹ is substituted with 0-3 substituents independently selected from —F, —Cl, methyl, —OCH₃, —CF₃, —CCl₃, —NHCH₃, and —N(CH₃)₂.

In various aspects, Cy¹ is a C2-C5 heterocycloalkyl substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In a still further aspect, Cy¹ is a C2-C5 heterocycloalkyl substituted with 0-3 substituents independently selected from halogen, hydroxyl, cyano, —NH₂, C1-C3 alkyl, C1-C3 alkoxy, C1-C3 haloalkyl, C1-C3 polyhaloalkyl, and C1-C3 alkylamino.

In a further aspect, Cy¹ is a C2-C5 heterocycloalkyl substituted with 0-3 substituents independently selected from —F, —Cl, hydroxyl, cyano, —NH₂, methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, 2,3-dimethylpentan-2-yl, —OCH₃, —OCH₂CH₃, —O(CH₂)₂CH₃, —OCH(CH₃)₂, —OCH(CH₂CH₃)₂(CH₃), —CH₂F, —CH₂Cl, —CH₂Br, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH2)2CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), and —N(CH₂CH₃)(CH(CH₃)₂).

In a further aspect, Cy¹ is a C2-C5 heterocycloalkyl substituted with 0-3 substituents independently selected from —F, —Cl, hydroxyl, cyano, —NH₂, methyl, ethyl, propyl, isopropyl, tert-butyl, sec-butyl, isobutyl, tert-butyl, —OCH₃, —OCH₂CH₃, —O(CH₂)₂CH₃, —OCH(CH₃)₂, —CH₂F, —CH₂Cl, —CH₂CH₂F, —CH₂CH₂Cl, —(CH₂)₂CH₂F, —(CH₂)₂CH₂Cl, —CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —NHCH₃, —NHCH₂CH₃, —NH(CH₂)₂CH₃, —NHCH(CH₃)₂, —N(CH₃)₂, —N(CH₃)CH₂CH₃, —N(CH₃)(CH₂)₂CH₃, —N(CH₃)CH(CH₃)₂, and —N(CH₂CH₃)₂.

In a further aspect, Cy¹ is a C2-C5 heterocycloalkyl substituted with 0-3 substituents independently selected from —F, —Cl, hydroxyl, cyano, —NH₂, methyl, ethyl, propyl, isopropyl, —OCH₃, —OCH₂CH₃, —OCH(CH₃)₂, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, —CH₂CCl₃, —NHCH₃, —NHCH₂CH₃, —N(CH₃)₂, —N(CH₃)CH₂CH₃, and —N(CH₃)CH(CH₃)₂.

In a further aspect, Cy¹ is a C2-C5 heterocycloalkyl substituted with 0-3 substituents independently selected from —F, —Cl, hydroxyl, —NH₂, methyl, ethyl, —OCH₃, —OCH₂CH₃, —CH₂F, —CH₂Cl, —CHF₂, —CF₃, —CH₂Cl, —CHCl₂, —CCl₃, —NHCH₃, and —N(CH₃)₂.

In a further aspect, Cy¹ is a C2-C5 heterocycloalkyl substituted with 0-3 substituents independently selected from —F, —Cl, methyl, —OCH₃, —CF₃, —CCl₃, —NHCH₃, and —N(CH₃)₂.

In one aspect Cy¹ is selected from pyrrolidinyl and piperidinyl, and wherein Cy¹ is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In a still further aspect, Cy¹ is selected from pyrrolidinyl and piperidinyl, and wherein Cy¹ is substituted with 0-3 substituents independently selected from halogen, hydroxyl, cyano, —NH₂, C1-C3 alkyl, C1-C3 alkoxy, C1-C3 haloalkyl, C1-C3 polyhaloalkyl, and C1-C3 alkylamino.

In a further aspect, Cy¹ is selected from pyrrolidinyl and piperidinyl, and wherein Cy¹ is substituted with 0-3 substituents independently selected from —F, —Cl, hydroxyl, cyano, —NH₂, methyl, ethyl, propyl, isopropyl, tert-butyl, sec-butyl, isobutyl, tert-butyl, neopentyl, isopentyl, sec-pentyl, tent-pentyl, 3,3-dimethylbutan-2-yl, 3,3-dimethylpentan-2-yl, 2,3-dimethylbutan-2-yl, 2,3-dimethylpentan-2-yl, —OCH₃, —OCH₂CH₃, —O(CH₂)₂CH₃, —OCH(CH₃)₂, —OCH(CH₂CH₃)₂(CH₃), —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), and —N(CH₂CH₃)(CH(CH₃)₂).

In a further aspect, Cy¹ is selected from pyrrolidinyl and piperidinyl, and wherein Cy¹ is substituted with 0-3 substituents independently selected from —F, —Cl, hydroxyl, cyano, —NH₂, methyl, ethyl, propyl, isopropyl, tert-butyl, sec-butyl, isobutyl, tert-butyl, —OCH₃, —OCH₂CH₃, —O(CH₂)₂CH₃, —OCH(CH₃)₂, —CH₂F, —CH₂Cl, —CH₂CH₂F, —CH₂CH₂Cl, —(CH₂)₂CH₂F, —(CH₂)₂CH₂Cl, —CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —NHCH₃, —NHCH₂CH₃, —NH(CH₂)₂CH₃, —NHCH(CH₃)₂, —N(CH₃)₂, —N(CH₃)CH₂CH₃, —N(CH₃)(CH₂)₂CH₃, —N(CH₃)CH(CH₃)₂, and —N(CH₂CH₃)₂.

In a further aspect Cy¹ is selected from pyrrolidinyl and piperidinyl, and wherein Cy¹ is substituted with 0-3 substituents independently selected from —F, —Cl, hydroxyl, cyano, —NH₂, methyl, ethyl, propyl, isopropyl, —OCH₃, —OCH₂CH₃, —OCH(CH₃)₂, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, —CH₂CCl₃, —NHCH₃, —NHCH₂CH₃, —N(CH₃)₂, —N(CH₃)CH₂CH₃, and —N(CH₃)CH(CH₃)₂.

In a further aspect, Cy¹ is selected from pyrrolidinyl and piperidinyl, and wherein Cy¹ is substituted with 0-3 substituents independently selected from —F, —Cl, hydroxyl, —NH₂, methyl, ethyl, —OCH₃, —OCH₂CH₃, —CH₂F, —CH₂Cl, —CHF₂, —CF₃, —CH₂Cl, —CHCl₂, —CCl₃, —NHCH₃, and —N(CH₃)₂.

In a further aspect, Cy¹ is selected from pyrrolidinyl and piperidinyl, and wherein Cy¹ is substituted with 0-3 substituents independently selected from —F, —Cl, methyl, —OCH₃, —CF₃, —CCl₃, —NHCH₃, and —N(CH₃)₂.

a. Leaving Groups

In one aspect, leaving groups can be selected from halogens. In a further aspect, a halogen is fluoro, chloro, bromo or iodo. In a still further aspect, halogen is fluoro, chloro, or bromo. In a yet further aspect, halogen is fluoro or chloro. In a further aspect, halogen is fluoro. In an even further aspect, halogen is chloro or bromo. In an even further aspect, halogen is chloro. In a yet further aspect, halogen is iodo. In a still further aspect, halogen is bromo.

2. Compound Examples

In one aspect, a compound is selected from:

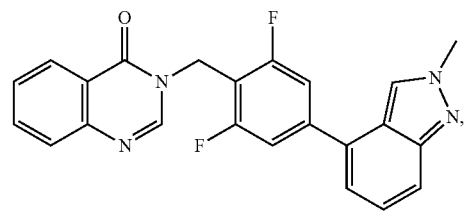

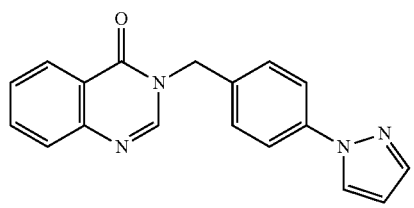
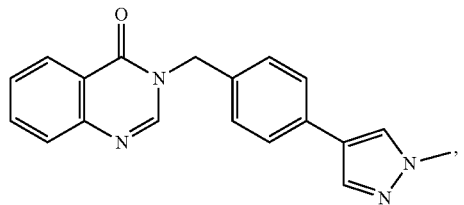
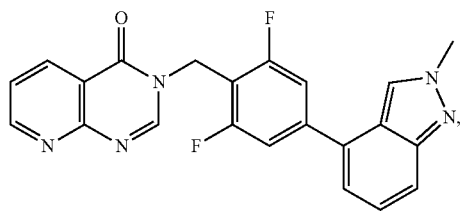
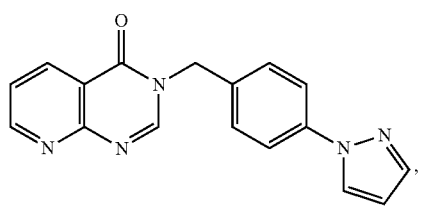
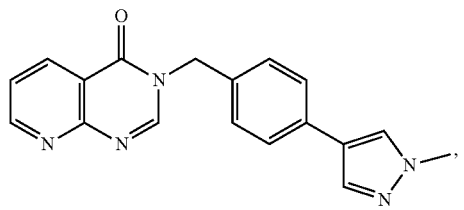
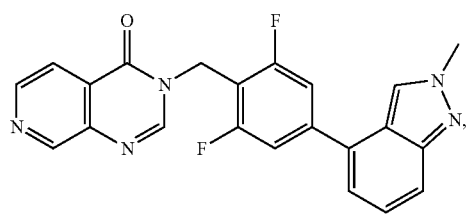
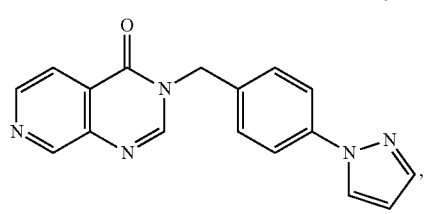
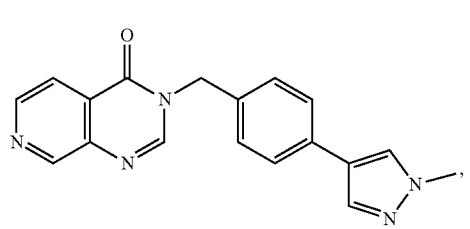
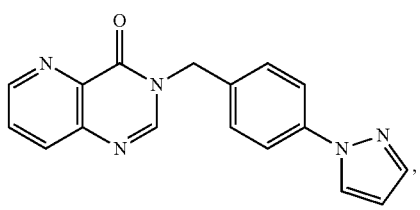
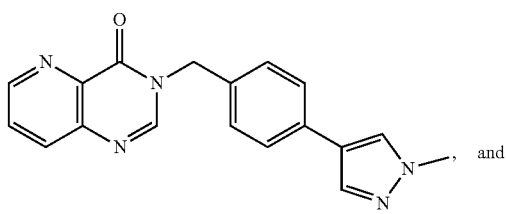, and
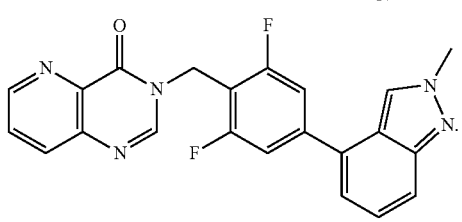
In a further aspect, a compound is selected from:
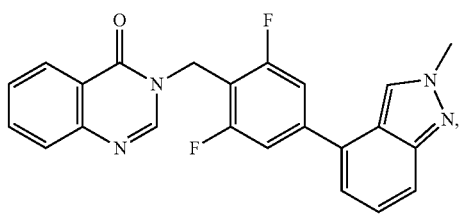
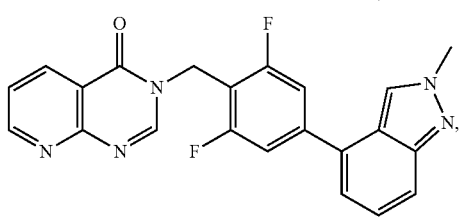
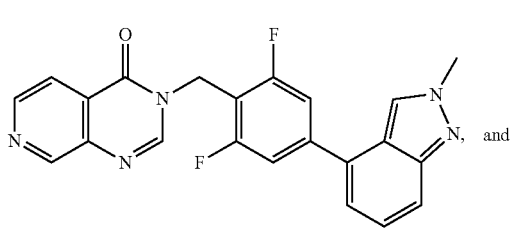, and
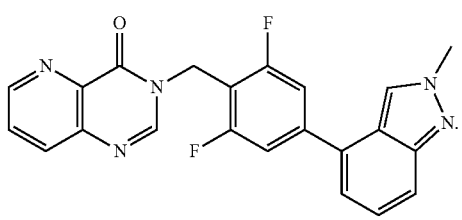

In a still further aspect, a compound is selected from:
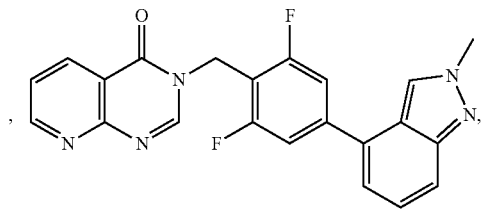
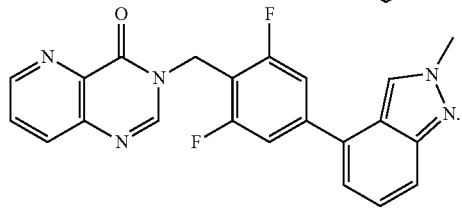, and
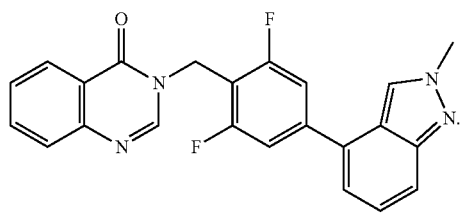 [SMILES: Cn1cc2c(-c3cc(F)c(Cn4cnc5ccccc5c4=O)c(F)c3)cccc2n1]
In yet a further aspect, a compound is:
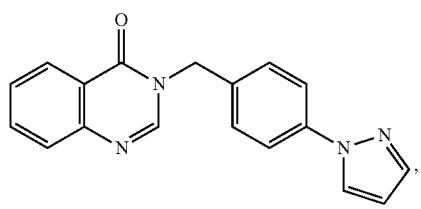
In a further aspect, a compound is selected from:
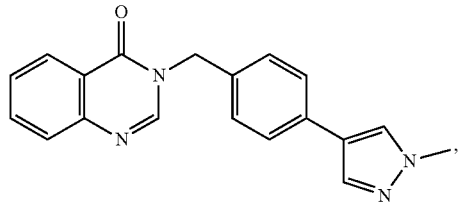,
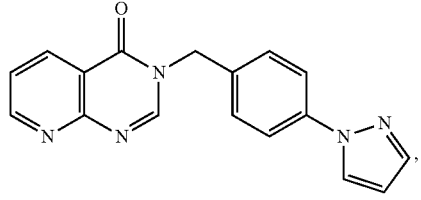,
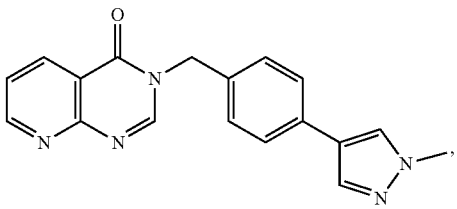,
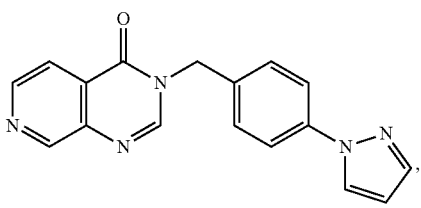,
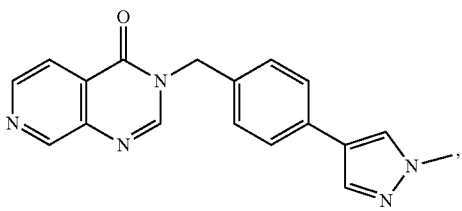,
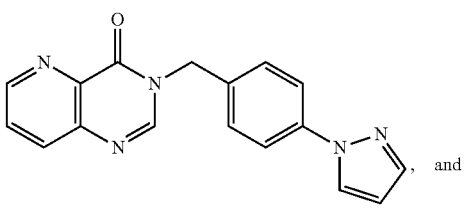,
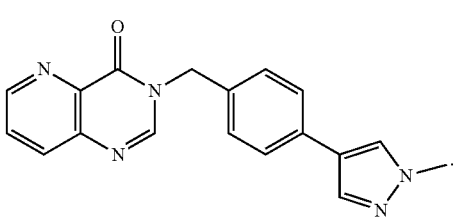, and
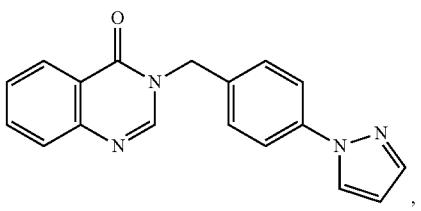.
In a still further aspect, a compound is selected from:
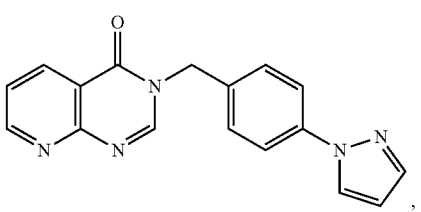, -continued
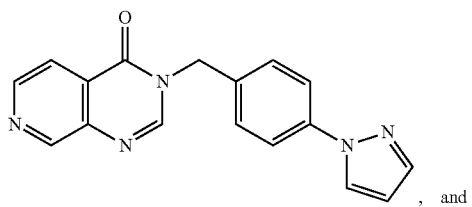, and
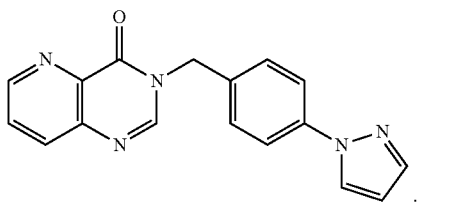.
In yet a further aspect, a compound is selected from:
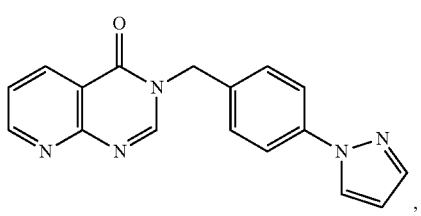,
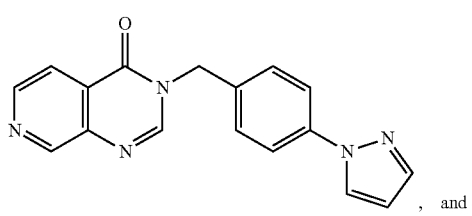, and
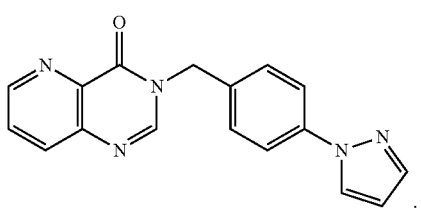.
In an even further aspect, a compound is:
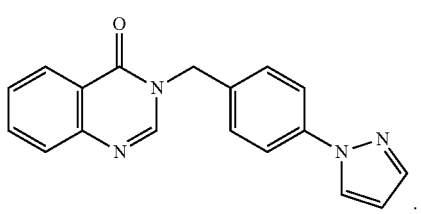 [SMILES: O=c1c2ccccc2ncn1Cc1ccc(-n2cccn2)cc1].
In a still further aspect, a compound is selected from:
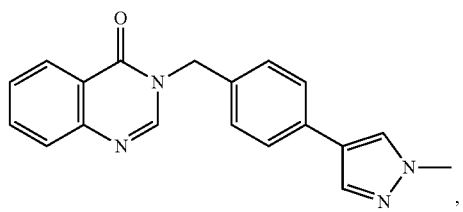,
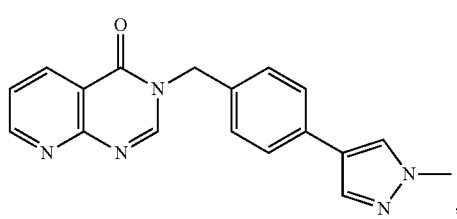,
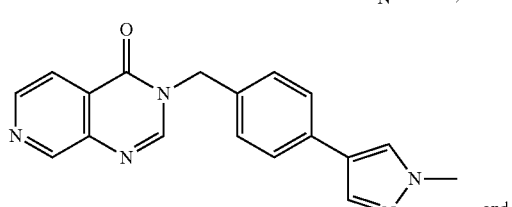, and
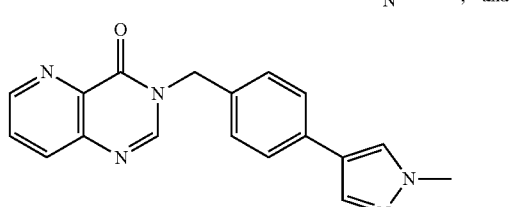.
In yet a further aspect, a compound is selected from:
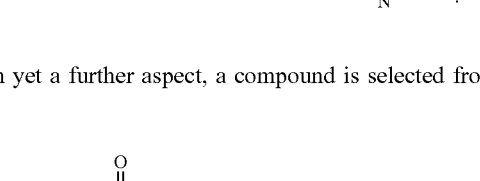,
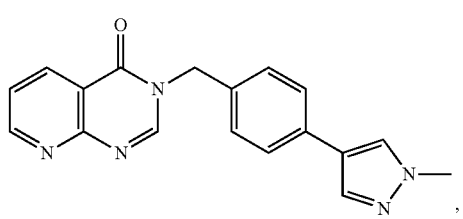, and
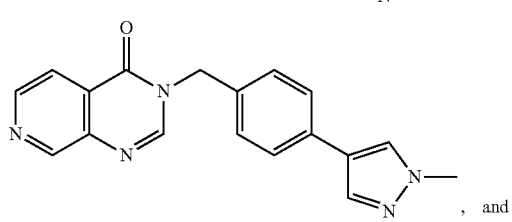
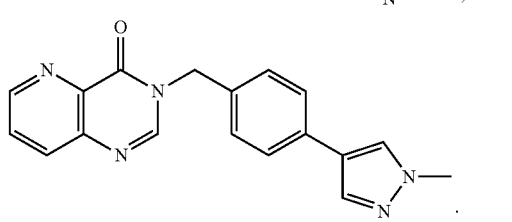.

In yet a further aspect, a compound is:

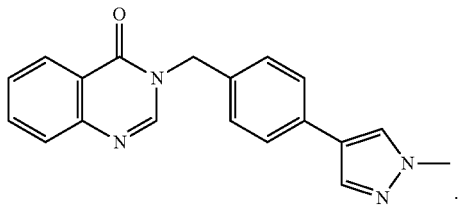 [SMILES: Cn1cc(-c2ccc(Cn3cnc4ccccc4c3=O)cc2)cn1]

3. Prophet Compound Examples

The following compound examples are prophetic, and can be prepared using the synthesis methods described herein above and other general methods as needed as would be known to one skilled in the art. It is anticipated that the prophetic compounds would be active as mAChR M1 positive allosteric modulators, and such activity can be determined using the assay methods described herein above.

In one aspect, a compound is selected from:

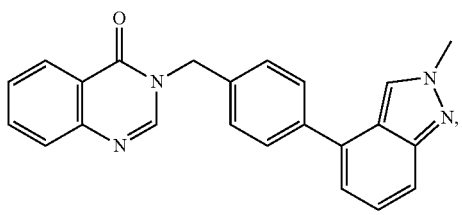

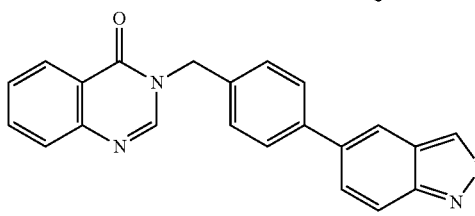

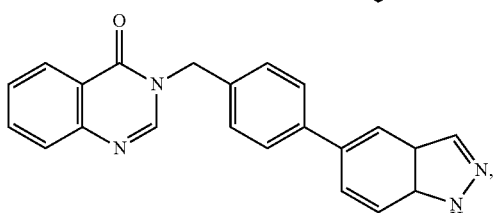

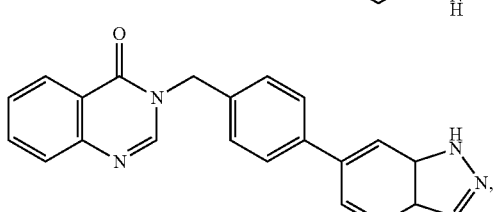

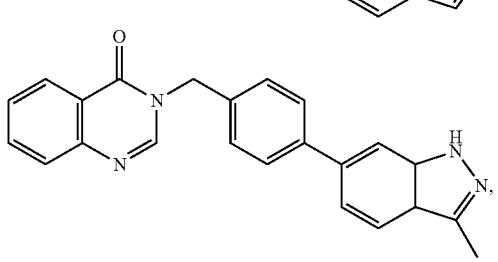

-continued

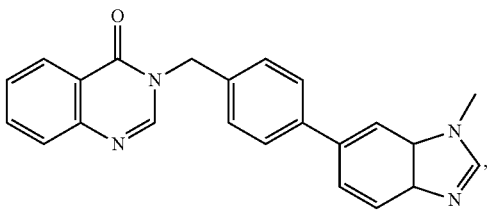

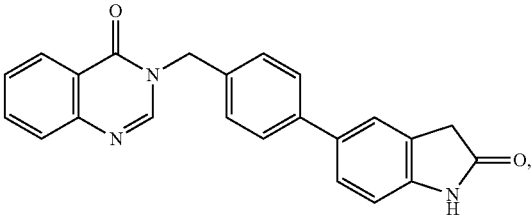

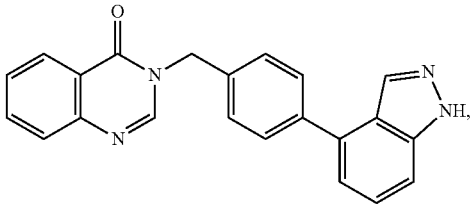

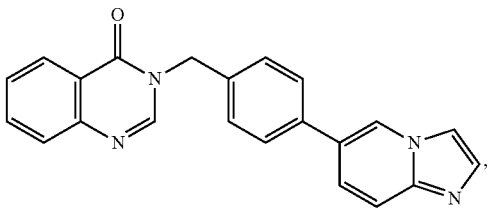

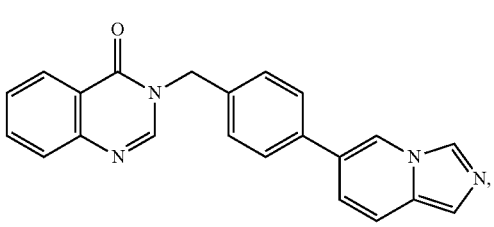

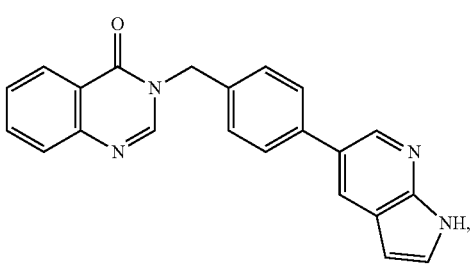

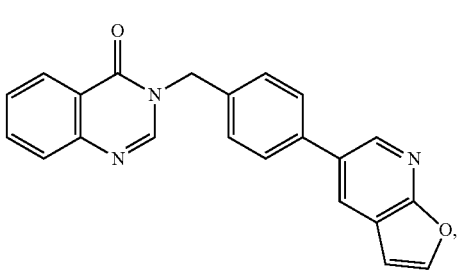

95
-continued
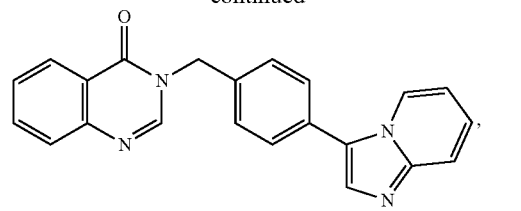
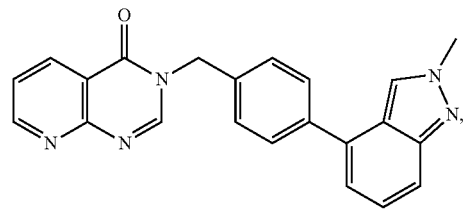
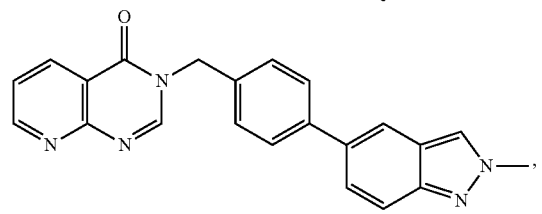
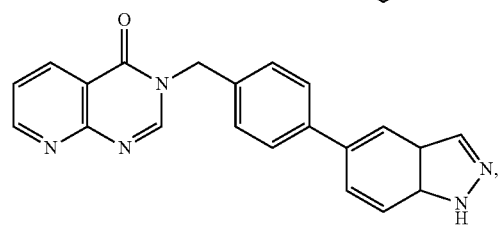
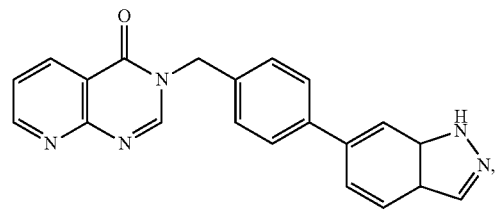
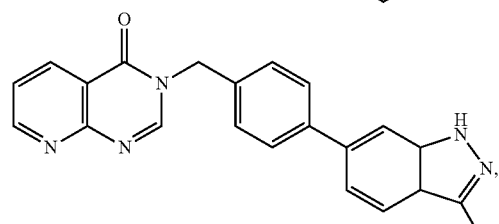
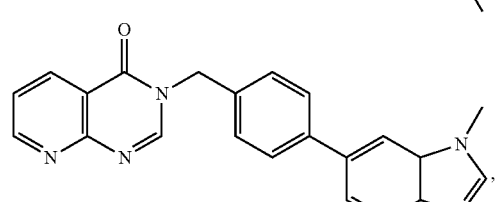
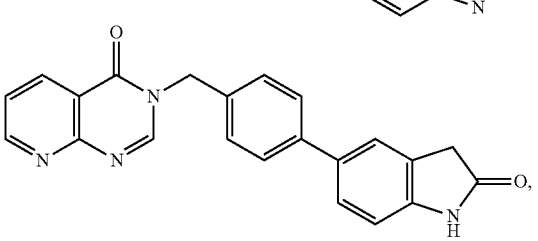
96
-continued
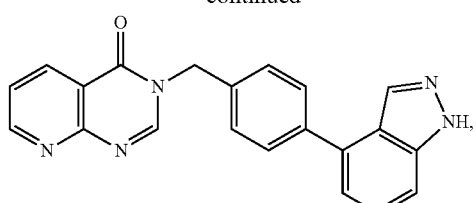
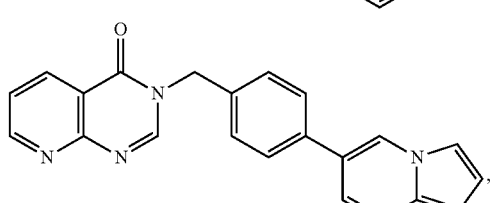
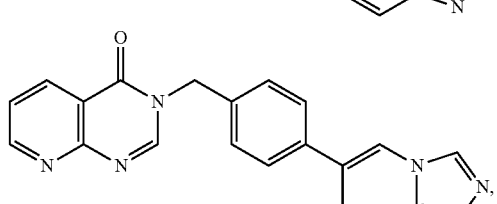
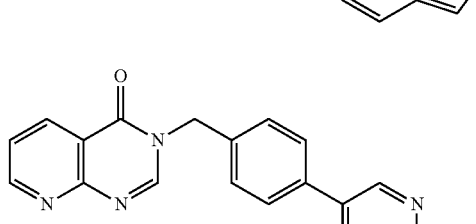
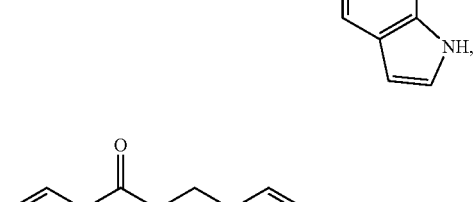
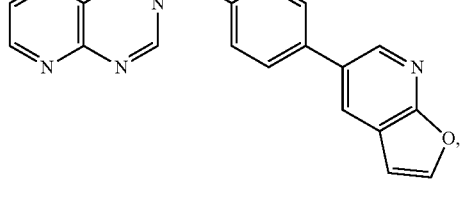
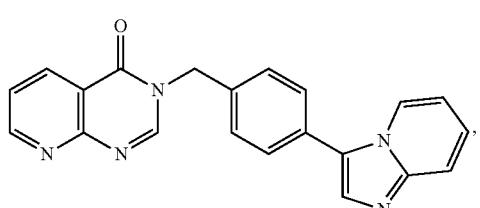
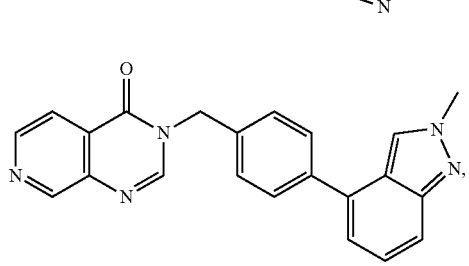

97
-continued
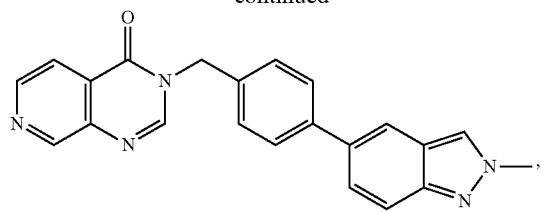
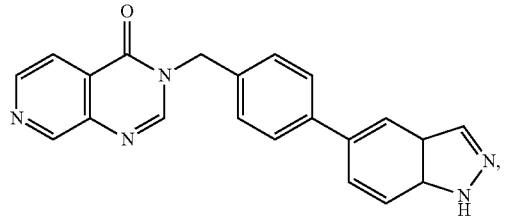
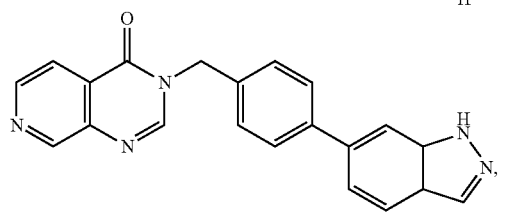
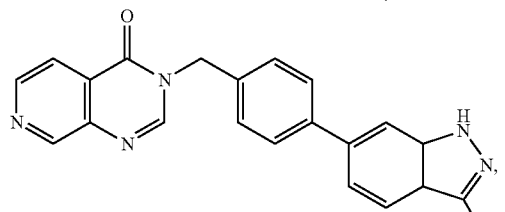
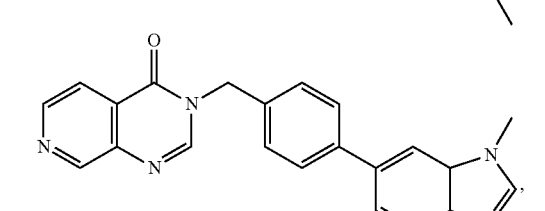
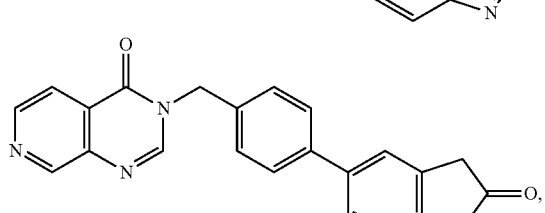
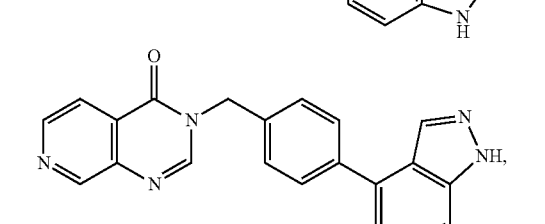
98
-continued
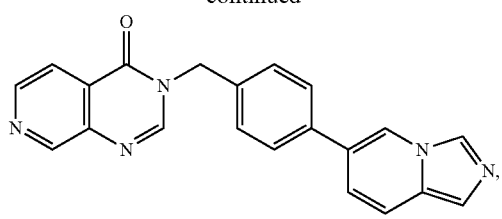
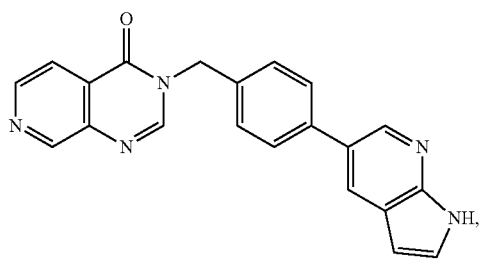
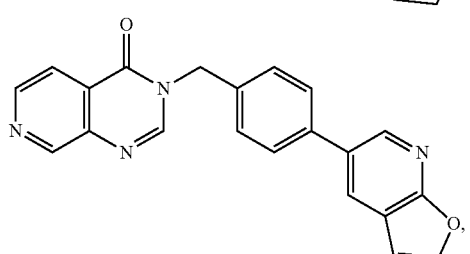
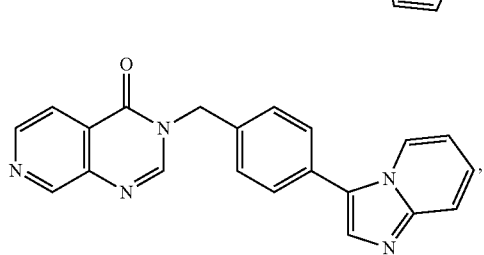
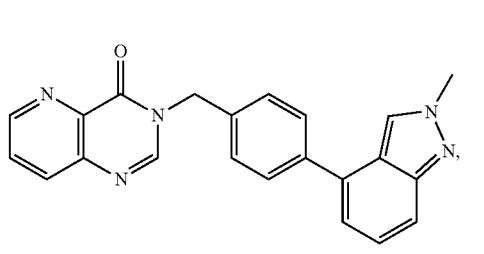
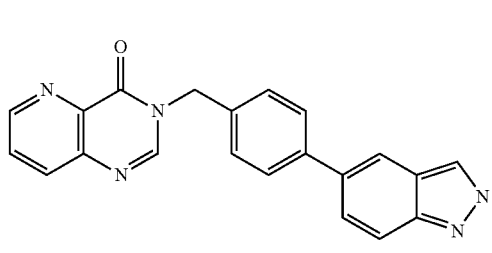
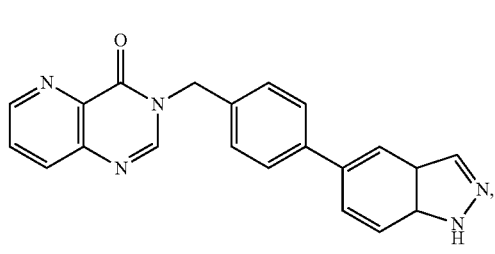

99
-continued
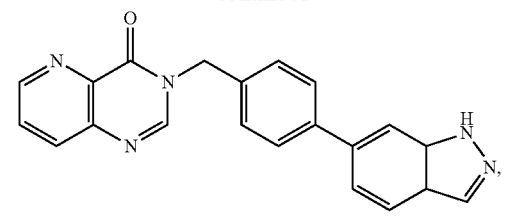
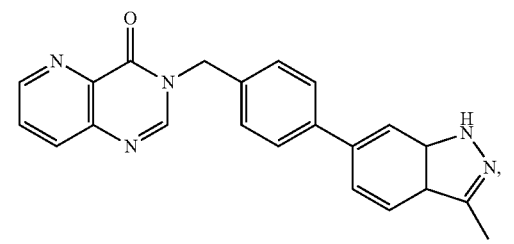
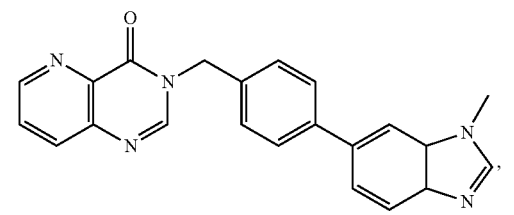
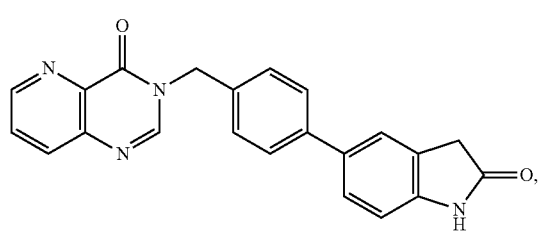
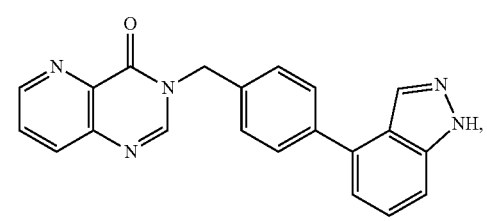
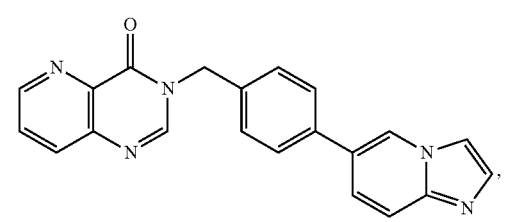
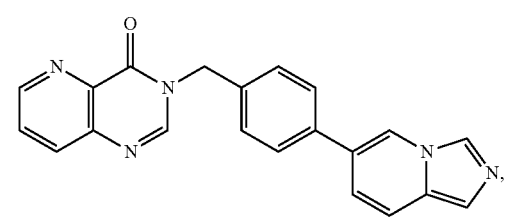
100
-continued
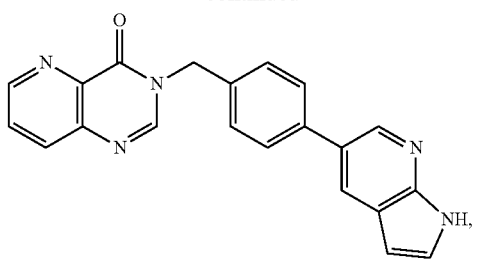
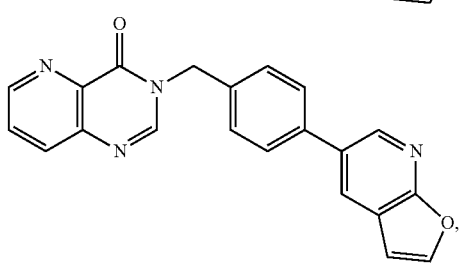
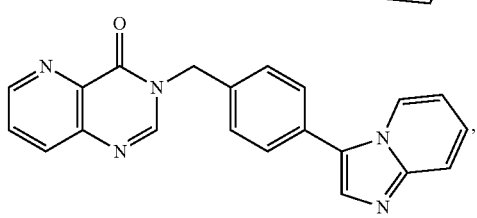
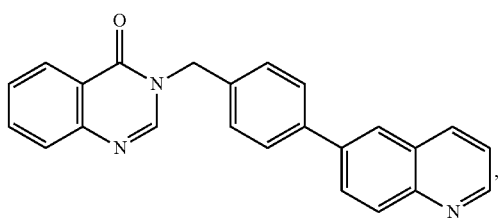
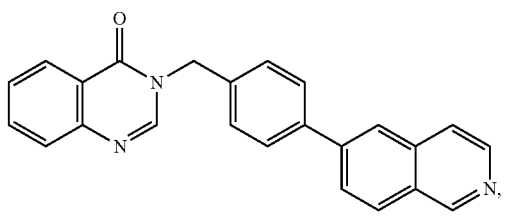
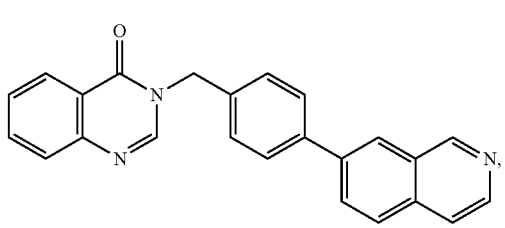
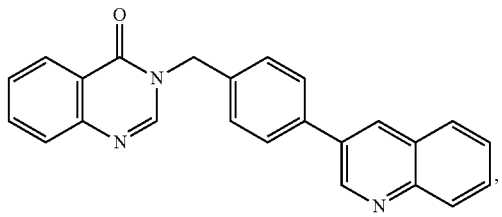

101
-continued
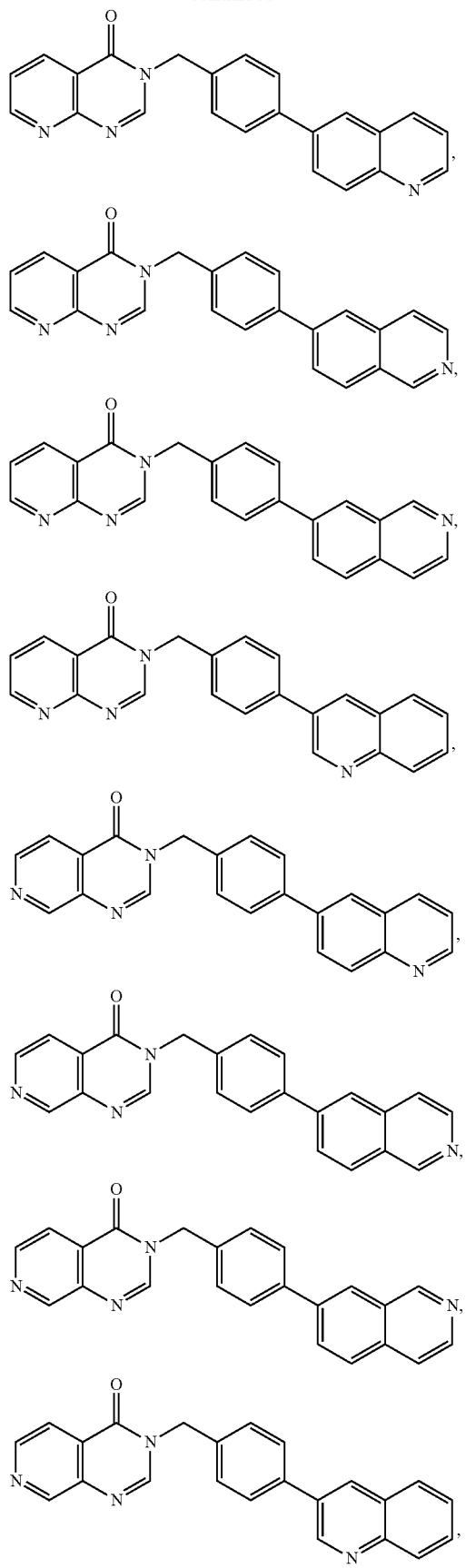
102
-continued
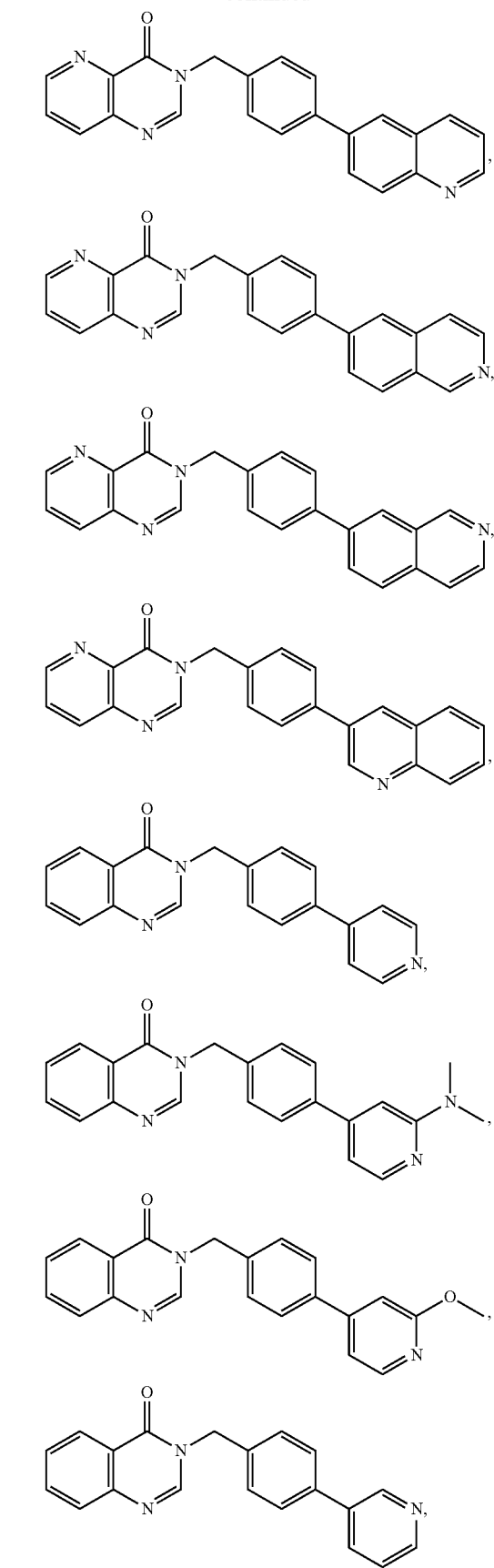

103
-continued
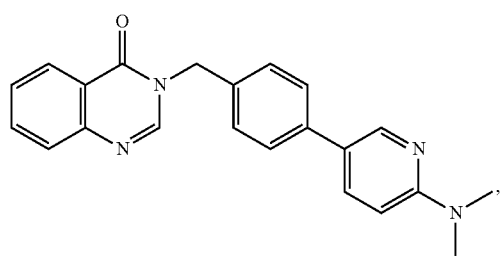
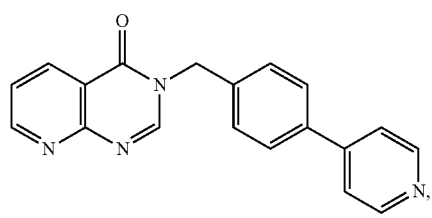
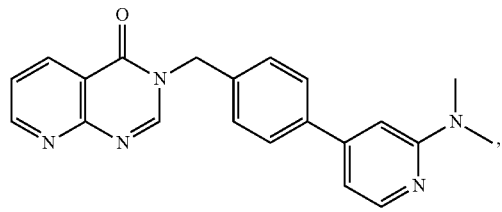
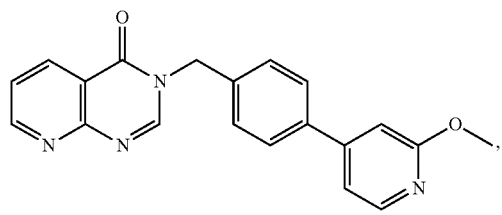
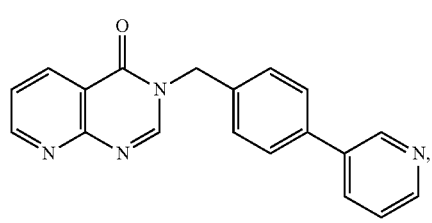
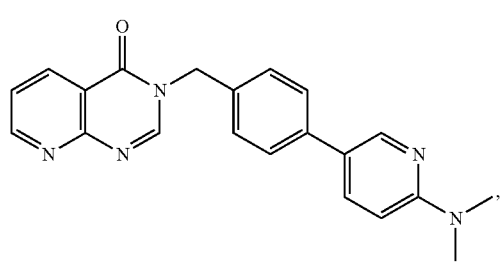
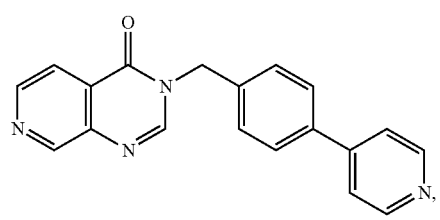
104
-continued
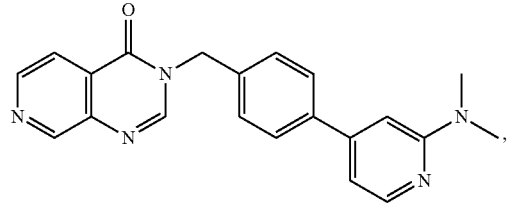
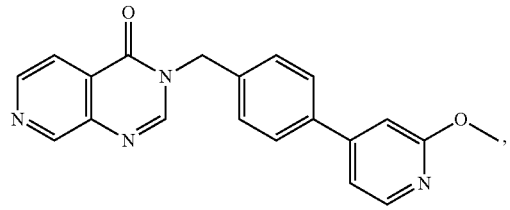
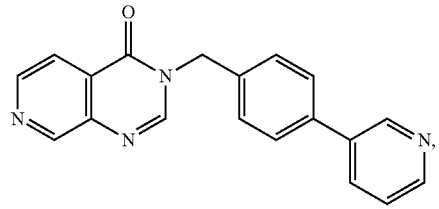
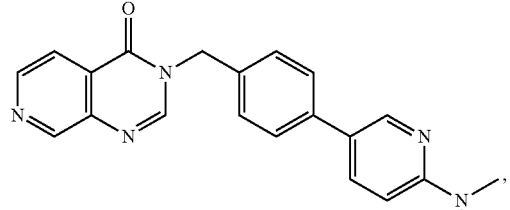
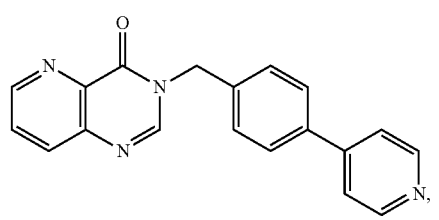
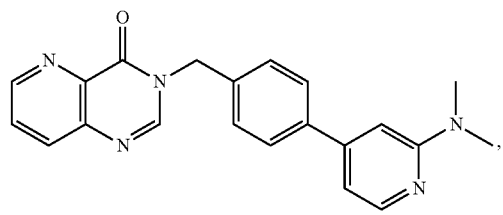
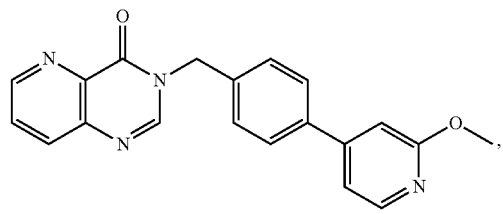
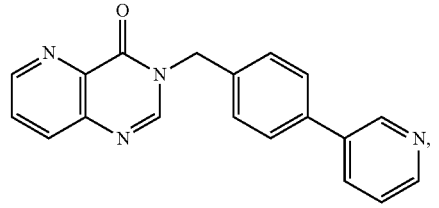

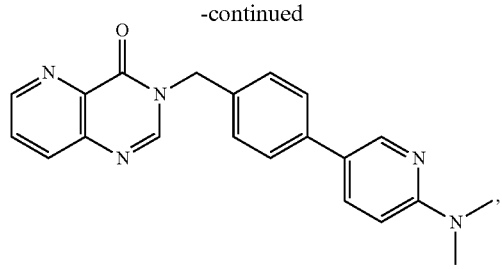
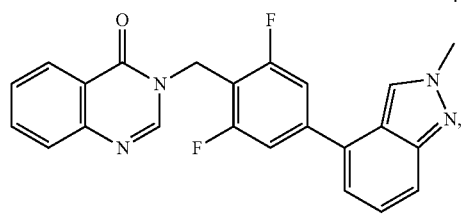
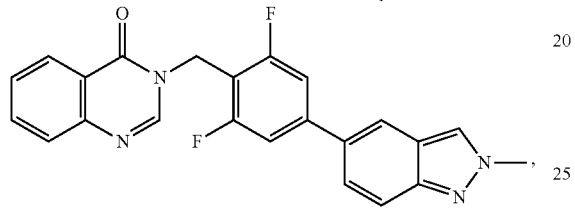
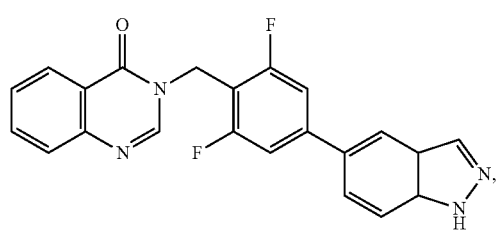
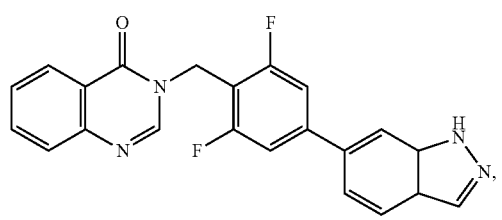
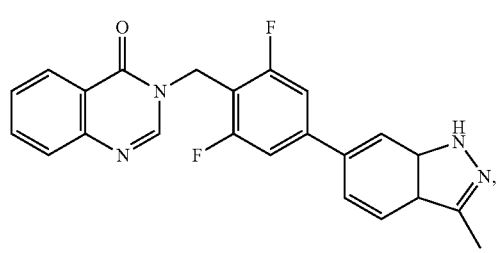
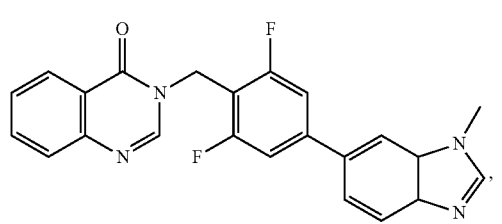
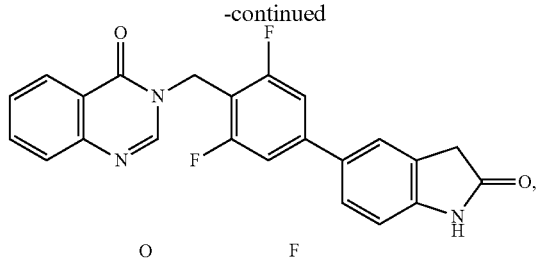
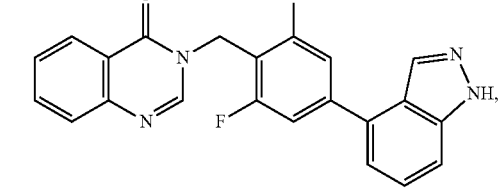
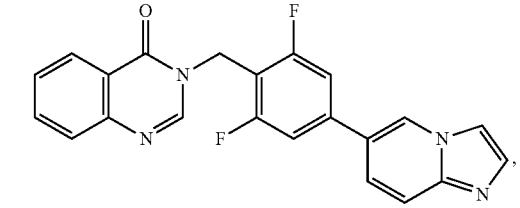
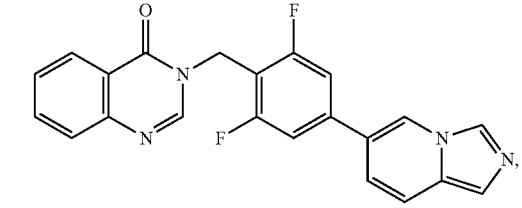
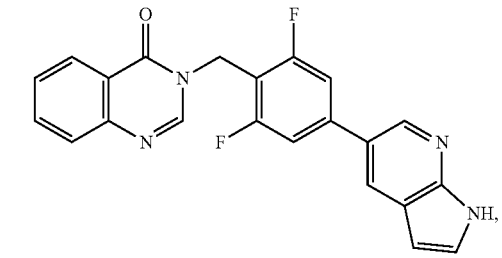
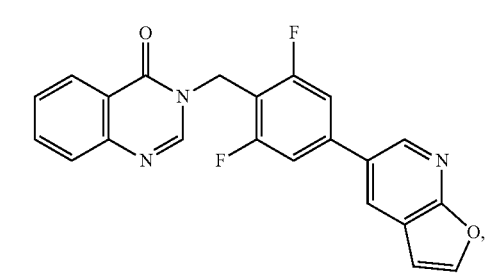
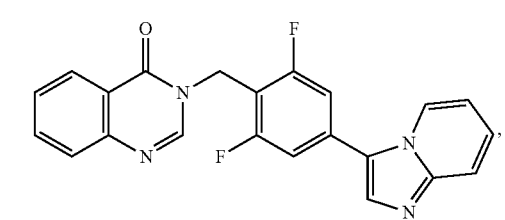

107
-continued
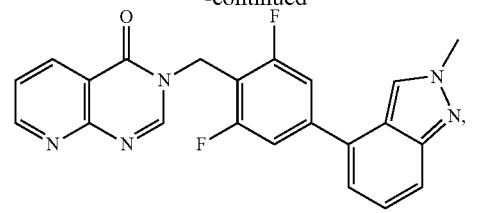
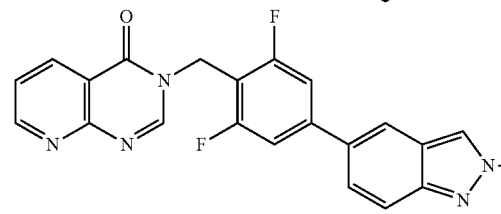
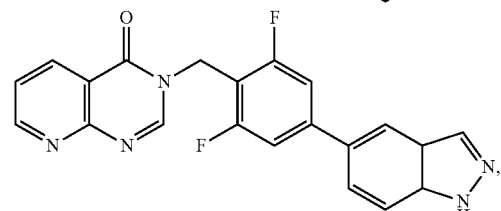
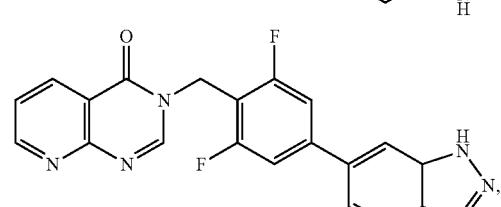
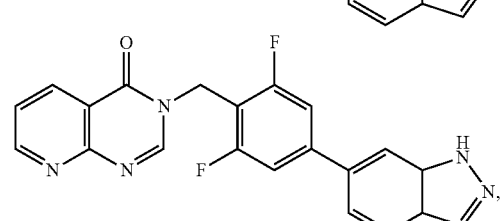
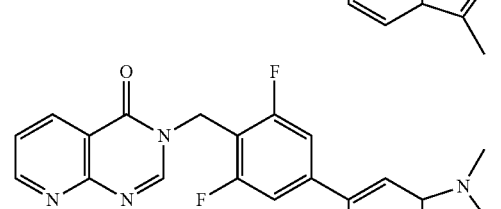
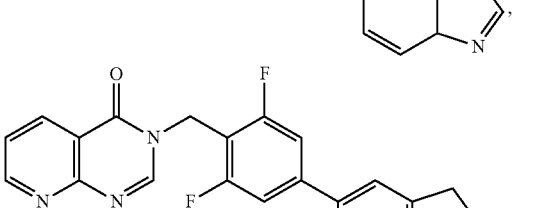
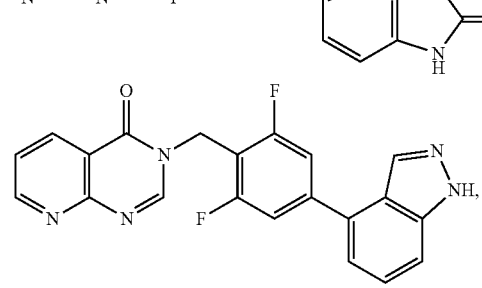
108
-continued
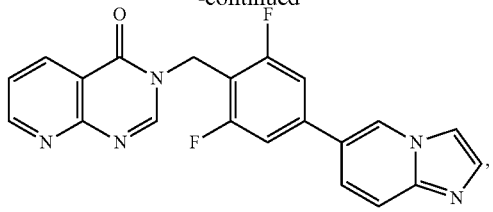
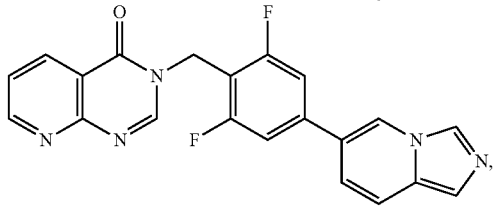
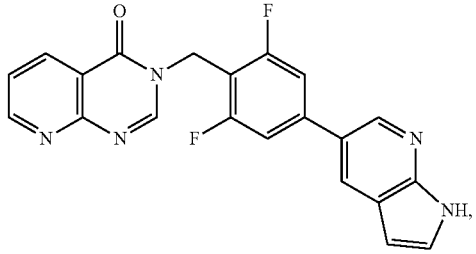
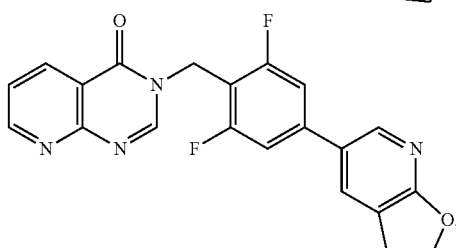
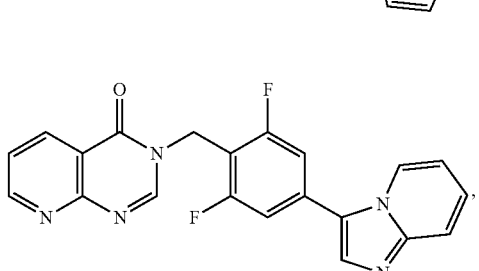
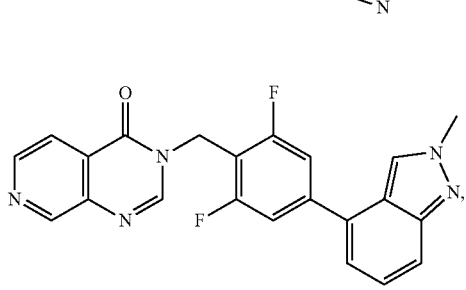
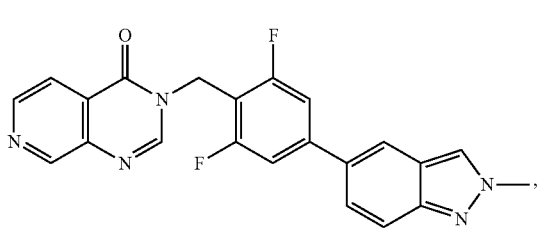

109
-continued
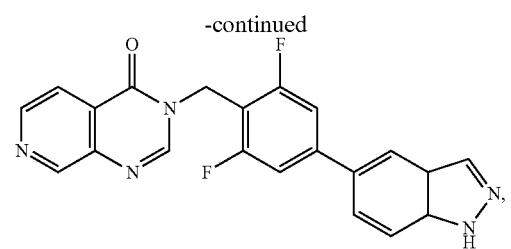
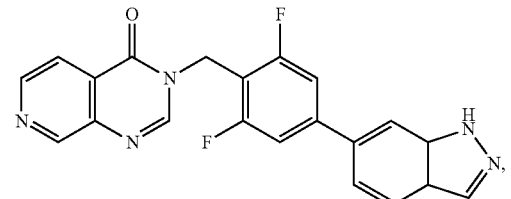
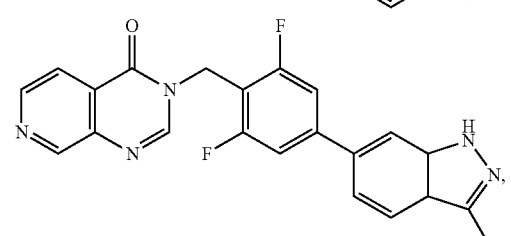
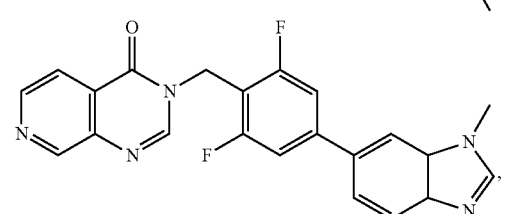
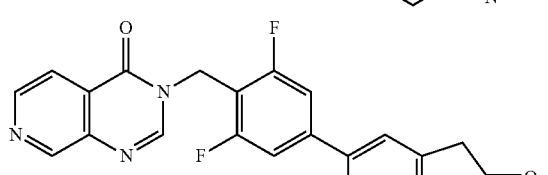
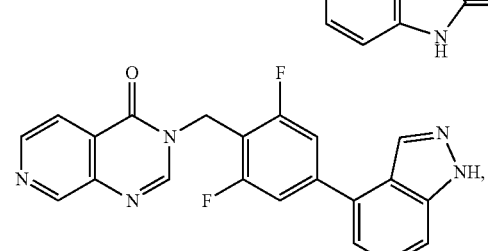
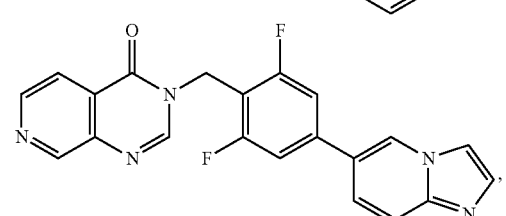
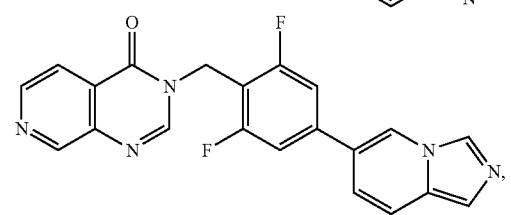
110
-continued
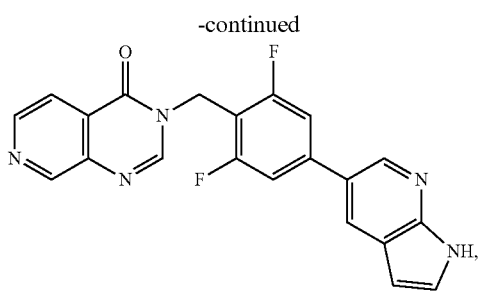
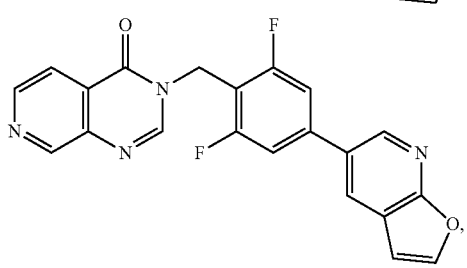
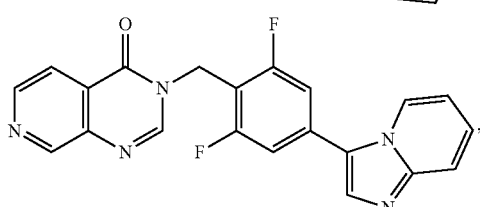
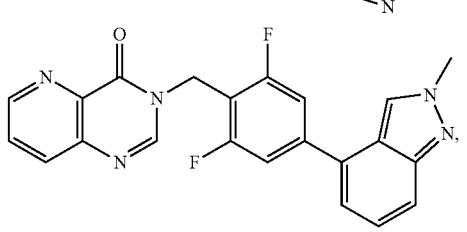
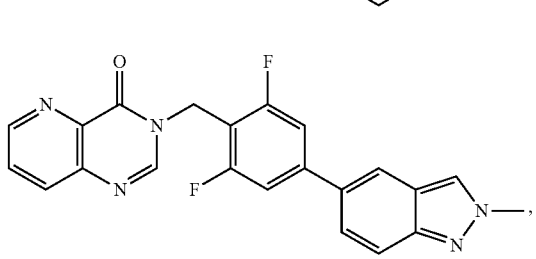
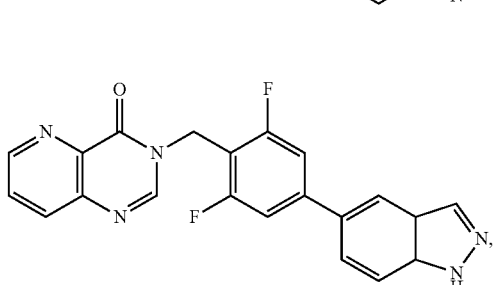
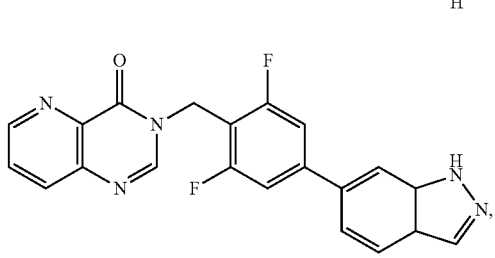

111
-continued
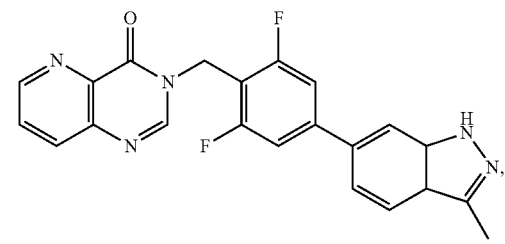
112
-continued
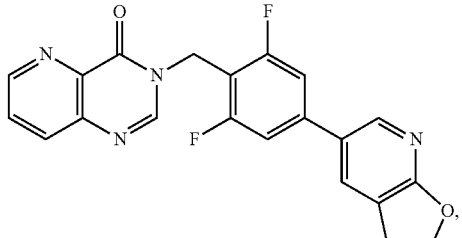
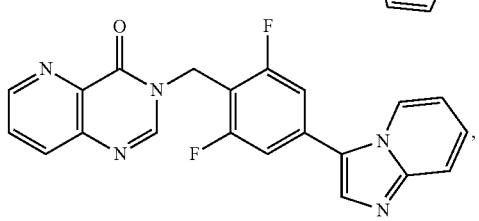
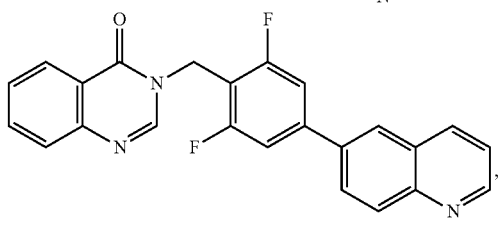
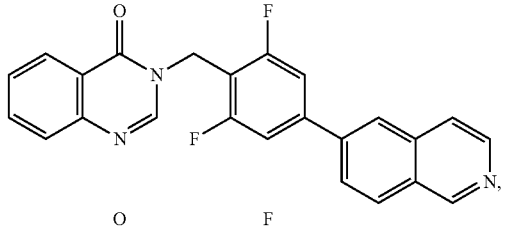
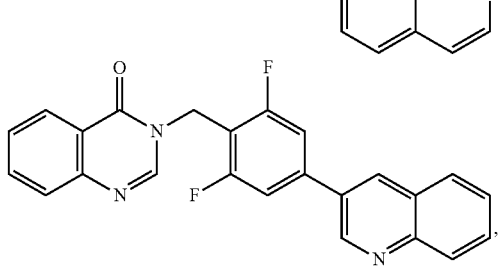
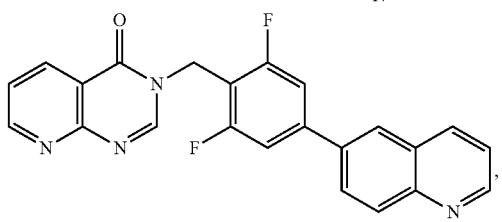
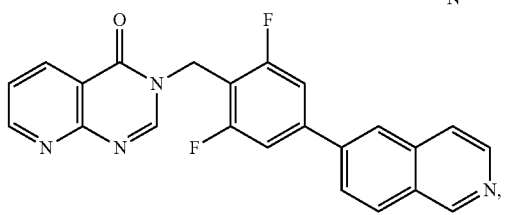

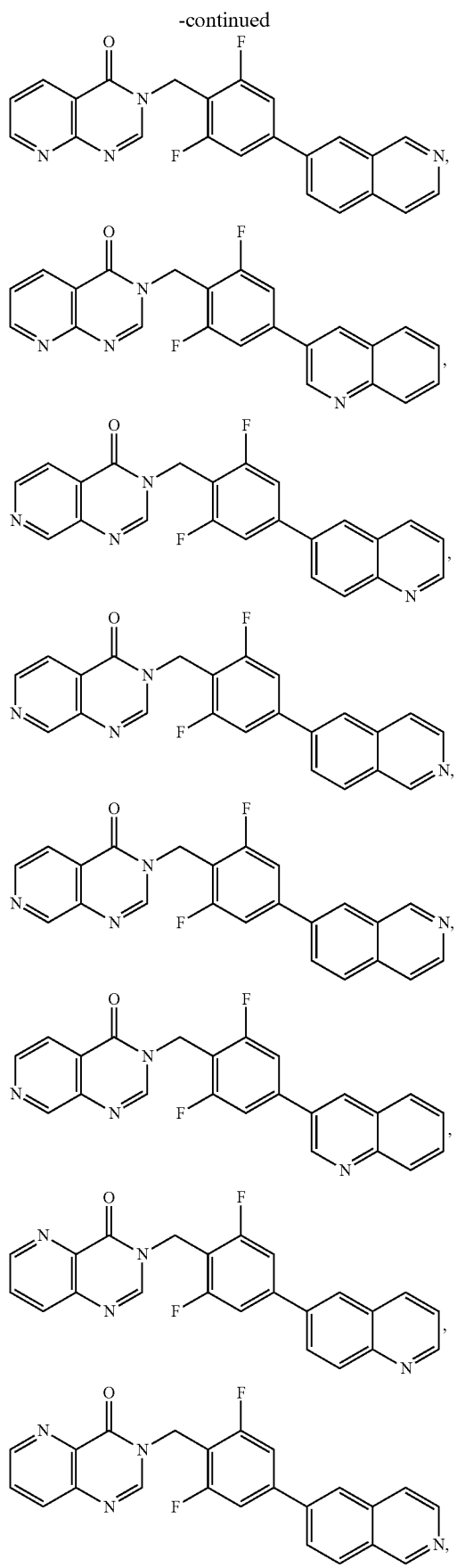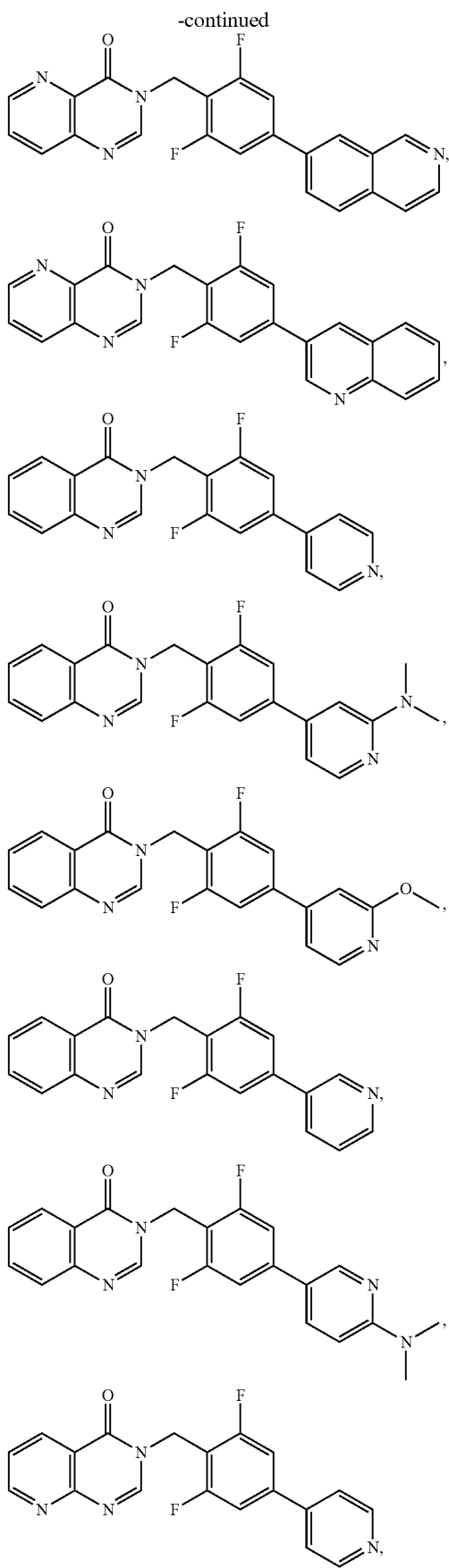

115
-continued
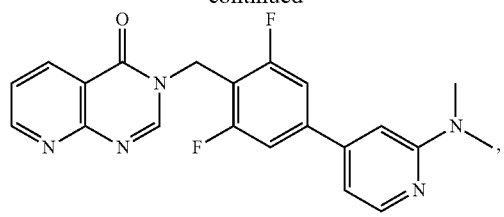
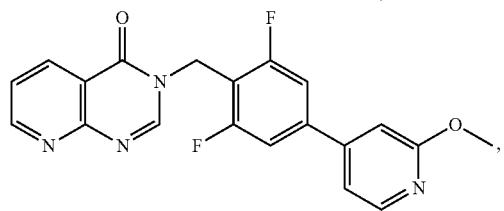
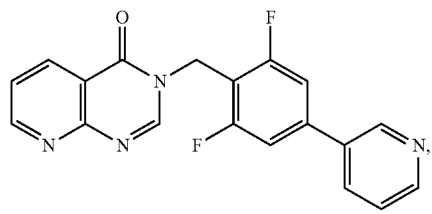
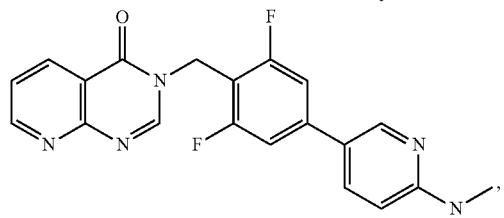
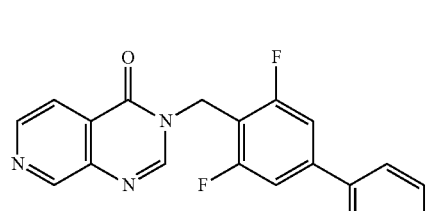
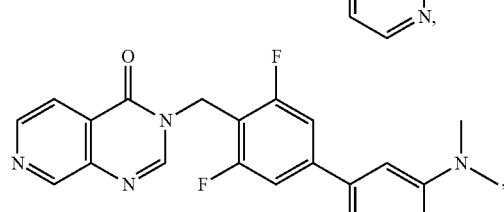
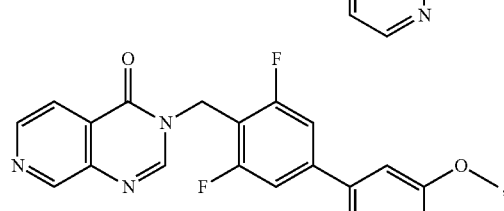
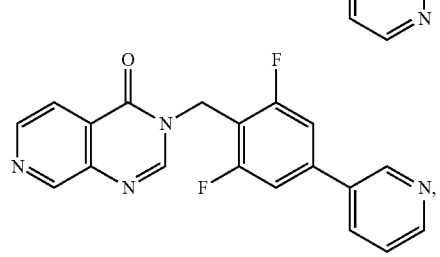
116
-continued
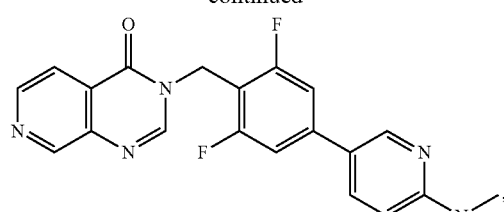
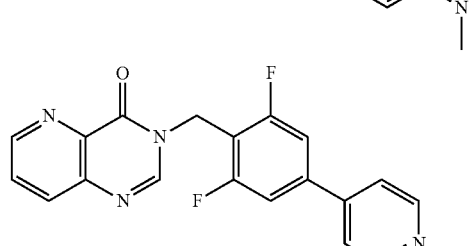
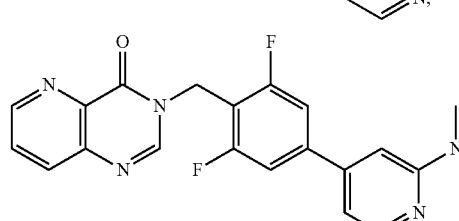
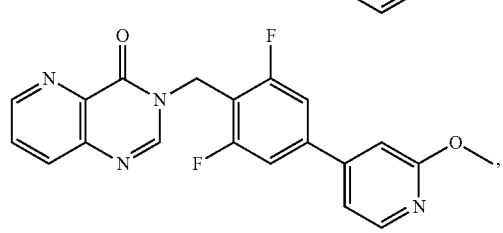
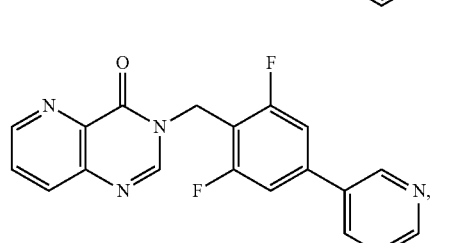
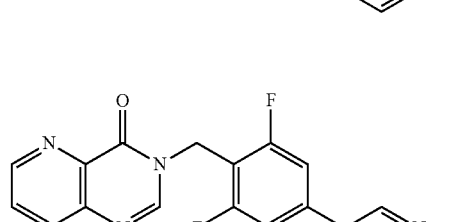
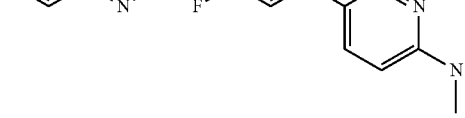
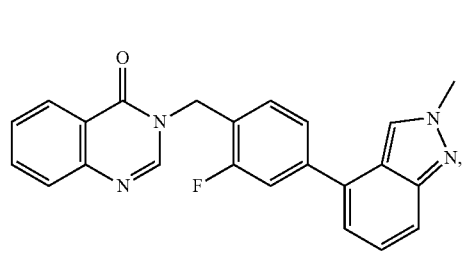

117
-continued
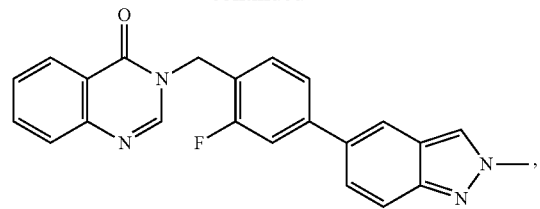
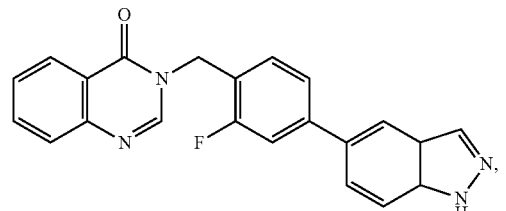
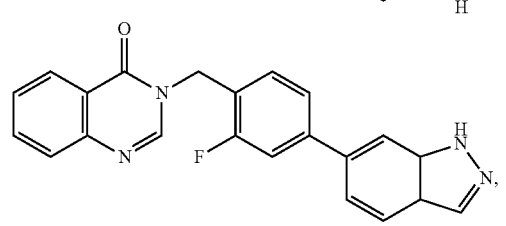
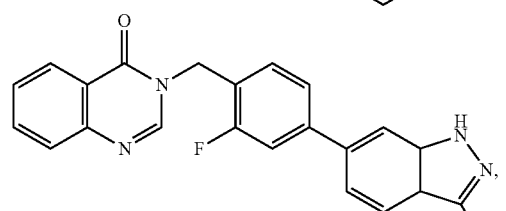
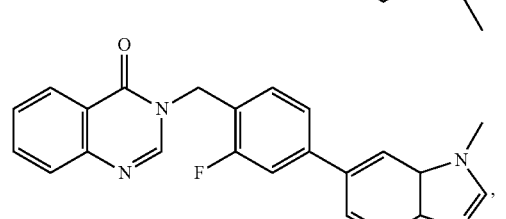
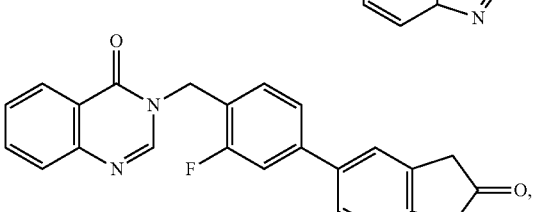
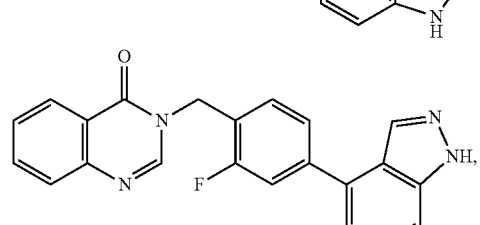
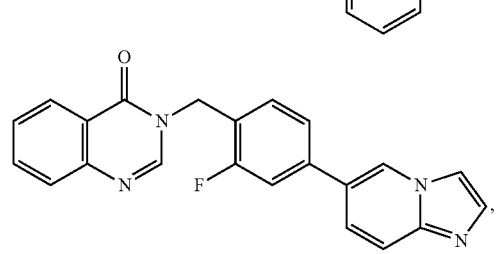
118
-continued
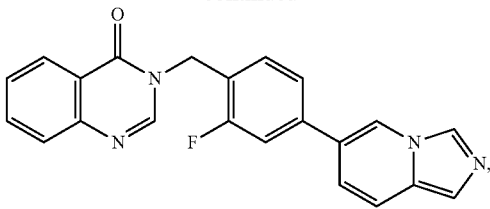
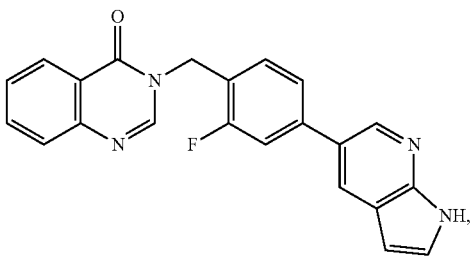
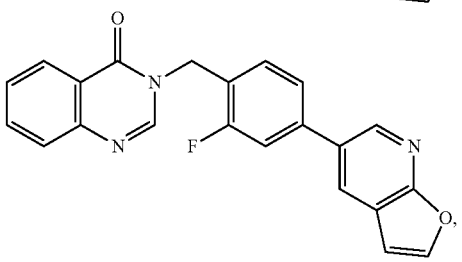
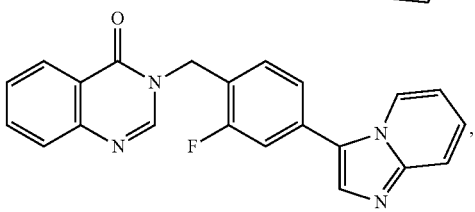
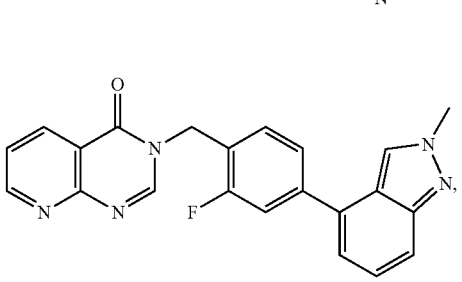
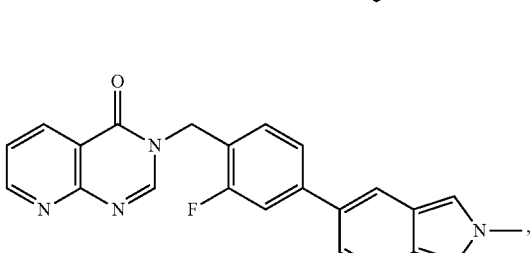
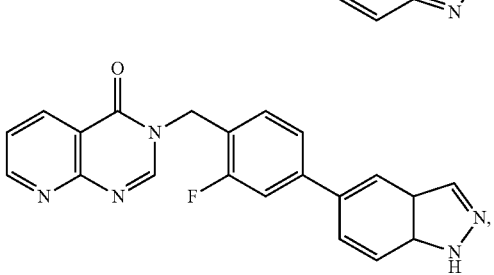

119
-continued
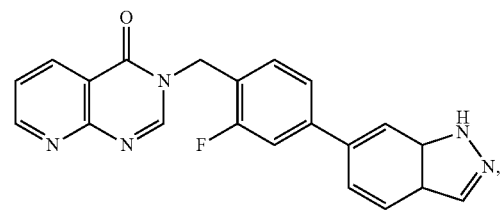
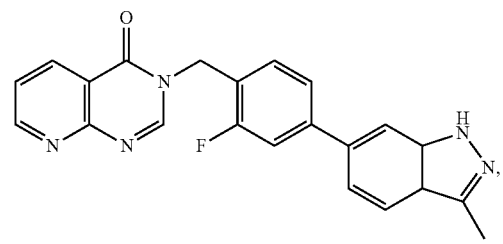
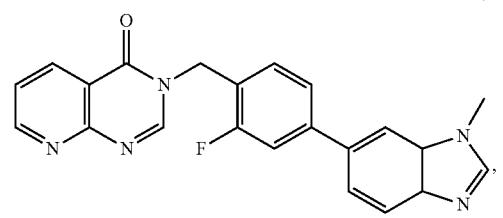
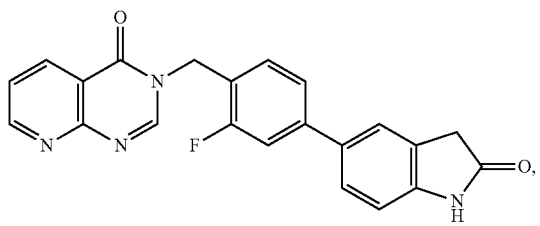
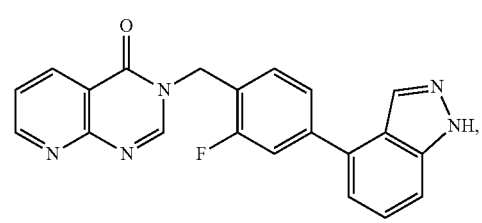
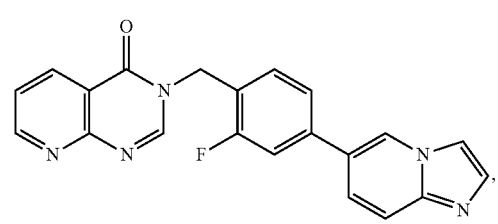
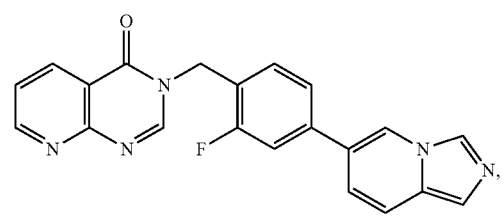
120
-continued
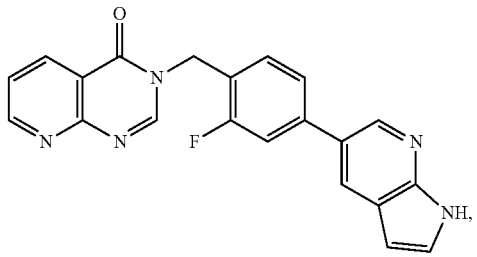
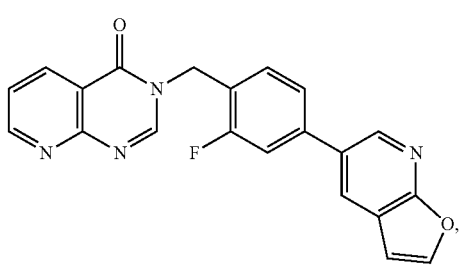
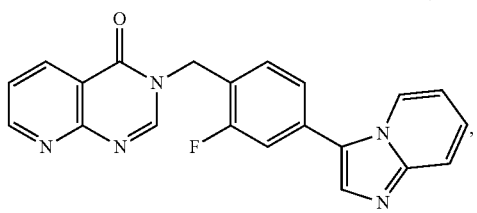
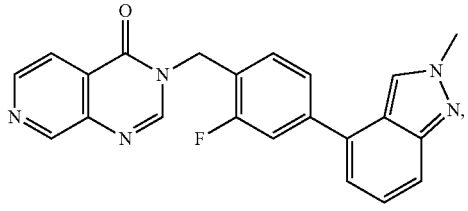
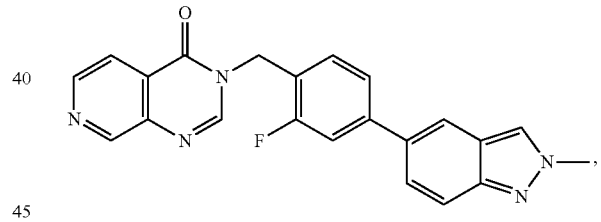
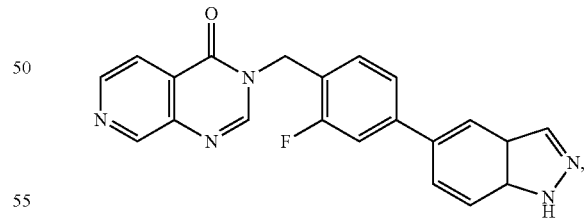
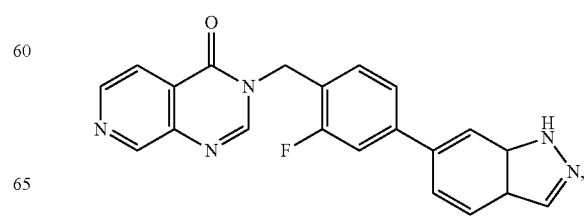

-continued

123
-continued
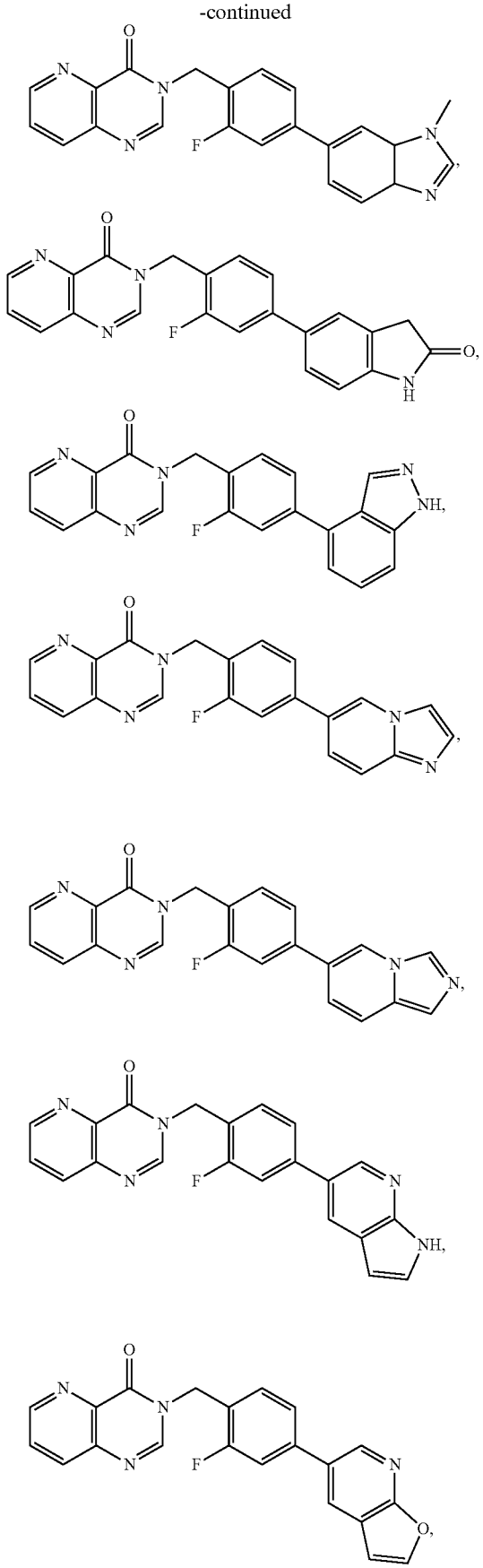
124
-continued
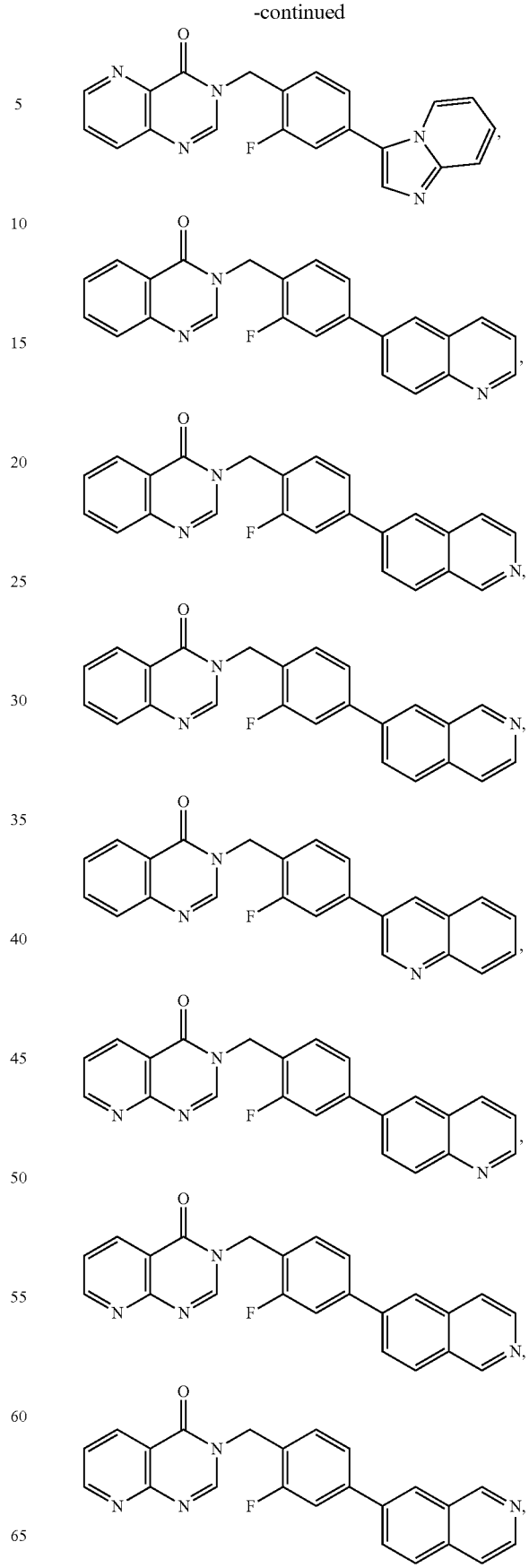

125
-continued
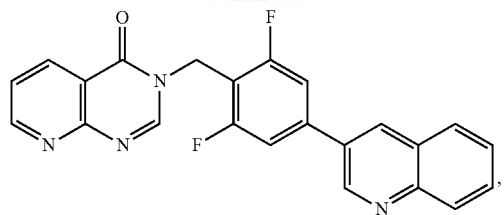
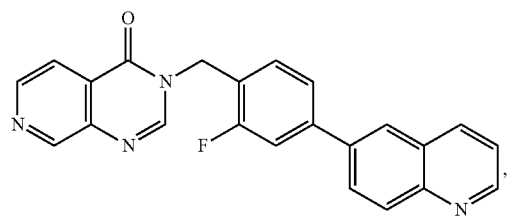
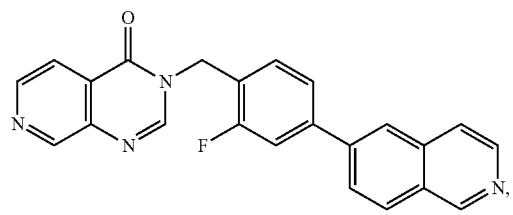
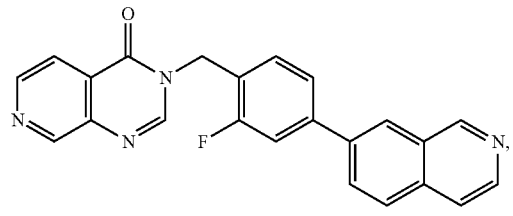
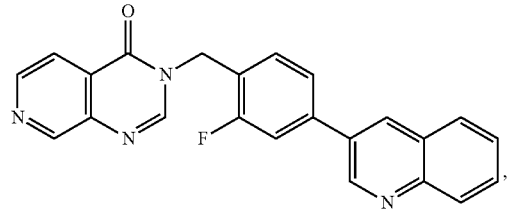
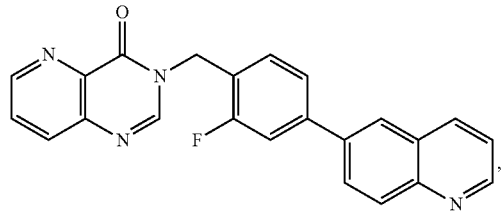
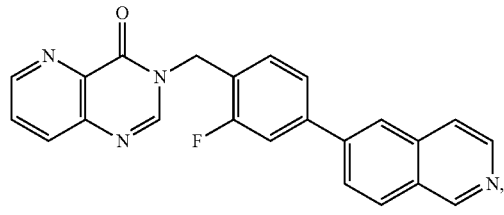
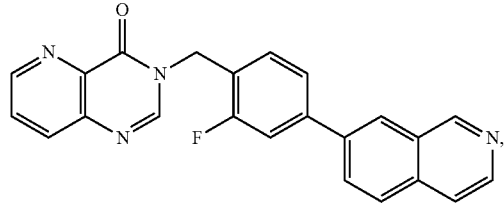
126
-continued
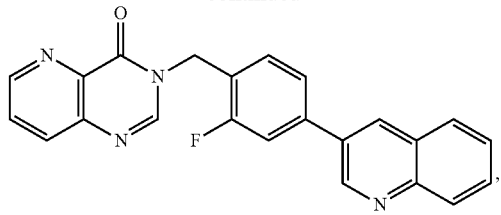
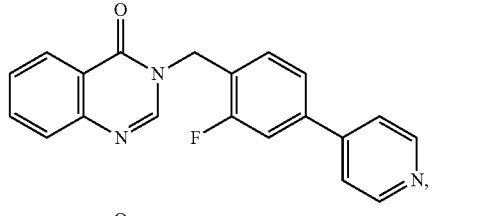
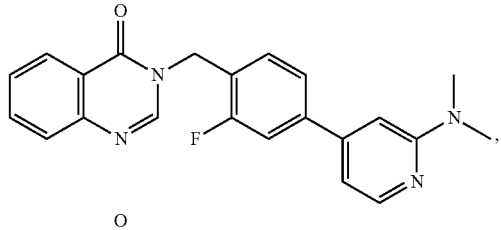
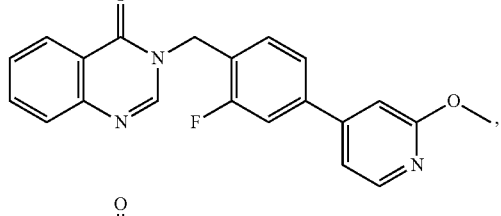
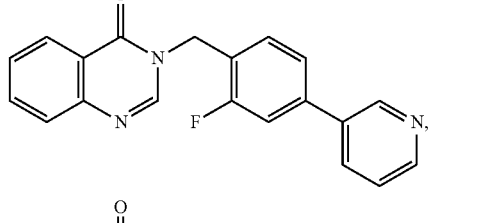
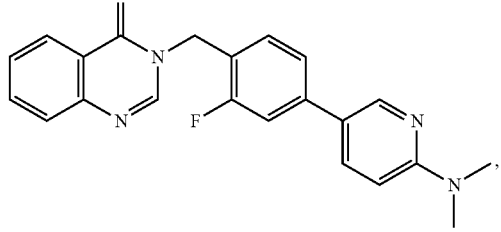
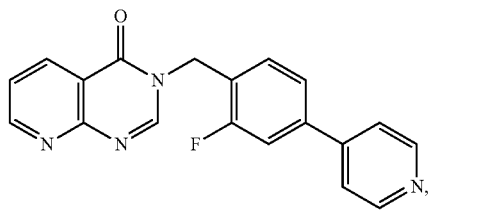
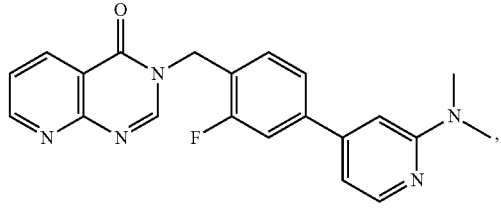

127
-continued
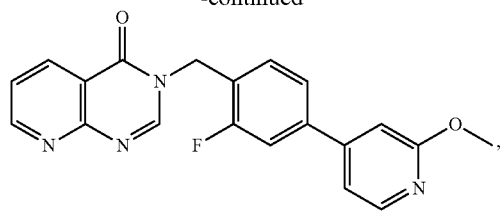
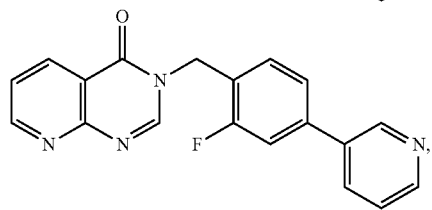
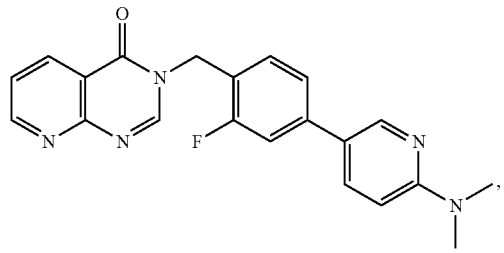
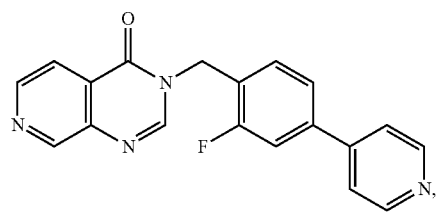
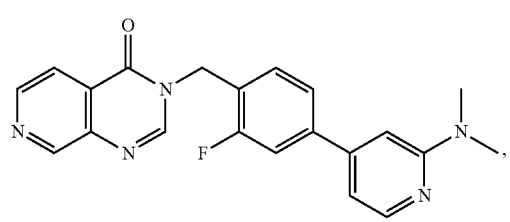
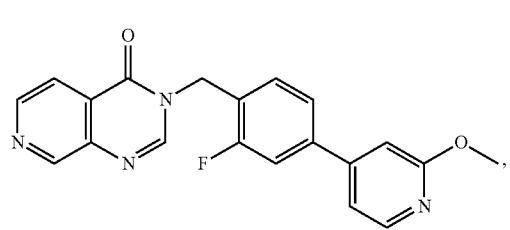
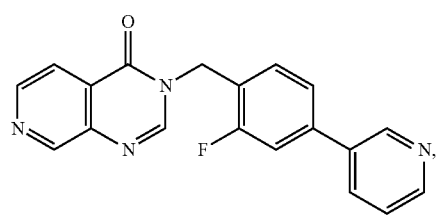
128
-continued
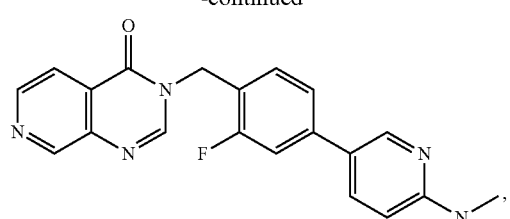
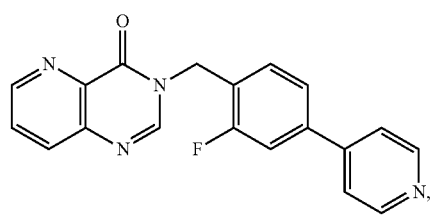
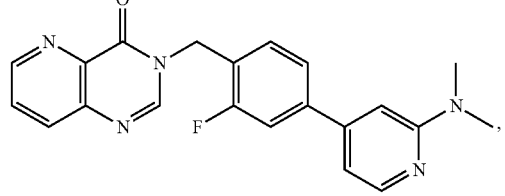
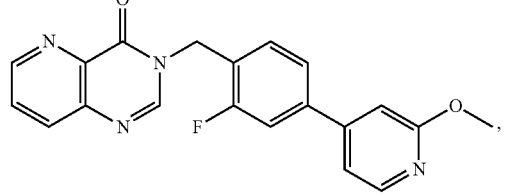
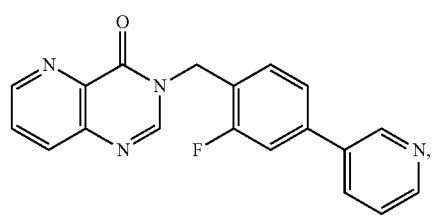
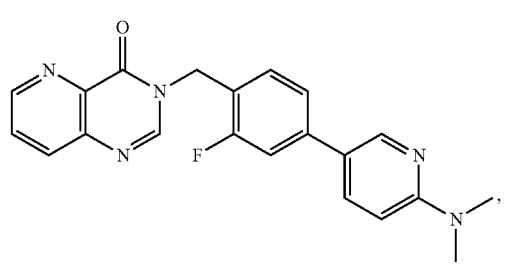
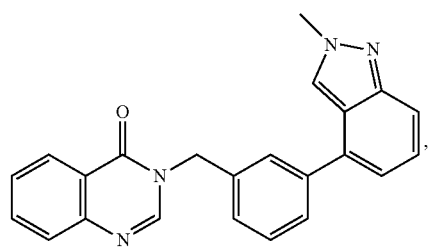

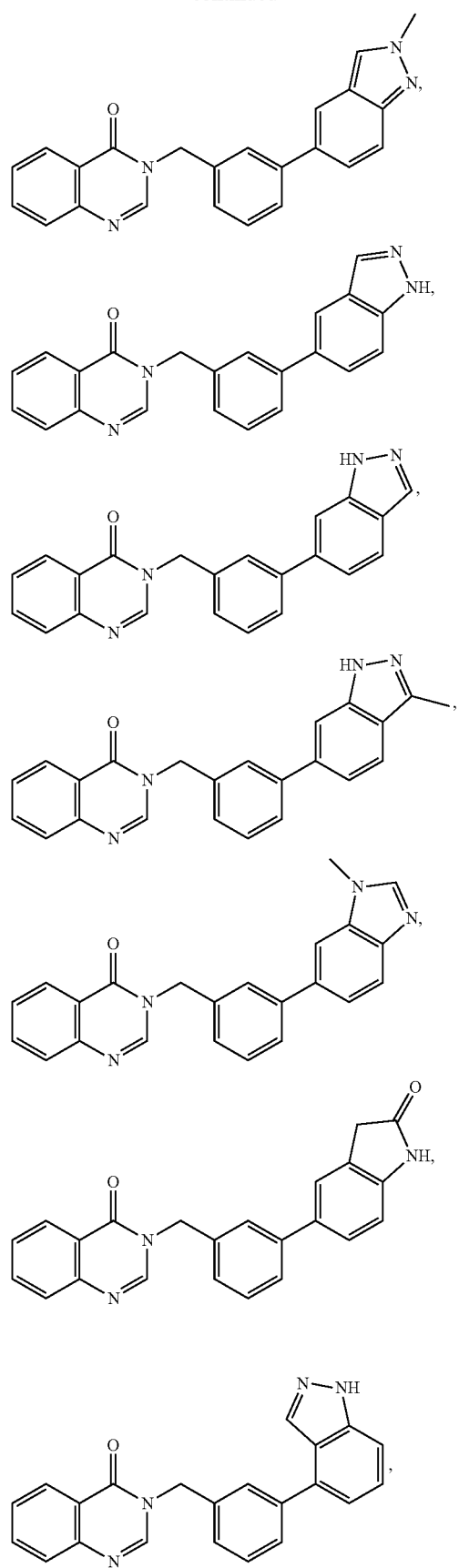
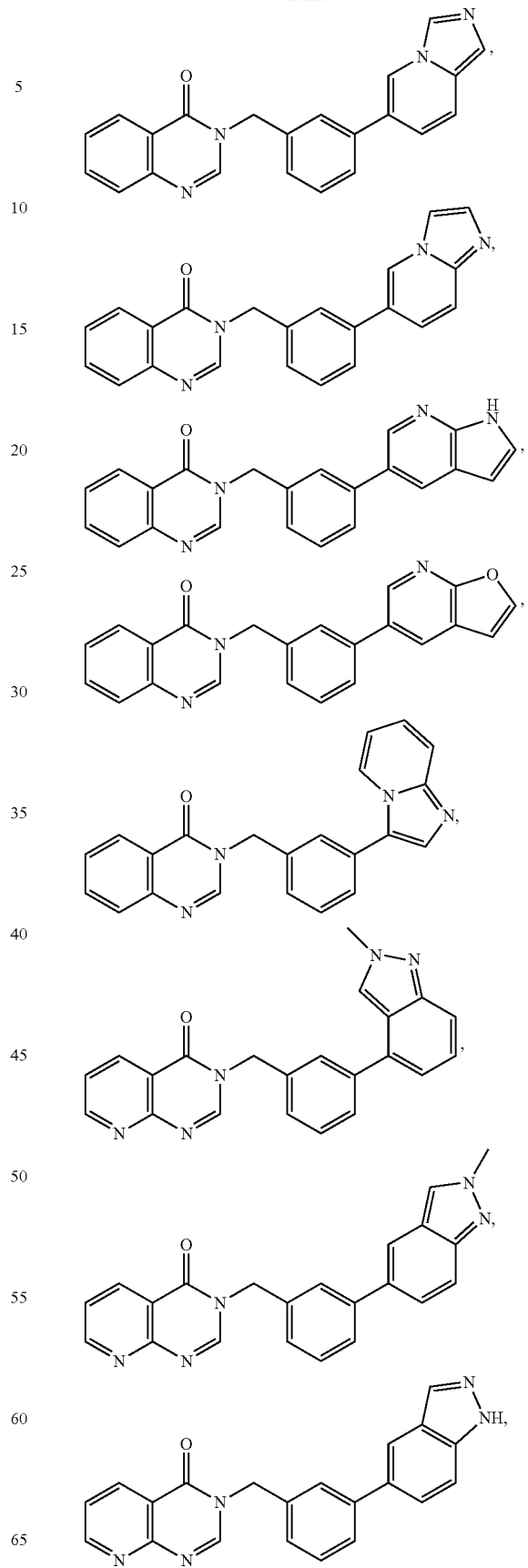

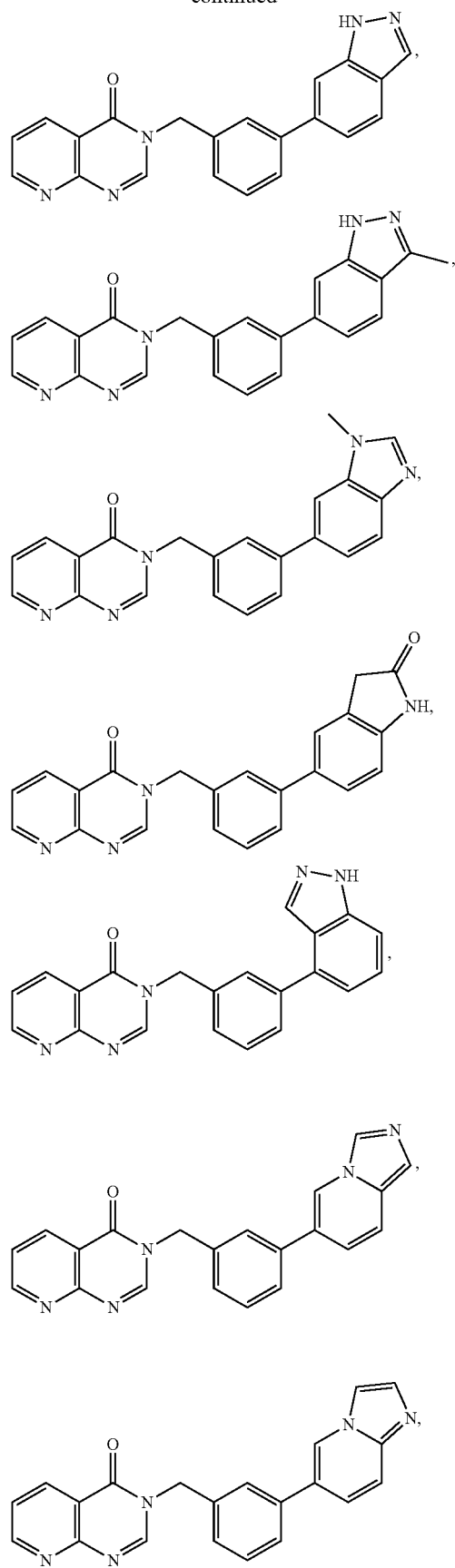
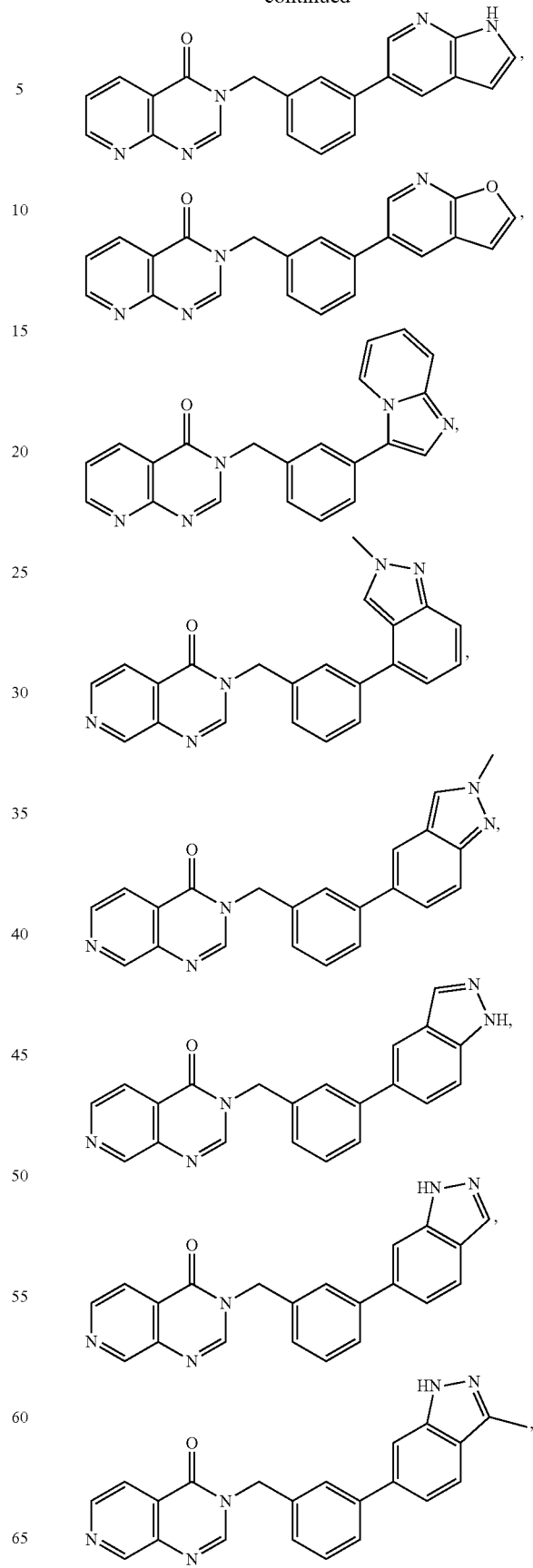

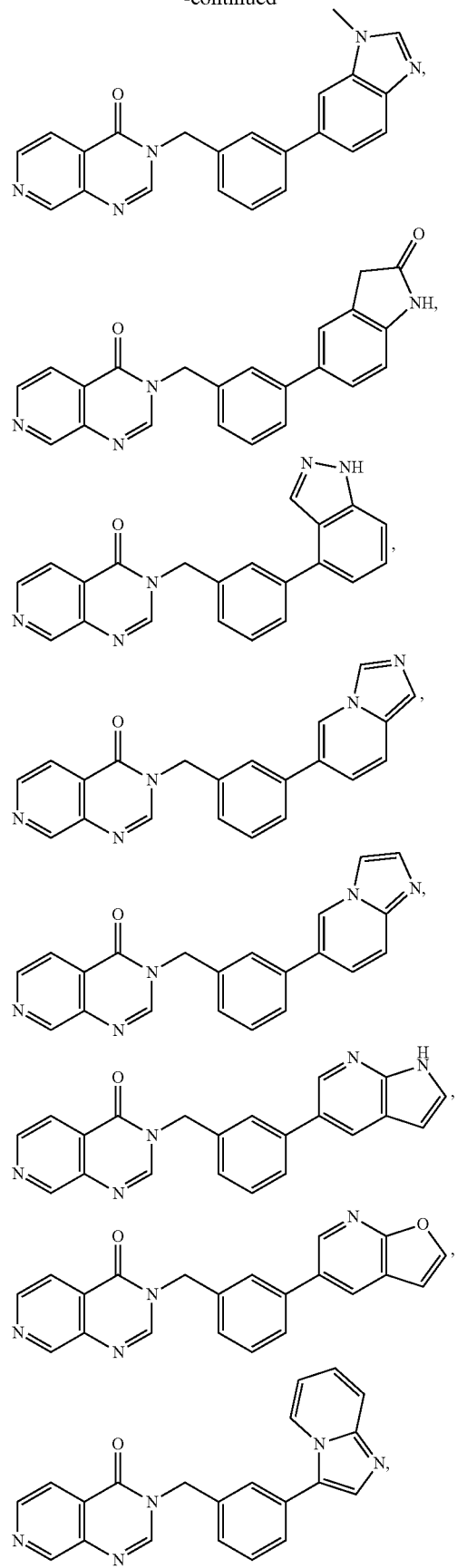
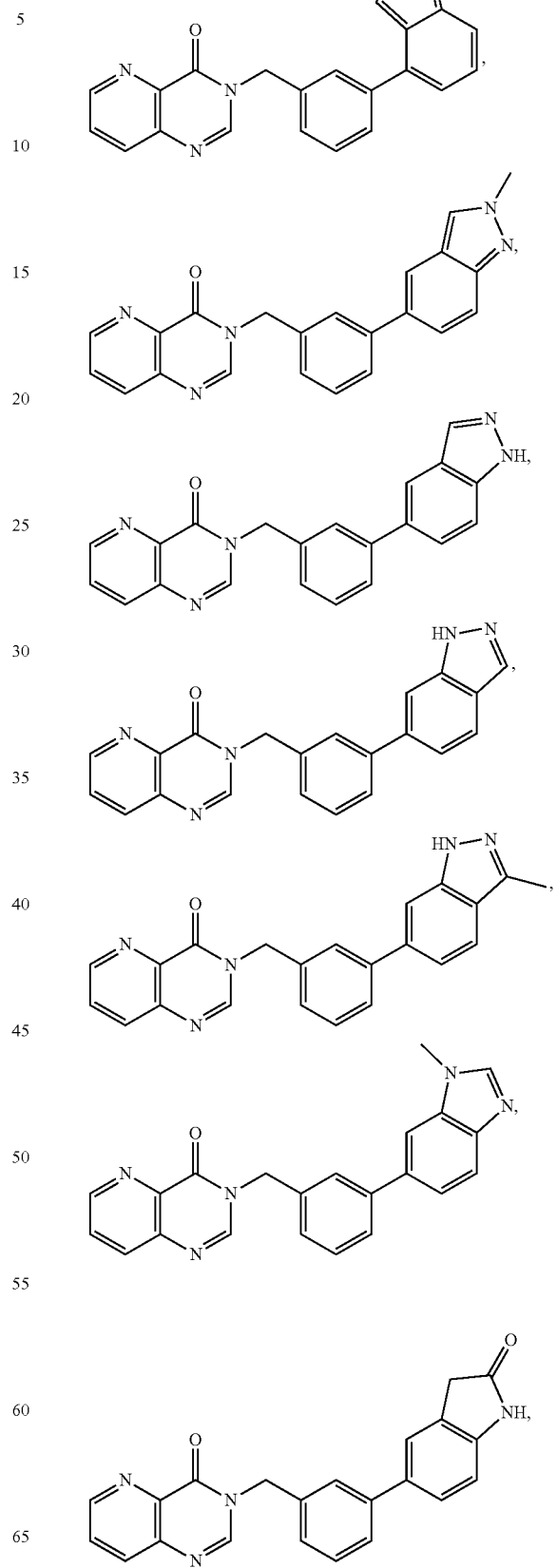

135
-continued
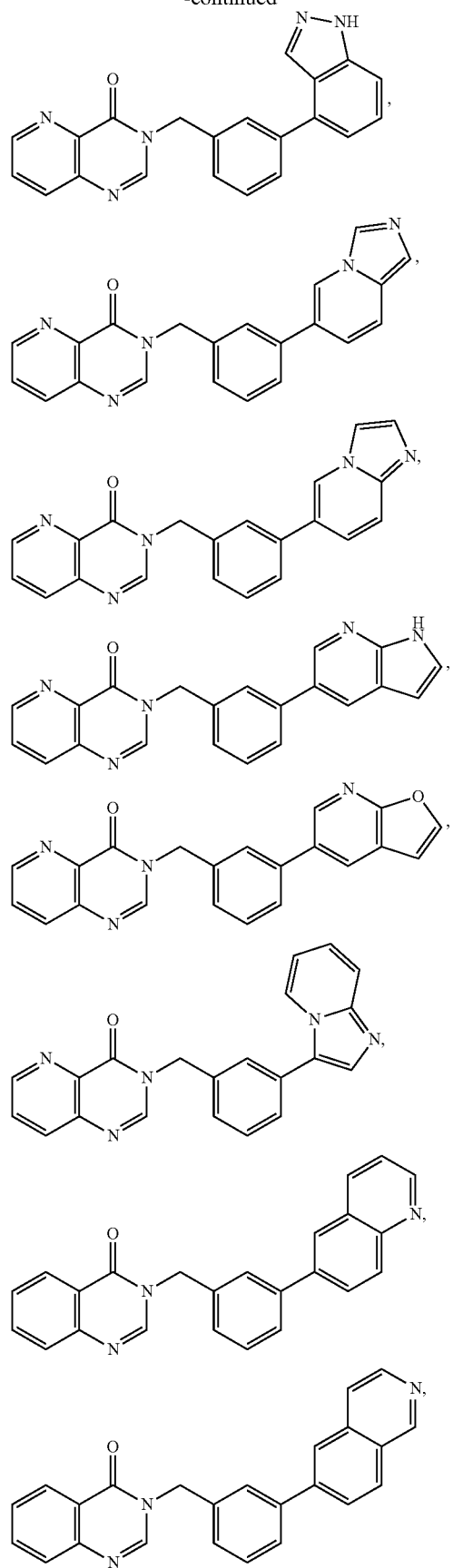
136
-continued
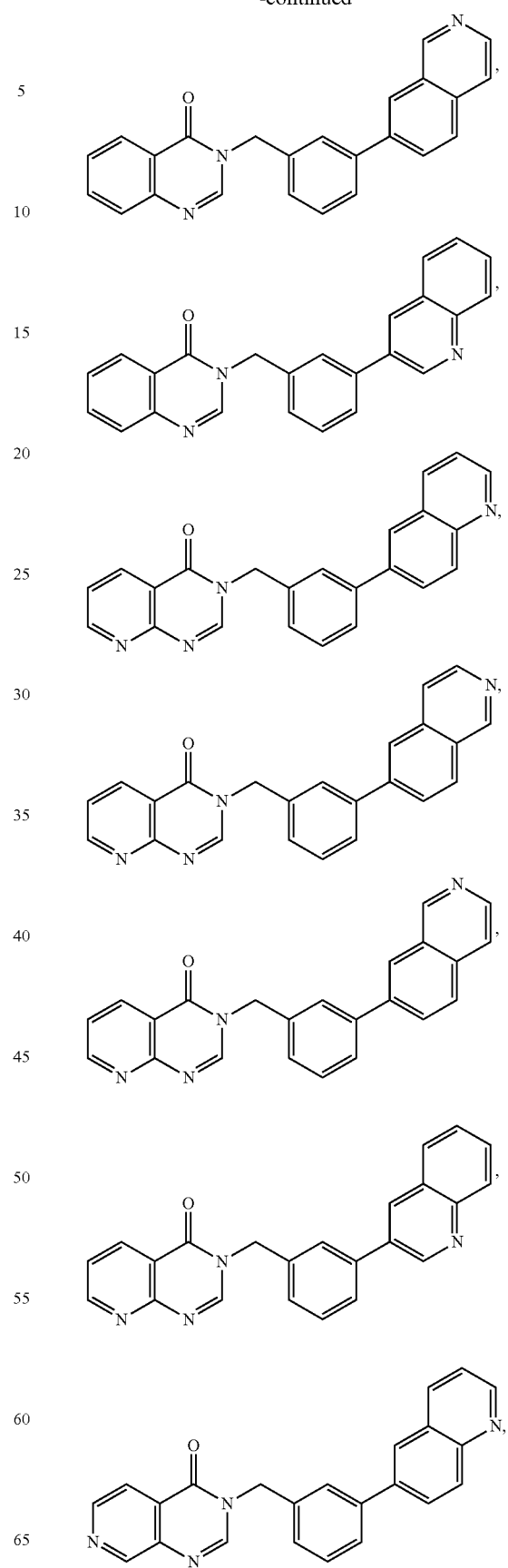

137
-continued
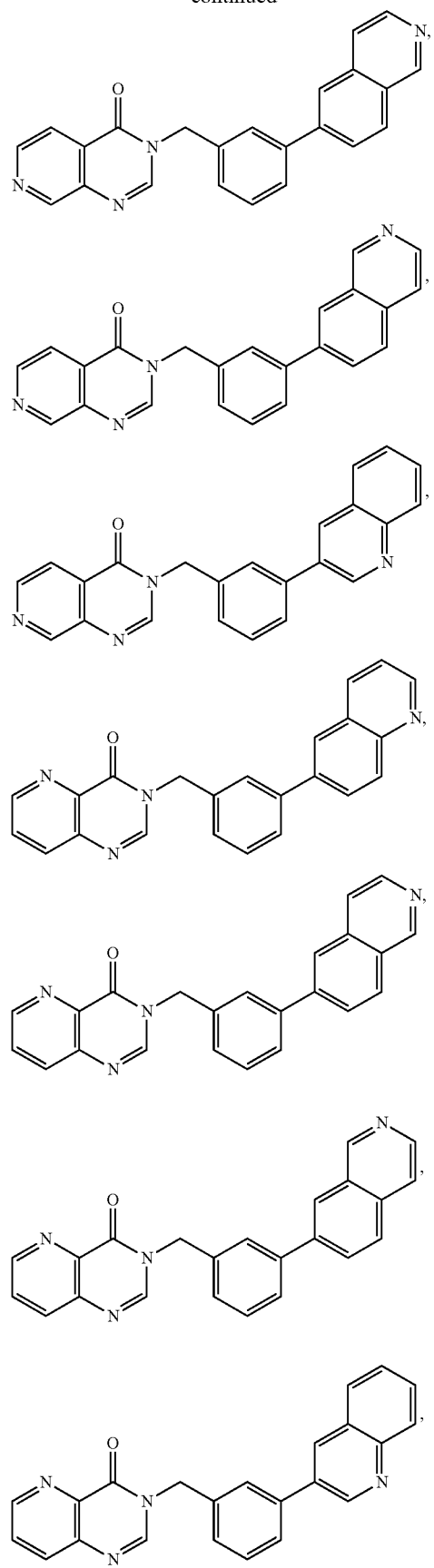
138
-continued
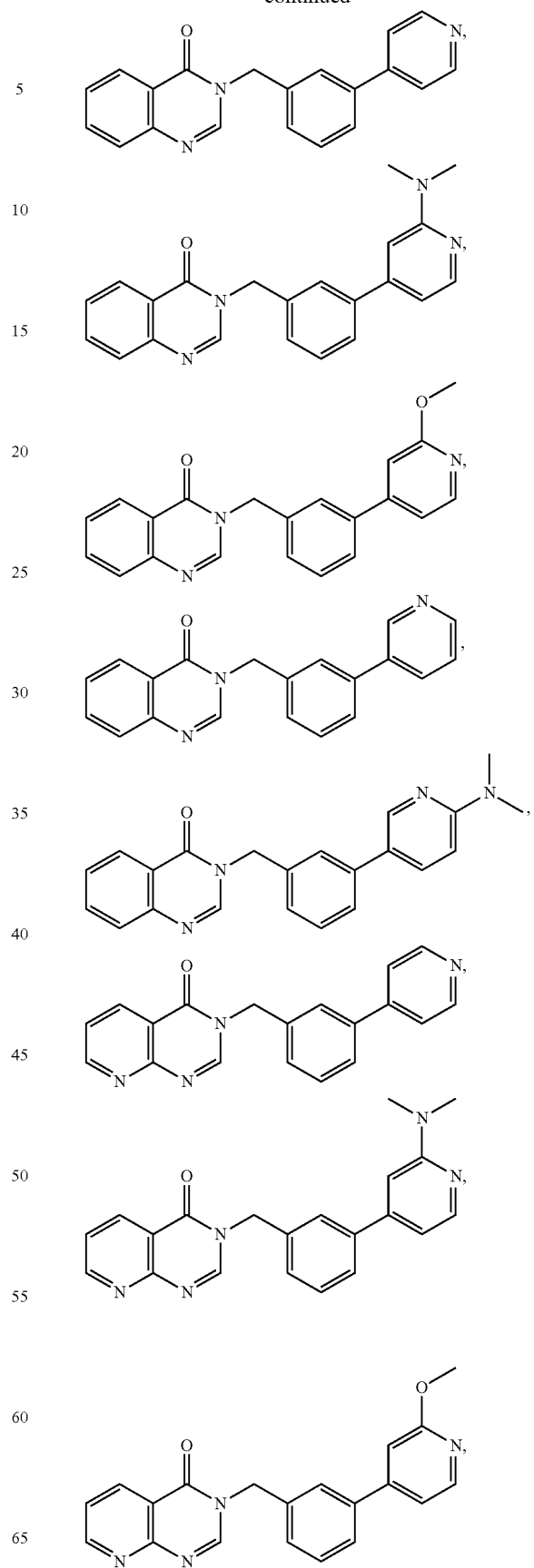

-continued

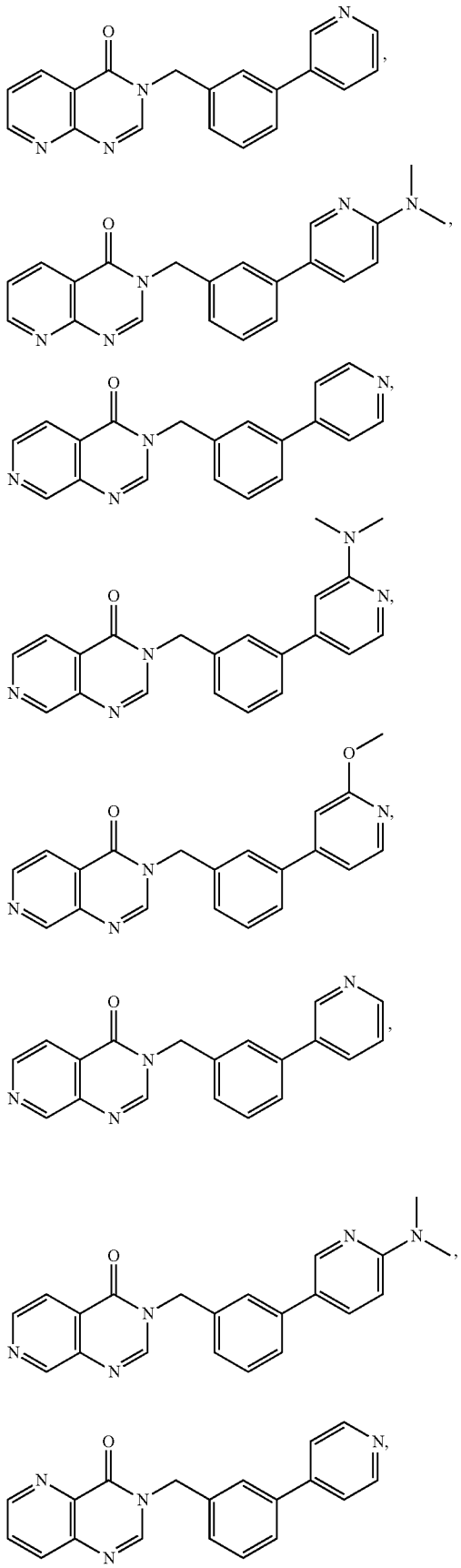

-continued

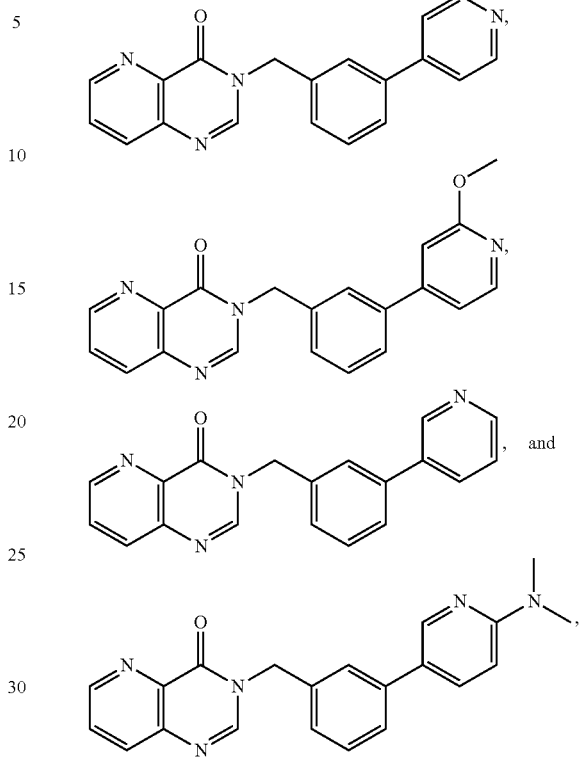

It is contemplated that one or more compounds can optionally be omitted from the disclosed invention.

It is understood that the disclosed compounds can be used in connection with the disclosed methods, compositions, kits, and uses.

It is understood that pharmaceutical acceptable derivatives of the disclosed compounds can be used also in connection with the disclosed methods, compositions, kits, and uses. The pharmaceutical acceptable derivatives of the compounds can include any suitable derivative, such as pharmaceutically acceptable salts as discussed below, isomers, radiolabeled analogs, tautomers, and the like.

4. Muscarinic Acetylcholine Receptor $M_1$ Modulation

The human muscarinic acetylcholine receptor $M_1$ (mAChR $M_1$) is a protein of 479 amino acids encoded by the CHRM1 gene. The molecular weight of the unglycosylated protein is about 51,421 kDa and it is a transmembrane GPCR. As described above, the mAChR $M_1$ is a member of the GPCR Class 1 family, or the rhodopsin-like GPCRs, which are characterized by structural features similar to rhodopsin such as seven transmembrane segments. The muscarinic acetylcholine receptors have the N-terminus oriented to the extracellular face of the membrane and the C-terminus located on the cytoplasmic face. The orthosteric binding for natural ligand, acetylcholine, for mAChRs is believed to be located within a pocket located within the transmembrane segments. The binding of ligands to the orthosteric and allosteric sites can be distinguished using methods such as those described herein and a variety of other methods known to one skilled in the art.

In one aspect, the disclosed compounds potentiate the agonist response (e.g., acetylcholine) of mAChR $M_1$. In a further aspect, the disclosed compounds increase mAChR $M_1$ response to non-maximal concentrations of agonist in the presence of compound compared to the response to agonist in the absence of compound. The potentiation of mAChR $M_1$ activity can be demonstrated by methodology known in the art. For example, activation of mAChR $M_1$ activity can be determined by measurement of calcium flux in response to agonist, e.g. acetylcholine, in cells loaded with a $Ca^{2+}$-sensitive fluorescent dye (e.g., Fluo-4). In a further aspect, the calcium flux was measured as an increase in fluorescent static ratio. In a yet further aspect, positive allosteric modulator activity was analyzed as a concentration-dependent increase in the $EC_{20}$ acetylcholine response (i.e. the response of mAChR $M_1$ at a concentration of acetylcholine that yields 20% of the maximal response).

In one aspect, the disclosed compounds activate mAChR $M_1$ response as an increase in calcium fluorescence in mAChR $M_1$-transfected CHO-K1 cells in the presence of the compound, compared to the response of equivalent CHO-K1 cells in the absence of the compound. For example, a disclosed compound can have an $EC_{50}$ of less than about 10 µM, of less than about 5 µM, of less than about 1 µM, of less than about 500 nM, of less than about 100 nM, or of less than about 50 nM. In a further aspect, the mAChR $M_1$-transfected CHO-K1 cells are transfected with human mAChR $M_1$. In a still further aspect, the mAChR $M_1$-transfected CHO-K1 cells are transfected with rat mAChR $M_1$.

In one aspect, the disclosed compounds exhibit potentiation of mAChR $M_1$ response to acetylcholine as an increase in response to non-maximal concentrations of acetylcholine in CHO-K1 cells transfected with a mammalian mAChR $M_1$ in the presence of the compound, compared to the response to acetylcholine in the absence of the compound. For example, CHO-K1 cells can be transfected with human mAChR $M_1$. For example, CHO-K1 cells can be transfected with rat mAChR $M_1$. For example, a compound can exhibit positive allosteric modulation of mAChR $M_1$ with an $EC_{50}$ of less than about 10,000 nM, of less than about 5,000 nM, of less than about 1,000 nM, of less than about 500 nM, or of less than about 100 nM. Alternatively, the disclosed compounds exhibit potentiation of mAChR $M_1$ response to acetylcholine as an increase in response to non-maximal concentrations of acetylcholine in CHO-K1 cells transfected with human mAChR $M_1$ in the presence of the compound, compared to the response to acetylcholine in the absence of the compound. For example, a compound can exhibit positive allosteric modulation of mAChR $M_1$ with an $EC_{50}$ of less than about 10,000 nM, of less than about 5,000 nM, of less than about 1,000 nM, of less than about 500 nM, of less than about 100 nM, or of less than about 50 nM.

In one aspect, the disclosed compounds are positive allosteric modulators of the mAChR $M_1$. Thus, the compounds of the invention can bind to the muscarinic receptor, and particularly to muscarinic receptor subtype $M_1$, which results in an increased efficacy at that receptor for the endogenous agonist. Thus, by positive allosteric modulation, the compounds indirectly activate the muscarinic receptor subtype $M_1$. In various further aspects, the disclosed compounds exhibit positive allosteric modulation of mAChR $M_1$ response to acetylcholine as an increase in response to non-maximal concentrations of acetylcholine in CHO-K1 cells transfected with a mAChR $M_1$ in the presence of the compound, compared to the response to acetylcholine in the absence of the compound. In a yet further aspect, the disclosed compounds exhibit positive allosteric modulation of the mAChR $M_1$ response to acetylcholine with an $EC_{50}$ of less than about 10,000 nM. In an even further aspect, the disclosed compounds exhibit positive allosteric modulation of the mAChR $M_1$ response to acetylcholine with an $EC_{50}$ of less than about 5,000 nM. In a still further aspect, the disclosed compounds exhibit positive allosteric modulation of the mAChR $M_1$ response to acetylcholine with an $EC_{50}$ of less than about 1,000 nM. In a yet further aspect, the disclosed compounds exhibit positive allosteric modulation of the mAChR $M_1$ response to acetylcholine with an $EC_{50}$ of less than about 500 nM. In an even further aspect, the disclosed compounds exhibit positive allosteric modulation of the mAChR $M_1$ response to acetylcholine with an $EC_{50}$ of less than about 100 nM. In a still further aspect, the $EC_{50}$ for positive allosteric modulation is determined in CHO-K1 cells are transfected with a mAChR $M_1$. In a yet further aspect, the CHO-K1 cells are transfected with a human mAChR $M_1$. In a still further aspect, the CHO-K1 cells are transfected with a rat mAChR $M_1$.

Without wishing to be bound by a particular theory, the disclosed compounds and products of the disclosed methods are believed to bind to an allosteric site distinct from the orthosteric binding site. Further, without wishing to be bound by particular theory, the disclosed compounds and products of the disclosed methods can bind to an allosteric site that comprises portions of one or more extracellular loops and/or transmembrane segments, and is distinct from the orthosteric binding site. In a further aspect, without wishing to be bound by a particular theory, the disclosed compounds and products of the disclosed methods can bind to an allosteric site that comprises portions of one or more intracellular loops and/or transmembrane segments, and is distinct from the orthosteric binding site. In a still further aspect, without wishing to be bound by particular theory, the disclosed compounds and products of the disclosed methods can bind to an allosteric site that comprises portions of segments, amino acids, or sub-domains of the mAChR $M_1$ protein that potentiates interactions of the protein with other proteins, e.g. G-proteins.

Previous attempts to develop agonists that are highly selective for individual mAChR subtypes have failed because of the high conservation of the orthosteric ACh binding site. To circumvent problems associated with targeting the highly conserved orthosteric ACh binding site, it is believed that developing compounds that act at less highly conserved allosteric mAChR sites will afford highly selective activators/modulators.

In various further aspects, the compound activates mAChR $M_1$ response in mAChR $M_1$-transfected CHO-K1 cells with an $EC_{50}$ less than the $EC_{50}$ for one or more of mAChR $M_2$, mAChR $M_3$, mAChR $M_4$, or mAChR $M_5$ response in mAChR $M_2$, $M_3$, $M_4$ or $M_5$-transfected CHO-K1 cells. That is, a disclosed compound can have selectivity for the mAChR $M_1$ receptor vis-á-vis one or more of the mAChR $M_2$, $M_3$, $M_4$ or $M_5$ receptors. For example, in one aspect, a disclosed compound can activate mAChR $M_1$ response with an $EC_{50}$ of about 5-fold less than that for mAChR $M_2$, of about 10-fold less than that for mAChR $M_2$, of about 20-fold less than that for mAChR $M_2$, of about 30-fold less than that for mAChR $M_2$, of about 50-fold less than that for mAChR $M_2$, of about 100-fold less than that for mAChR $M_2$, or of >100-fold less than that of that for mAChR $M_2$. In a further aspect, a disclosed compound can activate mAChR $M_1$ response with an $EC_{50}$ of about 5-fold less than that for mAChR $M_3$, of about 10-fold less than that for mAChR $M_3$, of about 20-fold less than that for $M_3$, of about 30-fold less than that for mAChR $M_3$, of about 50-fold less than that for mAChR $M_3$, of about 100-fold less than that for mAChR $M_3$, or of >100-fold less than that of that for mAChR $M_3$. In a further aspect, a disclosed compound can activate mAChR $M_1$ response with an $EC_{50}$ of about 5-fold less than that for mAChR $M_4$, of about 10-fold less than that for mAChR $M_4$, of about 20-fold less than that for $M_4$, of about 30-fold less than that for mAChR $M_4$, of about 50-fold less than that for mAChR $M_4$, of about 100-fold less than that for mAChR $M_4$, or of >100-fold less than that of that for mAChR $M_4$. In a further aspect, a disclosed compound can activate mAChR $M_1$ response with an $EC_{50}$ of about 5-fold less than that for mAChR $M_5$, of about 10-fold less than that for mAChR $M_5$, of about 20-fold less than that for mAChR $M_5$, of about 30-fold less than that for mAChR $M_5$, of about 50-fold less than that for mAChR $M_5$, of about 100-fold less than that for mAChR $M_5$, or of >100-fold less than that of that for mAChR $M_5$. In a further aspect, a disclosed compound can activate mAChR $M_1$ response with an $EC_{50}$ of about 5-fold less than that for the mAChR $M_2$, $M_3$, $M_4$ or $M_5$ receptors, of about 10-fold less than that for the mAChR $M_2$, $M_3$, $M_4$ or $M_5$ receptors, of about 20-fold less than that for the mAChR $M_2$, $M_3$, $M_4$ or $M_5$ receptors, of about 30-fold less than that for the mAChR $M_2$, $M_3$, $M_4$ or $M_5$ receptors, of about 50-fold less than that for the mAChR $M_2$, $M_3$, $M_4$ or $M_5$ receptors, of about 100-fold less than that for the mAChR $M_2$, $M_3$, $M_4$ or $M_5$ receptors, or of >100-fold than that for the mAChR $M_2$, $M_3$, $M_4$ or $M_5$ receptors. In various further aspects, the compound activates mAChR $M_1$ response in mAChR $M_1$-transfected CHO-K1 cells and is inactive for one or more of mAChR $M_1$, mAChR $M_3$, mAChR $M_4$, or mAChR $M_5$ response in mAChR $M_2$, $M_3$, $M_4$ or $M_5$-transfected CHO-K1 cells.

In various further aspects, the compound activates mAChR $M_1$ response in $M_1$-transfected CHO-K1 cells with an $EC_{50}$ of less than about 10 µM and exhibits a selectivity for the $M_1$ receptor vis-á-vis one or more of the mAChR $M_2$, $M_3$, $M_4$ or $M_5$ receptors. For example, in one aspect, the compound can have an $EC_{50}$ of less than about 10 µM, of less than about 5 µM, of less than about 1 µM, of less than about 500 nM, of less than about 100 nM, or of less than about 50 nM; and the compound can also activate mAChR $M_1$ response with an $EC_{50}$ of about 5-fold less than that for mAChR $M_2$, of about 10-fold less than that for mAChR $M_2$, of about 20-fold less than that for mAChR $M_2$, of about 30-fold less than that for mAChR $M_2$, or of about 50-fold less than that for mAChR $M_2$. In a further aspect, the compound can have an $EC_{50}$ of less than about 10 µM, of less than about 5 µM, of less than about 1 µM, of less than about 500 nM, of less than about 100 nM, or of less than about 50 nM; and the compound can also activate mAChR $M_1$ response with an $EC_{50}$ of about 5-fold less than that for mAChR $M_3$, of about 10-fold less than that for mAChR $M_3$, of about 20-fold less than that for mAChR $M_3$, of about 30-fold less than that for mAChR $M_3$, or of about 50-fold less than that for mAChR $M_3$. In a further aspect, the compound can have an $EC_{50}$ of less than about 10 µM, of less than about 5 µM, of less than about 1 µM, of less than about 500 nM, of less than about 100 nM, or of less than about 50 nM; and the compound can also activate mAChR $M_1$ response with an $EC_{50}$ of about 5-fold less than that for mAChR $M_4$, of about 10-fold less than that for mAChR $M_4$, of about 20-fold less than that for mAChR $M_4$, of about 30-fold less than that for mAChR $M_4$, or of about 50-fold less than that for mAChR $M_4$. In a further aspect, the compound can have an $EC_{50}$ of less than about 10 µM, of less than about 5 µM, of less than about 1 µM, of less than about 500 nM, of less than about 100 nM, or of less than about 50 nM; and the compound can also activate mAChR $M_1$ response with an $EC_{50}$ of about 5-fold less than that for mAChR $M_5$, of about 10-fold less than that for mAChR $M_5$, of about 20-fold less than that for mAChR $M_5$, of about 30-fold less than that for mAChR $M_5$, or of about 50-fold less than that for mAChR $M_5$. In a further aspect, the compound can have an $EC_{50}$ of less than about 10 µM, of less than about 5 µM, of less than about 1 µM, of less than about 500 nM, of less than about 100 nM, or of less than about 50 nM; and the compound can also activate mAChR $M_1$ response with an $EC_{50}$ of about 5-fold less than that for the mAChR $M_2$, $M_3$, $M_4$ or $M_5$ receptors, of about 10-fold less than that for the mAChR $M_2$, $M_3$, $M_4$ or $M_5$ receptors, of about 20-fold less than that for the mAChR $M_2$, $M_3$, $M_4$ or $M_5$ receptors, of about 30-fold less than that for the mAChR $M_2$, $M_3$, $M_4$ or $M_5$ receptors, or of about 50-fold less than that for the mAChR $M_2$, $M_3$, $M_4$ or $M_5$ receptors.

C. Methods of Making the Compounds

In one aspect, the invention relates to methods of making compounds useful as positive allosteric activators of the mAChR $M_1$ receptor, which can be useful in the treatment neurological and psychiatric disorders associated with muscarinic acetylcholine dysfunction and other diseases in which muscarinic acetylcholine receptors are involved. In one aspect, the invention relates to the disclosed synthetic manipulations. In a further aspect, the disclosed compounds comprise the products of the synthetic methods described herein.

In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one product of the disclosed methods with a pharmaceutically acceptable carrier or diluent.

The compounds of this invention can be prepared by employing reactions as shown in the disclosed schemes, in addition to other standard manipulations that are known in the literature, exemplified in the experimental sections or clear to one skilled in the art. For clarity, examples having a fewer substituent can be shown where multiple substituents are allowed under the definitions disclosed herein. Thus, the following examples are provided so that the invention might be more fully understood, are illustrative only, and should not be construed as limiting.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed compositions, kits, and uses.

1. Synthesis Route 1

In one aspect, substituted 3-benzylquinazolin-4(3H)-one analogues of the present invention can be prepared generically by the synthesis scheme as shown below. All positions are defined herein.

SCHEME 1A

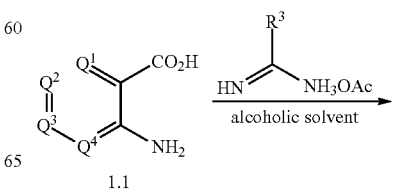

1.1

-continued

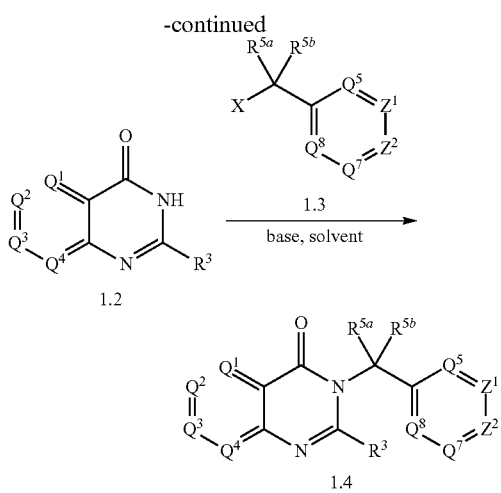

Compounds are represented in generic form, with substituents as noted in compound descriptions elsewhere herein. A more specific example is set forth below.

SCHEME 1B

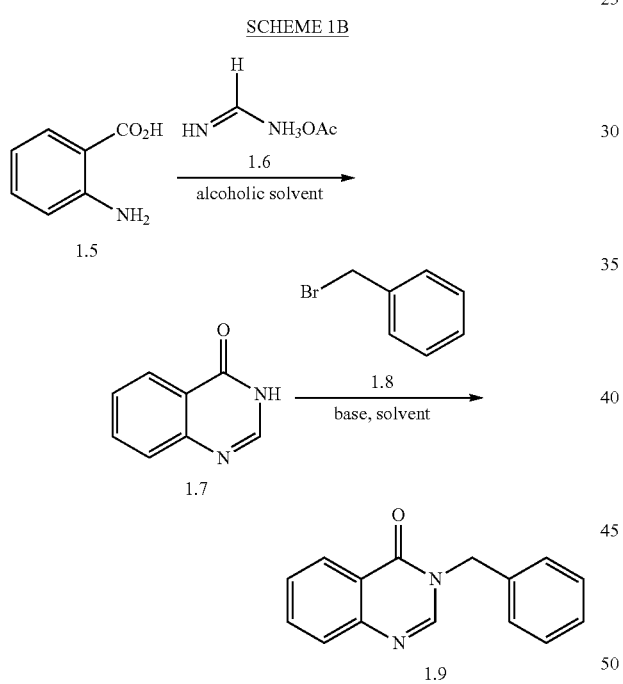

In one aspect, compounds of type 1.4, and similar compounds, can be prepared according to reaction Scheme 1B above. Thus, compounds of type 1.7 can be prepared by a condensation reaction of an appropriate anthranilic acid or heterocyclic 2-aminobenzoic acid derivative, e.g. 1.5 as shown above. Appropriate anthranilic acid or heterocyclic 2-aminobenzoic acid derivatives are commercially available or prepared by methods known to one skilled in the art. The reaction is carried out using an appropriate alcohol solvent, e.g. methanol or ethanol, in the presence of a suitable amidine acetate salt, e.g. 1.6 as shown above, which is commercially available or prepared by methods known to one skilled in the art. A compound of type 1.9 can be prepared by alkylation of a compound of type 1.7. For example, as shown above, such an alkylation reaction can be accomplished using a suitable base, e.g. potassium carbonate or cesium carbonate, in a suitable aprotic solvent, e.g. dimethylformamide or acetonitrile, and a functionalized bromide or mesylate intermediate, e.g. 1.8 as shown above. As can be appreciated by one skilled in the art, the above reaction provides an example of a generalized approach wherein compounds similar in structure to the specific reactants above (compounds similar to compounds of type 1.5, 1.6 and 1.8), can be substituted in the reaction to provide substituted 3-benzylquinazolin-4(3H)-one analogues similar to Formula 1.4.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

2. Synthesis Route 2

In one aspect, substituted 3-benzylquinazolin-4(3H)-one analogues of the present invention can be prepared generically by the synthesis scheme as shown below. All positions are defined herein.

SCHEME 2A

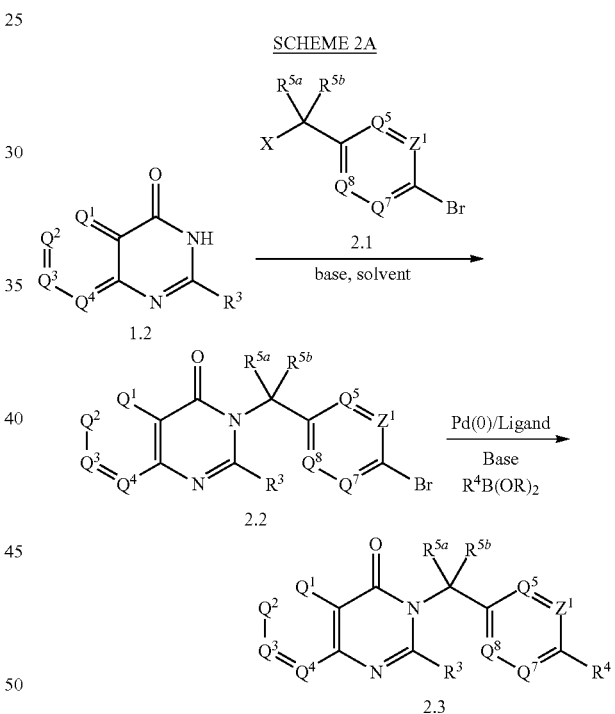

Compounds are represented in generic form, with substituents as noted in compound descriptions elsewhere herein. A more specific example is set forth below.

SCHEME 2B

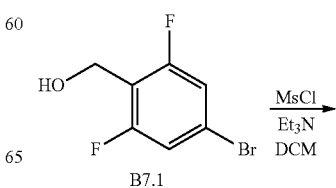

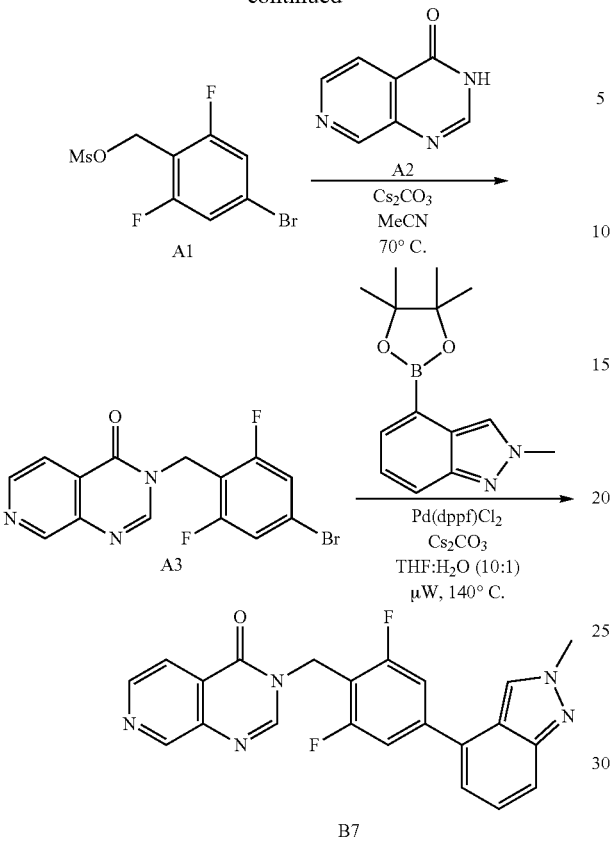

manipulation, and/or component can be optionally omitted from the invention. It is understood that a disclosed method can be used to provide the disclosed compounds. It is also understood that the products of the disclosed methods can be employed in the disclosed methods of using.

3. Intermediate Route

In one aspect, intermediates useful in the synthesis of substituted 3-benzylquinazolin-4(3H)-one analogues of the present invention can be prepared generically by the synthesis scheme as shown below. All positions are defined herein.

SCHEME 3A

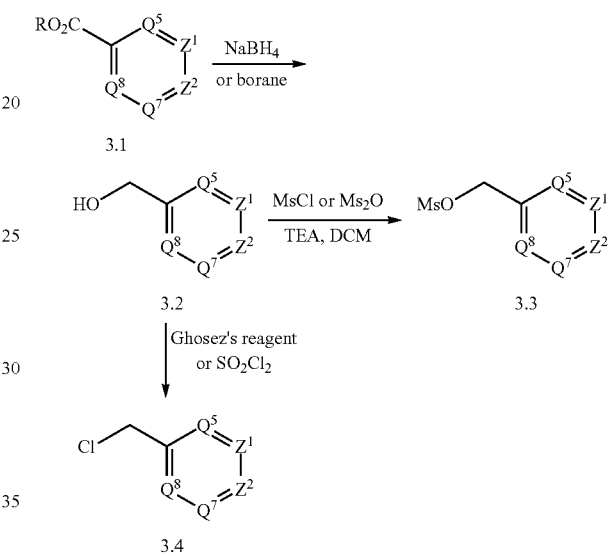

In one aspect, compounds of type 2.3, and similar compounds, can be prepared according to reaction Scheme 2B above. Thus, compounds of type A1 can be prepared by activating an appropriate alcohol derivative, e.g. B7.1 as shown above. Appropriate alcohol derivatives are commercially available or prepared by methods known to one skilled in the art. The reaction is carried out using a suitable sulfonyl chloride, e.g. mesyl chloride as shown above, in an appropriate solvent, e.g. dichloromethane, in the presence of a suitable base, e.g. triethylamine. A compound of type A3 can be prepared by alkylation of a compound of type A2. For example, as shown above, such an alkylation reaction can be accomplished using a suitable base, e.g. cesium carbonate, in a suitable aprotic solvent, e.g. acetonitrile, and a functionalized quinazoline intermediate, e.g. A2 as shown above. A compound of type B7 can be prepared by Suzuki reaction of a compound of type A3. For example, as shown above, such a Suzuki reaction can be accomplished using a suitable boronic acid derivative, e.g. 2-methyl-4-(4,4,5,5-tetramethyl-1,3,2-dioxaborolan-2-yl)-2H-indazole, with a suitable palladium catalyst, e.g. Pd(dppf)Cl$_2$, with a suitable base, e.g. cesium carbonate, in an appropriate solvent mixture, e.g. THF: H$_2$O 10:1, at a suitable temperature, e.g. 140° C. As can be appreciated by one skilled in the art, the above reaction provides an example of a generalized approach wherein compounds similar in structure to the specific reactants above (compounds similar to compounds of type B7.1 and A2), can be substituted in the reaction to provide substituted 3-benzylquinazolin-4(3H)-one analogues similar to Formula 2.3.

It is contemplated that each disclosed method can further comprise additional steps, manipulations, and/or components. It is also contemplated that any one or more step, Compounds are represented in generic form, with substituents as noted in compound descriptions elsewhere herein. A more specific example is set forth below.

SCHEME 3B

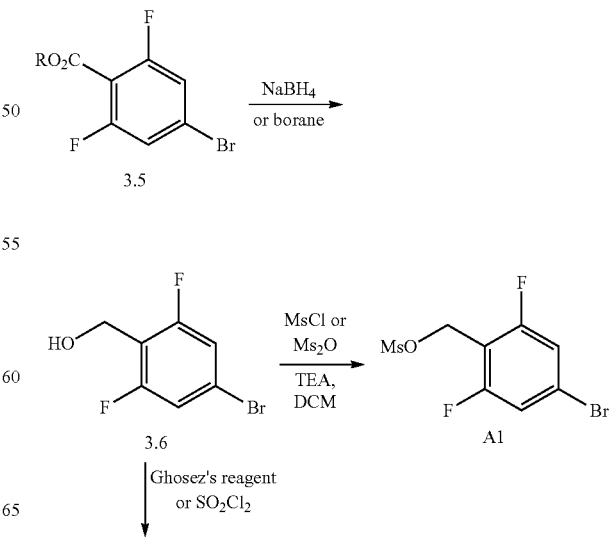

149

-continued

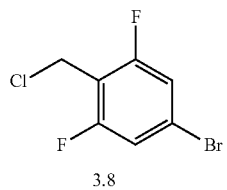

3.8

In one aspect, compounds of type 3.3 or 3.4, and similar compounds, can be prepared according to reaction Scheme 3B above. Thus, compounds of type 3.6 can be prepared by a reduction reaction of an appropriate carboxylic acid or ester derivative, e.g. 3.5 as shown above. Appropriate carboxylic acid or ester derivatives are commercially available or prepared by methods known to one skilled in the art. The reaction is carried out in the presence of a suitable reducing agent, e.g. sodium borohydride or borane as shown above. A compound of type A1 can be prepared by activation of a compound of type 3.6. For example, as shown above, such an activation can be accomplished using an activating agent, e.g. mesyl chloride or mesyl anhydride, in a suitable solvent, e.g. dichloromethane, with a suitable base, e.g. triethylamine as shown above. Alternatively, a compound of type 3.8 can be prepared by a substitution reaction of a compound of type 3.6. For example, as shown above, such a substitution reaction can be accomplished using an appropriate substitution reagent, e.g. Ghosez's reagent or thionyl chloride. As can be appreciated by one skilled in the art, the above reaction provides an example of a generalized approach wherein compounds similar in structure to the specific reactants above (compounds similar to compounds of type 3.5), can be substituted in the reaction to provide substituted 3-benzylquinazolin-4(3H)-one analogues similar to Formulas 3.3 or 3.4.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

4. Chiral Resolution

The disclosed methods of making can provide compounds that can contain one or more asymmetric centers and, thus, potentially give rise to enantiomers and diastereomers. Unless stated to the contrary, the compounds prepared by the disclosed methods include all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included.

In one aspect, the disclosed methods of making can provide racemic or scalemic mixtures that can be resolved to pure or substantially pure enantiomers using chiral phase chromatography or other suitable methods known to one skilled in the art. As known to one skilled in the art, a variety specific columns and/or mobile phases can affect the desired resolution of enantiomers, and the specific choice can be determined by one skilled in the art. As known to one skilled in the art, chiral chromatography can be carried out in a variety of formats (e.g. SFC, HPLC, and SMB), and other formats can be used to obtain similar results. Moreover, other suitable methods known to one skilled in the art for the separation and isolation of individual enantiomers from a racemic or scalemic mixture can be used to isolate specific enantiomers as needed

150

D. Pharmaceutical Compositions

In one aspect, the invention relates to pharmaceutical compositions comprising the disclosed compounds. That is, a pharmaceutical composition can be provided comprising an effective amount of at least one disclosed compound, at least one product of a disclosed method, or a pharmaceutically acceptable salt, solvate, hydrate, or polymorph thereof, and a pharmaceutically acceptable carrier. In one aspect, the invention relates to pharmaceutical compositions comprising a pharmaceutically acceptable carrier and an effective amount of at least one disclosed compound; or a pharmaceutically acceptable salt, hydrate, solvate, or polymorph thereof.

In one aspect, the invention relates to a pharmaceutical composition comprising a therapeutically effective amount of at least one compound having a structure represented by a formula:

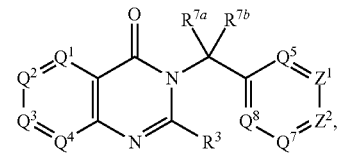

wherein each of $Z^1$ and $Z^2$ are independently selected from $Q^6$ or $CR^4$, provided that $Z^1$ and $Z^2$ are not simultaneously $Q^6$ or simultaneously $CR^4$; wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-1-C6 alkyl, C1-C6 polyhaloalkyl-oxy-1-C6 alkyl, and C1-CC6 dialkylamino; wherein $Q^5$ is selected from N and $CR^{2a}$; wherein $Q^6$ is selected from N and $CR^{2b}$; wherein $Q^7$ is selected from N and $CR^{2c}$; wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-1-C6 alkyl, C1-C6 dialkylamino, —C(OH)R$^{20a}$R$^{20b}$, and —SO$_2$R$^{30}$; wherein each of R$^{20a}$ and R$^{20b}$ is independently selected from hydrogen, C1-C3 alkyl, C1-C3 haloalkyl; and C1-C3 polyhaloalkyl; and wherein R$^3$ is selected from C1-C3 alkyl, C1-C3 haloalkyl; and C1-C3 polyhaloalkyl; wherein R$^3$ is selected from hydrogen, C1-C3 alkyl, C1-C3 haloalkyl, C1-C3 polyhaloalkyl, cyclopropyl, and Ar$^1$; wherein Ar$^1$ is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein R$^4$ is selected from Ar$^2$, —L$^2$—Ar$^2$, and Cy$^1$; wherein L$^2$ is selected from —CR$^{8a}$R$^{8b}$—, —O—, —NR$^9$—, —(S═O)—, and —(SO$_2$)—; wherein each of R$^{8a}$ and R$^{8b}$ is independently selected from hydrogen, C1-C6 alkyl, C1-C6 haloalkyl, and C1-C6 polyhaloalkyl; wherein $R^9$ is selected from hydrogen and C1-C6 alkyl; wherein $Ar^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2, 3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein $Ar^2$ is substituted with 0-3 substituents independently selected from halogen, hydroxyl, cyano, $-NH_2$, C1-C6 alkyl, C1-C6 alkoxy, C1-C6 haloalkyl, C1-C6 polyhaloalkyl, C1-C6 alkylamino, and C1-C6 dialkylamino; or wherein $Ar^2$ is pyrazolyl substituted with substituted with 1-3 substituents independently selected from halogen, hydroxyl, cyano, $-NH_2$, C1-C6 alkyl, C1-C6 alkoxy, C1-C6 haloalkyl, C1-C6 polyhaloalkyl, C1-C6 alkylamino, and C1-C6 dialkylamino; and wherein $Cy^1$ is a C2-C5 heterocycloalkyl or C2-C5 heterocycloalkenyl, and wherein $Cy^1$ is substituted with 0-3 substituents independently selected from halogen, hydroxyl, cyano, $-NH_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of $R^{7a}$ and $R^{7b}$ is independently selected from hydrogen, C1-C6 alkyl, C1-C6 haloalkyl, and C1-C6 polyhaloalkyl; or pharmaceutically acceptable salt, solvate, or polymorph thereof; and a pharmaceutically acceptable carrier.

In various aspects, the invention relates to a pharmaceutical composition comprising a therapeutically effective amount of at least one compound having a structure represented by a formula:

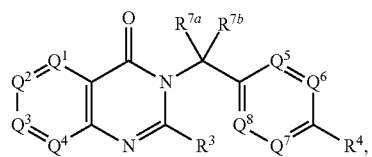

wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$; wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$ when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, $-C(OH)R^{20a}R^{20b}$, and $-SO_2R^{30}$; wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with 0-3 substituents independently selected from halogen, hydroxyl, cyano, $-NH_2$, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from $Ar^2$, $-L^2-Ar^2$, and $Cy^1$; wherein $L^2$ is selected from $-CR^{8a}R^{8b}-$, $-O-$, $-NR^9-$, $-S-$, $-(S=O)-$, and $-(SO_2)-$; wherein each of $R^{8a}$ and $R^{8b}$ is independently selected from hydrogen, C1-C6 alkyl, C1-C6 haloalkyl, and C1-C6 polyhaloalkyl; wherein $R^9$ is selected from hydrogen and C1-C6 alkyl; wherein $Ar^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2, 3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein $Ar^2$ is substituted with 0-3 substituents independently selected from halogen, hydroxyl, cyano, $-NH_2$, C1-C6 alkyl, C1-C6 alkoxy, C1-C6 haloalkyl, C1-C6 polyhaloalkyl, C1-C6 alkylamino, and C1-C6 dialkylamino; or wherein $Ar^2$ is pyrazolyl substituted with substituted with 1-3 substituents independently selected from halogen, hydroxyl, cyano, $-NH_2$, C1-C6 alkyl, C1-C6 alkoxy, C1-C6 haloalkyl, C1-C6 polyhaloalkyl, C1-C6 alkylamino, and C1-C6 dialkylamino; and wherein $Cy^1$ is a C2-C5 heterocycloalkyl or C2-C5 heterocycloalkenyl, and wherein $Cy^1$ is substituted with 0-3 substituents independently selected from halogen, hydroxyl, cyano, $-NH_2$, C1-C6 alkyl, C1-C6 alkoxy, C1-6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of $R^{7a}$ and $R^{7b}$ is independently selected from hydrogen, C1-C6 alkyl, C1-C6 haloalkyl, and C1-C6 polyhaloalkyl; or pharmaceutically acceptable salt, solvate, or polymorph thereof; and a pharmaceutically acceptable carrier.

In various aspects, the invention relates to a pharmaceutical composition comprising a therapeutically effective amount of at least one compound having a structure represented by a formula:

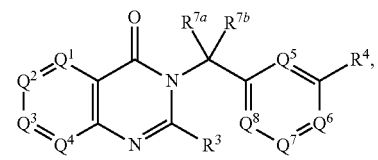

wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$; wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO$_2R^{30}$; wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from $Ar^2$, —$L^2$—$Ar^2$, and $Cy^1$; wherein $L^2$ is selected from —$CR^{8a}R^{8b}$—, —O—, —NR$^9$—, —S—, —(S=O)—, and —(SO$_2$)—; wherein each of $R^{8a}$ and $R^{8b}$ is independently selected from hydrogen, C1-C6 alkyl, C1-C6 haloalkyl, and C1-C6 polyhaloalkyl; wherein $R^9$ is selected from hydrogen and C1-C6 alkyl; wherein $Ar^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2,3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein $Ar^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein $Ar^2$ is pyrazolyl substituted with substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein $Cy^1$ is a C2-C5 heterocycloalkyl or C2-C5 heterocycloalkenyl, and wherein $Cy^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of $R^{7a}$ and $R^{7b}$ is independently selected from hydrogen, C1-C6 alkyl, C1-C6 haloalkyl, and C1-C6 polyhaloalkyl; or pharmaceutically acceptable salt, solvate, or polymorph thereof; and a pharmaceutically acceptable carrier.

In a further aspect, the effective amount is a therapeutically effective amount. In a still further aspect, the effective amount is a prophylactically effective amount. In a still further aspect, the pharmaceutical composition comprises a compound that is a product of a disclosed method of making.

In a further aspect, the pharmaceutical composition exhibits potentiation of mAChR $M_1$ with an $EC_{50}$ of less than about 10,000 nM. In a still further aspect, the pharmaceutical composition exhibits potentiation of mAChR $M_1$ with an $EC_{50}$ of less than about 5,000 nM. In an even further aspect the pharmaceutical composition exhibits positive allosteric modulation of mAChR $M_1$ with an $EC_{50}$ of less than about 1,000 nM. In a further aspect, the pharmaceutical composition exhibits potentiation of mAChR $M_1$ with an $EC_{50}$ of less than about 500 nM. In a yet further aspect, the pharmaceutical composition exhibits potentiation of mAChR $M_1$ with an $EC_{50}$ of less than about 100 nM. In a further aspect, the pharmaceutical composition exhibits potentiation of mAChR $M_1$ with an $EC_{50}$ of between from about 10,000 nM to about 1 nM. In a yet further aspect, the pharmaceutical composition exhibits potentiation of mAChR $M_1$ with an $EC_{50}$ of between from about 1,000 nM to about 1 nM. In a still further aspect, the pharmaceutical composition exhibits potentiation of mAChR $M_1$ with an $EC_{50}$ of between from about 100 nM to about 1 nM. In an even further aspect, the pharmaceutical composition exhibits potentiation of mAChR $M_1$ with an $EC_{50}$ of between from about 10 nM to about 1 nM. In a still further aspect, potentiation of the mAChR $M_1$ response is positive allosteric modulation of the mAChR $M_1$ response.

In one aspect, the pharmaceutical composition is used to treat a mammal. In a yet further aspect, the mammal is a human. In a further aspect, the mammal has been diagnosed with a need for treatment of the disorder prior to the administering step. In a further aspect, the mammal has been identified to be in need of treatment of the disorder. In a further aspect, the pharmaceutical composition is used to treat a neurological and/or psychiatric disorder. In a yet further aspect, the disorder is associated with mAChR $M_1$ dysfunction.

In a further aspect, the pharmaceutical composition is used to treat a neurological and/or psychiatric disorder. In a still further aspect, the disorder is Alzheimer's disease. In a yet further aspect, disorder is selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders. In an even further aspect, the disorder is a neurological and/or psychiatric disorder associated with $M_1$ receptor activity.

In a further aspect, the pharmaceutical composition is used to treat a disorder selected from conduct disorder, disruptive behavior disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require positive allosteric modulation of mAChR $M_1$ receptor activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for modulating mAChR $M_1$ receptor activity (e.g., treatment of one or more neurological and/or psychiatric disorder associated with mAChR $M_1$ receptor dysfunction) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

E. Methods of Using the Compounds and Compositions

Also provided is a method of use of a disclosed compound, composition, or medicament. In one aspect, the method of use is directed to the treatment of a disorder. In a further aspect, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

In one aspect, the compounds can be coadministered with anti-Alzheimer's agents, beta-secretase inhibitors, gamma-secretase inhibitors, orthosteric muscarinic agonists, muscarinic potentiators, cholinesterase inhibitors, HMG-CoA reductase inhibitors, NSAIDs and anti-amyloid antibodies. In a further aspect, the compounds can be administered in combination with sedatives, hypnotics, anxiolytics, antipsychotics (typical and atypical), selective serotonin reuptake inhibitors (SSRIs), monoamine oxidase inhibitors (MAOIs), 5-HT2 antagonists, GlyT1 inhibitors and the like such as, but not limited to: risperidone, clozapine, haloperidol, fluoxetine, prazepam, xanomeline, lithium, phenobarbitol, and salts thereof and combinations thereof.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of disorders wherein the patient or subject would benefit from selective positive allosteric modulation of the $M_1$ receptor. In one aspect, a treatment can include selective $M_1$ receptor modulation to an extent effective to affect cholinergic activity. Thus, a disorder can be associated with cholinergic activity, for example cholinergic hypofunction. In one aspect, provided is a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of one or more disorders, for which muscarinic receptor activation is predicted to be beneficial, in a subject comprising the step of administering to the subject at least one disclosed compound; at least one disclosed pharmaceutical composition; and/or at least one disclosed product in a dosage and amount effective to treat the disorder in the subject.

The invention is directed at the use of described chemical compositions to treat diseases or disorders in patients (preferably human) wherein muscarinic receptor activation would be predicted to have a therapeutic effect, such as Alzheimer's disease (both palliative cognitive and disease-modifying), cognitive impairment, schizophrenia, pain disorders (including acute pain, neuropathic pain and inflammatory pain), and sleep disorders, by administering one or more disclosed compounds or products.

In one aspect, provided is a method for treating or preventing anxiety, comprising: administering to a subject at least one disclosed compound; at least one disclosed pharmaceutical composition; and/or at least one disclosed product in a dosage and amount effective to treat the disorder in the subject. At present, the fourth edition of the *Diagnostic and Statistical Manual of Mental Disorders* (DSM-IV) (1994, American Psychiatric Association, Washington, D.C.), provides a diagnostic tool for disorders including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified.

Also provided is a method for the treatment of a disorder in a mammal comprising the step of administering to the mammal at least one disclosed compound, composition, or medicament.

In one aspect, the NMDA receptor is central to a wide range of CNS processes, and plays a role in a variety of disease states in humans or other species. The action of the $M_1$ receptor potentiates NMDA receptor function, which increases activation of the NMDA receptor following glutamate release from the presynaptic terminal. Changes in NMDA-mediated neurotransmission have been implicated in certain neuropsychiatric disorders such as dementia, depression and psychoses, for example schizophrenia, and learning and memory disorders, for example attention deficit disorders and autism.

In one aspect, the disclosed compounds have utility in treating a variety of neurological and psychiatric disorders, including one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anesthetics, amphetamine and other psychostimulants and cocaine) psychosis psychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age-related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa and compulsive eating disorders; bipolar disorders, mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorders; learning disorders, pervasive developmental disorder including autistic disorder, attention disorders including attention-deficit hyperactivity disorder (ADHD) and conduct disorder; NMDA receptor-related disorders such as autism, depression, benign forgetfulness, childhood learning disorders and closed head injury; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias [including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalized myoclonus and focal myoclonus), tics (including simple tics, complex tics and symptomatic tics), and dystonia (including generalized dystonia such as idiopathic dystonia, drug-induced dystonia, symptomatic dystonia and paroxysmal dystonia, and focal dystonia such as blepharospasm, oromandibular dystonia, spasmodic dysphonia, spasmodic torticollis, axial dystonia, dystonic writer's cramp and hemiplegic dystonia)]; urinary incontinence; neuronal damage including ocular damage, retinopathy or macular degeneration of the eye, tinnitus, hearing impairment and loss, and brain edema; emesis; and sleep disorders including insomnia and narcolepsy.

In a specific aspect, the present invention provides a method for treating cognitive disorders, comprising: administering to a patient in need thereof an effective amount of a compound of the present invention. Particular cognitive disorders are dementia, delirium, amnestic disorders and age-related cognitive decline. At present, the text revision of the fourth edition of the *Diagnostic and Statistical Manual of Mental Disorders* (DSM-IV-TR) (2000, American Psychiatric Association, Washington DC) provides a diagnostic tool that includes cognitive disorders including dementia, delirium, amnestic disorders and age-related cognitive decline. As used herein, the term "cognitive disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "cognitive disorders" is intended to include like disorders that are described in other diagnostic sources. In another specific embodiment, the present invention provides a method for treating anxiety disorders, comprising: administering to a patient in need thereof an effective amount of a compound of the present invention. Particular anxiety disorders are generalized anxiety disorder, obsessive-compulsive disorder and panic attack. At present, the text revision of the fourth edition of the *Diagnostic and Statistical Manual of Mental Disorders* (DSM-IV-TR) (2000, American Psychiatric Association, Washington D.C.) provides a diagnostic tool that includes anxiety disorders are generalized anxiety disorder, obsessive-compulsive disorder and panic attack. As used herein, the term "anxiety disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "anxiety disorders" is intended to include like disorders that are described in other diagnostic sources.

In a further specific aspect, the present invention provides a method for treating schizophrenia or psychosis comprising: administering to a patient in need thereof an effective amount of a compound of the present invention. Particular schizophrenia or psychosis pathologies are paranoid, disorganized, catatonic or undifferentiated schizophrenia and substance-induced psychotic disorder. At present, the text revision of the fourth edition of the *Diagnostic and Statistical Manual of Mental Disorders* (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-W-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

In a further specific aspect, the present invention provides a method for treating substance-related disorders and addictive behaviors, comprising: administering to a patient in need thereof an effective amount of a compound of the present invention. Particular substance-related disorders and addictive behaviors are persisting dementia, persisting amnestic disorder, psychotic disorder or anxiety disorder induced by substance abuse; and tolerance of, dependence on or withdrawal from substances of abuse. At present, the text revision of the fourth edition of the *Diagnostic and Statistical Manual of Mental Disorders* (DSM-IV-TR) (2000, American Psychiatric Association, Washington D.C.) provides a diagnostic tool that includes persisting dementia, persisting amnestic disorder, psychotic disorder or anxiety disorder induced by substance abuse; and tolerance of, dependence on or withdrawal from substances of abuse. As used herein, the term "substance-related disorders and addictive behaviors" includes treatment of those mental disorders as described in DSM -IV-TR. The skilled artisan will recognize that there are alternative nomenclatures, nosologies and classification systems for mental disorders, and that these systems evolve with medical and scientific progress. Thus the term "substance-related disorders and addictive behaviors" is intended to include like disorders that are described in other diagnostic sources.

In a still further aspect, the present invention provides a method for treating pain, comprising: administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In a further aspect, the present invention provides a method for treating obesity or eating disorders associated with excessive food intake and complications associated therewith, comprising: administering to a patient in need thereof an effective amount of a compound of the present invention. At present, obesity is included in the tenth edition of the *International Classification of Diseases and Related Health Problems* (ICD-10) (1992 World Health Organization) as a general medical condition. The text revision of the fourth edition of the *Diagnostic and Statistical Manual of Mental Disorders* (DSM-IV-TR) (2000, American Psychiatric Association, Washington D.C.) provides a diagnostic tool that includes obesity in the presence of psychological factors affecting medical condition. As used herein, the term "obesity or eating disorders associated with excessive food intake" includes treatment of those medical conditions and disorders described in ICD-10 and DSM-W-TR. The skilled artisan will recognize that there are alternative nomenclatures, nosologies and classification systems for general medical conditions, and that these systems evolve with medical and scientific progress. Thus, the term "obesity or eating disorders associated with excessive food intake" is intended to include like conditions and disorders that are described in other diagnostic sources.

The compounds are further useful in a method for the prevention, treatment, control, amelioration, or reduction of risk of the diseases, disorders and conditions noted herein. The compounds are further useful in a method for the prevention, treatment, control, amelioration, or reduction of risk of the aforementioned diseases, disorders and conditions in combination with other agents.

The present invention is further directed to administration of a selective $M_1$ receptor modulator for improving treatment outcomes in the context of cognitive or behavioral therapy. That is, in one aspect, the invention relates to a cotherapeutic method comprising the step of administering to a mammal an effective amount and dosage of at least one compound of the invention in connection with cognitive or behavioral therapy.

In a further aspect, administration improves treatment outcomes in the context of cognitive or behavioral therapy. Administration in connection with cognitive or behavioral therapy can be continuous or intermittent. Administration need not be simultaneous with therapy and can be before, during, and/or after therapy. For example, cognitive or behavioral therapy can be provided within 1, 2, 3, 4, 5, 6, 7 days before or after administration of the compound. As a further example, cognitive or behavioral therapy can be provided within 1, 2, 3, or 4 weeks before or after administration of the compound. As a still further example, cognitive or behavioral therapy can be provided before or after administration within a period of time of 1, 2, 3, 4, 5, 6, 7, 8, 9 or 10 half-lives of the administered compound.

In one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

Accordingly, the pharmaceutical compositions include those that contain one or more other active ingredients, in addition to a compound of the present invention.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In one aspect, the compound can be employed in combination with anti-Alzheimer's agents, beta-secretase inhibitors, gamma-secretase inhibitors, HMG-CoA reductase inhibitors, NSAIDs including ibuprofen, vitamin E, and anti-amyloid antibodies. In another embodiment, the subject compound can be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound can be administered in conjunction with the use of physical methods such as with light therapy or electrical stimulation.

In a further aspect, the compound can be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist can be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In a further aspect, the compound can be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound can be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound can be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In one aspect, the compound can be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT1A agonists or antagonists, especially 5-HT1A partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In the treatment of conditions which require activation of the muscarinic receptor an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one aspect, the invention relates to methods for activating or modulating muscarinic receptor in at least one cell, comprising the step of contacting the at least one cell with at least one compound of the invention, in an amount effective to modulate or activate mAChR $M_1$ activity response in the at least one cell. In a further aspect, the cell is mammalian, for example human. In a further aspect, the cell has been isolated from a subject prior to the contacting step. In a further aspect, contacting is via administration to a subject.

a. Treating a Disorder Associated with Muscarinic Acetylcholine Receptor Activity In one aspect, the invention relates to a method for the treatment of a neurological and/or psychiatric disorder associated with muscarinic acetylcholine receptor dysfunction in a mammal comprising the step of administering to the mammal an effective amount of at least one disclosed compound; or a pharmaceutically acceptable salt, hydrate, solvate, or polymorph thereof.

In one aspect, the invention relates to a method for the treatment of a neurological and/or psychiatric disorder associated with muscarinic acetylcholine receptor dysfunction in a mammal comprising the step of administering to the mammal an effective amount of at least one compound having a structure represented by a formula:

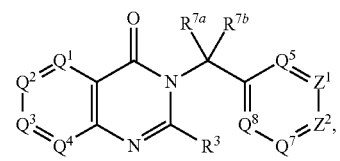

wherein each of $Z^1$ and $Z^2$ are independently selected from $Q^6$ or $CR^4$, provided that $Z^1$ and $Z^2$ are not simultaneously $Q^6$ or simultaneously $CR^4$; wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$; wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO$_2R^{30}$; wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-6 haloalkyl, C1-C6 polyhaloalkyl, C1-C6 alkylamino, and C1-C6 dialkylamino; wherein $R^4$ is selected from $Ar^2$, —$L^2$—$Ar^2$, and $Cy^1$; wherein $L^2$ is selected from —$CR^{8a}R^{8b}$—, —O—, —$NR^9$—, —S—, —(S=O)—, and —(SO$_2$)—; wherein each of $R^{8a}$ and $R^{8b}$ is independently selected from hydrogen, C1-C6 alkyl, C1-C6 haloalkyl, and C1-C6 polyhaloalkyl; wherein $R^9$ is selected from hydrogen and C1-C6 alkyl; wherein $Ar^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2, 3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein $Ar^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein $Ar^2$ is pyrazolyl substituted with substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein $Cy^1$ is a C2-C5 heterocycloalkyl or C2-C5 heterocycloalkenyl, and wherein $Cy^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of $R^{7a}$ and $R^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In various aspects, the invention relates to a method for the treatment of a neurological and/or psychiatric disorder associated with muscarinic acetylcholine receptor dysfunction in a mammal comprising the step of administering to the mammal an effective amount of at least one compound having a structure represented by a formula:

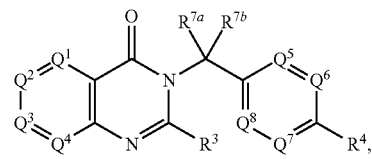

wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$, wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO$_2R^{30}$, wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from $Ar^2$, —$L^2$—$Ar^2$, and $Cy^1$; wherein $L^2$ is selected from —$CR^{8a}R^{8b}$—, —O—, —$NR^9$—, —S—, —(S=O)—, and —(SO$_2$)—; wherein each of $R^{8a}$ and $R^{8b}$ is independently selected from hydrogen, C1C6 alkyl, C1-C6 haloalkyl, and C1-C6 polyhaloalkyl; wherein $R^9$ is selected from hydrogen and C1-C6 alkyl; wherein $Ar^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2, 3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein $Ar^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein Ar$^2$ is pyrazolyl substituted with substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein Cy$^1$ is a C2-C5 heterocycloalkyl or C2-C5 heterocycloalkenyl, and wherein Cy$^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of R$^{7a}$ and R$^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In various aspects, the invention relates to a method for the treatment of a neurological and/or psychiatric disorder associated with muscarinic acetylcholine receptor dysfunction in a mammal comprising the step of administering to the mammal an effective amount of at least one compound having a structure represented by a formula:

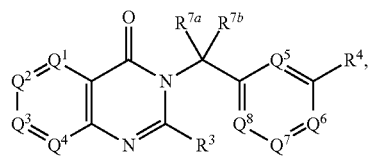

wherein Q$^1$ is selected from N and CR$^{1a}$; wherein Q$^2$ is selected from N and CR$^{1b}$; wherein Q$^3$ is selected from N and CR$^{1c}$; wherein Q$^4$ is selected from N and CR$^{1d}$; and wherein 0, 1, or 2 of Q$^1$, Q$^2$, Q$^3$, and Q$^4$ are N; wherein each of R$^{1a}$, R$^{1b}$, R$^{1c}$, and R$^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein Q$^5$ is selected from N and CR$^{2a}$; wherein Q$^6$ is selected from N and CR$^{2b}$; wherein Q$^7$ is selected from N and CR$^{2c}$, wherein Q$^8$ is selected from N and CR$^{2d}$; and wherein 0, 1, or 2 of Q$^5$, Q$^6$, Q$^7$, and Q$^8$ are N; wherein each of R$^{2a}$, R$^{2b}$, R$^{2c}$, and R$^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-1-C6 alkyl, C1-C6 polyhaloalkyl-oxy-C1-C6 alkyl, C1-C6 dialkylamino, —C(OH)R$^{20a}$R$^{20b}$, and —SO$_2$R$^{30}$; wherein each of R$^{20a}$ and R$^{20b}$ is independently selected from hydrogen, C1-C3 alkyl, C1-C3 haloalkyl; and C1-C3 polyhaloalkyl; and wherein R$^{30}$ is selected from C1-C3 alkyl, C1-C3 haloalkyl; and C1-C3 polyhaloalkyl; wherein R$^3$ is selected from hydrogen, C1-C3 alkyl, C1-C3 haloalkyl, C1-C3 polyhaloalkyl, cyclopropyl, and Ar$^1$; wherein Ar$^1$ is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein R$^4$ is selected from Ar$^2$, —L$^2$—Ar$^2$, and Cy$^1$;

wherein L$^2$ is selected from —CR$^{8a}$R$^{8b}$—, —O—, —NR$^9$—, —S—, —(S=O)—, and —(SO$_2$)—; wherein each of R$^{8a}$ and R$^{8b}$ is independently selected from hydrogen, C1-C6 alkyl, C1-C6 haloalkyl, and C1-C6 polyhaloalkyl; wherein R$^9$ is selected from hydrogen and C1-C6 alkyl; wherein Ar$^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2,3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein Ar$^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein Ar$^2$ is pyrazolyl substituted with substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein Cy$^1$ is a C2-C5 heterocycloalkyl or C2-C5 heterocycloalkenyl, and wherein Cy$^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of R$^{7a}$ and R$^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In a still further aspect, an effective amount is a therapeutically effective amount. In a yet further aspect, an effective amount is a prophylactically effective amount.

In a further aspect, the compound exhibits potentiation of mAChR M$_1$ activity with an EC$_{50}$ of less than about 10,000 nM. In a still further aspect, the compound exhibits potentiation of mAChR M$_1$ activity with an EC$_{50}$ of less than about 5,000 nM. In an even further aspect, the compound exhibits potentiation of mAChR M$_1$ activity with an EC$_{50}$ of less than about 1,000 nM. In a further aspect, the compound exhibits potentiation of mAChR M$_1$ activity with an EC$_{50}$ of less than about 500 nM. In a yet further aspect, the compound potentiation of mAChR M$_1$ activity with an EC$_{50}$ of less than about 100 nM.

In a further aspect, the compound exhibits potentiation of mAChR M$_1$ activity with an EC$_{50}$ of between from about 10,000 nM to about 1 nM. In a yet further aspect, the compound exhibits potentiation of mAChR M$_1$ activity with an EC$_{50}$ of between from about 1,000 nM to about 1 nM. In a still further aspect, the compound exhibits potentiation of mAChR M$_1$ activity with an EC$_{50}$ of between from about 100 nM to about 1 nM. In an even further aspect, the compound exhibits potentiation of mAChR M$_1$ activity with an EC$_{50}$ of between from about 10 nM to about 1 nM. In a yet further aspect, potent ion of mAChR M$_1$ activity is positive allosteric modulation of mAChR M$_1$ activity.

In one aspect, the mammal is a human. In a further aspect, the mammal has been diagnosed with a need for treatment of the disorder prior to the administering step. In a still further aspect, the method further comprises the step of identifying a mammal in need of treatment of the disorder.

In a further aspect, the disorder is a neurological and/or psychiatric disorder associated with mAChR M₁ dysfunction. In a still further aspect, the disorder is selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders. In a yet further aspect, the disorder is selected from Alzheimer's disease, schizophrenia, a sleep disorder, a pain disorder and a cognitive disorder. In an even further aspect, the disorder is Alzheimer's disease. In a still further aspect, the pain disorder is selected from neuropathic pain, central pain syndrome, postsurgical pain syndrome, bone and joint pain, repetitive motion pain, dental pain, cancer pain, myofascial pain, perioperative pain, chronic pain, dysmenorrhea, inflammatory pain, headache, migraine headache, cluster headache, headache, primary hyperalgesia, secondary hyperalgesia, primary allodynia, and secondary allodynia.

b. Potentiation of Muscarinic Acetylcholine Receptor Activity

In one aspect, the invention relates to a method for potentiation of muscarinic acetylcholine receptor activity in a mammal comprising the step of administering to the mammal an effective amount of at least one disclosed compound; or a pharmaceutically acceptable salt, hydrate, solvate, or polymorph thereof.

In one aspect, the invention relates to a method for potentiation of muscarinic acetylcholine receptor activity in a mammal comprising the step of administering to the mammal an effective amount of at least one compound having a structure represented by a formula:

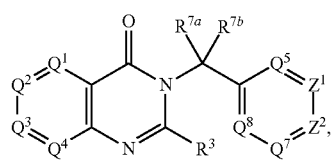

wherein each of $Z^1$ and $Z^2$ are independently selected from $Q^6$ or $CR^4$, provided that $Z^1$ and $Z^2$ are not simultaneously $Q^6$ or simultaneously $CR^4$; wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$; wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO₂$R^{30}$; wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from $Ar^2$, —$L^2$—$Ar^2$, and $Cy^1$; wherein $L^2$ is selected from —$CR^{8a}R^{8b}$—, —O—, —$NR^9$—, —S—, —(S=O)—, and —(SO₂)—; wherein each of $R^{8a}$ and $R^{8b}$ is independently selected from hydrogen, C1-C6 alkyl, C1-C6 haloalkyl, and C1-C6 polyhaloalkyl; wherein $R^9$ is selected from hydrogen and C1-C6 alkyl; wherein $Ar^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2, 3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein $Ar^2$ is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino; or wherein $Ar^2$ is pyrazolyl substituted with substituted with 1-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino; and wherein $Cy^1$ is a C2-C5 heterocycloalkyl or C2-C5 heterocycloalkenyl, and wherein $Cy^1$ is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of $R^{7a}$ and $R^{7b}$ is independently selected from hydrogen, C1-C6 alkyl, C1-C6 haloalkyl, and C1-C6 polyhaloalkyl; or a pharmaceutically acceptable salt, solvate, or polymorph thereof In various aspects, the invention relates to a method for potentiation of muscarinic acetylcholine receptor activity in a mammal comprising the step of administering to the mammal an effective amount of at least one compound having a structure represented by a formula:

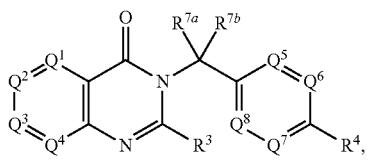

wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1- C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$, wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, $R^{2d}$, and when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO$_2R^{30}$, wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from $Ar^2$, —$L^2$—$Ar^2$, and $Cy^1$; wherein $L^2$ is selected from —$CR^{8a}R^{8b}$—, —O—, —$NR^9$—, —S—, —(S=O)—, and —(SO$_2$)—; wherein each of $R^{8a}$ and $R^{8b}$ is independently selected from hydrogen, C1-C6 alkyl, C1-C6 haloalkyl, and C1-C6 polyhaloalkyl; wherein $R^9$ is selected from hydrogen and C1-C6 alkyl; wherein $Ar^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2,3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein $Ar^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein $Ar^2$ is pyrazolyl substituted with substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein $Cy^1$ is a C2-C5 heterocycloalkyl or C2-C5 heterocycloalkenyl, and wherein $Cy^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of $R^{7a}$ and $R^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In various aspects, the invention relates to a method for potentiation of muscarinic acetylcholine receptor activity in a mammal comprising the step of administering to the mammal an effective amount of at least one compound having a structure represented by a formula:

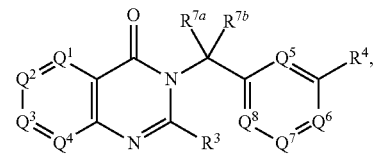

wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$; wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20b}R^{20b}$, and —SO$_2R^{30}$; wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from $Ar^2$, —$L^2$—$Ar^2$, and $Cy^1$; wherein $L^2$ is selected from —$CR^{8a}R^{8b}$—, —O—, —$NR^9$—, —S—, —(S=O)—, and —(SO$_2$)—; wherein each of $R^{8a}$ and $R^{8b}$ is independently selected from hydrogen, C1-C6 alkyl, C1-C6 haloalkyl, and C1-C6 polyhaloalkyl; wherein $R^9$ is selected from hydrogen and C1-C6 alkyl; wherein $Ar^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2,3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein $Ar^2$ is substituted with 0-3 substituents independently selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino; or wherein $Ar^2$ is pyrazolyl substituted with substituted with 1-3 substituents independently selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino; and wherein $Cy^1$ is a C2-C5 heterocycloalkyl or C2-C5 heterocycloalkenyl, and wherein $Cy^1$ is substituted with 0-3 substituents independently selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of $R^{7a}$ and $R^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In a further aspect, the compound administered is a product of a disclosed method of making a compound. In a still further aspect, an effective amount is a therapeutically effective amount. In a yet further aspect, an effective amount is a prophylactically effective amount.

In a further aspect, potentiation of muscarinic acetylcholine receptor activity increases muscarinic acetylcholine receptor activity. In a still further aspect, potentiation of muscarinic acetylcholine receptor activity is partial agonism of the muscarinic acetylcholine receptor. In a yet further aspect, potentiation of muscarinic acetylcholine receptor activity is positive allosteric modulation of the muscarinic acetylcholine receptor.

In a further aspect, the compound exhibits potentiation of mAChR $M_1$ activity with an $EC_{50}$ of less than about 10,000 nM. In a still further aspect, the compound exhibits potentiation of mAChR $M_1$ activity with an $EC_{50}$ of less than about 5,000 nM. In an even further aspect, the compound exhibits potentiation of mAChR $M_1$ activity with an $EC_{50}$ of less than about 1,000 nM. In a further aspect, the compound exhibits potentiation of mAChR $M_1$ activity with an $EC_{50}$ of less than about 500 nM. In a yet further aspect, the compound exhibits potentiation of mAChR $M_1$ activity with an $EC_{50}$ of less than about 100 nM.

In a further aspect, the compound exhibits potentiation of mAChR $M_1$ activity with an $EC_{50}$ of between from about 10,000 nM to about 1 nM. In a yet further aspect, the compound exhibits potentiation of mAChR $M_1$ activity with an $EC_{50}$ of between from about 1,000 nM to about 1 nM. In a still further aspect, the compound exhibits potentiation of mAChR $M_1$ activity with an $EC_{50}$ of between from about 100 nM to about 1 nM. In an even further aspect, the compound exhibits potentiation of mAChR $M_1$ activity with an $EC_{50}$ of between from about 10 nM to about 1 nM. In a yet further aspect, potentiation of mAChR $M_1$ activity is positive allosteric modulation of mAChR $M_1$ activity.

In one aspect, the mammal is a human. In a further aspect, the mammal has been diagnosed with a need for potentiation of muscarinic acetylcholine receptor activity prior to the administering step. In a still further aspect, the method further comprises the step of identifying a mammal in need of potentiating muscarinic acetylcholine receptor activity. In a yet further aspect, the muscarinic acetylcholine receptor is mAChR $M_1$. In an even further aspect, potentiation of mAChR $M_1$ activity treats a disorder associated with mAChR $M_1$ activity in the mammal.

In a further aspect, potentiation of muscarinic acetylcholine receptor activity in a mammal treats a neurological and/or psychiatric disorder. In a yet further aspect, the neurological and/or psychiatric disorder is associated with a mAChR $M_1$ dysfunction. In a still further aspect, the disorder is selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders. In a yet further aspect, the disorder is selected from Alzheimer's disease, schizophrenia, a sleep disorder, a pain disorder and a cognitive disorder. In an even further aspect, the disorder is Alzheimer's disease. In a still further aspect, the pain disorder is selected from neuropathic pain, central pain syndrome, postsurgical pain syndrome, bone and joint pain, repetitive motion pain, dental pain, cancer pain, myofascial pain, perioperative pain, chronic pain, dysmennorhea, inflammatory pain, headache, migraine headache, cluster headache, headache, primary hyperalgesia, secondary hyperalgesis, primary allodynia, and secondary allodynia.

c. Potentiating Muscarinic Acetylcholine Receptor Activity In Cells

In one aspect, the invention relates to a method for potentiation of muscarinic acetylcholine receptor activity in a mammal comprising the step of administering to the mammal an effective amount of at least one disclosed compound; or a pharmaceutically acceptable salt, hydrate, solvate, or polymorph thereof.

In various aspects, the invention relates to a method for potentiation of muscarinic acetylcholine receptor activity in at least one cell, comprising the step of contacting the cell with an effective amount of at least one compound having a structure represented by a formula:

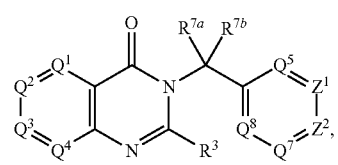

wherein each of $Z^1$ and $Z^2$ are independently selected from $Q^6$ or $CR^4$, provided that $Z^1$ and $Z^2$ are not simultaneously $Q^6$ or simultaneously $CR^4$; wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$, wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO$_2R^{30}$; wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with C0-C3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from $Ar^2$, —$L^2$—$Ar^2$, and $Cy^1$; wherein $L^2$ is selected from —$CR^{8a}R^{8b}$—, —O—, —$NR^9$—, —S—, —(S=O)—, and —(SO$_2$)—; wherein each of $R^{8a}$ and $R^{8b}$ is independently selected from hydrogen, C1-C6 alkyl, C1-C6 haloalkyl, and C1-C6 polyhaloalkyl; wherein $R^9$ is selected from hydrogen and C1-C6 alkyl; wherein $Ar^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2, 3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein $Ar^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein $Ar^2$ is pyrazolyl substituted with substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein $Cy^1$ is a C2-C5 heterocycloalkyl or C2-C5 heterocycloalkenyl, and wherein $Cy^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of $R^{7a}$ and $R^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In various aspects, the invention relates to a method for potentiation of muscarinic acetylcholine receptor activity in at least one cell, comprising the step of contacting the cell with an effective amount of at least one compound having a structure represented by a formula:

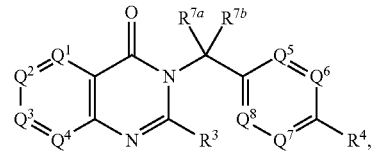

wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$; wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$ and —SO$_2R^{30}$; wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from $Ar^2$, —$L^2$—$Ar^2$, and $Cy^1$; wherein $L^2$ is selected from —$CR^{8a}R^{8b}$—, —O—, —$NR^9$—, —S—, —(S=O)—, and —(SO$_2$)—; wherein each of $R^{8a}$ and $R^{8b}$ is independently selected from hydrogen, C1-C6 alkyl, C1-C6 haloalkyl, and C1-C6 polyhaloalkyl; wherein $R^9$ is selected from hydrogen and C1-C6 alkyl; wherein $Ar^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2, 3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein $Ar^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein $Ar^2$ is pyrazolyl substituted with substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein $Cy^1$ is a C2-C5 heterocycloalkyl or C2-C5 heterocycloalkenyl, and wherein $Cy^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of $R^{7a}$ and $R^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In various aspects, the invention relates to a method for potentiation of muscarinic acetylcholine receptor activity in at least one cell, comprising the step of contacting the cell with an effective amount of at least one compound having a structure represented by a formula:

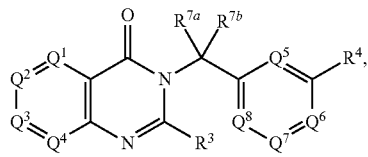

wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyloxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$; wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO$_2R^{30}$; wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from $Ar^2$, —L$^2$—$Ar^2$, and $Cy^1$; wherein $L^2$ is selected from —$CR^{8a}R^{8b}$—, —O—, —NR$^9$—, —S—, —(S=O)—, and —(SO$_2$)—; wherein each of $R^{8a}$ and $R^{8b}$ is independently selected from hydrogen, C1-C6 alkyl, C1-C6 haloalkyl, and C1-C6 polyhaloalkyl; wherein $R^9$ is selected from hydrogen and C1-C6 alkyl; wherein $Ar^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2,3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein $Ar^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein $Ar^2$ is pyrazolyl substituted with substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein $Cy^1$ is a C2-C5 heterocycloalkyl or C2-C5 heterocycloalkenyl, and wherein $Cy^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of $R^{7a}$ and $R^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In a still further aspect, an effective amount is a therapeutically effective amount. In a yet further aspect, an effective amount is a prophylactically effective amount.

In a further aspect, the muscarinic acetylcholine receptor is mAChR M$_1$.

In a further aspect, potentiation of the muscarinic acetylcholine receptor activity increases muscarinic acetylcholine receptor activity. In a still further aspect, potentiation of the muscarinic acetylcholine receptor activity is partial agonism of muscarinic acetylcholine receptor activity. In a yet further aspect, potentiation of muscarinic acetylcholine receptor activity is positive allosteric modulation of muscarinic acetylcholine receptor activity.

In a further aspect, the compound exhibits potentiation of mAChR M$_1$ activity with an EC$_{50}$ of less than about 10,000 nM. In a still further aspect, the compound exhibits potentiation of mAChR M$_1$ activity with an EC$_{50}$ of less than about 5,000 nM. In an even further aspect, the compound exhibits potentiation of mAChR M$_1$ activity with an EC$_{50}$ of less than about 1,000 nM. In a further aspect, the compound exhibits potentiation of mAChR M$_1$ activity with an EC$_{50}$ of less than about 500 nM. In a yet further aspect, the compound potentiation of mAChR M$_1$ activity with an EC$_{50}$ of less than about 100 nM.

In a further aspect, the compound exhibits potentiation of mAChR M$_1$ activity with an EC$_{50}$ of between from about 10,000 nM to about 1 nM. In a yet further aspect, the compound exhibits potentiation of activity mAChR M$_1$ with an EC$_{50}$ of between from about 1,000 nM to about 1 nM. In a still further aspect, the compound exhibits potentiation of mAChR M$_1$ activity with an EC$_{50}$ of between from about 100 nM to about 1 nM. In an even further aspect, the compound exhibits potentiation of mAChR M$_1$ activity with an EC$_{50}$ of between from about 10 nM to about 1 nM. In a yet further aspect, potentiation of mAChR M$_1$ activity is positive allosteric modulation of mAChR M$_1$ activity.

In one aspect, the cell is mammalian. In a still further aspect, the cell is human. In a yet further aspect, the cell has been isolated from a mammal prior to the contacting step. In an even further aspect, contacting is via administration to a mammal.

In a further aspect, the mammal has been diagnosed with a need for potentiation of muscarinic acetylcholine receptor activity prior to the administering step. In a still further aspect, the method further comprises the step of identifying a mammal in need of potentiating muscarinic acetylcholine receptor activity.

In a further aspect, the potentiation of muscarinic acetylcholine receptor activity treats a muscarinic acetylcholine receptor dysfunction. In a yet further aspect, the potentiation of muscarinic acetylcholine receptor activity treats a disorder associated with muscarinic acetylcholine receptor dysfunction in the mammal. In a still further aspect, the mammal has been diagnosed with a need for potentiation of muscarinic acetylcholine receptor activity prior to the administering step. In an even further aspect, treatment further comprises the step of identifying a mammal in need of potentiation of muscarinic acetylcholine receptor activity.

In a further aspect, potentiation of muscarinic acetylcholine receptor activity in at least one cell treats a neurological and/or psychiatric disorder. In a still further aspect, the neurological and/or psychiatric disorder is associated with a mAChR $M_1$ dysfunction. In a still further aspect, the disorder is selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders. In a yet further aspect, the disorder is selected from Alzheimer's disease, schizophrenia, a sleep disorder, a pain disorder and a cognitive disorder. In an even further aspect, the disorder is Alzheimer's disease. In a still further aspect, the pain disorder is selected from neuropathic pain, central pain syndrome, postsurgical pain syndrome, bone and joint pain, repetitive motion pain, dental pain, cancer pain, myofascial pain, perioperative pain, chronic pain, dysmennorhea, inflammatory pain, headache, migraine headache, cluster headache, headache, primary hyperalgesia, secondary hyperalgesis, primary allodynia, and secondary allodynia.

2. Cotherapeutic Methods

The present invention is further directed to administration of a selective mAChR $M_1$ potentiator for improving treatment outcomes in the context of cognitive or behavioral therapy. That is, in one aspect, the invention relates to a cotherapeutic method comprising the step of administering to a mammal an effective amount of at least one disclosed compound; or a pharmaceutically acceptable salt, hydrate, solvate, or polymorph thereof.

In a further aspect, the compound administered for the cotherapeutic method is a product of a disclosed method of making. In a still further aspect, an effective amount is a therapeutically effective amount. In a yet further aspect, an effective amount is a prophylactically effective amount.

In a further aspect, administration improves treatment outcomes in the context of cognitive or behavioral therapy. Administration in connection with cognitive or behavioral therapy can be continuous or intermittent. Administration need not be simultaneous with therapy and can be before, during, and/or after therapy. For example, cognitive or behavioral therapy can be provided within 1, 2, 3, 4, 5, 6, or 7 days before or after administration of the compound. As a further example, cognitive or behavioral therapy can be provided within 1, 2, 3, or 4 weeks before or after administration of the compound. As a still further example, cognitive or behavioral therapy can be provided before or after administration within a period of time of 1, 2, 3, 4, 5, 6, 7, 8, 9, or 10 half-lives of the administered compound. It is understood that the disclosed cotherapeutic methods can be used in connection with the disclosed compounds, compositions, kits, and uses.

3. Use of Compounds

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In one aspect, the invention relates to the use of a compound in the manufacture of a medicament for the treatment of a neurological and/or psychiatric disorder, wherein the compound has a structure represented by a formula:

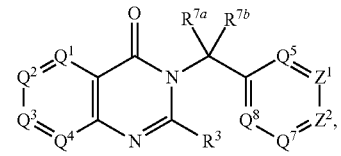

wherein each of $Z^1$ and $Z^2$ are independently selected from $Q^6$ or $CR^4$, provided that $Z^1$ and $Z^2$ are not simultaneously $Q^6$ or simultaneously $CR^4$; wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$, wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO$_2R^{30}$; wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from $Ar^2$, —$L^2$—$Ar^2$, and $Cy^1$; wherein $L^2$ is selected from —CR$^{8a}$R$^{8b}$—, —O—, —NR$^9$—, —S—, —(S=O)—, and —(SO$_2$)—; wherein each of R$^{8a}$ and R$^{8b}$ is independently selected from hydrogen, C1-C6 alkyl, C1-C6 haloalkyl, and C1-C6 polyhaloalkyl; wherein R$^9$ is selected from hydrogen and C1-C6 alkyl; wherein Ar$^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2, 3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein Ar$^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein Ar$^2$ is pyrazolyl substituted with substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein Cy$^1$ is a C2-C5 heterocycloalkyl or C2-C5 heterocycloalkenyl, and wherein Cy$^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of R$^{7a}$ and R$^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In various aspects, the invention relates to the use of a compound in the manufacture of a medicament for the treatment of a neurological and/or psychiatric disorder, wherein the compound has a structure represented by a formula:

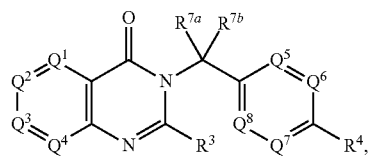

wherein Q$^1$ is selected from N and CR$^{1a}$; wherein Q$^2$ is selected from N and CR$^{1b}$; wherein Q$^3$ is selected from N and CR$^{1c}$; wherein Q$^4$ is selected from N and CR$^{1d}$; and wherein 0, 1, or 2 of Q$^1$, Q$^2$, Q$^3$, and Q$^4$ are N; wherein each of R$^{1a}$, R$^{1b}$, R$^{1c}$, and R$^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein Q$^5$ is selected from N and CR$^{2a}$; wherein Q$^6$ is selected from N and CR$^{2b}$; wherein Q$^7$ is selected from N and CR$^{2c}$; wherein Q$^8$ is selected from N and CR$^{2d}$; and wherein 0, 1, or 2 of Q$^5$, Q$^6$, Q$^7$, and Q$^8$ are N; wherein each of R$^{2a}$, R$^{2b}$, R$^{2c}$, and R$^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)R$^{20a}$R$^{20b}$, and —SO$_2$R$^{30}$; wherein each of R$^{20a}$ and R$^{20b}$ is independently selected from hydrogen, C1-C3 alkyl, C1-C3 haloalkyl; and C1-C3 polyhaloalkyl; and wherein R$^{30}$ is selected from C1-C3 alkyl, C1-C3 haloalkyl; and C1-C3 polyhaloalkyl; wherein R$^3$ is selected from hydrogen, C1-C3 alkyl, C1-C3 haloalkyl, C1-C3 polyhaloalkyl, cyclopropyl, and Ar$^1$; wherein Ar$^1$ is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-6 dialkylamino; wherein R$^4$ is selected from Ar$^2$, —L$^2$—Ar$^2$, and Cy$^1$; wherein L$^2$ is selected from —CR$^{8a}$R$^{8b}$—, —O—, —NR$^9$—, —S—, —(S=O)—, and —(SO$_2$)—; wherein each of R$^{8a}$ and R$^{8b}$ is independently selected from hydrogen, C1-C6 alkyl, C1-C6 haloalkyl, and C1-C6 polyhaloalkyl; wherein R$^9$ is selected from hydrogen and C1-C6 alkyl; wherein Ar$^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2, 3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein Ar$^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein Ar$^2$ is pyrazolyl substituted with substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein Cy$^1$ is a C2-C5 heterocycloalkyl or C2-C5 heterocycloalkenyl, and wherein Cy$^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of R$^{7a}$ and R$^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In various aspects, the invention relates to the use of a compound in the manufacture of a medicament for the treatment of a neurological and/or psychiatric disorder, wherein the compound has a structure represented by a formula:

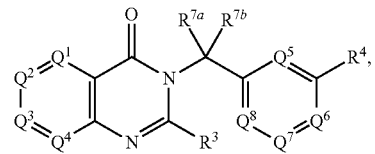

wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$, wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, a when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO$_2R^{30}$; wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from $Ar^2$, —L$^2$—$Ar^2$, and $Cy^1$; wherein $L^2$ is selected from —CR$^{8a}R^{8b}$—, —O—, —NR$^9$—, —S—, —(S=O)—, and —(SO$_2$)—; wherein each of $R^{8a}$ and $R^{8b}$ is independently selected from hydrogen, C1-C6 alkyl, C1-C6 haloalkyl, and C1-C6 polyhaloalkyl; wherein $R^9$ is selected from hydrogen and C1-C6 alkyl; wherein $Ar^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2,3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein $Ar^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein $Ar^2$ is pyrazolyl substituted with substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein $Cy^1$ is a C2-C5 heterocycloalkyl or C2-C5 heterocycloalkenyl, and wherein $Cy^1$ is substituted with 0-3 substituents independently selected from halogen, hydroxyl, cyano, —NH$_2$, C1-C6 alkyl, C1-C6 alkoxy, C1-6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of $R^{7a}$ and $R^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In various aspects, the invention relates to the use of a compound in the manufacture of a medicament for the potentiation of muscarinic acetylcholine receptor, wherein the compound has a structure represented by a formula:

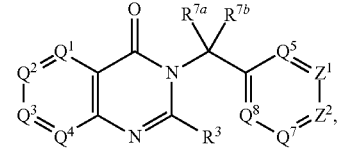

wherein each of $Z^1$ and $Z^2$ are independently selected from $Q^6$ or $CR^4$, provided that $Z^1$ and $Z^2$ are not simultaneously $Q^6$ or simultaneously $CR^4$; wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$, wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO$_2R^{30}$, wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from $Ar^2$, —L$^2$—$Ar^2$, and $Cy^1$; wherein $L^2$ is selected from —CR$^{8a}R^{8b}$—, —O—, —NR$^9$—, —S—, —(S=O)—, and —(SO$_2$)—; wherein each of $R^{8a}$ and $R^{8b}$ is independently selected from hydrogen, C1-C6 alkyl, C1-C6 haloalkyl, and C1-C6 polyhaloalkyl; wherein $R^9$ is selected from hydrogen and C1-C6 alkyl; wherein $Ar^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2,3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein $Ar^2$ is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-6 alkylamino, and C1-C6 dialkylamino; or wherein Ar² is pyrazolyl substituted with substituted with 1-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino; and wherein Cy¹ is a C2-C5 heterocycloalkyl or C2-C5 heterocycloalkenyl, and wherein Cy¹ is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of $R^{7a}$ and $R^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In various aspects, the invention relates to the use of a compound in the manufacture of a medicament for the potentiation of muscarinic acetylcholine receptor, wherein the compound has a structure represented by a formula:

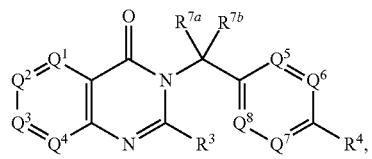

wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$, wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO₂$R^{30}$; wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and Ar¹; wherein Ar¹ is selected from phenyl, indenyl, and naphthalenyl; and substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from Ar², —L²—Ar², and Cy¹; wherein L² is selected from —$CR^{8a}R^{8b}$—, —O—, —$NR^9$—, —S—, —S—, —(S═O)—; and —(SO₂)—; wherein each of $R^{8a}$ and $R^{8b}$ is independently selected from hydrogen, C1-C6 alkyl, C1-C6 haloalkyl, and C1-C6 polyhaloalkyl; wherein $R^9$ is selected from hydrogen and C1-C6 alkyl; wherein Ar² is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2, 3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein Ar² is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino; or wherein Ar² is pyrazolyl substituted with substituted with 1-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino; and wherein Cy¹ is a C2-C5 heterocycloalkyl or C2-C5 heterocycloalkenyl, and wherein Cy¹ is substituted with 0-3 substituents independently selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of $R^{7a}$ and $R^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In various aspects, the invention relates to the use of a compound in the manufacture of a medicament for the potentiation of muscarinic acetylcholine receptor, wherein the compound has a structure represented by a formula:

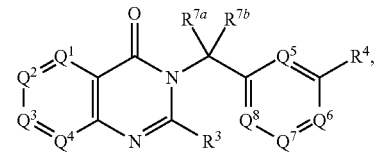

wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$, wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$; when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO$_2$R$^{30}$, wherein each of R$^{20a}$ and R$^{20b}$ is independently selected from hydrogen, C1-C3 alkyl, C1-C3 haloalkyl; and C1-C3 polyhaloalkyl; and wherein R$^{30}$ is selected from C1-C3 alkyl, C1-C3 haloalkyl; and C1-C3 polyhaloalkyl; wherein R$^3$ is selected from hydrogen, C1-C3 alkyl, C1-C3 haloalkyl, C1-C3 polyhaloalkyl, cyclopropyl, and Ar$^1$; wherein Ar$^1$ is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein R$^4$ is selected from Ar$^2$, —L$^2$—Ar$^2$, and Cy$^1$; wherein L$^2$ is selected from —CR$^{8a}$R$^{8b}$—, —O—, —NR$^9$—, —S—, —(S=O)—, and —(SO$_2$)—; wherein each of R$^{8a}$ and R$^{8b}$ is independently selected from hydrogen, C1-C6 alkyl, C1-C6 haloalkyl, and C1-C6 polyhaloalkyl; wherein R$^9$ is selected from hydrogen and C1-C6 alkyl; wherein Ar$^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2, 3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein Ar$^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein Ar$^2$ is pyrazolyl substituted with substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein Cy$^1$ is a C2-C5 heterocycloalkyl or C2-C5 heterocycloalkenyl, and wherein Cy$^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of R$^{7a}$ and R$^{7b}$ is independently selected from hydrogen, C1-C6 alkyl, C1-C6 haloalkyl, and C1-C6 polyhaloalkyl; or a pharmaceutically acceptable salt, solvate, or polymorph thereof.

In a further aspect, the compound used exhibits potentiation of mAChR M$_1$ activity with an EC$_{50}$ of less than about 10,000 nM. In a still further aspect, the compound used exhibits potentiation of mAChR M$_1$ activity with an EC$_{50}$ of less than about 5,000 nM. In an even further aspect, the compound used exhibits potentiation of mAChR M$_1$ with an EC$_{50}$ of less than about 1,000 nM. In a further aspect, the compound used exhibits potentiation of mAChR M$_1$ activity with an EC$_{50}$ of less than about 500 nM. In a yet further aspect, the compound used potentiation of mAChR M$_1$ activity with an EC$_{50}$ of less than about 100 nM.

In a further aspect, the compound used exhibits potentiation of mAChR M$_1$ activity with an EC$_{50}$ of between from about 10,000 nM to about 1 nM. In a yet further aspect, the compound used exhibits potentiation of mAChR M$_1$ activity with an EC$_{50}$ of between from about 1,000 nM to about 1 nM. In a still further aspect, the compound used exhibits potentiation of mAChR M$_1$ activity with an EC$_{50}$ of between from about 100 nM to about 1 nM. In an even further aspect, the compound used exhibits potentiation of mAChR M$_1$ activity with an EC$_{50}$ of between from about 10 nM to about 1 nM. In a yet further aspect, potentiation of mAChR M$_1$ activity is positive allosteric modulation of mAChR M$_1$ activity.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of a disorder in a mammal. Also disclosed is the use of a compound for mAChR M$_1$ receptor activation. In one aspect, the use is characterized in that the mammal is a human. In one aspect, the use is characterized in that the disorder is a neurological and/or psychiatric disorder associated with a muscarinic acetylcholine receptor dysfunction. In one aspect, the neurological and/or psychiatric disorder associated with muscarinic acetylcholine receptor dysfunction is treated by potentiation of muscarinic acetylcholine receptor activity in a mammal.

In a further aspect, the use relates to the manufacture of a medicament for the treatment of a disorder associated with a muscarinic acetylcholine receptor dysfunction in a mammal. In a further aspect, the medicament is used in the treatment of a neurological and/or psychiatric disorder associated with a muscarinic acetylcholine receptor dysfunction in a mammal.

In a further aspect, the use relates to potentiation of muscarinic acetylcholine receptor activity in a mammal. In a further aspect, the use relates to partial agonism of muscarinic acetylcholine receptor activity in a mammal. In a further aspect, the use relates to modulating mAChR M$_1$ activity in a mammal. In a still further aspect, the use relates to modulating mAChR M$_1$ activity in a cell. In a yet further aspect, the use relates to partial allosteric agonism of mAChR M$_1$ in a cell. In an even further aspect, the mammal is a human.

In a further aspect, the use is treatment of a neurological and/or psychiatric disorder. In an even further aspect, the disorder is a neurological and/or psychiatric disorder associated with M$_1$ receptor activity. In a yet further aspect, disorder is selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, movement disorders associated dyskinesias, attention deficit hyperactivity disorder, cognitive disorders, dementias, and memory disorders. In an even further aspect, the disorder is selected from Alzheimer's disease, schizophrenia, a sleep disorder, a pain disorder and a cognitive disorder. In a still further aspect, the disorder is Alzheimer's disease. In a still further aspect, wherein the pain disorder is selected from neuropathic pain, central pain syndrome, postsurgical pain syndrome, bone and joint pain, repetitive motion pain, dental pain, cancer pain, myofascial pain, perioperative pain, chronic pain, dysmennorhea, inflammatory pain, headache, migraine headache, cluster headache, headache, primary hyperalgesia, secondary hyperalgesis, primary allodynia, and secondary allodynia.

It is understood that the disclosed uses can be employed in connection with the disclosed compounds, methods, compositions, and kits. In a further aspect, the invention relates to the use of a disclosed compound or a disclosed product in the manufacture of a medicament for the treatment of a disorder associated with mAChR $M_1$ receptor dysfunction in a mammal. In a further aspect, the disorder is a neurological and/or psychiatric disorder 4. Kits In one aspect, the invention relates to kits comprising at least one disclosed compound; or a pharmaceutically acceptable salt, hydrate, solvate, or polymorph thereof, and one or more of:

(a) at least one agent known to increase mAChR $M_1$ activity;
(b) at least one agent known to decrease mAChR $M_1$ activity;
(c) at least one agent known to treat a disorder associated with cholinergic activity;
(d) instructions for treating a disorder associated with cholinergic activity;
(e) instructions for treating a disorder associated with mAChR $M_1$ receptor activity; or
(f) instructions for administering the compound in connection with cognitive or behavioral therapy.

In various further aspects, the invention relates to kits comprising at least one product of a disclosed method of making and at least one agent known to have $M_1$ receptor agonist activity. In a further aspect, the kit comprises a disclosed compound or a product of a disclosed method.

In one aspect, the invention relates to a kit comprising at least one compound having a structure represented by a formula:

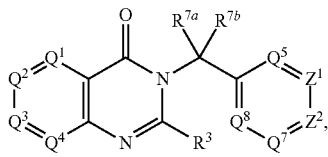

wherein each of $Z^1$ and $Z^2$ are independently selected from $Q^6$ or $CR^4$, provided that $Z^1$ and $Z^2$ are not simultaneously $Q^6$ or simultaneously $CR^4$; wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$; wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —$SO_2R^{30}$; wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with 0-3 substituents independently selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from $Ar^2$, —$L^2$—$Ar^2$, and $Cy^1$; wherein $L^2$ is selected from —$CR^{8a}R^{8b}$—, —O—, —$NR^9$—, —S—, —(S=O)—, and —($SO_2$)—; wherein each of $R^{8a}$ and $R^{8b}$ is independently selected from hydrogen, C1-C6 alkyl, C1-C6 haloalkyl, and C1-C6 polyhaloalkyl; wherein R9 is selected from hydrogen and C1-C6 alkyl; wherein $Ar^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2,3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein $Ar^2$ is substituted with 0-3 substituents independently selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino; or wherein $Ar^2$ is pyrazolyl substituted with substituted with 1-3 substituents independently selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino; and wherein $Cy^1$ is a C2-C5 heterocycloalkyl or C2-C5 heterocycloalkenyl, and wherein $Cy^1$ is substituted with 0-3 substituents independently selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of $R^{7a}$ and $R^{7b}$ is independently selected from hydrogen, C1-C6 alkyl, C1-C6 haloalkyl, and C1-C6 polyhaloalkyl; or a pharmaceutically acceptable salt, solvate, or polymorph thereof; and one or more of:

(a) at least one agent known to increase mAChR $M_1$ activity;
(b) at least one agent known to decrease mAChR $M_1$ activity;
(c) at least one agent known to treat a disorder associated with cholinergic activity;
(d) instructions for treating a disorder associated with cholinergic activity;
(e) instructions for treating a disorder associated with mAChR $M_1$ receptor activity; or (f) instructions for administering the compound in connection with cognitive or behavioral therapy.

In various aspects, the invention relates to a kit comprising at least one compound having a structure represented by a formula:

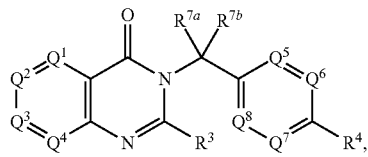

wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ and N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$; wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO$_2R^{30}$; wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and $Ar^1$; wherein $Ar^1$ is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein $R^4$ is selected from $Ar^2$, —$L^2$—$Ar^2$, and $Cy^1$; wherein $L^2$ is selected from —$CR^{8a}R^{8b}$—, —O—, —$NR^9$—, —S—, —(S=O)—, and —(SO$_2$)—; wherein each of $R^{8a}$ and $R^{8b}$ is independently selected from hydrogen, C1-C6 alkyl, C1-C6 haloalkyl, and C1-C6 polyhaloalkyl; wherein $R^9$ is selected from hydrogen and C1-C6 alkyl; wherein $Ar^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'oxospiro[1,3]dioxolane-2,3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein $Ar^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein $Ar^2$ is pyrazolyl substituted with substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein $Cy^1$ is a C2-C5 heterocycloalkyl or C2-C5 heterocycloalkenyl, and wherein $Cy^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3-6-membered fused ring group; wherein each of $R^{7a}$ and $R^{7b}$ is independently selected from hydrogen, C1-C6 alkyl, C1-C6 haloalkyl, and C1-C6 polyhaloalkyl; or a pharmaceutically acceptable salt, solvate, or polymorph thereof; and one or more of:

(a) at least one agent known to increase mAChR $M_1$ activity;
(b) at least one agent known to decrease mAChR $M_1$ activity;
(c) at least one agent known to treat a disorder associated with cholinergic activity;
(d) instructions for treating a disorder associated with cholinergic activity;
(e) instructions for treating a disorder associated with mAChR $M_1$ receptor activity; or
(f) instructions for administering the compound in connection with cognitive or behavioral therapy.

In various aspects, the invention relates to a kit comprising at least one compound having a structure represented by a formula:

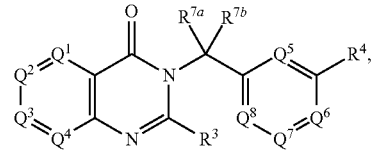

wherein $Q^1$ is selected from N and $CR^{1a}$; wherein $Q^2$ is selected from N and $CR^{1b}$; wherein $Q^3$ is selected from N and $CR^{1c}$; wherein $Q^4$ is selected from N and $CR^{1d}$; and wherein 0, 1, or 2 of $Q^1$, $Q^2$, $Q^3$, and $Q^4$ are N; wherein each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $Q^5$ is selected from N and $CR^{2a}$; wherein $Q^6$ is selected from N and $CR^{2b}$; wherein $Q^7$ is selected from N and $CR^{2c}$, wherein $Q^8$ is selected from N and $CR^{2d}$; and wherein 0, 1, or 2 of $Q^5$, $Q^6$, $Q^7$, and $Q^8$ are N; wherein each of $R^{2a}$, $R^{2b}$, $R^{2c}$, and $R^{2d}$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, C1-C6 dialkylamino, —C(OH)$R^{20a}R^{20b}$, and —SO$_2R^{30}$, wherein each of $R^{20a}$ and $R^{20b}$ is independently selected from hydrogen, C1-C3 alkyl, C1-C3 haloalkyl; and C1-C3 polyhaloalkyl; and wherein $R^{30}$ is selected from C1-C3 alkyl, C1-C3 haloalkyl; and C1-C3 polyhaloalkyl; wherein $R^3$ is selected from hydrogen, C1-C3 alkyl, C1-C3 haloalkyl, C1-C3 polyhaloalkyl, cyclopropyl, and Ar$^1$; wherein Ar$^1$ is selected from phenyl, indenyl, and naphthalenyl; and substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein R$^4$ is selected from Ar$^2$, —L$^2$—Ar$^2$, and Cy$^1$; wherein L$^2$ is selected from —CR$^{8a}$R$^{8b}$—, —O—, —NR$^9$—, —S—, —(S═O)—, and —(SO$_2$)—; wherein each of R$^{8a}$ and R$^{8b}$ is independently selected from hydrogen, C1-C6 alkyl, C1-C6 haloalkyl, and C1-C6 polyhaloalkyl; wherein R$^9$ is selected from hydrogen and C1-C6 alkyl; wherein Ar$^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2, 3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl; and wherein Ar$^2$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or wherein Ar$^2$ is pyrazolyl substituted with substituted with 1-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein Cy$^1$ is a C2-C5 heterocycloalkyl or C2-C5 heterocycloalkenyl, and wherein Cy$^1$ is substituted with 0-3 substituents independently selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, and wherein two of the substituents are optionally covalently bonded, and together with the intermediate atoms, comprise an optionally substituted 3- to 6-membered fused ring group; wherein each of R$^{7a}$ and R$^{7b}$ is independently selected from hydrogen, C1-C6 alkyl, C1-C6 haloalkyl, and C1-C6 polyhaloalkyl; or a pharmaceutically acceptable salt, solvate, or polymorph thereof; and one or more of:
  (a) at least one agent known to increase mAChR M$_1$ activity;
  (b) at least one agent known to decrease mAChR M$_1$ activity;
  (c) at least one agent known to treat a disorder associated with cholinergic activity;
  (d) instructions for treating a disorder associated with cholinergic activity;
  (e) instructions for treating a disorder associated with mAChR M$_1$ receptor activity; or
  (f) instructions for administering the compound in connection with cognitive or behavioral therapy.

In a further aspect, the at least one compound and the at least one agent are co-formulated. In a still further aspect, the at least one compound and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

5. Subjects

The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

In some aspects of the disclosed methods, the subject has been diagnosed with a need for treatment prior to the administering step. In some aspects of the disclosed method, the subject has been diagnosed with a disorder treatable by activation or modulation of the muscarinic receptor and/or a need for activation or modulation of muscarinic receptor activity prior to the administering step. In some aspects of the disclosed method, the subject has been diagnosed with anxiety or a related disorder prior to the administering step. In some aspects of the disclosed methods, the subject has been identified with a need for treatment prior to the administering step. In some aspects of the disclosed method, the subject has been identified with a disorder treatable by activation of the muscarinic receptor and/or or a need for activation/modulation of muscarinic activity prior to the administering step. In some aspects of the disclosed method, the subject has been identified with anxiety or a related disorder prior to the administering step. In one aspect, a subject can be treated prophylactically with a compound or composition disclosed herein, as discussed herein elsewhere.

F. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein. The Examples are provided herein to illustrate the invention, and should not be construed as limiting the invention in any way. The Examples are typically depicted in free base form, according to the IUPAC naming convention. Examples are provided herein to illustrate the invention, and should not be construed as limiting the invention in any way.

As indicated, some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

1. General Methods

Hereinafter, the term "EtOAc" means ethyl acetate, "DCM" means dichloromethane, "DIPEA" means N,N-diisopropylethylamine, "DMF" means N,N-dimethylformamide, "DTBAD" means di-tert-butyl azodicarboxylate, "HATU" means 2-(7-aza-1H-benzotriazole-1-yl)-1,1,3,3-tetramethyluronium hexafluorophosphate, "LCMS" means liquid chromatography/mass spectrometry, "MeOH" means methanol, "[M+H]+" means the protonated mass of the free base of the compound, "M. p." means melting point, "NMR" means nuclear magnetic resonance, "$R_t$" means retention time (in minutes), "THF" means tetrahydrofuran $^1$H NMR spectra were recorded either on a Bruker DPX-400 or on a Bruker AV-500 spectrometer with standard pulse sequences, operating at 400 MHz and 500 MHz respectively. Chemical shifts (δ) are reported in parts per million (ppm) downfield from tetramethylsilane (TMS), which was used as internal standard.

Microwave assisted reactions were performed in a single-mode reactor: Emrys™ Optimizer microwave reactor (Personal Chemistry A.B., currently Biotage).

Analytical thin layer chromatography was performed on Analtech silica gel GF 250 micron plates using reagent grade solvents. Normal phase flash silica gel-based column chromatography was performed using ready-to-connect cartridges from ISCO, on irregular silica gel, particle size 15-40 μm on a Combi-flash Companion chromatography system from ISCO.

Hydrogenation reactions were performed in a continuous flow hydrogenator H -CUBE® from ThalesNano Nanotechnology Inc. or using a Parr hydrogenation shaker apparatus.

Low resolution mass spectra were obtained on an Agilent 1200 series 6130 mass spectrometer. High resolution mass spectra were recorded on a Waters Q-TOF API-US.

Analytical HPLC was performed on an HP1100 with UV detection at 214 and 254 nm along with ELSD detection, LC/MS (J-Sphere80-C18, 3.0×50 mm, 4.1 min gradient, 5%[0.05%TFA/CH$_3$CN]:95%[0.05%TFA/H$_2$O] to 100% [0.05%TFA/CH$_3$CN]. Preparative RP-HPLC purification was performed on a custom HP1100 automated purification system with collection triggered by mass detection or using a Gilson Inc. preparative UV-based system using a Phenomenex Luna C18 column (50×30 mm I.D., 5 μm) with an acetonitrile (unmodified)-water (0.1% TFA) custom gradient.

Chiral purification of racemic mixtures was readily accomplished using a supercritical fluid chromatography (SFC) instrument from Thar Scientific Instruments. Chiral analytical and semi-prep SFC purification columns were from Chiral Technologies.

2. LC-MS Methods

For LC-MS-characterization of the compounds of the present invention, the following methods were used.

In Method 1, the HPLC measurement was performed using an Agilent 1200 system comprising a binary pump with degasser, an autosampler, a column oven, a diode-array detector (DAD) and a column as specified in the respective methods below. Flow from the column was split to a SQ mass spectrometer and Polymer Labs ELSD. The MS detector was configured with an ES ionization source. Nitrogen was used as the nebulizer gas. The source temperature was maintained at 350° C. Data acquisition was performed with Agilent Chemstation software. Reverse phase HPLC was carried out on a Kinetex C18 column (2.6 μm, 2.1×30 μm) from Phenomenex, with a flow rate of 1.5 mL/min, at 45° C. The gradient conditions used were as follows: 93% A (water+0.1% TFA), 7% B (acetonitrile), to 95% B in 1.1 minutes, returning to initial conditions at 1.11 minutes. The injection volume was 1 μL. Low-resolution mass spectra (single quadruple MSD detector) were acquired in electrospray mode by scanning from 100 to 700 in 0.25 seconds, step size of 0.1 and peak width of 0.03 minutes. The capillary needle voltage was 3.0 kV and the fragmentor voltage was 100 V.Method 2 was performed using the same instrument and column conditions as in Method 1. The gradient conditions used were as follows: 93% A (water+0.1% TFA), 7% B (acetonitrile), to 95% B in 2.0 minutes, returning to initial conditions at 2.11 minutes. The injection volume was 1 μL. Low-resolution mass spectra (single quadruple MSD detector) were acquired in electrospray mode by scanning from 100 to 700 in 0.25 seconds, step size of 0.1 and peak width of 0.03 minutes. The capillary needle voltage was 3.0 kV and the fragmentor voltage was 100 V.

3. Intermediate A1: Preparation of 4-Bromo-2,6-Difluorobenzyl Methanesulfonate

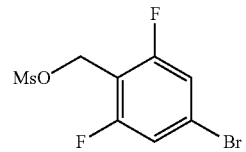 [SMILES: CS(=O)(=O)OCc1c(F)cc(Br)cc1F]

A flame-dried flask was charged with (4-bromo-2,6-difluorophenyl)methanol (223 mg, 1.0 mmol) and DCM (5 mL) under an inert argon atmosphere. After cooling to 0° C., triethylamine (279 μL, 2.0 mmol) and methanesulfonyl chloride (93 μL, 1.2 mmol) were added. The reaction mixture was allowed to reach r.t. and monitored by TLC. After 30 min, ethyl acetate (5 mL) and water (5 mL) were added. The organic layer was removed and washed successively with 1 M HCl (5 mL), sat. NaHCO$_3$ (5 mL), and brine. The organic layer was dried (MgSO$_4$), filtered, and concentrated. The residue was purified on silica gel (1:1 EtOAc: hexanes) to provide mesylate intermediate A1 as a white solid (215 mg, 72%): LC—MS (>98%) m/z=204.9 [M+H] not observed, $R_f$=0.968; $^1$H NMR (500 MHz, CDCl$_3$) δ 7.18 (d, J=7.0 Hz, 2H), 5.28 (s, 1H), 3.05 (s, 3H).

4. Intermediate A2: Preparation of Pyrido[3,4-D]Pyrimidin-4(3H)-One.

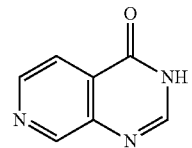 [SMILES: O=c1[nH]cnc2cnccc12]

A Biotage microwave vial was charged with 3-aminoisonicotinic acid (691 mg, 5.0 mmol), formamidine acetate (573 mg, 5.5 mmol), and ethanol (10 mL). The reaction mixture was heated in the microwave at 160° C. for 30 min, diluted with H$_2$O (20 mL), and cooled to 0° C. The suspension was filtered and the solids were washed with cold H$_2$O (10 mL) to provide quinazoline A2 (259 mg, 35%) as a white solid: LC—MS (>98%) m/z=148.0 [M+H], $R_f$=0.604.

5. Intermediate A3: Preparation of 3-(4-Bromo-2,6-Difluorobenzyl)Pyrido[3,4-D]Pyrimidin-4(3H)-One.

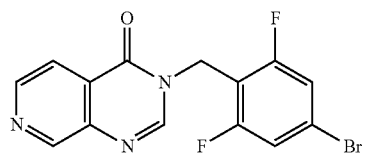 [SMILES: O=c1c2ccncc2ncn1Cc1c(F)cc(Br)cc1F]

A vial was charged with mesylate A1(522 mg, 1.7 mmol), quinazoline A2 (256 mg, 1.7 mmol), Cs$_2$CO$_3$ (1.1 g, 3.4 mmol), and acetonitrile (10 mL). The reaction mixture was heated at 70° C. for 3 h, cooled to r.t., and filtered. After washing with acetonitrile (2×10 mL), the filtrate was concentrated. The residue was purified on silica gel (EtOAc) to provide benzyl quinazoline intermediate A3 as a white solid (453 mg, 74%): LC—MS (>98%) m/z=351.7 [M+H], R$_f$=0.895; $^1$H NMR (500 MHz, CDCl$_3$)δ9.15 (s, 1H), 8.71 (d, J=5.2 Hz, 1H), 8.25 (s, 1H), 8.04 (d, J=5.2 Hz, 1H), 7.14 (d, J=7.5 Hz, 2H), 5.19 (s, 2H).

6. Method A: Preparation of 3-(2,6-Difluoro-4-(2-Methyl-2H-Indazol-4-yl)Benzyl)Pyrido[3,4-D]Pyrimidin-4(3H)-one(B7).

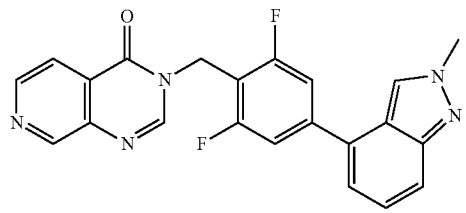 [SMILES: Cn1cc2c(-c3cc(F)c(Cn4cnc5cnccc5c4=O)c(F)c3)cccc2n1]

A microwave vial was charged with 3-(4-bromo-2,6-difluorobenzyl)pyrido[3,4-d]pyrimidin-4(3H)-one (A3, 18 mg, 0.05 mmol), (2-methyl-2H-indazol-4-yl)boronic acid (14 mg, 0.055 mmol), Cs$_2$CO$_3$ (49 mg, 0.15 mmol), [1,1'-bis(diphenylphosphino)ferrocene]palladium(II) dichloride (2.1 mg, 0.0025 mmol), water (0.1 mL), and THF (1 mL). The reaction mixture was heated in the microwave at 140° C. for 10 min, cooled to r.t., and filtered. After washing with methanol (2×3 mL), the filtrate was concentrated. The residue was purified on reverse-phase HPLC (1% aq. NH$_4$OH: acetonitrile) to provide title compound B7 as a white solid (14 mg, 70%): LC—MS (>98%) m/z=403.8 [M+H], Rt=0.915; $^1$H NMR(500 MHz, CDCl$_3$)δ 9.16 (s, 1H), 8.71 (d, J=5.3 Hz, 1H), 8.34 (s, 1H), 8.07 (dd, J=0.6, 5.3 Hz, 1H), 8.02 (s, 1H), 7.74 (d, J=8.7 Hz, 1H), 7.34 (dd, J=7.0, 8.7 Hz, 1H), 7.27-7.25 (m, 2H), 7.13 (d, J=6.9 Hz, 1H).

7. Characterization of Exemplary Compounds

The compounds in Table I were synthesized with methods identical or analogous to those described herein. The Synthetic Example indicated in Table I refers to the compound identified above and corresponding synthetic method described therein. The requisite starting materials were commercially available, described in the literature, or readily synthesized by one skilled in the art of organic synthesis. The mass spectrometry data were obtained using either General LC-MS Method 1 or General LC-MS Method 2 as described above. LC-MS [M+H]$^+$ means the protonated mass of the free base of the compound.

TABLE I

| No. | Compound | LC-MS [M + H]$^+$ | LC-MS Method | Retention time | Synthesis Example/ Scheme* |
|---|---|---|---|---|---|
| B1 | | 402.8 | 1 | 1.011 | Ex. 2/Schemes 1-3 |
| B2 | | 302.9 | 1 | 0.891 | Ex. 2/Scheme 1, 3 |

TABLE I-continued

| No. | Compound | LC-MS [M + H]+ | LC-MS Method | Retention time | Synthesis Example/ Scheme* |
|---|---|---|---|---|---|
| B3 | | 316.9 | 1 | 0.863 | Ex. 2/Schemes 1-3 |
| B4 | | 403.8 | 1 | 0.892 | Ex. 2/Schemes 1-3 |
| B5 | | 303.9 | 1 | 0.712 | Ex. 2/Scheme 1, 3 |
| B6 | | 317.9 | 1 | 0.711 | Ex. 2/Schemes 1-3 |
| B7 | | 403.8 | 1 | 0.915 | Ex. 2 |
| B8 | | 303.9 | 1 | 0.757 | Ex. 2/Scheme 1, 3 |
| B9 | | 317.9 | 1 | 0.762 | Ex. 2/Schemes 1-3 |

TABLE I-continued

| No. | Compound | LC-MS [M + H]+ | LC-MS Method | Retention time | Synthesis Example/ Scheme* |
|---|---|---|---|---|---|
| B10 | (structure) | 303.9 | 1 | 0.73 | Ex. 2/Schemes 1-3 |
| B11 | (structure) | 317.9 | 1 | 0.711 | Ex. 2/Schemes 1-3 |
| B12 | (structure) | 403.8 | 1 | 0.873 | Ex. 2/Schemes 1-3 |

*Synthesis Examples refer to the indicated methods above, e.g. Synthesis Example "2" corresponds to "Method A" described above. Specifically, the examples are as follows: Synthesis Example "2" corresponds to Method A (synthesis of Compound B7; 3-(2,6-difluoro-4-(2-methyl-2H-indazol-4-yl)benzyl)quinazolin-4(3H)-one).

8. Cell Lines Expressing Muscarinic Acetylcholine Receptors

Chinese hamster ovary (CHO-K1) cells stably expressing rat (r)$M_1$ were purchased from the American Type Culture Collection and cultured according to their indicated protocol. CHO cells stably expressing human (h)$M_2$, h$M_3$, and h$M_5$ were described previously (Levey, A. I., et al., *J Neurosci.* 1991, 11, 3218-3226.); h$M_1$ and h$M_4$ cDNAs were purchased from Missouri S&T cDNA Resource; r$M_4$ cDNA was provided by T. I. Bonner (National Institutes of Health, Bethesda, Md.). r$M_2$ and r$M_3$ were cloned from a rat brain cDNA library and sequence verified. h$M_1$, r$M_2$, r$M_3$, h$M_4$, and r$M_4$ cDNAs were used to stably transfect CHO-K1 cells purchased from the American Type Culture Collection using Lipofectamine® 2000 (Thermo Fisher Scientific Inc.). To make stable r$M_2$, h$M_2$, h$M_4$, and r$M_4$ cell lines for use in calcium mobilization assays, these cells also were stably transfected with a chimeric G-protein ($G_{qi5}$) (provided by B. R. Conklin, University of California, San Francisco) using Lipofectamine® 2000. r$M_1$, h$M_1$, r$M_3$, h$M_3$, r$M_5$, and h$M_5$ cells were grown in Ham's F-12 medium containing 10% heat-inactivated fetal bovine serum (FBS), 20 mM HEPES, and 50 μg/mL G418 sulfate. r$M_2$-$G_{qi5}$, h$M_2$-$G_{qi5}$, and h$M_4$-$G_{qi5}$ cells were grown in the same medium also containing 500 μg/mL hygromycin B. Stable r$M_4$-$G_{qi5}$ cells were grown in DMEM containing 10% heat-inactivated FBS, 20 mM HEPES, 400 μg/mL G418 sulfate, and 500 μg/mL hygromycin B.

9. Cell-Based Functional Assay of Muscarinic Acetylcholine Receptor Activity

For high throughput measurement of agonist-evoked increases in intracellular calcium, CHO-K1 cells stably expressing muscarinic receptors were plated in growth medium lacking G418 and hygromycin B at 15,000 cells/20 μL/well in Greiner 384-well black-walled, tissue culture (TC)-treated, clear-bottom plates (VWR). Cells were incubated overnight at 37° C. and 5% $CO_2$. The next day, cells were washed using an ELX 405 (BioTek) with four washes (80 μL) of assay buffer then aspirated to 20 μL. Next, 20 μL of 16 μM Fluo-4/acetoxymethyl ester (Invitrogen, Carlsbad, Calif.) prepared as a 2.3 mM stock in DMSO and mixed in a 1:1 ratio with 10% (w/v) Pluronic F-127 and diluted in assay buffer was added to the wells and the cell plates were incubated for 50 min at 37° C. and 5% $CO_2$. Dye was removed by washing with the ELX 405 (four 80 μL washes of assay buffer) then aspirated to 20 μL. Compound master plates were formatted in an 11 point CRC format (1:3 dilutions) in 100% DMSO with a starting concentration of 10 mM using the BRAVO liquid handler (Agilent). Test compound CRCs were then transferred to daughter plates (240 nL) using the Echo acoustic plate reformatter (Labcyte, Sunnyvale, Calif.) and then diluted into assay buffer (40 μL) to a 2× stock using a Thermo Fisher Combi (Thermo Fisher Scientific, Waltham, Mass.).

Calcium flux was measured using the Functional Drug Screening System (FDSS) 6000 (Hamamatsu Corporation, Tokyo, Japan) as an increase in the fluorescent static ratio. Compounds were applied to cells (20 μL, 2X) using the automated system of the FDSS 6000 at 4 s into the 300 s protocol and the data were collected at 1 Hz. At 144 s into the 300 s protocol, 10 μL of an $EC_{20}$ concentration of the muscarinic receptor agonist acetylcholine was added (5X), followed by the addition of 12 μL, an $EC_{80}$ concentration of acetylcholine at the 230 s time point (5X). Agonist activity was analyzed as a concentration—dependent increase in calcium mobilization upon compound addition. Positive allosteric modulator activity was analyzed as a concentration-dependent increase in the $EC_{20}$ acetylcholine response. Antagonist activity was analyzed as a concentration-dependent decrease in the $EC_{80}$ acetylcholine response. Concentration-response curves were generated using a four-parameter logistical equation in XLFit curve fitting software (IDBS, Bridgewater, N.J.) for Excel (Microsoft, Redmond, Wash.) or Prism (GraphPad Software, Inc., San Diego, Calif.).

The above described assay was also operated in a second mode where an appropriate fixed concentration of the present compounds were added to the cells after establishment of a fluorescence baseline for about 3 seconds, and the response in cells was measured. 140 s later the appropriate concentration of agonist was added and readings taken for an additional 106 s. Data were reduced as described above and the $EC_{50}$ values for the agonist in the presence of test compound were determined by nonlinear curve fitting. A decrease in the $EC_{50}$ value of the agonist with increasing concentrations of the present compounds (a leftward shift of the agonist concentration-response curve) is an indication of the degree of muscarinic positive allosteric modulation at a given concentration of the present compound. An increase in the $EC_{50}$ value of the agonist with increasing concentrations of the present compounds (a rightward shift of the agonist concentration response curve) is an indication of the degree of muscarinic antagonism at a given concentration of the present compound. The second mode also indicates whether the present compounds also affect the maximum response of the muscarinic receptor to agonists.

The calcium mobilization assay was also used to determine "efficacy". In the context of the assays carried out for the data in Table II, "efficacy" (%ACh at 30 μM) is defined as the maximal response in the calcium flux as determined by the sigmoidal curve fit of the concentration response curve, or in the absence of an acceptable curve fit, the response recorded at 30 μM test compound, stated as a percentage of the response elicited by a concentration of Ach that induces approximately 80% of a maximal (i.e. saturating) ACh response.

10. Activity of Compounds in Cell-Based Assays

Substituted 3-benzylquinazolin-4(3H)-one analogs were synthesized as described above. Activity ($EC_{50}$ and $E_{max}$) was determined in the mAChR $M_1$ cell-based functional assay as described above and the data are shown in Table II. The compound number corresponds to the compound numbers used in Table I.

TABLE II

| No. | $EC_{50}$ (μM) |
| --- | --- |
| B1 | 10 |
| B2 | >10 |
| B3 | >10 |
| B4 | 10 |
| B5 | >10 |
| B6 | >10 |
| B7 | 0.6 |
| B8 | >10 |
| B9 | 4.9 |
| B10 | >10 |
| B11 | >10 |
| B12 | 3.6 |

For compounds showing low potency (as indicated by a lack of a plateau in the concentration response curve) but greater than a 20% increase in ACh response, a potency of >10 μM ($pEC_{50}$<5) is estimated.

The selectivity of the disclosed compounds for mAChR $M_1$ compared to mAChR $M_2$, $M_3$, $M_4$, and $M_5$ was determined using the cell-based functional assay described below using the appropriate cell-lines (prepared as described below). The $EC_{50}$ for each of mAChR $M_2$, $M_3$, $M_4$, and $M_5$ was greater than at least 30 μM for representative compounds (i.e., there was no receptor response up to a concentration of about 30 μM, the upper limit of compound used in the assay).

11. Prophetic Pharmaceutical Composition Examples

"Active ingredient" as used throughout these examples relates to one or more disclosed compounds or products of disclosed methods of making as described hereinbefore, or a pharmaceutically acceptable salt, hydrate, solvate, or polymorph thereof. The following examples of the formulation of the compounds of the present invention in tablets, suspension, injectables and ointments are prophetic. Typical examples of recipes for the formulation of the invention are as given below.

Typical examples of recipes for the formulation of the invention are as given below. Various other dosage forms can be applied herein such as a filled gelatin capsule, liquid emulsion/suspension, ointments, suppositories or chewable tablet form employing the disclosed compounds in desired dosage amounts in accordance with the present invention. Various conventional techniques for preparing suitable dosage forms can be used to prepare the prophetic pharmaceutical compositions, such as those disclosed herein and in standard reference texts, for example the British and U.S. Pharmacopoeias, *Remington's Pharmaceutical Sciences* (Mack Publishing Co.) and *Martindale The Extra Pharmacopoeia* (London The Pharmaceutical Press).

The disclosure of this reference is hereby incorporated herein by reference.

a. Pharmaceutical Composition for Oral Administration

A tablet can be prepared as follows:

| Component | Amount |
| --- | --- |
| Active ingredient | 10 to 500 mg |
| Lactose | 100 mg |
| Crystalline cellulose | 60 mg |
| Magnesium stearate | 5 |
| Starch (e.g. potato starch) | Amount necessary to yield total weight indicated below |
| Total (per capsule) | 1000 mg |

Alternatively, about 100 mg of a disclosed compound, 50 mg of lactose (monohydrate), 50 mg of maize starch (native), 10 mg of polyvinylpyrrolidone (PVP 25) (e.g. from BASF, Ludwigshafen, Germany) and 2 mg of magnesium stearate are used per tablet. The mixture of active component, lactose and starch is granulated with a 5% solution (m/m) of the PVP in water. After drying, the granules are mixed with magnesium stearate for 5 min. This mixture is molded using a customary tablet press (e.g. tablet format: diameter 8 mm, curvature radius 12 mm). The molding force applied is typically about 15 kN.

Alternatively, a disclosed compound can be administered in a suspension formulated for oral use. For example, about 100-5000 mg of the desired disclosed compound, 1000 mg of ethanol (96%), 400 mg of xanthan gum, and 99 g of water are combined with stirring. A single dose of about 10-500 mg of the desired disclosed compound according can be provided by 10 ml of oral suspension.

In these Examples, active ingredient can be replaced with the same amount of any of the compounds according to the present invention, in particular by the same amount of any of the exemplified compounds. In some circumstances it may be desirable to use a capsule, e.g. a filled gelatin capsule, instead of a tablet form. The choice of tablet or capsule will depend, in part, upon physicochemical characteristics of the particular disclosed compound used.

Examples of alternative useful carriers for making oral preparations are lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. These alternative carriers can be substituted for those given above as required for desired dissolution, absorption, and manufacturing characteristics.

The amount of a disclosed compound per tablet for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

b. Pharmaceutical Composition for Injectable Use

A parenteral composition can be prepared as follows:

| Component | Amount* |
| --- | --- |
| Active ingredient | 10 to 500 mg |
| Sodium carbonate | 560 mg* |
| Sodium hydroxide | 80 mg* |
| Distilled, sterile water | Quantity sufficient to prepare total volume indicated below. |
| Total (per capsule) | 10 ml per ampule |

*Amount adjusted as required to maintain physiological pH in the context of the amount of active ingredient, and form of active ingredient, e.g. a particular salt form of the active ingredient.

Alternatively, a pharmaceutical composition for intravenous injection can be used, with composition comprising about 100-5000 mg of a disclosed compound, 15 g polyethylene glycol 400 and 250 g water in saline with optionally up to about 15% Cremophor EL, and optionally up to 15% ethyl alcohol, and optionally up to 2 equivalents of a pharmaceutically suitable acid such as citric acid or hydrochloric acid are used. The preparation of such an injectable composition can be accomplished as follows: The disclosed compound and the polyethylene glycol 400 are dissolved in the water with stirring. The solution is sterile filtered (pore size 0.22 µm) and filled into heat sterilized infusion bottles under aseptic conditions. The infusion bottles are sealed with rubber seals.

In a further example, a pharmaceutical composition for intravenous injection can be used, with composition comprising about 10-500 mg of a disclosed compound, standard saline solution, optionally with up to 15% by weight of Cremophor EL, and optionally up to 15% by weight of ethyl alcohol, and optionally up to 2 equivalents of a pharmaceutically suitable acid such as citric acid or hydrochloric acid. Preparation can be accomplished as follows: a desired disclosed compound is dissolved in the saline solution with stirring. Optionally Cremophor EL, ethyl alcohol or acid are added. The solution is sterile filtered (pore size 0.22 µm) and filled into heat sterilized infusion bottles under aseptic conditions. The infusion bottles are sealed with rubber seals.

In this example, active ingredient can be replaced with the same amount of any of the compounds according to the present invention, in particular by the same amount of any of the exemplified compounds.

The amount of a disclosed compound per ampule for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

Carriers suitable for parenteral preparations are, for example, water, physiological saline solution, etc. which can be used with tris(hydroxymethyl)aminomethane, sodium carbonate, sodium hydroxide or the like serving as a solubilizer or pH adjusting agent. The parenteral preparations contain preferably 50 to 1000 mg of a disclosed compound per dosage unit.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

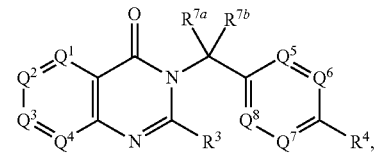

wherein:
$Q^1$ is selected from N and $CR^{1a}$;
$Q^2$ is $CR^{1b}$;
$Q^3$ is selected from N and $CR^{1c}$;
$Q^4$ is selected from N and $CR^{1d}$;
provided that 0 or 1 of $Q^1$, $Q^3$, and $Q^4$ is N;
each of $R^{1a}$, $R^{1b}$, $R^{1c}$, and $R^{1d}$, when present, is independently selected from hydrogen, halogen, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino;
$Q^5$ is selected from N and $CR^{2a}$;
$Q^6$ is selected from N and $CR^{2b}$;
$Q^7$ is selected from N and $CR^{2c}$;
$Q^8$ is selected from N and $CR^{2d}$;
provided that 0, 1 or 2 of $Q^5$, $Q^6$, $Q^7$, and $Q^8$ are N;
each of $R^{2a}$, $R^{2b}$, $R^{2c}$, and $R^d$, when present, is independently selected from hydrogen, halogen, cyano, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy C1-C6 alkyl, C1-C6 polyhaloalkyl-oxy-C1-C6 alkyl, C1-C6 dialkylamino, —C(OH)$R^{20a}R^{20b}$, and —SO$_2R^{30}$;

each of $R^{20a}$ and $R^{20b}$ is independently selected from hydrogen, C1-C3 alkyl, C1-C3 haloalkyl, and C1-C3 polyhaloalkyl;
$R^{30}$ is selected from C1-C3 alkyl, C1-C3 haloalkyl, and C1-C3 polyhaloalkyl;
$R^3$ is selected from hydrogen, C1-C3 alkyl, C1-C3 haloalkyl, C1-C3 polyhaloalkyl, cyclopropyl, and $Ar^1$;
wherein $Ar^1$ is selected from phenyl, indenyl, and naphthalenyl;
wherein $Ar^1$ is substituted with 0-3 substituents selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino;
$R^4$ is selected from $Ar^2$, —$L^2$—$Ar^2$, and $Cy^1$;
$L^2$ is selected from —$CR^{8a}R^{8b}$—, —O—, —$NR^9$—, —S—, —(S=O)—, and —(SO$_2$)—;
each of $R^{8a}$ and $R^{8b}$ is independently selected from hydrogen, C1-C6 alkyl, C1-C6 haloalkyl, and C1-C6 polyhaloalkyl;
$R^9$ is selected from hydrogen and C1-C6 alkyl;
$Ar^2$ is selected from benzodioxolyl, benzofuranyl, benzoimidazolyl, benzoisoxazolyl, benzooxadiazolyl, benzooxazolyl, benzothiazolyl, benzothiophenyl, dihydrobenzodioxinyl, dihydrobenzofuranyl, dihydroisobenzofuranyl, furanyl, furopyridinyl, imidazolyl, imidazopyrazinyl, imidazopyridinyl, indazolyl, indolinyl, indolyl, isoindolinyl, isoquinolinyl, naphthyridinyl, oxadiazolyl, oxazolyl, oxoindolinyl, 2'-oxospiro[1,3]dioxolane-2,3'-indolinyl, pyrazinyl, pyridinyl, pyrimidinyl, pyrrolopyridinyl, pyrrolyl, quinazolinyl, quinolinyl, quinoxalinyl, tetrahydroquinolinyl, thiadiazolyl, thiazolyl, triazopyridinyl, and triazolyl;
wherein $Ar^2$ is substituted with 0-3 substituents selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or
$Ar^2$ is pyrazolyl substituted with 1-3 substituents selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino;
$Cy^1$ is C2-C5 heterocycloalkyl or C2-C5 heterocycloalkenyl; wherein $Cy^1$ is substituted with 0-3 substituents selected from halogen, hydroxyl, cyano, —NH$_2$, C1-C6 alkyl, C1-C6 alkoxy, C1-C6 haloalkyl, C1-C6 polyhaloalkyl, C1C6 alkylamino, and C1-C6 dialkylamino, and wherein two of the substituents are optionally covalently bonded, and together with the intermediate atoms, comprise a 3- to 6-membered fused ring group;
and each of $R^{7a}$ and $R^{7b}$ is independently selected from hydrogen, C1-C6 alkyl, C1-C6 haloalkyl, and C1-C6 polyhaloalkyl;
or a pharmaceutically acceptable salt, thereof.

2. The compound of claim 1, wherein each of $R^{1a}$, $R^{1b}$, $R^{1c}$, and $R^{1d}$, when present, is hydrogen.

3. The compound of claim 1, having a structure represented by a formula:

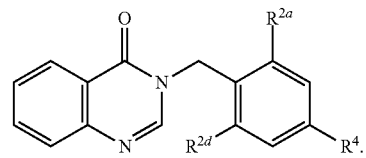

4. The compound of claim 1, having a structure represented by a formula:

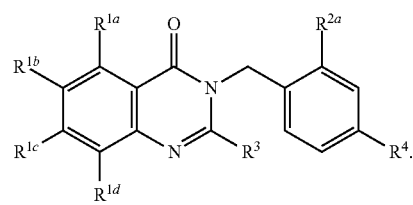

5. The compound of claim 1, having a structure represented by a formula:

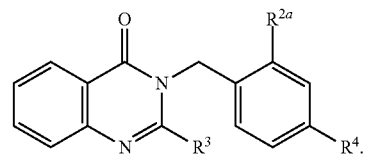

6. The compound of claim 1, having a structure represented by a formula:

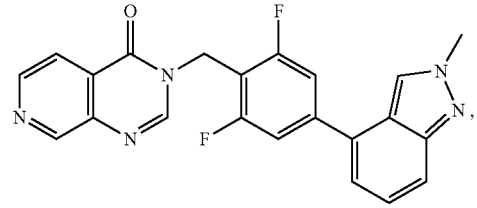

7. The compound of claim 1, having a structure selected from:

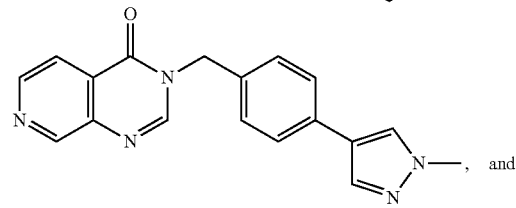

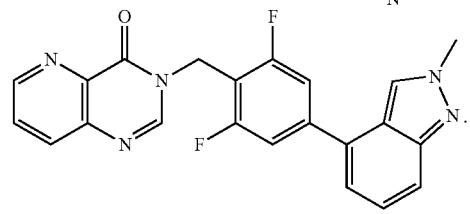

8. A pharmaceutical composition comprising a therapeutically effective amount of at least one compound of claim 1, or pharmaceutically acceptable salt thereof, and a pharmaceutically acceptable carrier.

9. A method for modulating muscarinic acetylcholine receptor activity in a mammal;
the method comprising the step of administering to the mammal an effective amount of at least one compound of claim 1, or a pharmaceutically acceptable salt thereof.

10. The method of claim 9, wherein the mammal has a disorder selected from psychosis, schizophrenia, conduct disorder, disruptive behavior disorder, bipolar disorder, psychotic episodes of anxiety, anxiety associated with psychosis, psychotic mood disorders, severe major depressive disorder, mood disorders associated with psychotic disorders, acute mania, depression associated with bipolar disorder, mood disorders associated with schizophrenia, behavioral manifestations of mental retardation, conduct disorder, autistic disorder, movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders.

11. The method of claim 9, wherein the mammal has a disorder selected from Alzheimer's disease, schizophrenia, a sleep disorder, a pain disorder and a cognitive disorder.

12. The method of claim 11, wherein the disorder is Alzheimer's disease.

* * * * *

UNITED STATES PATENT AND TRADEMARK OFFICE
CERTIFICATE OF CORRECTION

PATENT NO. : 9,540,371 B2  
APPLICATION NO. : 14/787722  
DATED : January 10, 2017  
INVENTOR(S) : Craig W. Lindsley et al.

Page 1 of 1

It is certified that error appears in the above-identified patent and that said Letters Patent is hereby corrected as shown below:

In the Claims

Claim 1, Column 208, Line 60:  Replace [[0, 1 or 2]]
with --0, 1, or 2--

Claim 1, Column 208, Line 61:  Replace [[R2a, R2b, R2c, and Rd]]
with --R2a, R2b, R2c, and R2d--

Claim 1, Column 209, Line 44:  Replace [[C1C6 alkylamino]]
with --C1-C6 alkylamino--

Signed and Sealed this
Sixteenth Day of May, 2017

Michelle K. Lee
*Director of the United States Patent and Trademark Office*